US011253587B2

(12) United States Patent
Anderson et al.

(10) Patent No.: US 11,253,587 B2
(45) Date of Patent: Feb. 22, 2022

(54) VACCINE COMPOSITIONS FOR THE TREATMENT OF CORONAVIRUS

(71) Applicant: Variation Biotechnologies Inc., Ottawa (CA)

(72) Inventors: David Evander Anderson, Newton, MA (US); Anne-Catherine Fluckiger, Saint Genis les Ollières (FR)

(73) Assignee: Variation Biotechnologies Inc., Ottawa (CA)

( * ) Notice: Subject to any disclaimer, the term of this patent is extended or adjusted under 35 U.S.C. 154(b) by 0 days.

(21) Appl. No.: 17/218,148

(22) Filed: Mar. 30, 2021

(65) Prior Publication Data

US 2021/0353741 A1 Nov. 18, 2021

Related U.S. Application Data

(60) Provisional application No. 63/070,150, filed on Aug. 25, 2020, provisional application No. 63/002,237, filed on Mar. 30, 2020.

(51) Int. Cl.

*A61K 39/12* (2006.01)
*A61K 39/00* (2006.01)
*C12N 7/00* (2006.01)
*C07K 14/005* (2006.01)
*A61K 39/21* (2006.01)
*A61K 39/215* (2006.01)

(52) U.S. Cl.

CPC .............. *A61K 39/215* (2013.01); *C12N 7/00* (2013.01); *A61K 2039/55505* (2013.01); *C12N 2740/13034* (2013.01); *C12N 2760/20234* (2013.01); *C12N 2770/20034* (2013.01)

(58) Field of Classification Search

CPC ............ A61K 39/12; A61K 2039/5258; C07K 14/005; C07K 2319/00; C12N 7/00

See application file for complete search history.

(56) References Cited

U.S. PATENT DOCUMENTS 5,500,161 A 3/1996 Andrianov et al.
8,920,812 B2 12/2014 Haynes

FOREIGN PATENT DOCUMENTS

WO WO-2005/118813 A2 12/2005
WO WO-2010/059689 A2 5/2010
WO WO-2011/115583 A1 9/2011
WO WO2011115583 * 9/2011

OTHER PUBLICATIONS

Allison, A.C., The Mode of Action of Immunological Adjuvants, Dev. Biol. Stand., 92:3-11 (1998).

Altschul, S. F. et al., Basic local alignment search tool, J. Mol. Biol., 215(3):403-410 (1990).

Altschul, S.F. et al., Gapped BLAST and PSI-BLAST: a new generation of protein database search programs, Nucleic Acids Res., 25(17):3389-3402 (1997).

Bachmann, M. F. et al., The influence of antigen organization on B cell responsiveness, Science, 262(5138):1448-1451 (1993).

Broer, R. et al., Important Role for the Transmembrane Domain of Severe Acute Respiratory Syndrome Coronavirus Spike Protein during Entry, J. Vir., 80(3):1302-1310 (2006).

Compton, T. et al., A sorting signal for the basolateral delivery of the vesicular stomatitis virus (VSV) G protein lies in its luminal domain: Analysis of the targeting of VSV G-influenza hemagglutinin chimeras, Proc Natl Acad Sci USA, 86:4112-4116 (1989).

Fontanet, A. et al., SARS-CoV-2 variants and ending the COVID-19 pandemic, The Lancet, 397(10278):952-954 (2021).

Garrone, P. et al., A Prime-Boost Strategy Using Virus-Like Particles Pseudotyped for HCV Proteins Triggers Broadly Neutralizing Antibodies in Macaques, Science Trans. Med., 3(94): 1-8 (2011).

Graham, F. L. et al., Characteristics of a Human Cell Line Transformed by DNA from Human Adenovirus Type 5, J. Gen Virol., 36:59-74 (1977).

Kirchmeier, M. et al., Enveloped Virus-Like Particle Expression of Human Cytomegalovirus Glycoprotein B Antigen Induces Antibodies with Potent and Broad Neutralizing Activity, CVI 21(2): 174-180 (2014).

Korber, B. et al, Tracking Changes in SARS-CoV-2 Spike: Evidence that D614G Increases Infectivity of the COVID-19 Virus, Cell, 182(4):812-827 (2020).

Lemaitre, M. et al., Seasonal H1N1 2007 influenza virus infection is associated with elevated pre-exposure antibody titers to the 2009 pandemic influenza A (H1N1) virus, Clin Microbiol Infect., 17(5):732-737 (2011).

Levy, C. et al., Virus-like particle vaccine induces cross-protection against human metapneumovirus infections in mice, Vaccine, 31(25):2778-2785 (2013).

Madhi, S. A. et al., Safety and efficacy of the ChAdOx1 nCoV-19 (AZD1222) Covid-19 vaccine against the B.1.351 variant in South Africa, N.E.J.M. DOI: 10.1056/NEJMoa2102214 (2021).

Mammano, F. et al., Truncation of the human immunodeficiency virus type 1 envelope glycoprotein allows efficient pseudotyping of Moloney murine leukemia virus particles and gene transfer into CD4+ cells, J Virol, 71(4):3341-3345 (1997).

Mather, J. P. et al., Culture of testicular cells in hormone-supplemented serum-free medium, *Annals N.Y. Acad. Sci.*, 383:44-68 (1982).

Mather, J. P., Establishment and characterization of two distinct mouse testicular epithelial cell lines, Biol. Reprod. 23(1):243-251 (1980).

(Continued)

*Primary Examiner* — Barry A Chestnut

(74) *Attorney, Agent, or Firm* — Choate, Hall & Stewart LLP; Rolando Medina

(57) ABSTRACT

The present disclosure provides compositions and methods useful for preventing and/or treating coronavirus infection. As described herein, the compositions and methods are based on development of immunogenic compositions that include virus-like particles (VLPs) which comprise one or more Moloney Murine leukemia virus (MMLV) core proteins and include one or more coronavirus epitopes, such as, for example, from SARS-Cov-2 spike protein.

20 Claims, 2 Drawing Sheets

Specification includes a Sequence Listing.

(56) References Cited

OTHER PUBLICATIONS

Pallesen, J. et al., Immunogenicity and structures of a rationally designed prefusion MERS-CoV spike antigen, PNAS, 114(35): E7348-E7357 (2017).
Phillips, N. C. and Emili, A., Enhanced antibody response to liposome-associated protein antigens: preferential stimulation of IgG2a/b production, Vaccine, 10(3):151-158 (1992).
Sharma, S. et al., Noninfectious virus-like particles produced by Moloney murine leukemia virus-based retrovirus packaging cells deficient in viral envelope become infectious in the presence of lipofection reagents, Proc. Natl. Acad. Sci. USA 94(20):10803-8 (1997).
Unkeless, J. C. et al., Structure and function of human and murine receptors for IgG, Annu. Rev. Immunol., 6:251-281 (1988).
Urlaub, G. and Chasin, L.A., Isolation of Chinese Hamster Cell Mutants Deficient in Dihydrofolate Reductase Activity, Proc. Natl. Acad. Sci. USA, 77(7):4216-4220 (1980).
Wan, Y. et al., Receptor Recognition by the Novel Coronavirus from Wuhan: an Analysis Based on Decade-Long Structural Studies of SARS Coronavirus, J. Vir. 94(7):1-9 (2020).
Wrapp, D. et al., Cryo-EM structure of the 2019-nCoV spike in the prefusion conformation, Science, 367(6483):1260-1263 (2020).
International Search Report for PCT/US21/000190, 4 pages (dated Jun. 25, 2021).
Written Opinion for PCT/US21/000190, 4 pages (dated Jun. 25, 2021).

* cited by examiner

VBI Constructs of full length Spike CoV

S from Covid-19
Ward, 2020
1
SS
NTD
RBD
SD1
SD2
S1/S2
S2'
FP
HR1
CH
CD
1208
TM
HR2
CT
1273

COVID-S
S1
S2
TMCyt
1
685
1273
SARS-S
S1
S2
TMCyt
1
667
1255
MERS-S
S1
S2
TMCyt
1
751
1353

SEQUENCE LISTING

```
<160> NUMBER OF SEQ ID NOS: 44

<210> SEQ ID NO 1
<211> LENGTH: 538
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255

Glu Ser Val Leu Ile Thr His Gln Pro Thr Trp Asp Asp Cys Gln Gln
```

```
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
    290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365

Leu Glu Arg Leu Lys Glu Ala Tyr Arg Arg Tyr Thr Pro Tyr Asp Pro
    370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Glu Arg Ile Arg Arg Glu Thr
        435                 440                 445

Glu Glu Lys Glu Glu Arg Arg Arg Thr Glu Asp Glu Gln Lys Glu Lys
    450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg Arg
                485                 490                 495

Ser Gln Leu Asp Arg Asp Gln Cys Ala Tyr Cys Lys Glu Lys Gly His
            500                 505                 510

Trp Ala Lys Asp Cys Pro Lys Lys Pro Arg Gly Pro Arg Gly Pro Arg
        515                 520                 525

Pro Gln Thr Ser Leu Leu Thr Leu Asp Asp
    530                 535


<210> SEQ ID NO 2
<211> LENGTH: 1614
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

atgggccaga ctgttaccac tcccttaagt ttgaccttag gtcactggaa agatgtcgag      60

cggatcgctc acaaccagtc ggtagatgtc aagaagagac gttgggttac cttctgctct     120

gcagaatggc caacctttaa cgtcggatgg ccgcgagacg gcacctttaa ccgagacctc     180

atcacccagg ttaagatcaa ggtcttttca cctggcccgc atggacaccc agaccaggtc     240

ccctacatcg tgacctggga agccttggct tttgaccccc ctccctgggt caagcccttt     300

gtacacccta agcctccgcc tcctcttcct ccatccgccc cgtctctccc ccttgaacct     360

cctcgttcga ccccgcctcg atcctcccct tatccagccc tcactccttc tctaggcgcc     420

aaacctaaac ctcaagttct ttctgacagt ggggggccgc tcatcgacct acttacagaa     480
```

gaccccccgc cttataggga cccaagacca ccccccttccg acagggacgg aaatggtgga 540
gaagcgaccc ctgcgggaga ggcaccggac ccctccccaa tggcatctcg cctacgtggg 600
agacgggagc cccctgtggc cgactccact acctcgcagg cattcccccct ccgcgcagga 660 ggaaacggac agcttcaata ctggccgttc tcctcttctg acctttacaa ctggaaaaat 720
aataaccctt ctttttctga agatccaggt aaactgacag ctctgatcga gtctgttctc 780
atcacccatc agcccacctg ggacgactgt cagcagctgt tggggactct gctgaccgga 840
gaagaaaaac aacgggtgct cttagaggct agaaaggcgg tgcggggcga tgatgggcgc 900
cccactcaac tgcccaatga agtcgatgcc gcttttcccc tcgagcgccc agactgggat 960
tacaccaccc aggcaggtag gaaccaccta gtccactatc gccagttgct cctagcgggt 1020
ctccaaaacg cgggcagaag ccccaccaat ttggccaagg taaaaggaat aacacaaggg 1080
cccaatgagt ctccctcggc cttcctagag agacttaagg aagcctatcg caggtacact 1140
ccttatgacc ctgaggaccc agggcaagaa actaatgtgt ctatgtcttt catttggcag 1200
tctgccccag acattgggag aaagttagag aggttagaag atttaaaaaa caagacgctt 1260
ggagatttgg ttagagaggc agaaaagatc tttaataaac gagaaacccc ggaagaaaga 1320
gaggaacgta tcaggagaga aacagaggaa aaagaagaac gccgtaggac agaggatgag 1380
cagaaagaga aagaaagaga tcgtaggaga catagagaga tgagcaagct attggccact 1440
gtcgttagtg gacagaaaca ggatagacag ggaggagaac gaaggaggtc ccaactcgat 1500
cgcgaccagt gtgcctactg caaagaaaag gggcactggg ctaaagattg tcccaagaaa 1560
ccacgaggac ctcggggacc aagaccccag acctccctcc tgaccctaga tgac 1614

<210> SEQ ID NO 3
<211> LENGTH: 1614
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
atgggacaga ccgtcacaac acccctgagc ctgaccctgg gacattggaa agacgtggag 60
aggatcgcac ataaccagag cgtggacgtg aagaaacgga gatgggtcac attctgcagt 120
gctgagtggc caacttttaa tgtgggatgg ccccgagacg gcactttcaa cagggatctg 180
atcacccagg tgaagatcaa ggtctttagc ccaggacctc acggacatcc agaccaggtg 240
ccttatatcg tcacctggga ggcactggcc ttcgatcccc ctccatgggt gaagccattt 300
gtccacccaa aaccacctcc accactgcct ccaagtgccc cttcactgcc actggaacca 360
ccccggagca caccaccccg cagctccctg tatcctgctc tgactccatc tctgggcgca 420
aagccaaaac cacaggtgct gagcgactcc ggaggaccac tgattgacct gctgacagag 480 gacccccccac cataccgaga tcctcggcct ccaccaagcg accgcgatgg aaatggagga 540
gaggctactc ctgccggcga agcccctgac ccatctccaa tggctagtag gctgcgcggc 600
aggcgcgagc ctccagtggc agatagcacc acatcccagg ccttccctct gagggctggg 660
ggaaatgggc agctccagta ttggccattt tctagttcag acctgtacaa ctggaagaac 720
aataacccct ctttcagtga ggaccccggc aaactgaccg ccctgatcga atccgtgctg 780
attacccatc agcccacatg ggacgattgt cagcagctcc tgggcaccct gctgaccgga 840
gaggaaaagc agcgcgtgct gctggaggct cgcaaagcag tccgagggga cgatggacgg 900

```
cccacacagc tccctaatga ggtggacgcc gcttttccac tggaaagacc cgactgggat    960

tatactaccc aggcagggag aaaccacctg gtccattaca ggcagctcct gctggcaggc   1020

ctgcagaatg ccgggagatc ccccaccaac ctggccaagg tgaaaggcat cacacagggg   1080

cctaatgagt caccaagcgc ctttctggag aggctgaagg aagcttaccg acggtatacc   1140

ccatacgacc ctgaggaccc cggacaggaa acaaacgtct ccatgtcttt catctggcag   1200

tctgccccag acattgggcg gaagctggag agactggaag acctgaagaa caagaccctg   1260

ggcgacctgg tgcgggaggc tgaaaagatc ttcaacaaac gggagacccc cgaggaaaga   1320

gaggaaagga ttagaaggga aactgaggaa aaggaggaac gccgacggac cgaggacgaa   1380

cagaaggaga aagaacgaga tcggcggcgg caccgggaga tgtcaaagct gctggccacc   1440

gtggtcagcg gacagaaaca ggacagacag ggaggagagc gacggagaag ccagctcgac   1500

agggatcagt gcgcatactg taaggaaaaa ggccattggg ccaaggattg ccccaaaaag   1560

ccaagaggac caagaggacc aagaccacag acatcactgc tgaccctgga cgac         1614
```

```
<210> SEQ ID NO 4
<211> LENGTH: 1273
<212> TYPE: PRT
<213> ORGANISM: Severe acute respiratory syndrome coronavirus 2

<400> SEQUENCE: 4

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
```

-continued

```
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670
```

-continued

```
Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080
```

-continued

```
Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 5
<211> LENGTH: 3822
<212> TYPE: DNA
<213> ORGANISM: Severe acute respiratory syndrome coronavirus 2

<400> SEQUENCE: 5

atgtttgttt ttcttgtttt attgccacta gtctctagtc agtgtgttaa tcttacaacc     60

agaactcaat tacccccctgc atacactaat tctttcacac gtggtgttta ttaccctgac    120

aaagttttca gatcctcagt tttacattca actcaggact tgttcttacc tttcttttcc    180

aatgttactt ggttccatgc tatacatgtc tctgggacca atggtactaa gaggtttgat    240

aaccctgtcc taccatttaa tgatggtgtt tattttgctt ccactgagaa gtctaacata    300

ataagaggct ggatttttgg tactacttta gattcgaaga cccagtccct acttattgtt    360

aataacgcta ctaatgttgt tattaaagtc tgtgaatttc aattttgtaa tgatccattt    420

ttgggtgttt attaccacaa aaacaacaaa agttggatgg aaagtgagtt cagagtttat    480

tctagtgcga ataattgcac ttttgaatat gtctctcagc cttttcttat ggaccttgaa    540

ggaaaacagg gtaatttcaa aaatcttagg gaatttgtgt ttaagaatat tgatggttat    600

tttaaaatat attctaagca cacgcctatt aatttagtgc gtgatctccc tcagggtttt    660

tcggctttag aaccattggt agatttgcca ataggtatta acatcactag gtttcaaact    720

ttacttgctt tacatagaag ttatttgact cctggtgatt cttcttcagg ttggacagct    780

ggtgctgcag cttattatgt gggttatctt caacctagga cttttctatt aaaatataat    840

gaaaatggaa ccattacaga tgctgtagac tgtgcacttg accctctctc agaaacaaag    900

tgtacgttga aatccttcac tgtagaaaaa ggaatctatc aaacttctaa ctttagagtc    960
```

```
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
```

```
tttgtgtctg gtaactgtga tgttgtaata ggaattgtca acaacacagt ttatgatcct   3420

ttgcaacctg aattagactc attcaaggag gagttagata aatattttaa gaatcataca   3480

tcaccagatg ttgatttagg tgacatctct ggcattaatg cttcagttgt aaacattcaa   3540

aaagaaattg accgcctcaa tgaggttgcc aagaatttaa atgaatctct catcgatctc   3600

caagaacttg gaaagtatga gcagtatata aaatggccat ggtacatttg gctaggtttt   3660

atagctggct tgattgccat agtaatggtg acaattatgc tttgctgtat gaccagttgc   3720

tgtagttgtc tcaagggctg ttgttcttgt ggatcctgct gcaaatttga tgaagacgac   3780

tctgagccag tgctcaaagg agtcaaatta cattacacat aa                      3822
```

<210> SEQ ID NO 6
<211> LENGTH: 3822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atgttcgtgt ttctggtgct gctgcctctg gtgagctccc agtgcgtgaa cctgaccaca     60

aggacccagc tcccccctgc ctataccaat tccttcacac ggggcgtgta ctatcccgac    120

aaggtgttta gatctagcgt gctgcactcc acacaggatc tgtttctgcc tttcttttct    180

aacgtgacct ggttccacgc catccatgtg agcggcacca atggcacaaa gcggttcgac    240

aatccagtgc tgccctttaa cgatggcgtg tacttcgcct ccaccgagaa gtctaacatc    300

atcagaggct ggatctttgg caccacactg gacagcaaga cacagtccct gctgatcgtg    360

aacaatgcca ccaacgtggt catcaaggtg tgcgagttcc agttttgtaa tgatccattc    420

ctgggcgtgt actatcacaa gaacaataag tcttggatgg agagcgagtt tcgcgtgtat    480

tcctctgcca acaattgcac atttgagtac gtgtcccagc ccttcctgat ggacctggag    540

ggcaagcagg gcaatttcaa gaacctgagg gagttcgtgt ttaagaatat cgatggctac    600

ttcaagatct actccaagca caccccaatc aacctggtgc gcgacctgcc acagggcttc    660

tctgccctgg agccactggt ggatctgccc atcggcatca acatcacccg gtttcagaca    720

ctgctggccc tgcacagaag ctacctgaca ccaggcgaca gctcctctgg atggaccgcc    780

ggggccgccg cctactatgt gggctatctg cagcccagga ccttcctgct gaagtacaac    840

gagaatggca ccatcacaga cgcagtggat tgcgccctgg accccctgtc tgagaccaag    900

tgtacactga agagctttac cgtggagaag ggcatctatc agacaagcaa tttcagggtg    960

cagcctaccg agtccatcgt gcgctttccc aatatcacaa acctgtgccc ttttggcgag   1020

gtgttcaacg caaccaggtt cgccagcgtg tacgcatgga ataggaagcg catctccaac   1080

tgcgtggccg actattctgt gctgtacaac agcgcctcct tctctacctt taagtgctat   1140

ggcgtgagcc ccacaaagct gaatgacctg tgctttacca acgtgtacgc cgattccttc   1200

gtgatcaggg gcgacgaggt gcgccagatc gcaccaggac agacaggcaa gatcgcagac   1260

tacaattata agctgcctga cgatttcacc ggctgcgtga tcgcctggaa ctctaacaat   1320

ctggatagca aagtgggcgg caactacaat tatctgtacc ggctgtttag aaagtctaat   1380

ctgaagccat tcgagaggga catctccaca gagatctacc aggccggctc taccccctgc   1440

aatggcgtgg agggctttaa ctgttatttc cctctgcaga gctacggctt ccagccaaca   1500

aacggcgtgg gctatcagcc ctaccgcgtg gtggtgctgt cttttgagct gctgcacgca   1560
```

```
cctgcaacag tgtgcggacc aaagaagagc accaatctgg tgaagaacaa gtgcgtgaac   1620
ttcaacttca acggcctgac cggcacaggc gtgctgaccg agtccaacaa gaagttcctg   1680
ccttttcagc agttcggcag ggacatcgca gataccacag acgccgtgcg cgaccctcag   1740
accctggaga tcctggacat cacaccatgc tccttcggcg gcgtgtctgt gatcacacca   1800
ggcaccaata caagcaacca ggtggccgtg ctgtatcagg acgtgaattg taccgaggtg   1860
cccgtggcca tccacgcaga tcagctcacc cctacatggc gggtgtactc taccggcagc   1920
aacgtgttcc agacaagagc cggctgcctg atcggagccg agcatgtgaa caatagctat   1980
gagtgcgaca tccctatcgg agccggcatc tgtgcctcct accagaccca gacaaactcc   2040
ccacggagag cccggtctgt ggccagccag tccatcatcg cctataccat gagcctgggg   2100
gccgagaaca gcgtggccta ctccaacaat tctatcgcca tccctaccaa cttcacaatc   2160
tccgtgacca cagagatcct gccagtgagc atgaccaaga catccgtgga ctgcacaatg   2220
tatatctgtg gcgattccac cgagtgctct aacctgctgc tgcagtacgg ctctttttgt   2280
acccagctca acagagccct gacaggcatc gccgtggagc aggacaagaa cacacaggag   2340
gtgttcgccc aggtgaagca gatctacaag accccaccca tcaaggactt tggcggcttc   2400
aacttcagcc agatcctgcc cgatcctagc aagccatcca agcggtcttt tatcgaggac   2460
ctgctgttca acaaggtgac cctggccgat gccggcttca tcaagcagta tggcgattgc   2520
ctgggcgaca tcgccgccag agacctgatc tgtgcccaga agtttaatgg cctgaccgtg   2580
ctgcctccac tgctgacaga tgagatgatc gcccagtaca catctgccct gctggccggc   2640
accatcacaa gcggatggac cttcggggcc ggggccgccc tgcagatccc ctttgccatg   2700
cagatggcct atcggttcaa cggcatcggc gtgacccaga atgtgctgta cgagaaccag   2760
aagctgatcg ccaatcagtt taactccgcc atcggcaaga tccaggactc tctgagctcc   2820
acagccagcg ccctgggcaa gctgcaggat gtggtgaatc agaacgccca ggccctgaat   2880
accctggtga agcagctcag cagcaacttc ggggccatca gcagcgtgct gaacgacatc   2940
ctgagccggc tggacaaggt ggaggcagag gtgcagatcg accggctgat cacaggcaga   3000
ctgcagtccc tgcagaccta cgtgacacag cagctcatca gggccgccga gatcagggcc   3060
tctgccaatc tggccgccac caagatgagc gagtgcgtgc tgggccagtc caagagagtg   3120
gacttttgtg gcaagggcta tcacctgatg agcttcccac agtccgcccc tcacggagtg   3180
gtgtttctgc atgtgaccta cgtgccagcc caggagaaga acttcaccac agcccccgca   3240
atctgccacg atggcaaggc acactttccc cgggagggcg tgttcgtgag caacggcacc   3300
cactggtttg tgacacagcg caatttctac gagccacaga tcatcaccac agacaataca   3360
ttcgtgtccg gcaactgtga cgtggtcatc ggcatcgtga acaataccgt gtatgatcct   3420
ctgcagccag agctggactc ttttaaggag gagctggata agtacttcaa gaatcacacc   3480
agccccgacg tggatctggg cgacatctct ggcatcaatg ccagcgtggt gaacatccag   3540
aaggagatcg acaggctgaa cgaggtggcc aagaatctga acgagtccct gatcgatctg   3600
caggagctgg gcaagtatga gcagtacatc aagtggccct ggtatatctg gctgggcttc   3660
atcgccggcc tgatcgccat cgtgatggtg accatcatgc tgtgctgtat gacaagctgc   3720
tgttcctgcc tgaagggctg ctgttcttgt ggctcctgct gtaagtttga tgaggacgat   3780
agcgagcctg tgctgaaggg cgtgaagctg cactacacct ga                       3822
```

<210> SEQ ID NO 7

<211> LENGTH: 1255
<212> TYPE: PRT
<213> ORGANISM: Severe acute respiratory syndrome-related coronavirus

<400> SEQUENCE: 7

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
```

```
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815
```

```
Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                 1005

Thr Lys  Met Ser Glu Cys Val  Leu Gly Gln Ser Lys  Arg Val Asp
    1010                 1015                 1020

Phe Cys  Gly Lys Gly Tyr His  Leu Met Ser Phe Pro  Gln Ala Ala
    1025                 1030                 1035

Pro His  Gly Val Val Phe Leu  His Val Thr Tyr Val  Pro Ser Gln
    1040                 1045                 1050

Glu Arg  Asn Phe Thr Thr Ala  Pro Ala Ile Cys His  Glu Gly Lys
    1055                 1060                 1065

Ala Tyr  Phe Pro Arg Glu Gly  Val Phe Val Phe Asn  Gly Thr Ser
    1070                 1075                 1080

Trp Phe  Ile Thr Gln Arg Asn  Phe Phe Ser Pro Gln  Ile Ile Thr
    1085                 1090                 1095

Thr Asp  Asn Thr Phe Val Ser  Gly Asn Cys Asp Val  Val Ile Gly
    1100                 1105                 1110

Ile Ile  Asn Asn Thr Val Tyr  Asp Pro Leu Gln Pro  Glu Leu Asp
    1115                 1120                 1125

Ser Phe  Lys Glu Glu Leu Asp  Lys Tyr Phe Lys Asn  His Thr Ser
    1130                 1135                 1140

Pro Asp  Val Asp Leu Gly Asp  Ile Ser Gly Ile Asn  Ala Ser Val
    1145                 1150                 1155

Val Asn  Ile Gln Lys Glu Ile  Asp Arg Leu Asn Glu  Val Ala Lys
    1160                 1165                 1170

Asn Leu  Asn Glu Ser Leu Ile  Asp Leu Gln Glu Leu  Gly Lys Tyr
    1175                 1180                 1185

Glu Gln  Tyr Ile Lys Trp Pro  Trp Tyr Val Trp Leu  Gly Phe Ile
    1190                 1195                 1200

Ala Gly  Leu Ile Ala Ile Val  Met Val Thr Ile Leu  Leu Cys Cys
    1205                 1210                 1215
```

```
Met Thr  Ser Cys Cys Ser Cys  Leu Lys Gly Ala Cys  Ser Cys Gly
    1220                1225                1230

Ser Cys  Cys Lys Phe Asp Glu  Asp Asp Ser Glu Pro  Val Leu Lys
    1235                1240                1245

Gly Val  Lys Leu His Tyr Thr
    1250                1255
```

<210> SEQ ID NO 8
<211> LENGTH: 3768
<212> TYPE: DNA
<213> ORGANISM: Severe acute respiratory syndrome-related coronavirus

<400> SEQUENCE: 8

```
atgtttattt tcttattatt tcttactctc actagtggta gtgaccttga ccggtgcacc     60

acttttgatg atgttcaagc tcctaattac actcaacata cttcatctat gaggggggtt    120

tactatcctg atgaaatttt tagatcagac actctttatt taactcagga tttatttctt    180

ccattttatt ctaatgttac agggtttcat actattaatc atacgtttgg caaccctgtc    240

atacctttta aggatggtat ttattttgct gccacagaga aatcaaatgt tgtccgtggt    300

tgggtttttg gttctaccat gaacaacaag tcacagtcgg tgattattat taacaattct    360

actaatgttg ttatacgagc atgtaacttt gaattgtgtg acaacccttt ctttgctgtt    420

tctaaaccca tgggtacaca gacacatact atgatattcg ataatgcatt taattgcact    480

ttcgagtaca tatctgatgc cttttcgctt gatgtttcag aaaagtcagg taattttaaa    540

cacttacgag agtttgtgtt taaaaataaa gatgggtttc tctatgttta taagggctat    600

caacctatag atgtagttcg tgatctacct tctggtttta acactttgaa acctattttt    660

aagttgcctc ttggtattaa cattacaaat tttagagcca ttcttacagc cttttcacct    720

gctcaagaca tttggggcac gtcagctgca gcctattttg ttggctattt aaagccaact    780

acatttatgc tcaagtatga tgaaaatggt acaatcacag atgctgttga ttgttctcaa    840

aatccacttg ctgaactcaa atgctctgtt aagagctttg agattgacaa aggaatttac    900

cagacctcta atttcagggt tgttccctca ggagatgttg tgagattccc taatattaca    960

aacttgtgtc cttttggaga ggtttttaat gctactaaat tcccttctgt ctatgcatgg   1020

gagagaaaaa aaatttctaa ttgtgttgct gattactctg tgctctacaa ctcaacattt   1080

ttttcaacct ttaagtgcta tggcgtttct gccactaagt tgaatgatct ttgcttctcc   1140

aatgtctatg cagattcttt tgtagtcaag ggagatgatg taagacaaat agcgccagga   1200

caaactggtg ttattgctga ttataattat aaattgccag atgatttcat gggttgtgtc   1260

cttgcttgga atactaggaa cattgatgct acttcaactg gtaattataa ttataaatat   1320

aggtatctta gacatggcaa gcttaggccc tttgagagag acatatctaa tgtgcctttc   1380

tcccctgatg gcaaaccttg caccccacct gctcttaatt gttattggcc attaaatgat   1440

tatggttttt acaccactac tggcattggc taccaacctt acagagttgt agtactttct   1500

tttgaacttt taaatgcacc ggccacggtt tgtggaccaa aattatccac tgaccttatt   1560

aagaaccagt gtgtcaattt taattttaat ggactcactg gtactggtgt gttaactcct   1620

tcttcaaaga gatttcaacc atttcaacaa tttggccgtg atgtttctga tttcactgat   1680

tccgttcgag atcctaaaac atctgaaata ttagacattt caccttgctc ttttgggggt   1740

gtaagtgtaa ttacacctgg aacaaatgct tcatctgaag ttgctgttct atatcaagat   1800

gttaactgca ctgatgtttc tacagcaatt catgcagatc aactcacacc agcttggcgc   1860
```

atatattcta ctggaaacaa tgtattccag actcaagcag gctgtcttat aggagctgag 1920
catgtcgaca cttcttatga gtgcgacatt cctattggag ctggcatttg tgctagttac 1980
catacagttt ctttattacg tagtactagc caaaaatcta ttgtggctta tactatgtct 2040
ttaggtgctg atagttcaat tgcttactct aataacacca ttgctatacc tactaacttt 2100
tcaattagca ttactacaga agtaatgcct gtttctatgg ctaaaacctc cgtagattgt 2160
aatatgtaca tctgcggaga ttctactgaa tgtgctaatt tgcttctcca atatggtagc 2220
ttttgcacac aactaaatcg tgcactctca ggtattgctg ctgaacagga tcgcaacaca 2280
cgtgaagtgt tcgctcaagt caaacaaatg tacaaaaccc caactttgaa atattttggt 2340
ggttttaatt tttcacaaat attacctgac cctctaaagc caactaagag gtcttttatt 2400
gaggacttgc tctttaataa ggtgacactc gctgatgctg gcttcatgaa gcaatatggc 2460
gaatgcctag gtgatattaa tgctagagat ctcatttgtg cgcagaagtt caatggactt 2520
acagtgttgc cacctctgct cactgatgat atgattgctg cctacactgc tgctctagtt 2580
agtggtactg ccactgctgg atggacattt ggtgctggcg ctgctcttca aatacctttt 2640
gctatgcaaa tggcatatag gttcaatggc attggagtta cccaaaatgt tctctatgag 2700
aaccaaaaac aaatcgccaa ccaatttaac aaggcgatta gtcaaattca agaatcactt 2760
acaacaacat caactgcatt gggcaagctg caagacgttg ttaaccagaa tgctcaagca 2820
ttaaacacac ttgttaaaca acttagctct aattttggtg caatttcaag tgtgctaaat 2880
gatatccttt cgcgacttga taaagtcgag gcggaggtac aaattgacag gttaattaca 2940
ggcagacttc aaagccttca aacctatgta acacaacaac taatcagggc tgctgaaatc 3000
agggcttctg ctaatcttgc tgctactaaa atgtctgagt gtgttcttgg acaatcaaaa 3060
agagttgact tttgtggaaa gggctaccac cttatgtcct tcccacaagc agccccgcat 3120
ggtgttgtct tcctacatgt cacgtatgtg ccatcccagg agaggaactt caccacagcg 3180
ccagcaattt gtcatgaagg caaagcatac ttccctcgtg aaggtgtttt tgtgtttaat 3240
ggcacttctt ggtttattac acagaggaac ttcttttctc cacaaataat tactacagac 3300
aatacatttg tctcaggaaa ttgtgatgtc gttattggca tcattaacaa cacagtttat 3360
gatcctctgc aacctgagct tgactcattc aaagaagagc tggacaagta cttcaaaaat 3420
catacatcac cagatgttga tcttggcgac atttcaggca ttaacgcttc tgtcgtcaac 3480
attcaaaaag aaattgaccg cctcaatgag gtcgctaaaa atttaaatga atcactcatt 3540
gaccttcaag aattgggaaa atatgagcaa tatattaaat ggccttggta tgtttggctc 3600
ggcttcattg ctggactaat tgccatcgtc atggttacaa tcttgctttg ttgcatgact 3660
agttgttgca gttgcctcaa gggtgcatgc tcttgtggtt cttgctgcaa gtttgatgag 3720
gatgactctg agccagttct caagggtgtc aaattacatt acacataa 3768

<210> SEQ ID NO 9
<211> LENGTH: 3768
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
atgttcatct ttctgctgtt cctgaccctg acaagcggct ccgacctgga taggtgcacc 60
acatttgacg atgtgcaggc ccccaactac acacagcaca ccagctccat gaggggcgtg 120

-continued

```
tactatcctg atgagatctt ccgctctgac acactgtacc tgacccagga cctgttcctg    180
ccttttata gcaatgtgac aggcttccac accatcaatc acacatttgg caacccgtg    240
atccctttca aggatggcat ctactttgcc gccaccgaga agtctaacgt ggtgcgggga    300
tgggtgttcg gcagcacaat gaacaataag tctcagagcg tgatcatcat caacaatagc    360
accaacgtgg tcatcagagc ctgcaatttt gagctgtgcg acaacccctt ctttgccgtg    420
tccaagccta tgggcaccca gacacacacc atgatctttg ataatgcctt caactgtacc    480
tttgagtaca tcagcgatgc cttttccctg gacgtgtctg agaagtccgg caacttcaag    540
cacctgaggg agttcgtgtt taagaataag gacggcttcc tgtacgtgta taagggctat    600
cagcccatcg atgtggtgcg cgacctgcct tccggcttca acaccctgaa gccaatcttt    660
aagctgcccc tgggcatcaa tatcaccaac ttcagggcca tcctgacagc ctttagccca    720
gcacaggaca tctggggcac cagcgccgcc gcctacttcg tgggctatct gaagcccacc    780
accttcatgc tgaagtacga tgagaacggc acaatcaccg acgccgtgga ttgcagccag    840
aatccactgg ccgagctgaa gtgttccgtg aagtctttcg agatcgacaa gggcatctat    900
cagacctcca actttagggt ggtgccatct ggcgatgtgg tgcgcttccc aaatatcacc    960
aacctgtgcc ccttcggcga ggtgtttaat gccacaaagt tccccagcgt gtacgcctgg   1020
gagcgcaaga agatcagcaa ctgcgtggcc gactactccg tgctgtataa tagcaccttc   1080
ttcagcacct tcaagtgcta cggcgtgagc gccaccaagc tgaatgacct gtgcttctct   1140
aacgtgtatg ccgatagctt tgtggtgaag ggcgacgatg tgaggcagat cgcacctgga   1200
cagaccggcg tgatcgcaga ctacaactat aagctgccag acgatttcat gggctgcgtg   1260
ctggcctgga atacacgcaa catcgatgcc acatccaccg gcaactacaa ttataagtac   1320
cggtatctga gacacggcaa gctgcggccc ttcgagagag acatctccaa tgtgccattt   1380
tctccagatg gcaagccatg caccccacct gccctgaatt gttactggcc tctgaacgac   1440
tacggcttct ataccacaac cggcatcggc taccagcctt atagggtggt ggtgctgtcc   1500
tttgagctgc tgaacgcacc tgcaaccgtg tgcggaccaa agctgtctac agatctgatc   1560
aagaatcagt gcgtgaactt caacttcaac ggcctgacag gcaccggcgt gctgacccct   1620
tctagcaagc ggttccagcc atttcagcag ttcggcagag acgtgagcga tttcaccgac   1680
tccgtgcgcg acccaaagac atccgagatc ctggacatca gcccctgctc ctttggcggc   1740
gtgtctgtga tcacacctgg caccaacgcc tcctctgagg tggccgtgct gtaccaggat   1800
gtgaattgta ccgacgtgag cacagcaatc cacgcagacc agctcacccc agcatggcgg   1860
atctattcca ccggcaacaa cgtgttccag acacaggcag gatgcctgat cggagccgag   1920
catgtggata caagctacga gtgcgacatc cccatcggag ccggcatctg tgcctcttat   1980
cacaccgtga gcctgctgag atccacatct cagaagtcta tcgtggccta caccatgagc   2040
ctgggggccg atagctccat cgcctattcc aacaatacca tcgccatccc aacaaacttc   2100
agcatctcca tcacaaccga agtgatgccc gtgtccatgg ccaagacctc tgtggactgc   2160
aacatgtaca tctgtggcga tagcacagag tgcgccaatc tgctgctgca gtatggctcc   2220
ttttgtaccc agctcaaccg ggccctgtct ggaatcgccg ccgagcagga caggaataca   2280
cgcgaggtgt tcgcccaggt gaagcagatg tacaagacac ctaccctgaa gtattttggc   2340
ggcttcaact tttctcagat cctgcctgat ccactgaagc caaccaagcg gagcttcatc   2400
gaggacctgc tgtttaataa ggtgacactg gccgatgccg gcttcatgaa gcagtacggc   2460
gagtgcctgg gcgacatcaa cgccagagac ctgatctgtg cccagaagtt taatggcctg   2520
```

```
accgtgctgc cacccctgct gacagacgat atgatcgcag catataccgc cgccctggtg   2580

tccggcacag ccaccgccgg ctggaccttc ggggccgggg ccgccctgca gatccctttc   2640

gccatgcaga tggcctaccg gtttaacggc atcggcgtga cccagaatgt gctgtatgag   2700

aaccagaagc agatcgccaa tcagtttaac aaggccatca gccagatcca ggagtccctg   2760

acaaccacat ctaccgccct gggcaagctg caggacgtgg tgaatcagaa cgcccaggcc   2820

ctgaatacac tggtgaagca gctcagcagc aacttcgggg ccatcagcag cgtgctgaac   2880

gacatcctga gccggctgga caaggtggag gcagaggtgc agatcgatag gctgatcacc   2940

ggcagactgc agtctctgca gacatacgtg acccagcagc tcatcagggc cgccgagatc   3000

agagccagcg ccaacctggc cgccacaaag atgtccgagt gcgtgctggg ccagtctaag   3060

agggtggact tctgtggcaa gggctaccac ctgatgtcct ttccacaggc cgcccctcac   3120

ggagtggtgt tcctgcatgt gacctatgtg ccttctcagg agcgcaactt taccacagcc   3180

ccagcaatct gccacgaggg caaggcatac ttcccccggg agggcgtgtt cgtgtttaac   3240

ggcacctcct ggtttatcac acagagaaat ttcttttccc ctcagatcat caccacagac   3300

aataccttcg tgagcggcaa ctgtgacgtg gtcatcggca tcatcaacaa tacagtgtac   3360

gatcctctgc agccagagct ggacagcttc aaggaggagc tggataagta cttcaagaac   3420

cacacctccc ccgacgtgga tctgggcgac atcagcggca tcaatgcctc cgtggtgaac   3480

atccagaagg agatcgacag actgaatgag gtggccaaga atctgaacga gtccctgatc   3540

gatctgcagg agctgggcaa gtacgagcag tatatcaagt ggccatggta cgtgtggctg   3600

ggcttcatcg ccggcctgat cgccatcgtg atggtgacca tcctgctgtg ctgtatgaca   3660

tcttgctgta gctgcctgaa gggagcctgc tcctgtggct cttgctgtaa gtttgacgag   3720

gacgatagcg agcccgtgct gaagggcgtg aagctgcact atacctga               3768


<210> SEQ ID NO 10
<211> LENGTH: 1353
<212> TYPE: PRT
<213> ORGANISM: Middle East respiratory syndrome-related coronavirus

<400> SEQUENCE: 10

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
    50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
            100                 105                 110

Ala Asn Gly Phe Val Val Arg Ile Gly Ala Ala Ala Asn Ser Thr Gly
        115                 120                 125

Thr Val Ile Ile Ser Pro Ser Thr Ser Ala Thr Ile Arg Lys Ile Tyr
    130                 135                 140

Pro Ala Phe Met Leu Gly Ser Ser Val Gly Asn Phe Ser Asp Gly Lys
```

-continued

```
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
            180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
            260                 265                 270

Leu Tyr Gly Gly Asn Met Phe Gln Phe Ala Thr Leu Pro Val Tyr Asp
        275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
            340                 345                 350

Ser Phe Asp Val Glu Ser Gly Val Tyr Ser Val Ser Ser Phe Glu Ala
        355                 360                 365

Lys Pro Ser Gly Ser Val Val Glu Gln Ala Glu Gly Val Glu Cys Asp
    370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
            420                 425                 430

Ile Ala Ser Asn Cys Tyr Ser Ser Leu Ile Leu Asp Tyr Phe Ser Tyr
        435                 440                 445

Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575
```

```
Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
            660                 665                 670

Leu Phe Gly Ser Val Ala Cys Glu His Ile Ser Ser Thr Met Ser Gln
        675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
865                 870                 875                 880

Thr Gly Ser Arg Ser Ala Arg Ser Ala Ile Glu Asp Leu Leu Phe Asp
                885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
        915                 920                 925

Val Ala Gly Tyr Lys Val Leu Pro Pro Leu Met Asp Val Asn Met Glu
    930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
                965                 970                 975

Phe Tyr Arg Leu Asn Gly Val Gly Ile Thr Gln Gln Val Leu Ser Glu
            980                 985                 990
```

```
Asn Gln Lys Leu Ile Ala Asn Lys  Phe Asn Gln Ala Leu  Gly Ala Met
        995                  1000                 1005

Gln Thr  Gly Phe Thr Thr Thr  Asn Glu Ala Phe Gln  Lys Val Gln
    1010                 1015                 1020

Asp Ala  Val Asn Asn Asn Ala  Gln Ala Leu Ser Lys  Leu Ala Ser
    1025                 1030                 1035

Glu Leu  Ser Asn Thr Phe Gly  Ala Ile Ser Ala Ser  Ile Gly Asp
    1040                 1045                 1050

Ile Ile  Gln Arg Leu Asp Val  Leu Glu Gln Asp Ala  Gln Ile Asp
    1055                 1060                 1065

Arg Leu  Ile Asn Gly Arg Leu  Thr Thr Leu Asn Ala  Phe Val Ala
    1070                 1075                 1080

Gln Gln  Leu Val Arg Ser Glu  Ser Ala Ala Leu Ser  Ala Gln Leu
    1085                 1090                 1095

Ala Lys  Asp Lys Val Asn Glu  Cys Val Lys Ala Gln  Ser Lys Arg
    1100                 1105                 1110

Ser Gly  Phe Cys Gly Gln Gly  Thr His Ile Val Ser  Phe Val Val
    1115                 1120                 1125

Asn Ala  Pro Asn Gly Leu Tyr  Phe Met His Val Gly  Tyr Tyr Pro
    1130                 1135                 1140

Ser Asn  His Ile Glu Val Val  Ser Ala Tyr Gly Leu  Cys Asp Ala
    1145                 1150                 1155

Ala Asn  Pro Thr Asn Cys Ile  Ala Pro Val Asn Gly  Tyr Phe Ile
    1160                 1165                 1170

Lys Thr  Asn Asn Thr Arg Ile  Val Asp Glu Trp Ser  Tyr Thr Gly
    1175                 1180                 1185

Ser Ser  Phe Tyr Ala Pro Glu  Pro Ile Thr Ser Leu  Asn Thr Lys
    1190                 1195                 1200

Tyr Val  Ala Pro Gln Val Thr  Tyr Gln Asn Ile Ser  Thr Asn Leu
    1205                 1210                 1215

Pro Pro  Pro Leu Leu Gly Asn  Ser Thr Gly Ile Asp  Phe Gln Asp
    1220                 1225                 1230

Glu Leu  Asp Glu Phe Phe Lys  Asn Val Ser Thr Ser  Ile Pro Asn
    1235                 1240                 1245

Phe Gly  Ser Leu Thr Gln Ile  Asn Thr Thr Leu Leu  Asp Leu Thr
    1250                 1255                 1260

Tyr Glu  Met Leu Ser Leu Gln  Gln Val Val Lys Ala  Leu Asn Glu
    1265                 1270                 1275

Ser Tyr  Ile Asp Leu Lys Glu  Leu Gly Asn Tyr Thr  Tyr Tyr Asn
    1280                 1285                 1290

Lys Trp  Pro Trp Tyr Ile Trp  Leu Gly Phe Ile Ala  Gly Leu Val
    1295                 1300                 1305

Ala Leu  Ala Leu Cys Val Phe  Phe Ile Leu Cys Cys  Thr Gly Cys
    1310                 1315                 1320

Gly Thr  Asn Cys Met Gly Lys  Leu Lys Cys Asn Arg  Cys Cys Asp
    1325                 1330                 1335

Arg Tyr  Glu Glu Tyr Asp Leu  Glu Pro His Lys Val  His Val His
    1340                 1345                 1350
```

<210> SEQ ID NO 11
<211> LENGTH: 4062
<212> TYPE: DNA
<213> ORGANISM: Middle East respiratory syndrome-related coronavirus

<400> SEQUENCE: 11

-continued

```
atgatacact cagtgtttct actgatgttc ttgttaacac ctacagaaag ttacgttgat     60
gtagggccag attctgttaa gtctgcttgt attgaggttg atatacaaca gactttcttt    120
gataaaactt ggcctaggcc aattgatgtt tctaaggctg acggtattat ataccctcaa    180
ggccgtacat attctaacat aactatcact tatcaaggtc tttttcccta tcagggagac    240
catggtgata tgtatgttta ctctgcagga catgctacag gcacaactcc acaaaagttg    300
tttgtagcta actattctca ggacgtcaaa cagtttgcta atgggtttgt cgtccgtata    360
ggagcagctg ccaattccac tggcactgtt attattagcc catctaccag cgctactata    420
cgaaaaattt accctgcttt tatgctgggt tcttcagttg gtaatttctc agatggtaaa    480
atgggccgct tcttcaatca tactctagtt cttttgcccg atggatgtgg cactttactt    540
agagcttttt attgtattct agagcctcgc tctggaaatc attgtcctgc tggcaattcc    600
tatacttctt ttgccactta tcacactcct gcaacagatt gttctgatgg caattacaat    660
cgtaatgcca gtctgaactc ttttaaggag tattttaatt tacgtaactg cacctttatg    720
tacacttata acattaccga agatgagatt ttagagtggt ttggcattac acaaactgct    780
caaggtgttc acctcttctc atctcggtat gttgatttgt acggcggcaa tatgtttcaa    840
tttgccacct tgcctgttta tgatactatt aagtattatt ctatcattcc tcacagtatt    900
cgttctatcc aaagtgatag aaaagcttgg gctgccttct acgtatataa acttcaaccg    960
ttaactttcc tgttggattt ttctgttgat ggttatatac gcagagctat agactgtggt   1020
tttaatgatt tgtcacaact ccactgctca tatgaatcct tcgatgttga atctggagtt   1080
tattcagttt cgtctttcga agcaaaacct tctggctcag ttgtggaaca ggctgaaggt   1140
gttgaatgtg atttttcacc tcttctgtct ggcacacctc ctcaggttta taatttcaag   1200
cgtttggttt ttaccaattg caattataat cttaccaaat tgctttcact tttttctgtg   1260
aatgatttta cttgtagtca aatatctcca gcagcaattg ctagcaactg ttattcttca   1320
ctgattttgg attacttttc atacccactt agtatgaaat ccgatctcag tgttagttct   1380
gctggtccaa tatcccagtt taattataaa cagtcctttt ctaatcccac atgtttgatt   1440
ttagcgactg ttcctcataa ccttactact attactaagc ctcttaagta cagctatatt   1500
aacaagtgct ctcgtcttct ttctgatgat cgtactgaag tacctcagtt agtgaacgct   1560
aatcaatact caccctgtgt atccattgtc ccatccactg tgtgggaaga cggtgattat   1620
tataggaaac aactatctcc acttgaaggt ggtggctggc ttgttgctag tggctcaact   1680
gttgccatga ctgagcaatt acagatgggc tttggtatta cagttcaata tggtacagac   1740
accaatagtg tttgccccaa gcttgaattt gctaatgaca caaaaattgc ctctcaatta   1800
ggcaattgcg tggaatattc cctctatggt gtttcgggcc gtggtgtttt tcagaattgc   1860
acagctgtag gtgttcgaca gcagcgcttt gtttatgatg cgtaccagaa tttagttggc   1920
tattattctg atgatggcaa ctactactgt ttgcgtgctt gtgttagtgt tcctgtttct   1980
gtcatctatg ataaagaaac taaaacccac gctactctat ttggtagtgt tgcatgtgaa   2040
cacatttctt ctaccatgtc tcaatactcc cgttctacgc gatcaatgct taaacggcga   2100
gattctacat atggcccccct tcagacacct gttggttgtg tcctaggact tgttaattcc   2160
tctttgttcg tagaggactg caagttgcct cttggtcaat ctctctgtgc tcttcctgac   2220
acacctagta ctctcacacc tcgcagtgtg cgctctgttc caggtgaaat gcgcttggca   2280
tccattgctt ttaatcatcc tattcaggtt gatcaactta atagtagtta ttttaaatta   2340
```

agtataccca ctaatttttc ctttggtgtg actcaggagt acattcagac aaccattcag 2400
aaagttactg ttgattgtaa acagtacgtt tgcaatggtt tccagaagtg tgagcaatta 2460
ctgcgcgagt atggccagtt ttgttccaaa ataaaccagg ctctccatgg tgccaattta 2520
cgccaggatg attctgtacg taatttgttt gcgagcgtga aaagctctca atcatctcct 2580
atcataccag gttttggagg tgactttaat ttgacacttc tagaacctgt ttctatatct 2640
actggcagtc gtagtgcacg tagtgctatt gaggatttgc tatttgacaa agtcactata 2700
gctgatcctg gttatatgca aggttacgat gattgcatgc agcaaggtcc agcatcagct 2760
cgtgatctta tttgtgctca atatgtggct ggttacaaag tattacctcc tcttatggat 2820
gttaatatgg aagccgcgta tacttcatct ttgcttggca gcatagcagg tgttggctgg 2880
actgctggct tatcctcctt tgctgctatt ccatttgcac agagtatctt ttataggtta 2940
aacggtgttg gcattactca acaggttctt tcagagaacc aaaagcttat tgccaataag 3000
tttaatcagg ctctgggagc tatgcaaaca ggcttcacta caactaatga agcttttcag 3060
aaggttcagg atgctgtgaa caacaatgca caggctctat ccaaattagc tagcgagcta 3120
tctaatactt ttggtgctat ttccgcctct attggagaca tcatacaacg tcttgatgtt 3180
ctcgaacagg acgcccaaat agacagactt attaatggcc gtttgacaac actaaatgct 3240
tttgttgcac agcagcttgt tcgttccgaa tcagctgctc tttccgctca attggctaaa 3300
gataaagtca atgagtgtgt caaggcacaa tccaagcgtt ctggattttg cggtcaaggc 3360
acacatatag tgtcctttgt tgtaaatgcc cctaatggcc tttacttcat gcatgttggt 3420
tattacccta gcaaccacat tgaggttgtt tctgcttatg gtctttgcga tgcagctaac 3480
cctactaatt gtatagcccc tgttaatggc tactttatta aaactaataa cactaggatt 3540
gttgatgagt ggtcatatac tggctcgtcc ttctatgcac ctgagcccat tacctccctt 3600
aatactaagt atgttgcacc acaggtgaca taccaaaaca tttctactaa cctccctcct 3660
cctcttctcg gcaattccac cgggattgac ttccaagatg agttggatga gtttttcaaa 3720
aatgttagca ccagtatacc taattttggt tccctaacac agattaatac tacattactc 3780
gatcttacct acgagatgtt gtctcttcaa caagttgtta aagcccttaa tgagtcttac 3840
atagacctta aagagcttgg caattatact tattacaaca aatggccgtg gtacatttgg 3900
cttggtttca ttgctgggct tgttgcctta gctctatgcg tcttcttcat actgtgctgc 3960
actggttgtg gcacaaactg tatgggaaaa cttaagtgta atcgttgttg tgatagatac 4020
gaggaatacg acctcgagcc gcataaggtt catgttcact aa 4062

<210> SEQ ID NO 12
<211> LENGTH: 4062
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
atgatccaca gcgtgttcct gctgatgttt ctgctgacac ctaccgagtc ctacgtggat 60
gtgggcccag actctgtgaa gagcgcctgc atcgaggtgg acatccagca gacattcttt 120
gacaagacct ggcccagacc catcgacgtg agcaaggcag acggaatcat ctacccacag 180
ggacgcacat atagcaacat cacaatcacc taccagggcc tgttccctta tcagggcgac 240
cacggcgata tgtacgtgta tagcgccggc cacgcaaccg gcaccacacc acagaagctg 300

-continued

```
tttgtggcca attattccca ggacgtgaag cagttcgcca acggatttgt ggtgcggatc    360
ggggccgccg ccaacagcac aggcaccgtg atcatctctc ccagcacatc cgccaccatc    420
agaaagatct accctgcctt tatgctgggc agctccgtgg gcaacttctc cgatggcaag    480
atgggcaggt tctttaatca cacactggtg ctgctgccag acggatgcgg caccctgctg    540
agggccttct actgtatcct ggagccccgc tctggaaatc actgccctgc cggcaactcc    600
tacacctctt ttgccacata tcacacccct gccacagact gttccgatgg caattataac    660
cggaatgcca gcctgaactc cttcaaggag tactttaatc tgagaaactg caccttcatg    720
tacacatata atatcaccga ggatgagatc ctggagtggt tcggcatcac acagaccgcc    780
cagggcgtgc acctgttttc tagcagatac gtggatctgt atggcggcaa catgttccag    840
tttgccacac tgccagtgta tgacaccatc aagtactata gcatcatccc ccactctatc    900
cggagcatcc agtccgacag aaaggcctgg gccgccttct acgtgtataa gctgcagccc    960
ctgaccttcc tgctggattt ttccgtggac ggctacatcc ggagagccat cgattgcggc   1020
tttaacgacc tgtctcagct ccactgttct tatgagagct tcgatgtgga gtctggcgtg   1080
tacagcgtgt cctcttttga ggccaagcca tctggcagcg tggtggagca ggcagaggga   1140
gtggagtgcg acttctcccc actgctgtct ggcacaccac ctcaggtgta taatttcaag   1200
aggctggtgt ttacaaactg taattacaac ctgaccaagc tgctgtccct gttctctgtg   1260
aacgacttta cctgcagcca gatctcccct gccgccatcg cctccaattg ttatagctcc   1320
ctgatcctgg attacttctc ttatcccctg tctatgaaga gcgacctgtc cgtgtctagc   1380
gccggcccta tcagccagtt taattacaag cagtccttct ctaaccccac atgcctgatc   1440
ctggccaccg tgcctcacaa cctgaccaca atcacaaagc cactgaagta ctcctatatc   1500
aataagtgca gcaggctgct gtccgacgat cgcaccgagg tgcctcagct cgtgaacgcc   1560
aaccagtact ctccatgcgt gagcatcgtg ccatccaccg tgtgggagga cggcgattac   1620
tatagaaagc agctcagccc actggaggga ggaggatggc tggtggccag cggctccaca   1680
gtggccatga ccgagcagct ccagatgggc ttcggcatca cagtgcagta cggcacagat   1740
accaatagcg tgtgccccaa gctggagttt gccaacgaca ccaagatcgc ctcccagctc   1800
ggcaattgcg tggagtactc cctgtatggc gtgtctggca gaggcgtgtt ccagaactgt   1860
acagccgtgg gcgtgcggca gcagcggttc gtgtacgatg cctatcagaa cctggtgggc   1920
tactatagcg acgatggcaa ttactattgc ctgagggcat gcgtgagcgt gcccgtgagc   1980
gtgatctacg acaaggagac aaagacccac gccaccctgt tcggctccgt ggcctgcgag   2040
cacatctcct ctacaatgtc tcagtattct aggagcaccc gctctatgct gaagaggcgc   2100
gacagcacat acggaccact gcagacccct gtgggatgcg tgctgggcct ggtgaacagc   2160
agcctgtttg tggaggattg caagctgcca ctgggccagt ctctgtgcgc actgccagac   2220
acccccagca cactgacccc acggtctgtg agaagcgtgc ccggagagat gagactggcc   2280
agcatcgcct tcaatcaccc tatccaggtg gatcagctca acagcagcta ctttaagctg   2340
agcatcccaa caaacttctc ctttggcgtg acccaggagt atatccagac cacaatccag   2400
aaggtgaccg tggactgcaa gcagtacgtg tgcaatggct tccagaagtg cgagcagctc   2460
ctgagggagt atggccagtt ttgttccaag atcaatcagg ccctgcacgg agccaacctg   2520
aggcaggacg attccgtgag aaacctgttc gcctctgtga agtcctctca gagctcccct   2580
atcatcccag gcttcggcgg cgacttcaac ctgaccctgc tggagcccgt gtccatctct   2640
accggcagca ggtccgcccg cagcgccatc gaggatctgc tgtttgacaa ggtgaccatc   2700
```

```
gccgacccag gctacatgca gggctatgac gattgcatgc agcagggacc agcctccgcc   2760

cgcgatctga tctgtgccca gtacgtggcc ggctataagg tgctgccacc cctgatggac   2820

gtgaacatgg aggccgccta tacatctagc ctgctgggca gcatcgcagg agtgggatgg   2880

accgccggcc tgtcctcttt cgccgcaatc ccttttgccc agtctatctt ctaccggctg   2940

aacggcgtgg gcatcacaca gcaggtgctg agcgagaatc agaagctgat cgccaataag   3000

ttcaaccagg ccctgggggc catgcagacc ggctttacca caaccaacga ggccttccag   3060

aaggtgcagg atgccgtgaa caataacgca caggccctgt ccaagctggc ctccgagctg   3120

tctaatacct tcggggccat cagcgccagc atcggcgaca tcatccagcg cctggacgtg   3180

ctggagcagg atgcccagat cgacaggctg atcaatggcc gcctgacaac cctgaacgcc   3240

tttgtggcac agcagctcgt gcggagcgag tctgccgccc tgagcgccca gctcgccaag   3300

gacaaggtga acgagtgcgt gaaggcccag agcaagcggt ccggcttttg tggccagggc   3360

acccacatcg tgtccttcgt ggtgaatgcc cctaacggcc tgtactttat gcatgtgggc   3420

tactatccaa gcaaccacat cgaggtggtg tccgcctatg gcctgtgcga tgccgccaat   3480

cctacaaact gtatcgcccc agtgaatggc tacttcatca agaccaataa cacacggatc   3540

gtggacgagt ggtcctacac cggcagctcc ttttatgccc ccgagcctat cacatctctg   3600

aacaccaagt acgtggcccc acaggtgaca tatcagaata tcagcaccaa cctgcctcca   3660

cccctgctgg gcaattccac cggcatcgac ttccaggatg agctggacga gttctttaag   3720

aatgtgagca catccatccc caactttggc agcctgaccc agatcaacac aaccctgctg   3780

gatctgacat acgagatgct gtctctgcag caggtggtga aggccctgaa tgagagctac   3840

atcgacctga aggagctggg caattatacc tactataaca agtggccttg gtacatctgg   3900

ctgggcttca tcgcaggcct ggtggccctg gccctgtgcg tgttctttat cctgtgctgt   3960

acaggctgcg gcaccaattg tatgggcaag ctgaagtgta accggtgctg tgatagatac   4020

gaggagtatg acctggagcc acacaaggtg catgtgcact ga                     4062
```

<210> SEQ ID NO 13
<211> LENGTH: 1273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110
```

```
Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
```

-continued

```
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960
```

```
Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 14
<211> LENGTH: 3822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atgtttgttt ttcttgtttt attgccacta gtctctagtc agtgtgttaa tcttacaacc      60

agaactcaat taccccctgc atacactaat tctttcacac gtggtgttta ttaccctgac     120
```

```
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatttaa tgatggtgtt tattttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
```

```
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgaccctcc tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaatg cttcagttgt aaacattcaa   3540
aaagaaattg accgcctcaa tgaggttgcc aagaatttaa atgaatctct catcgatctc   3600
caagaacttg gaaagtatga gcagtatata aaatggccat ggtacatttg gctaggtttt   3660
atagctggct tgattgccat agtaatggtg acaattatgc tttgctgtat gaccagttgc   3720
tgtagttgtc tcaagggctg ttgttcttgt ggatcctgct gcaaatttga tgaagacgac   3780
tctgagccag tgctcaaagg agtcaaatta cattacacat aa                      3822
```

<210> SEQ ID NO 15
<211> LENGTH: 3822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atgttcgtgt ttctggtgct gctgcctctg gtgagctccc agtgcgtgaa cctgaccaca     60
aggacccagc tcccccctgc ctataccaat tccttcacac ggggcgtgta ctatccagac    120
aaggtgttta gatctagcgt gctgcactcc acacaggatc tgtttctgcc cttcttttct    180
aacgtgacct ggttccacgc catccatgtg agcggcacca atggcacaaa gcggttcgac    240
aatcctgtgc tgcccttcaa cgatggcgtg tacttcgcct ccaccgagaa gtctaacatc    300
atcagaggct ggatctttgg caccacactg gacagcaaga cacagtccct gctgatcgtg    360
aacaatgcca ccaacgtggt catcaaggtg tgcgagttcc agttttgtaa tgatcctttc    420
ctgggcgtgt actatcacaa gaacaataag tcttggatgg agagcgagtt tcgcgtgtat    480
tcctctgcca acaattgcac atttgagtac gtgtcccagc cattcctgat ggacctggag    540
ggcaagcagg gcaatttcaa gaacctgagg gagttcgtgt ttaagaatat cgatggctac    600
ttcaagatct actccaagca cacccctatc aacctggtgc gcgacctgcc acagggcttc    660
tctgccctgg agcctctggt ggatctgcca atcggcatca acatcacccg gtttcagaca    720
```

```
ctgctggccc tgcacagaag ctacctgaca cctggcgaca gctcctctgg atggaccgcc    780
ggggccgccg cctactatgt gggctatctg cagccaagga ccttcctgct gaagtacaac    840
gagaatggca ccatcacaga cgcagtggat tgcgccctgg accccctgtc tgagaccaag    900
tgtacactga agagctttac cgtggagaag ggcatctatc agacaagcaa tttcagggtg    960
cagcccaccg agtccatcgt gcgctttcca aatatcacaa acctgtgccc ctttggcgag   1020
gtgttcaacg caaccaggtt cgccagcgtg tacgcatgga ataggaagcg catctccaac   1080
tgcgtggccg actattctgt gctgtacaac agcgcctcct tctctacctt taagtgctat   1140
ggcgtgagcc ccacaaagct gaatgacctg tgctttacca acgtgtacgc cgattccttc   1200
gtgatcaggg gcgacgaggt gcgccagatc gcaccaggac agacaggcaa gatcgccgac   1260
tacaattata agctgcccga cgatttcacc ggctgcgtga tcgcctggaa ctctaacaat   1320
ctggatagca aagtgggcgg caactacaat tatctgtacc ggctgtttag aaagtctaat   1380
ctgaagcctt tcgagaggga catctccaca gagatctacc aggccggctc taccccatgc   1440
aatggcgtgg agggctttaa ctgttatttc cccctgcaga gctacggctt ccagcctaca   1500
aacggcgtgg gctatcagcc ataccgcgtg gtggtgctgt cttttgagct gctgcacgca   1560
ccagcaacag tgtgcggacc taagaagagc accaatctgg tgaagaacaa gtgcgtgaac   1620
ttcaacttca acggcctgac cggcacaggc gtgctgaccg agtccaacaa gaagttcctg   1680
ccctttcagc agttcggcag ggacatcgca gataccacag acgccgtgcg cgacccccag   1740
accctggaga tcctggacat cacaccttgc tccttcggcg gcgtgtctgt gatcacacct   1800
ggcaccaata caagcaacca ggtggccgtg ctgtatcagg acgtgaattg taccgaggtg   1860
ccagtggcca tccacgccga tcagctcacc cccacatggc gggtgtactc taccggcagc   1920
aacgtgttcc agacaagagc cggctgcctg atcggagccg agcatgtgaa caatagctat   1980
gagtgcgaca tccccatcgg agccggcatc tgtgcctcct accagaccca gacaaactcc   2040
cctcggagag cccggtctgt ggccagccag tccatcatcg cctataccat gagcctgggg   2100
gccgagaaca gcgtggccta ctccaacaat tctatcgcca tccccaccaa cttcacaatc   2160
tccgtgacca cagagatcct gcctgtgagc atgaccaaga catccgtgga ctgcacaatg   2220
tatatctgtg gcgattccac cgagtgctct aacctgctgc tgcagtacgg ctctttttgt   2280
acccagctca acagagccct gacaggcatc gccgtggagc aggacaagaa cacacaggag   2340
gtgttcgccc aggtgaagca gatctacaag accccaccca tcaaggactt tggcggcttc   2400
aacttcagcc agatcctgcc agatcccagc aagccttcca agcggtcttt tatcgaggac   2460
ctgctgttca acaaggtgac cctggccgat gccggcttca tcaagcagta tggcgattgc   2520
ctgggcgaca tcgccgccag agacctgatc tgtgcccaga agtttaatgg cctgaccgtg   2580
ctgcctccac tgctgacaga tgagatgatc gcccagtaca catctgccct gctggccggc   2640
accatcacaa gcggatggac cttcggggcc ggggccgccc tgcagatccc atttgccatg   2700
cagatggcct atcggttcaa cggcatcggc gtgacccaga atgtgctgta cgagaaccag   2760
aagctgatcg ccaatcagtt taactccgcc atcggcaaga tccaggactc tctgagctcc   2820
acagccagcg ccctgggcaa gctgcaggat gtggtgaatc agaacgccca ggccctgaat   2880
accctggtga agcagctcag cagcaacttc ggggccatca gcagcgtgct gaacgacatc   2940
ctgagccggc tggacccccc tgaggcagag gtgcagatcg accggctgat cacaggcaga   3000
ctgcagtccc tgcagaccta cgtgacacag cagctcatca gggccgccga gatcagggcc   3060
```

-continued

```
tctgccaatc tggccgccac caagatgagc gagtgcgtgc tgggccagtc caagagagtg   3120

gacttttgtg gcaagggcta tcacctgatg agcttcccac agtccgcccc ccacggagtg   3180

gtgtttctgc atgtgaccta cgtgcctgcc caggagaaga acttcaccac agccccagcc   3240

atctgccacg atggcaaggc ccactttccc agggagggcg tgttcgtgag caacggcacc   3300

cactggtttg tgacacagcg caatttctac gagcctcaga tcatcaccac agacaataca   3360

ttcgtgtccg gcaactgtga cgtggtcatc ggcatcgtga acaataccgt gtatgatccc   3420

ctgcagcctg agctggactc ttttaaggag gagctggata agtacttcaa gaatcacacc   3480

agccccgacg tggatctggg cgacatctct ggcatcaatg ccagcgtggt gaacatccag   3540

aaggagatcg acaggctgaa cgaggtggcc aagaatctga acgagtccct gatcgatctg   3600

caggagctgg gcaagtatga gcagtacatc aagtggccat ggtatatctg gctgggcttc   3660

atcgccggcc tgatcgccat cgtgatggtg accatcatgc tgtgctgtat gacaagctgc   3720

tgttcctgcc tgaagggctg ctgttcttgt ggctcctgct gtaagtttga tgaggacgat   3780

agcgagcccg tgctgaaggg cgtgaagctg cactacacct ga                      3822
```

<210> SEQ ID NO 16
<211> LENGTH: 1273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220
```

-continued

```
Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
```

```
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065
```

```
Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270

<210> SEQ ID NO 17
<211> LENGTH: 3822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

atgtttgttt ttcttgtttt attgccacta gtctctagtc agtgtgttaa tcttacaacc      60

agaactcaat taccccctgc atacactaat tctttcacac gtggtgttta ttaccctgac     120

aaagttttca gatcctcagt tttacattca actcaggact tgttcttacc tttcttttcc     180

aatgttactt ggttccatgc tatacatgtc tctgggacca atggtactaa gaggtttgat     240

aaccctgtcc taccatttaa tgatggtgtt tattttgctt ccactgagaa gtctaacata     300

ataagaggct ggatttttgg tactacttta gattcgaaga cccagtccct acttattgtt     360

aataacgcta ctaatgttgt tattaaagtc tgtgaatttc aattttgtaa tgatccattt     420

ttgggtgttt attaccacaa aaacaacaaa agttggatgg aaagtgagtt cagagtttat     480

tctagtgcga ataattgcac ttttgaatat gtctctcagc cttttcttat ggaccttgaa     540

ggaaaacagg gtaatttcaa aaatcttagg gaatttgtgt ttaagaatat tgatggttat     600

tttaaaatat attctaagca cacgcctatt aatttagtgc gtgatctccc tcagggtttt     660

tcggctttag aaccattggt agatttgcca ataggtatta acatcactag gtttcaaact     720

ttacttgctt tacatagaag ttatttgact cctggtgatt cttcttcagg ttggacagct     780
```

ggtgctgcag cttattatgt gggttatctt caacctagga cttttctatt aaaatataat 840
gaaaatggaa ccattacaga tgctgtagac tgtgcacttg accctctctc agaaacaaag 900
tgtacgttga aatccttcac tgtagaaaaa ggaatctatc aaacttctaa ctttagagtc 960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
tataattata aattaccaga tgattttaca ggctgcgtta tagcttggaa ttctaacaat 1320
cttgattcta aggttggtgg taattataat tacctgtata gattgtttag gaagtctaat 1380
ctcaaacctt ttgagagaga tatttcaact gaaatctatc aggccggtag cacaccttgt 1440
aatggtgttg aaggttttaa ttgttacttt cctttacaat catatggttt ccaacccact 1500
aatggtgttg gttaccaacc atacagagta gtagtacttt cttttgaact tctacatgca 1560
ccagcaactg tttgtggacc taaaaagtct actaatttgg ttaaaaacaa atgtgtcaat 1620
ttcaacttca atggtttaac aggcacaggt gttcttactg agtctaacaa aaagtttctg 1680
cctttccaac aatttggcag agacattgct gacactactg atgctgtccg tgatccacag 1740
acacttgaga ttcttgacat tacaccatgt tcttttggtg gtgtcagtgt tataacacca 1800
ggaacaaata cttctaacca ggttgctgtt ctttatcagg atgttaactg cacagaagtc 1860
cctgttgcta ttcatgcaga tcaacttact cctacttggc gtgtttattc tacaggttct 1920
aatgtttttc aaacacgtgc aggctgttta ataggggctg aacatgtcaa caactcatat 1980
gagtgtgaca tacccattgg tgcaggtata tgcgctagtt atcagactca gactaattct 2040
cctggtagtg caagtagtgt agctagtcaa tccatcattg cctacactat gtcacttggt 2100
gcagaaaatt cagttgctta ctctaataac tctattgcca tacccacaaa ttttactatt 2160
agtgttacca cagaaattct accagtgtct atgaccaaga catcagtaga ttgtacaatg 2220
tacatttgtg gtgattcaac tgaatgcagc aatcttttgt tgcaatatgg cagtttttgt 2280
acacaattaa accgtgcttt aactggaata gctgttgaac aagacaaaaa cacccaagaa 2340
gtttttgcac aagtcaaaca aatttacaaa acaccaccaa ttaaagattt tggtggtttt 2400
aatttttcac aaatattacc agatccatca aaaccaagca agaggtcatt tattgaagat 2460
ctacttttca acaaagtgac acttgcagat gctggcttca tcaaacaata tggtgattgc 2520
cttggtgata ttgctgctag agacctcatt tgtgcacaaa agtttaacgg ccttactgtt 2580
ttgccacctt tgctcacaga tgaaatgatt gctcaataca cttctgcact gttagcgggt 2640
acaatcactt ctggttggac ctttggtgca ggtgctgcat tacaaatacc atttgctatg 2700
caaatggctt ataggtttaa tggtattgga gttacacaga atgttctcta tgagaaccaa 2760
aaattgattg ccaaccaatt taatagtgct attggcaaaa ttcaagactc actttcttcc 2820
acagcaagtg cacttggaaa acttcaagat gtggtcaacc aaaatgcaca agctttaaac 2880
acgcttgtta aacaacttag ctccaatttt ggtgcaattt caagtgtttt aaatgatatc 2940
ctttcacgtc ttgacaaagt tgaggctgaa gtgcaaattg ataggttgat cacaggcaga 3000
cttcaaagtt tgcagacata tgtgactcaa caattaatta gagctgcaga aatcagagct 3060
tctgctaatc ttgctgctac taaaatgtca gagtgtgtac ttggacaatc aaaaagagtt 3120

```
gatttttgtg gaaagggcta tcatcttatg tccttccctc agtcagcacc tcatggtgta   3180

gtcttcttgc atgtgactta tgtccctgca caagaaaaga acttcacaac tgctcctgcc   3240

atttgtcatg atggaaaagc acactttcct cgtgaaggtg tctttgtttc aaatggcaca   3300

cactggtttg taacacaaag gaatttttat gaaccacaaa tcattactac agacaacaca   3360

tttgtgtctg gtaactgtga tgttgtaata ggaattgtca acaacacagt ttatgatcct   3420

ttgcaacctg aattagactc attcaaggag gagttagata aatattttaa gaatcataca   3480

tcaccagatg ttgatttagg tgacatctct ggcattaatg cttcagttgt aaacattcaa   3540

aaagaaattg accgcctcaa tgaggttgcc aagaatttaa atgaatctct catcgatctc   3600

caagaacttg gaaagtatga gcagtatata aaatggccat ggtacatttg gctaggtttt   3660

atagctggct tgattgccat agtaatggtg acaattatgc tttgctgtat gaccagttgc   3720

tgtagttgtc tcaagggctg ttgttcttgt ggatcctgct gcaaatttga tgaagacgac   3780

tctgagccag tgctcaaagg agtcaaatta cattacacat aa                      3822
```

<210> SEQ ID NO 18
<211> LENGTH: 3822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atgttcgtgt ttctggtgct gctgcctctg gtgagctccc agtgcgtgaa cctgaccaca     60

aggacccagc tcccccctgc ctataccaat tccttcacaa ggggcgtgta ctatcccgac    120

aaggtgtttc gctctagcgt gctgcacagc acacaggatc tgtttctgcc tttcttttcc    180

aacgtgacct ggttccacgc catccatgtg agcggcacca atggcacaaa gaggttcgac    240

aatccagtgc tgccctttaa cgatggcgtg tacttcgcct ctaccgagaa gagcaacatc    300

atccgcggct ggatctttgg caccacactg gactccaaga cacagtctct gctgatcgtg    360

aacaatgcca ccaacgtggt catcaaggtg tgcgagttcc agttttgtaa tgatccattc    420

ctgggcgtgt actatcacaa gaacaataag agctggatgg agtccgagtt tcgcgtgtat    480

tcctctgcca acaattgcac atttgagtac gtgtcccagc ccttcctgat ggacctggag    540

ggcaagcagg gcaatttcaa gaacctgcgg gagttcgtgt ttaagaatat cgatggctac    600

ttcaagatct acagcaagca caccccaatc aacctggtga gagacctgcc acagggcttc    660

tccgccctgg agccactggt ggatctgccc atcggcatca acatcaccag gtttcagaca    720

ctgctggccc tgcaccgcag ctacctgaca ccaggcgaca gctcctctgg atggaccgcc    780

ggggccgccg cctactatgt gggctatctg cagccccgga ccttcctgct gaagtacaac    840

gagaatggca ccatcacaga cgcagtggat tgcgccctgg accccctgtc cgagaccaag    900

tgtacactga agtcttttac cgtggagaag ggcatctatc agacatctaa tttccgggtg    960

cagcctaccg agagcatcgt gagatttccc aatatcacaa acctgtgccc ttttggcgag   1020

gtgttcaacg ccaccagatt cgccagcgtg tacgcctgga atcggaagag aatcagcaac   1080

tgcgtggccg actattccgt gctgtacaac tctgccagct tctccacctt taagtgctat   1140

ggcgtgtctc ccacaaagct gaatgacctg tgctttacca acgtgtacgc cgatagcttc   1200

gtgatcaggg gcgacgaggt gagacagatc gcaccaggac agacaggcaa gatcgcagac   1260

tacaattata agctgcctga cgatttcacc ggctgcgtga tcgcctggaa cagcaacaat   1320
```

-continued

```
ctggattcca aagtgggcgg caactacaat tatctgtaca ggctgtttcg caagtccaat   1380
ctgaagccat tcgagcggga catcagcaca gagatctacc aggcaggctc caccccatgc   1440
aatggagtgg agggctttaa ctgttatttc cctctgcagt cttacggctt ccagccaaca   1500
aacggcgtgg gctatcagcc ctacagagtg gtggtgctgt cctttgagct gctgcacgca   1560
cctgcaacag tgtgcggacc aaagaagtct accaatctgg tgaagaacaa gtgcgtgaac   1620
ttcaacttca acggcctgac cggcacaggc gtgctgaccg agtccaacaa gaagttcctg   1680
ccttttcagc agttcggcag agacatcgcc gataccacag acgccgtgag agaccctcag   1740
accctggaga tcctggacat cacaccatgc tctttcggcg gcgtgagcgt gatcacacca   1800
ggcaccaata caagcaacca ggtggccgtg ctgtatcagg acgtgaattg taccgaggtg   1860
cccgtggcca tccacgcaga tcagctcacc cctacatgga gggtgtactc caccggctct   1920
aacgtgttcc agacacgcgc cggatgcctg atcggagccg agcatgtgaa caattcttat   1980
gagtgcgaca tccctatcgg agccggcatc tgtgccagct accagaccca gacaaacagc   2040
ccaggctccg ccagctccgt ggcctctcag agcatcatcg cctataccat gagcctgggg   2100
gccgagaata gcgtggccta ctctaacaat agcatcgcca tccctaccaa cttcacaatc   2160
tccgtgacca cagagatcct gccagtgtcc atgaccaaga catctgtgga ctgcacaatg   2220
tatatctgtg gcgattctac cgagtgcagc aacctgctgc tgcagtacgg cagcttttgt   2280
acccagctca accgggccct gacaggaatc gcagtggagc aggacaagaa cacacaggag   2340
gtgttcgccc aggtgaagca gatctacaag accccaccca tcaaggactt tggcggcttc   2400
aacttcagcc agatcctgcc cgatccttcc aagccatcta agaggagctt tatcgaggac   2460
ctgctgttca acaaggtgac cctggccgat gccggcttca tcaagcagta tggcgattgc   2520
ctgggcgaca tcgcagcccg cgacctgatc tgtgcccaga agtttaatgg cctgaccgtg   2580
ctgcctccac tgctgacaga tgagatgatc gcacagtaca catccgccct gctggccggc   2640
accatcacat ctggatggac cttcggggcc ggggccgccc tgcagatccc ctttgccatg   2700
cagatggcct atagattcaa cggcatcggc gtgacccaga atgtgctgta cgagaaccag   2760
aagctgatcg ccaatcagtt taactccgcc atcggcaaga tccaggactc cctgtctagc   2820
acagcctctg ccctgggcaa gctgcaggat gtggtgaatc agaacgccca ggccctgaat   2880
accctggtga agcagctcag cagcaacttc ggggccatca gcagcgtgct gaacgacatc   2940
ctgagccggc tggacaaggt ggaggcagag gtgcagatcg acaggctgat cacaggccgc   3000
ctgcagagcc tgcagaccta cgtgacacag cagctcatca gggccgccga gatcagagcc   3060
tccgccaatc tggccgccac caagatgtct gagtgcgtgc tgggccagag caagcgcgtg   3120
gacttttgtg gcaagggcta tcacctgatg tccttcccac agtctgcccc tcacggagtg   3180
gtgtttctgc atgtgaccta cgtgccagcc caggagaaga acttcaccac agccccccgca   3240
atctgccacg atggcaaggc acactttcct cgggagggcg tgttcgtgtc taacggcacc   3300
cactggtttg tgacacagag aaatttctac gagccacaga tcatcaccac agacaataca   3360
ttcgtgagcg gcaactgtga cgtggtcatc ggcatcgtga acaataccgt gtatgatcct   3420
ctgcagccag agctggactc ctttaaggag gagctggata agtacttcaa gaatcacacc   3480
tctcccgacg tggatctggg cgacatcagc ggcatcaatg cctccgtggt gaacatccag   3540
aaggagatcg acaggctgaa cgaggtggcc aagaatctga acgagtccct gatcgatctg   3600
caggagctgg gcaagtatga gcagtacatc aagtggccct ggtatatctg gctgggcttc   3660
atcgccggcc tgatcgccat cgtgatggtg accatcatgc tgtgctgtat gacatcctgc   3720
```

tgttcttgcc tgaagggctg ctgtagctgt ggctcctgct gtaagtttga tgaggacgat 3780
agcgagcctg tgctgaaggg cgtgaagctg cactacacct ga 3822

<210> SEQ ID NO 19
<211> LENGTH: 1273
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Arg Val
305 310 315 320

Gln Pro Thr Glu Ser Ile Val Arg Phe Pro Asn Ile Thr Asn Leu Cys
325 330 335

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
```

```
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170
```

```
Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 20
<211> LENGTH: 3822
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

atgtttgttt ttcttgtttt attgccacta gtctctagtc agtgtgttaa tcttacaacc     60

agaactcaat taccccctgc atacactaat tctttcacac gtggtgttta ttaccctgac    120

aaagttttca gatcctcagt tttacattca actcaggact tgttcttacc tttcttttcc    180

aatgttactt ggttccatgc tatacatgtc tctgggacca atggtactaa gaggtttgat    240

aaccctgtcc taccatttaa tgatggtgtt tattttgctt ccactgagaa gtctaacata    300

ataagaggct ggatttttgg tactacttta gattcgaaga cccagtccct acttattgtt    360

aataacgcta ctaatgttgt tattaaagtc tgtgaatttc aattttgtaa tgatccattt    420

ttgggtgttt attaccacaa aaacaacaaa agttggatgg aaagtgagtt cagagtttat    480

tctagtgcga ataattgcac ttttgaatat gtctctcagc cttttcttat ggaccttgaa    540

ggaaaacagg gtaatttcaa aaatcttagg gaatttgtgt ttaagaatat tgatggttat    600

tttaaaatat attctaagca cacgcctatt aatttagtgc gtgatctccc tcagggtttt    660

tcggctttag aaccattggt agatttgcca ataggtatta acatcactag gtttcaaact    720

ttacttgctt tacatagaag ttatttgact cctggtgatt cttcttcagg ttggacagct    780

ggtgctgcag cttattatgt gggttatctt caacctagga cttttctatt aaaatataat    840

gaaaatggaa ccattacaga tgctgtagac tgtgcacttg accctctctc agaaacaaag    900

tgtacgttga aatccttcac tgtagaaaaa ggaatctatc aaacttctaa ctttagagtc    960

caaccaacag aatctattgt tagatttcct aatattacaa acttgtgccc ttttggtgaa   1020

gtttttaacg ccaccagatt tgcatctgtt tatgcttgga acaggaagag aatcagcaac   1080

tgtgttgctg attattctgt cctatataat tccgcatcat tttccacttt taagtgttat   1140

ggagtgtctc ctactaaatt aaatgatctc tgctttacta atgtctatgc agattcattt   1200

gtaattagag gtgatgaagt cagacaaatc gctccagggc aaactggaaa gattgctgat   1260

tataattata aattaccaga tgattttaca ggctgcgtta tagcttggaa ttctaacaat   1320

cttgattcta aggttggtgg taattataat tacctgtata gattgtttag gaagtctaat   1380
```

```
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctggtagtg caagtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgaccctcc tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaatg cttcagttgt aaacattcaa   3540
aaagaaattg accgcctcaa tgaggttgcc aagaatttaa atgaatctct catcgatctc   3600
caagaacttg gaaagtatga gcagtatata aaatggccat ggtacatttg gctaggtttt   3660
atagctggct tgattgccat agtaatggtg acaattatgc tttgctgtat gaccagttgc   3720
tgtagttgtc tcaagggctg ttgttcttgt ggatcctgct gcaaatttga tgaagacgac   3780
```

tctgagccag tgctcaaagg agtcaaatta cattacacat aa 3822

<210> SEQ ID NO 21
<211> LENGTH: 3822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21
atgttcgtgt ttctggtgct gctgcctctg gtgagctccc agtgcgtgaa cctgaccaca 60
aggacccagc tccccccctgc ctataccaat tccttcacaa ggggcgtgta ctatccagac 120
aaggtgtttc gctctagcgt gctgcacagc acacaggatc tgtttctgcc cttcttttcc 180
aacgtgacct ggttccacgc catccatgtg agcggcacca atggcacaaa gaggttcgac 240
aatcctgtgc tgcccttcaa cgatggcgtg tacttcgcct ctaccgagaa gagcaacatc 300
atccgcggct ggatctttgg caccacactg gactccaaga cacagtctct gctgatcgtg 360
aacaatgcca ccaacgtggt catcaaggtg tgcgagttcc agttttgtaa tgatcctttc 420
ctgggcgtgt actatcacaa gaacaataag agctggatgg agtccgagtt tcgcgtgtat 480
tcctctgcca acaattgcac atttgagtac gtgtcccagc cattcctgat ggacctggag 540
ggcaagcagg gcaatttcaa gaacctgcgg gagttcgtgt ttaagaatat cgatggctac 600
ttcaagatct acagcaagca cacccctatc aacctggtga gagacctgcc acagggcttc 660
tccgccctgg agcctctggt ggatctgcca atcggcatca acatcaccag gtttcagaca 720
ctgctggccc tgcaccgcag ctacctgaca cctggcgaca gctcctctgg atggaccgcc 780
ggggccgccg cctactatgt gggctatctg cagccacgga ccttcctgct gaagtacaac 840
gagaatggca ccatcacaga cgcagtggat tgcgccctgg accccctgtc cgagaccaag 900
tgtacactga agtcttttac cgtggagaag ggcatctatc agacatctaa tttccgggtg 960
cagcccaccg agagcatcgt gagatttcca aatatcacaa acctgtgccc ctttggcgag 1020
gtgttcaacg ccaccagatt cgccagcgtg tacgcctgga atcggaagag aatcagcaac 1080
tgcgtggccg actattccgt gctgtacaac tctgccagct tctccacctt taagtgctat 1140
ggcgtgtctc ccacaaagct gaatgacctg tgctttacca acgtgtacgc cgatagcttc 1200
gtgatcaggg gcgacgaggt gagacagatc gcaccaggcc agacaggcaa gatcgccgac 1260
tacaattata agctgcccga cgatttcacc ggctgcgtga tcgcctggaa cagcaacaat 1320
ctggattcca aagtgggcgg caactacaat tatctgtaca ggctgtttcg caagtccaat 1380
ctgaagcctt tcgagcggga catcagcaca gagatctacc aggccggctc caccccatgc 1440
aatggcgtgg agggctttaa ctgttatttc cccctgcagt cttacggctt ccagcctaca 1500
aacggcgtgg gctatcagcc atacagagtg gtggtgctgt cctttgagct gctgcacgca 1560
ccagcaacag tgtgcggacc taagaagtct accaatctgg tgaagaacaa gtgcgtgaac 1620
ttcaacttca acggcctgac cggcacaggc gtgctgaccg agtccaacaa gaagttcctg 1680
ccctttcagc agttcggcag agacatcgcc gataccacag acgccgtgag agacccccag 1740
accctggaga tcctggacat cacaccttgc tctttcggcg gcgtgagcgt gatcacacct 1800
ggcaccaata caagcaacca ggtggccgtg ctgtatcagg acgtgaattg taccgaggtg 1860
ccagtggcca tccacgccga tcagctcacc cccacatgga gggtgtactc caccggctct 1920
aacgtgttcc agacacgcgc cggatgcctg atcggagccg agcatgtgaa caattcttat 1980

```
gagtgcgaca tccccatcgg agccggcatc tgtgccagct accagaccca gacaaacagc   2040
cctggctccg ccagctccgt ggcctctcag agcatcatcg cctataccat gagcctgggg   2100
gccgagaata gcgtggccta ctctaacaat agcatcgcca tccccaccaa cttcacaatc   2160
tccgtgacca cagagatcct gcccgtgagc atgaccaaga catctgtgga ctgcacaatg   2220
tatatctgtg gcgattctac cgagtgcagc aacctgctgc tgcagtacgg cagcttttgt   2280
acccagctca accgggccct gacaggaatc gcagtggagc aggacaagaa cacacaggag   2340
gtgttcgccc aggtgaagca gatctacaag accccaccca tcaaggactt tggcggcttc   2400
aacttcagcc agatcctgcc agatccctcc aagccttcta agaggagctt tatcgaggac   2460
ctgctgttca acaaggtgac cctggccgat gccggcttca tcaagcagta tggcgattgc   2520
ctgggcgaca tcgcagcccg cgacctgatc tgtgcccaga agtttaatgg cctgaccgtg   2580
ctgcctccac tgctgacaga tgagatgatc gcacagtaca catccgccct gctggccggc   2640
accatcacat ctggatggac cttcggggcc ggggccgccc tgcagatccc atttgccatg   2700
cagatggcct atagattcaa cggcatcggc gtgacccaga atgtgctgta cgagaaccag   2760
aagctgatcg ccaatcagtt taactccgcc atcggcaaga tccaggactc cctgtctagc   2820
acagcctctg ccctgggcaa gctgcaggat gtggtgaatc agaacgccca ggccctgaat   2880
accctggtga agcagctcag cagcaacttc ggggccatca gcagcgtgct gaacgacatc   2940
ctgagccggc tggacccccc tgaggcagag gtgcagatcg acaggctgat cacaggccgc   3000
ctgcagagcc tgcagaccta cgtgacacag cagctcatca gggccgccga gatcagagcc   3060
tccgccaatc tggccgccac caagatgtct gagtgcgtgc tgggccagag caagcgcgtg   3120
gacttttgtg gcaagggcta tcacctgatg tccttcccac agtctgcccc ccacggagtg   3180
gtgtttctgc atgtgaccta cgtgcctgcc caggagaaga acttcaccac agccccagcc   3240
atctgccacg atggcaaggc acactttccc cgggagggcg tgttcgtgtc taacggcacc   3300
cactggtttg tgacacagag aaatttctac gagcctcaga tcatcaccac agacaataca   3360
ttcgtgagcg gcaactgtga cgtggtcatc ggcatcgtga acaataccgt gtatgatccc   3420
ctgcagcctg agctggactc ctttaaggag gagctggata agtacttcaa gaatcacacc   3480
tctcccgacg tggatctggg cgacatcagc ggcatcaatg cctccgtggt gaacatccag   3540
aaggagatcg acaggctgaa cgaggtggcc aagaatctga acgagtccct gatcgatctg   3600
caggagctgg gcaagtatga gcagtacatc aagtggccat ggtatatctg gctgggcttc   3660
atcgccggcc tgatcgccat cgtgatggtg accatcatgc tgtgctgtat gacatcctgc   3720
tgttcttgcc tgaagggctg ctgtagctgt ggctcctgct gtaagtttga tgaggacgat   3780
agcgagcccg tgctgaaggg cgtgaagctg cactacacct ga                      3822
```

<210> SEQ ID NO 22
<211> LENGTH: 1255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30
```

-continued

```
Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445
```

```
Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
```

-continued

```
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Phe Phe Phe Ile  Ile Gly Leu
    1205                 1210                 1215

Ile Ile  Gly Leu Phe Leu Val  Leu Arg Val Gly Ile  His Leu Cys
    1220                 1225                 1230

Ile Lys  Leu Lys His Thr Lys  Lys Arg Gln Ile Tyr  Thr Asp Ile
    1235                 1240                 1245

Glu Met  Asn Arg Leu Gly Lys
    1250                 1255
```

<210> SEQ ID NO 23

<211> LENGTH: 3768
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
atgtttgttt ttcttgtttt attgccacta gtctctagtc agtgtgttaa tcttacaacc     60
agaactcaat taccccctgc atacactaat tctttcacac gtggtgttta ttaccctgac    120
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatttaa tgatggtgtt tattttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctggtagtg caagtagtgt agctagtcaa tccatcattg cctacactat gtcacttggt   2100
```

```
gcagaaaatt cagttgctta ctctaataac tctattgcca tacccacaaa ttttactatt   2160

agtgttacca cagaaattct accagtgtct atgaccaaga catcagtaga ttgtacaatg   2220

tacatttgtg gtgattcaac tgaatgcagc aatcttttgt tgcaatatgg cagtttttgt   2280

acacaattaa accgtgcttt aactggaata gctgttgaac aagacaaaaa cacccaagaa   2340

gtttttgcac aagtcaaaca aatttacaaa acaccaccaa ttaaagattt tggtggtttt   2400

aatttttcac aaatattacc agatccatca aaaccaagca agaggtcatt tattgaagat   2460

ctacttttca acaaagtgac acttgcagat gctggcttca tcaaacaata tggtgattgc   2520

cttggtgata ttgctgctag agacctcatt tgtgcacaaa agtttaacgg ccttactgtt   2580

ttgccacctt tgctcacaga tgaaatgatt gctcaataca cttctgcact gttagcgggt   2640

acaatcactt ctggttggac ctttggtgca ggtgctgcat tacaaatacc atttgctatg   2700

caaatggctt ataggtttaa tggtattgga gttacacaga atgttctcta tgagaaccaa   2760

aaattgattg ccaaccaatt taatagtgct attggcaaaa ttcaagactc actttcttcc   2820

acagcaagtg cacttggaaa acttcaagat gtggtcaacc aaaatgcaca agctttaaac   2880

acgcttgtta aacaacttag ctccaatttt ggtgcaattt caagtgtttt aaatgatatc   2940

ctttcacgtc ttgaccctcc tgaggctgaa gtgcaaattg ataggttgat cacaggcaga   3000

cttcaaagtt tgcagacata tgtgactcaa caattaatta gagctgcaga aatcagagct   3060

tctgctaatc ttgctgctac taaaatgtca gagtgtgtac ttggacaatc aaaaagagtt   3120

gatttttgtg gaaagggcta tcatcttatg tccttccctc agtcagcacc tcatggtgta   3180

gtcttcttgc atgtgactta tgtccctgca caagaaaaga acttcacaac tgctcctgcc   3240

atttgtcatg atggaaaagc acactttcct cgtgaaggtg tctttgtttc aaatggcaca   3300

cactggtttg taacacaaag gaatttttat gaaccacaaa tcattactac agacaacaca   3360

tttgtgtctg gtaactgtga tgttgtaata ggaattgtca acaacacagt ttatgatcct   3420

ttgcaacctg aattagactc attcaaggag gagttagata aatattttaa gaatcataca   3480

tcaccagatg ttgatttagg tgacatctct ggcattaatg cttcagttgt aaacattcaa   3540

aaagaaattg accgcctcaa tgaggttgcc aagaatttaa atgaatctct catcgatctc   3600

caagaacttg gaaagtatga gcagtatata aaattttttct ttatcatagg gttaatcatt   3660

ggactattct tggttctccg agttggtatc catctttgca ttaaattaaa gcacaccaag   3720

aaaagacaga tttatacaga catagagatg aaccgacttg gaaagtaa                3768
```

<210> SEQ ID NO 24
<211> LENGTH: 3768
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
atgttcgtgt tcctggtgct gctgcctctg gtgagctccc agtgcgtgaa cctgaccaca     60

aggacccagc tcccccctgc ctataccaat tcctttacaa ggggcgtgta ctatccagac    120

aaggtgttcc gctctagcgt gctgcactct acacaggatc tgttcctgcc cttctttagc    180

aacgtgacct ggtttcacgc catccatgtg agcggcacca atggcacaaa gcggtttgac    240

aatcctgtgc tgccattcaa cgatggcgtg tactttgcct ccaccgagaa gtctaacatc    300

atcagaggct ggatcttcgg caccacactg gacagcaaga cacagtccct gctgatcgtg    360
```

-continued

```
aacaatgcca ccaacgtggt catcaaggtg tgcgagtttc agttctgtaa tgatcctttt    420
ctgggcgtgt actatcacaa gaacaataag tcttggatgg agagcgagtt ccgcgtgtat    480
tcctctgcca acaattgtac attcgagtac gtgtcccagc catttctgat ggacctggag    540
ggcaagcagg gcaacttcaa gaacctgcgg gagttcgtgt tcaagaatat cgatggctat    600
ttcaagatct actctaagca cacccctatc aacctggtgc gcgacctgcc acagggcttt    660
agcgccctgg agcctctggt ggatctgcca atcggcatca acatcaccag gttccagaca    720
ctgctggccc tgcaccgcag ctacctgaca cctggcgaca gctcctctgg atggaccgcc    780
ggggccgccg cctactatgt gggctatctg cagccacgga cctttctgct gaagtacaac    840
gagaatggca ccatcacaga cgcagtggat tgcgccctgg accccctgag cgagaccaag    900
tgtacactga agtccttcac cgtggagaag ggcatctatc agacatccaa ttttcgggtg    960
cagcccaccg agtctatcgt gagattccca aatatcacaa acctgtgccc cttcggcgag   1020
gtgtttaacg ccaccagatt cgccagcgtg tacgcctgga atcggaagag aatctctaac   1080
tgcgtggccg actatagcgt gctgtacaac tctgccagct tttccacctt caagtgctat   1140
ggcgtgtccc ccacaaagct gaatgacctg tgcttcacca acgtgtacgc cgattctttt   1200
gtgatcaggg gcgacgaggt gagacagatc gcaccaggcc agacaggcaa gatcgccgac   1260
tacaattata agctgcccga cgatttcacc ggctgcgtga tcgcctggaa ctctaacaat   1320
ctggatagca aagtgggcgg caactacaat tatctgtaca ggctgttccg caagagcaat   1380
ctgaagcctt ttgagcggga catctctaca gagatctacc aggccggcag caccccatgc   1440
aatggcgtgg agggcttcaa ctgttatttt cccctgcagt cctacggctt tcagcctacc   1500
aacggcgtgg gctatcagcc atacagagtg gtggtgctga gcttcgagct gctgcacgca   1560
ccagcaacag tgtgcggacc taagaagtcc accaatctgg tgaagaacaa gtgcgtgaac   1620
ttcaacttca acggcctgac cggcacaggc gtgctgaccg agtccaataa gaagtttctg   1680
cccttccagc agtttggccg ggacatcgcc gataccacag acgccgtgag agacccccag   1740
accctggaga tcctggacat cacaccttgc tccttcggcg gcgtgtctgt gatcacacct   1800
ggcaccaata caagcaacca ggtggccgtg ctgtatcagg acgtgaattg taccgaggtg   1860
ccagtggcca tccacgccga tcagctcacc cccacatggc gggtgtactc caccggctct   1920
aacgtgttcc agacaagagc cggctgcctg atcggagccg agcatgtgaa caattcctat   1980
gagtgcgaca tccccatcgg agccggcatc tgtgcctctt accagaccca gacaaacagc   2040
cctggctccg ccagctccgt ggcctctcag agcatcatcg cctataccat gagcctgggg   2100
gccgagaaca gcgtggccta ctctaacaat agcatcgcca tccccaccaa ctttacaatc   2160
tctgtgacca cagagatcct gcctgtgagc atgaccaaga catccgtgga ctgcacaatg   2220
tatatctgtg gcgattccac cgagtgctct aacctgctgc tgcagtacgg cagcttctgt   2280
acccagctca accgggccct gacaggaatc gcagtggagc aggacaagaa cacacaggag   2340
gtgtttgccc aggtgaagca gatctacaag accccaccca tcaaggactt cggcggcttt   2400
aatttctccc agatcctgcc agatccctcc aagccatcta agcggagctt catcgaggac   2460
ctgctgttta acaaggtgac cctggccgat gccggcttta tcaagcagta tggcgattgc   2520
ctgggcgaca tcgccgccag agacctgatc tgtgcccaga agttcaatgg cctgaccgtg   2580
ctgcctccac tgctgacaga tgagatgatc gcacagtaca caagcgccct gctggccggc   2640
accatcacat ccggatggac cttcggggcc ggggccgccc tgcagatccc cttcgccatg   2700
cagatggcct ataggtttaa cggcatcggc gtgacccaga atgtgctgta cgagaaccag   2760
```

```
aagctgatcg ccaatcagtt caactccgcc atcggcaaga tccaggacag cctgtctagc   2820

acagcctccg ccctgggcaa gctgcaggat gtggtgaatc agaacgccca ggccctgaat   2880

accctggtga agcagctcag cagcaacttc ggggccatca gcagcgtgct gaacgacatc   2940

ctgagccggc tggacccccc tgaggcagag gtgcagatcg acaggctgat cacaggccgc   3000

ctgcagtctc tgcagaccta tgtgacacag cagctcatca gggccgccga gatcagagcc   3060

agcgccaatc tggccgccac caagatgtcc gagtgcgtgc tgggccagtc taagcgcgtg   3120

gacttctgtg gcaagggcta tcacctgatg agctttccac agtccgcccc ccacggagtg   3180

gtgttcctgc atgtgaccta cgtgcctgcc caggagaaga actttaccac agccccagcc   3240

atctgccacg atggcaaggc acacttcccc agggagggcg tgttcgtgag caacggcacc   3300

cactggttcg tgacacagcg caacttctac gagcctcaga tcatcaccac agacaataca   3360

ttcgtgtctg gcaactgtga cgtggtcatc ggcatcgtga acaataccgt gtatgatccc   3420

ctgcagcctg agctggacag cttcaaggag gagctggata agtactttaa gaatcacacc   3480

tcccccgacg tggatctggg cgacatctct ggcatcaatg ccagcgtggt gaacatccag   3540

aaggagatcg acaggctgaa cgaggtggcc aagaatctga acgagagcct gatcgatctg   3600

caggagctgg gcaagtatga gcagtacatc aagttctttt tcatcatcgg cctgatcatc   3660

ggcctgttcc tggtgctgcg cgtgggcatc cacctgtgca tcaagctgaa gcacaccaag   3720

aagaggcaga tctacacaga catcgagatg aaccgcctgg gcaagtga                3768
```

<210> SEQ ID NO 25
<211> LENGTH: 1255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175
```

```
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
```

```
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020
```

```
Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Phe Phe Phe Ile  Ile Gly Leu
    1205                 1210                 1215

Ile Ile  Gly Leu Phe Leu Val  Leu Arg Val Gly Ile  His Leu Cys
    1220                 1225                 1230

Ile Lys  Leu Lys His Thr Lys  Lys Arg Gln Ile Tyr  Thr Asp Ile
    1235                 1240                 1245

Glu Met  Asn Arg Leu Gly Lys
    1250                 1255
```

<210> SEQ ID NO 26
<211> LENGTH: 3819
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
ctcgaggttt aaacgaattc cgccaccatg tttgtttttc ttgttttatt gccactagtc     60

tctagtcagt gtgttaatct tacaaccaga actcaattac cccctgcata cactaattct    120

ttcacacgtg gtgtttatta ccctgacaaa gttttcagat cctcagtttt acattcaact    180

caggacttgt tcttaccttt cttttccaat gttacttggt tccatgctat acatgtctct    240

gggaccaatg gtactaagag gtttgataac cctgtcctac catttaatga tggtgtttat    300

tttgcttcca ctgagaagtc taacataata agaggctgga tttttggtac tactttagat    360

tcgaagaccc agtccctact tattgttaat aacgctacta atgttgttat taaagtctgt    420

gaatttcaat tttgtaatga tccatttttg ggtgtttatt accacaaaaa caacaaaagt    480

tggatggaaa gtgagttcag agtttattct agtgcgaata attgcacttt tgaatatgtc    540

tctcagcctt ttcttatgga ccttgaagga aaacagggta atttcaaaaa tcttagggaa    600
```

```
tttgtgttta agaatattga tggttatttt aaaatatatt ctaagcacac gcctattaat    660
ttagtgcgtg atctccctca gggtttttcg gctttagaac cattggtaga tttgccaata    720
ggtattaaca tcactaggtt tcaaacttta cttgctttac atagaagtta tttgactcct    780
ggtgattctt cttcaggttg gacagctggt gctgcagctt attatgtggg ttatcttcaa    840
cctaggactt ttctattaaa atataatgaa aatggaacca ttacagatgc tgtagactgt    900
gcacttgacc ctctctcaga aacaaagtgt acgttgaaat ccttcactgt agaaaaagga    960
atctatcaaa cttctaactt tagagtccaa ccaacagaat ctattgttag atttcctaat   1020
attacaaact tgtgcccttt tggtgaagtt tttaacgcca ccagatttgc atctgtttat   1080
gcttggaaca ggaagagaat cagcaactgt gttgctgatt attctgtcct atataattcc   1140
gcatcatttt ccacttttaa gtgttatgga gtgtctccta ctaaattaaa tgatctctgc   1200
tttactaatg tctatgcaga ttcatttgta attagaggtg atgaagtcag acaaatcgct   1260
ccagggcaaa ctggaaagat tgctgattat aattataaat taccagatga ttttacaggc   1320
tgcgttatag cttggaattc taacaatctt gattctaagg ttggtggtaa ttataattac   1380
ctgtatagat tgtttaggaa gtctaatctc aaaccttttg agagagatat ttcaactgaa   1440
atctatcagg ccggtagcac accttgtaat ggtgttgaag gttttaattg ttactttcct   1500
ttacaatcat atggtttcca acccactaat ggtgttggtt accaaccata cagagtagta   1560
gtactttctt ttgaacttct acatgcacca gcaactgttt gtggacctaa aaagtctact   1620
aatttggtta aaaacaaatg tgtcaatttc aacttcaatg gtttaacagg cacaggtgtt   1680
cttactgagt ctaacaaaaa gtttctgcct ttccaacaat ttggcagaga cattgctgac   1740
actactgatg ctgtccgtga tccacagaca cttgagattc ttgacattac accatgttct   1800
tttggtggtg tcagtgttat aacaccagga acaaatactt ctaaccaggt tgctgttctt   1860
tatcaggatg ttaactgcac agaagtccct gttgctattc atgcagatca acttactcct   1920
acttggcgtg tttattctac aggttctaat gtttttcaaa cacgtgcagg ctgtttaata   1980
ggggctgaac atgtcaacaa ctcatatgag tgtgacatac ccattggtgc aggtatatgc   2040
gctagttatc agactcagac taattctcct cggcgggcac gtagtgtagc tagtcaatcc   2100
atcattgcct acactatgtc acttggtgca gaaaattcag ttgcttactc taataactct   2160
attgccatac ccacaaattt tactattagt gttaccacag aaattctacc agtgtctatg   2220
accaagacat cagtagattg tacaatgtac atttgtggtg attcaactga atgcagcaat   2280
cttttgttgc aatatggcag tttttgtaca caattaaacc gtgctttaac tggaatagct   2340
gttgaacaag acaaaaacac ccaagaagtt tttgcacaag tcaaacaaat ttacaaaaca   2400
ccaccaatta aagattttgg tggttttaat ttttcacaaa tattaccaga tccatcaaaa   2460
ccaagcaaga ggtcatttat tgaagatcta cttttcaaca aagtgacact tgcagatgct   2520
ggcttcatca aacaatatgg tgattgcctt ggtgatattg ctgctagaga cctcatttgt   2580
gcacaaaagt ttaacggcct tactgttttg ccacctttgc tcacagatga aatgattgct   2640
caatacactt ctgcactgtt agcgggtaca atcacttctg gttggacctt tggtgcaggt   2700
gctgcattac aaataccatt tgctatgcaa atggcttata ggtttaatgg tattggagtt   2760
acacagaatg ttctctatga gaaccaaaaa ttgattgcca accaatttaa tagtgctatt   2820
ggcaaaattc aagactcact ttcttccaca gcaagtgcac ttggaaaact tcaagatgtg   2880
gtcaaccaaa atgcacaagc tttaaacacg cttgttaaac aacttagctc caattttggt   2940
```

```
gcaatttcaa gtgttttaaa tgatatcctt tcacgtcttg acaaagttga ggctgaagtg   3000

caaattgata ggttgatcac aggcagactt caaagtttgc agacatatgt gactcaacaa   3060

ttaattagag ctgcagaaat cagagcttct gctaatcttg ctgctactaa aatgtcagag   3120

tgtgtacttg gacaatcaaa aagagttgat ttttgtggaa agggctatca tcttatgtcc   3180

ttccctcagt cagcacctca tggtgtagtc ttcttgcatg tgacttatgt ccctgcacaa   3240

gaaaagaact tcacaactgc tcctgccatt tgtcatgatg gaaaagcaca ctttcctcgt   3300

gaaggtgtct ttgtttcaaa tggcacacac tggtttgtaa cacaaaggaa tttttatgaa   3360

ccacaaatca ttactacaga caacacattt gtgtctggta actgtgatgt tgtaatagga   3420

attgtcaaca acacagttta tgatcctttg caacctgaat tagactcatt caaggaggag   3480

ttagataaat attttaagaa tcatacatca ccagatgttg atttaggtga catctctggc   3540

attaatgctt cagttgtaaa cattcaaaaa gaaattgacc gcctcaatga ggttgccaag   3600

aatttaaatg aatctctcat cgatctccaa gaacttggaa agtatgagca gtatataaaa   3660

tggccatttt tctttatcat agggttaatc attggactat tcttggttct ccgagttggt   3720

atccatcttt gcattaaatt aaagcacacc aagaaaagac agatttatac agacatagag   3780

atgaaccgac ttggaaagta agaattccac gtgggatcc                          3819
```

<210> SEQ ID NO 27
<211> LENGTH: 3819
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
ctcgaggttt aaacgaattc cgccaccatg ttcgtgttcc tggtgctgct gcccctggtg     60

tccagccagt gcgtgaatct gaccacccgg acccaactgc ctcccgccta cacaaactct    120

ttcaccagag ggtttatta ccccgataag gtgttcagaa gctcagtgct tcattctacc    180

caggacctgt ttctgccttt tttcagcaac gtcacatggt tccacgccat ccacgtcagc    240

ggaaccaacg gcacgaagcg gttcgacaat cctgtgctgc cttttaacga cggcgtctac    300

tttgccagca cggaaaagag caacattatc cggggatgga tcttcggcac caccctggac    360

tctaaaaccc agagcctgtt gatcgtgaac aacgcaacca atgtggtgat caaggtctgc    420

gagttccaat tttgcaacga tcctttcctg ggcgtgtact accacaagaa caacaagtct    480

tggatggaat ctgagttccg cgtctacagc agcgcaaaca actgcacatt tgagtacgtg    540

tctcagcctt ttctgatgga cctggaagga aagcagggaa atttcaagaa cctgcgggag    600

ttcgtgttca agaacatcga cggctacttc aagatctaca gcaagcacac ccccatcaac    660

ctcgtgagag acctgcccca gggcttcagc gccctggaac ccctggtgga ccttcccata    720

ggaatcaaca tcacacggtt ccagacactg ctggccctgc atagaagcta cctgacccct    780

ggagattcta gcagcggctg gaccgccggc gctgccgctt actacgtcgg atacctgcag    840

cctagaacct tcctgttgaa gtacaacgag aacggcacca tcacagatgc cgtggactgc    900

gccctggacc ccctgagcga gacaaagtgc accctgaaga gcttcaccgt ggagaagggc    960

atctaccaga caagcaactt cagagtgcag cctaccgagt caatcgtgag attcccaaac   1020

atcaccaacc tttgtccttt cggcgaggta tttaacgcca cccggttcgc cagcgtgtac   1080

gcctggaata ggaagcggat cagcaactgc gtggccgatt acagcgtgct ctataacagc   1140
```

-continued

```
gccagtttta gcactttcaa gtgctacgga gtctctccta caaagctgaa cgacctgtgc   1200
ttcaccaacg tgtatgccga cagcttcgtc atccggggcg acgaggtgcg acagatcgct   1260
cctggccaga ccggcaagat agccgactac aactacaagc tgcctgacga cttcacaggc   1320
tgcgtgatcg cttggaacag caacaatctg gatagcaaag tgggcggcaa ctataactac   1380
ctgtacagac tgttccggaa gtccaatctc aagccgtttg agagagacat cagcaccgaa   1440
atctaccagg ctggatctac accctgcaac ggcgtcgaag gcttcaattg ttacttccct   1500
ctgcaatctt acggcttcca gcccaccaac ggcgtgggct accagcccta cagagtggtt   1560
gtgctgagct tcgagctgct gcacgcccca gctacagtgt gcggccctaa gaaatctaca   1620
aacctggtca agaacaagtg tgtgaacttc aacttcaatg gcctgacggg caccggcgtg   1680
ctgacagaga gcaacaagaa gttcctgcct ttccagcaat ttggcagaga catcgccgac   1740
accaccgacg ccgtgcgcga ccctcagacc ctggaaattc tggacatcac cccatgttct   1800
ttcggcggcg tgtccgtcat tacgccaggc accaatacca gcaaccaggt ggccgtgctt   1860
tatcaggatg tgaattgtac cgaagttcct gttgcaatcc acgccgacca actgaccccc   1920
acatggagag tgtactctac cggcagcaac gtgttccaaa cgagagccgg atgcctgatt   1980
ggagctgagc atgtgaacaa cagctacgag tgcgatattc caatcggagc cggcatctgc   2040
gcctcctacc aaacacaaac caactcccct cgtagagcga gaagcgtggc ctctcagagc   2100
atcatcgcct acaccatgag cctgggtgcc gaaaactccg tggcttactc caacaacagc   2160
atcgccatcc ctacaaattt caccatcagc gtgacaaccg agatcctgcc tgtgtccatg   2220
accaagacca gcgtggactg cacgatgtac atctgcggag atagcaccga gtgcagcaat   2280
ctgctactgc agtatggcag cttctgcacc caactgaaca gagcactgac cggcattgct   2340
gtggaacagg acaagaatac ccaggaggtg ttcgcccaag tgaagcagat ttacaagaca   2400
ccccctatca aggacttcgg aggcttcaac ttcagccaga tcctgcctga ccctagcaag   2460
ccaagcaaaa gatcctttat cgaagatctg ctgtttaaca aggtgacact ggccgatgcc   2520
ggctttatca agcagtacgg cgactgcctg ggagacatcg ccgccagaga cctgatctgt   2580
gctcagaaat ttaacgggct gaccgtgctg ccacctctgc tgacagatga gatgatcgct   2640
cagtacacca gcgccctgct ggccggcaca attacctccg gctggacctt cggagccgga   2700
gccgccctgc agatcccctt cgccatgcag atggcctacc ggttcaatgg catcggcgtc   2760
acccaaaacg tgctctatga gaaccagaag ctgatcgcaa accagttcaa ctccgccatc   2820
ggtaagatcc aggacagtct gagcagcacg gcgtctgccc tgggcaagct ccaggacgtg   2880
gtgaaccaga acgcccaggc ccttaacacc ctggtgaaac aactgagcag caacttcggt   2940
gccatttcca gcgttctcaa tgacatcctg agcagactgg ataaggtgga agccgaggtg   3000
cagatcgacc ggctgatcac cggacggctg cagagcctgc agacgtacgt gacccagcaa   3060
ttaatcagag ctgccgagat cagagccagc gccaatctgg ctgccaccaa aatgagcgaa   3120
tgtgtgctgg gccagtcaaa gagagtggat ttttgtggca aaggctacca cctgatgtcc   3180
ttccctcagt ctgcccctca cggcgtggtg ttcctccatg tgacctatgt gcctgctcag   3240
gagaagaact ttaccacagc ccctgctatc tgccacgacg gaaaggccca cttccccaga   3300
gagggcgtgt ttgtgtccaa tggcacacac tggttcgtga cccaaagaaa cttctacgag   3360
ccccagatca tcaccacaga caacaccttc gtgagcggca actgcgacgt ggtgatcggc   3420
atcgtgaaca acacagtgta cgaccccctg caacctgagc tggacagctt caaagaggaa   3480
ctggacaaat acttcaagaa tcacaccagc cctgatgtgg atctgggcga catcagcggc   3540
```

atcaacgcca gcgtcgtgaa catccagaag gaaatcgaca gactgaacga agtggccaag 3600
aacctgaacg agagcctcat cgatctgcag gagctgggca agtacgagca gtacatcaaa 3660
tggcctttct tcttcatcat cggcctgatt atcggcctgt tcctcgtgct gagagtgggc 3720
atccacctgt gcatcaagct taagcacaca aaaaagcggc agatttacac cgacatcgag 3780
atgaaccggc tgggcaaatg agaattccac gtgggatcc 3819

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
acaggtacgt taatagttaa tagcgt 26

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
atattgcagc agtacgcaca ca 22

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 30
acactagcca tccttactgc gcttcg 26

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ccacggagaa agacctcatc tg 22

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gggtcacctc atgttggaaa taaa 24

<210> SEQ ID NO 33
<211> LENGTH: 24

<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gttgccaaac cttatcagaa atga 24

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
ttctggcccg tggttctct 19

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
aaatggcggg ttctgtgc 18

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
aatatcctct gggtcttgta gatgg 25

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ggagtggctg agccatcgt 19

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
agctggttgt ctttgagaga catg 24

<210> SEQ ID NO 39
<211> LENGTH: 20
<212> TYPE: DNA

<213> ORGANISM: Artificial Sequence
<220> FEATURE:
<223> OTHER INFORMATION: Description of Artificial Sequence: Synthetic
primer

<400> SEQUENCE: 39
ggccatccag aggagcatag 20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
tttctccatg ctgctgttga a 21

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
actgccgcat cctcttcct 19

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
tcgttgccaa tggtgatgac 20

<210> SEQ ID NO 43
<211> LENGTH: 4
<212> TYPE: PRT
<213> ORGANISM: Severe acute respiratory syndrome coronavirus 2

<400> SEQUENCE: 43

Arg Arg Ala Arg
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Gly Ser Ala Ser
1

VACCINE COMPOSITIONS FOR THE TREATMENT OF CORONAVIRUS

CROSS REFERENCE TO RELATED APPLICATIONS

This application claims the benefit of U.S. Provisional Application No. 63/002,237, filed Mar. 30, 2020, and of U.S. Provisional Application No. 63/070,150, filed Aug. 25, 2020, the contents of both of which are hereby incorporated herein in their entireties.

SEQUENCE LISTING

The instant application contains a Sequence Listing which has been submitted electronically in ASCII format and is hereby incorporated by reference in its entirety. Said ASCII copy, created on Apr. 28, 2021, is named 2007801-0140_SL.txt and is 184,699 bytes in size.

FIELD OF THE INVENTION

This invention is in the field of vaccines, in particular virus like particle vaccines for coronavirus.

BACKGROUND

Coronaviruses are spherical, enveloped viruses, ranging from 160-180 nm in diameter and containing a positive-stranded RNA genome. With their genome of approximately 30,000 bases, they are considered the largest of the known RNA viruses. Like influenza viruses they have the ability to genetically recombine with other members of the coronavirus family. Coronaviruses fall into four major genera. Coronaviruses are believed to be the causative agents of several severe diseases in many animals, for example, infectious bronchitis virus, feline infectious peritonitis virus and transmissible gastroenteritis virus. Coronaviruses also cause a range of illnesses in humans from the common cold to severe respiratory infections. Four human coronaviruses, HCoV-OC43, HCoV-HKU1 (betacoronaviruses), and HCoV-NL63, HCoV-229E (alphacoronaviruses), contribute to 15%-30% of common colds (Fung et al (2019) Annu. Rev. Microbiol. 73:2-529-557). In recent years, beta-coronaviruses have been responsible for three significant outbreaks of disease in humans.

In the early 2000s, a beta coronavirus known as SARS-CoV caused an outbreak of respiratory disease referred to as severe acute respiratory syndrome (SARS). The main symptoms included fever, dry cough, headache, shortness of breath and difficulty of breathing. Many of those infected developed viral pneumonia resulting in infection of the lower respiratory tract. SARS is highly contagious, and is spread by droplets caused by coughing or sneezing or through other methods such as fecal contamination. SARS was fatal in around 9.14% of all cases. The global outbreak of SARS was contained in July 2003 and there have been no reported cases since 2004 (Peeri et al Int. J. Epi, Feb. 10, 2020).

In 2012, another novel coronavirus emerged in Saudi Arabia which is now known as Middle East Respiratory Syndrome coronavirus (MERS-CoV). MERS-CoV is also beta coronavirus. Subsequent cases of MERS-CoV infection were reported and the outbreak spread to 27 countries in the Middle East, Europe, Asia and North America. Infection with MERS-CoV presented as a severe acute respiratory illness with symptoms of fever, cough, and shortness of breath. About 34% of reported cases of MERS-CoV infection resulted in death. Only a small number of reported cases involved subjects with mild respiratory illness.

In late 2019, a respiratory infection appeared in Wuhan, China which was quickly identified as caused by a novel coronavirus strain called SARS-CoV-2. The infection, known as COVID-19 is highly infectious and causes severe pneumonia, particularly in elderly patients. Mortality rates vary significantly by country, with estimates ranging from 13.7% in Italy to 1.9% in Japan. As of March 2021, the fatality rate in the United States was approximately 1.8% (Johns Hopkins Coronavirus Research Centre, Update as of Mar. 30, 2021). COVID-19 quickly spread throughout the world resulting in a significant threat to human health and a massive slowdown in economic activity. As of Feb. 1, 2021, more than 100 million people had contracted COVID-19, and over 2 million had died.

In late 2020, several vaccines against COVID-19 were approved for emergency use. These vaccines target a protein on the surface of SARS-CoV-2 known as the spike protein and utilized novel platforms, sometimes for the first time for human use. These vaccines were shown to be highly effective in clinical trials, but distribution has been slow in many parts of the world due to manufacturing challenges and, in some cases, the requirement for storage at ultra-low temperatures. Furthermore, while several new vaccines have proven to be safe, some have been associated with rare but deadly side effects that have restricted their use in certain countries.

During the second half of 2020, variants of SARS-CoV-2 emerged which cause COVID-19 disease. Three variants rapidly became dominant in the countries where they emerged, B.1.1.7 (also known as the UK variant), 501Y.V2 (also known as the South Africa variant), and P.1 (as known as the Brazil variant). These variants have proven to be highly infectious due to increased binding affinity of the viral receptor-binding domain to the receptor known as angiotensin-converting enzyme 2 (ACE2). The rapid spread of the new variants, and the possible emergence of new variants has raised significant concerns regarding reinfection and the effectiveness of the recently approved vaccines, all of which were developed against the original strain of SARS-CoV-2.

As a result, there is an urgent need to develop new vaccines which induce strong immunity against SARS-CoV-2 while being safe and easy to store and distribute. Furthermore, there is an urgent need to ensure that vaccines against SARS-CoV-2 provide broad immunity so as to protect patients against mutated forms of the virus.

Accordingly, a need exists for a vaccine against human coronaviruses which provides broad immunity against coronavirus antigens.

SUMMARY

The present disclosure provides methods and compositions useful for prophylaxis of infection cause by human coronaviruses. More particularly, the present disclosure provides methods for production of, and compositions comprising, virus like particles (VLPs) expressing antigens from human coronaviruses which are useful for prevention, treatment, and/or diagnosis of infections caused by coronaviruses.

The present disclosure provides virus-like particles which comprise one or more Moloney Murine leukemia virus (MMLV) core proteins and are surrounded by a lipid bilayer membrane. The VLPs include one or more envelope polypeptides from human coronaviruses (e.g., one or more coronavirus polypeptide epitopes) that play a role in induction of virus-neutralizing antibodies.

In some embodiments, the present disclosure provides VLPs having an envelope that comprises a wild type human coronavirus envelope glycoprotein. In some embodiments, the polypeptide is from SARS-CoV. In some embodiments, the polypeptide is from MERS-CoV. In some embodiments, the polypeptide is from SARS-CoV-2. In some embodiments, the VLPs include polypeptides from more than one of SARS-CoV, MERS-CoV and SARS-CoV-2. In some embodiments, the VLPs include polypeptides from all three of SARS-CoV, MERS-CoV and SARS-CoV-2.

In some embodiments, the present disclosure provides VLPs having an envelope that comprises a modified human coronavirus envelope glycoprotein. In an embodiment, the present disclosure encompasses production of VLPs having envelopes that include a coronavirus polypeptide in a premature conformation. In a specific embodiment, the modified envelope glycoprotein lacks a furin cleavage site. In some embodiments, the polypeptide lacking a furin cleavage site is from SARS-CoV. In some embodiments, the polypeptide lacking a furin cleavage site is from MERS-CoV. In some embodiments, the polypeptide lacking a furin cleavage site is from SARS-CoV-2. In some embodiments, the VLPs include polypeptides from more than one of SARS-CoV, MERS-CoV and SARS-CoV-2, wherein the polypeptides lack a furin cleavage site. In some embodiments, the VLPs include polypeptides from all three of SARS-CoV, MERS-CoV and SARS-CoV-2, wherein the polypeptides lack a furin cleavage site.

In another embodiment, the present disclosure encompasses production of VLPs having envelopes that include a coronavirus polypeptide having a modified amino acid sequence. In a specific embodiment, the modified envelope glycoprotein has a lysine and valine residue substituted for proline residues. In some embodiments, the polypeptide having a proline substitution is from SARS-CoV. In some embodiments, the polypeptide having a proline substitution is from MERS-CoV. In some embodiments, the polypeptide having a proline substitution is from SARS-CoV-2. In some embodiments, the VLPs include polypeptides from more than one of SARS-CoV, MERS-CoV and SARS-CoV-2, wherein the polypeptides have a proline substitution. In some embodiments, the VLPs include polypeptides from all three of SARS-CoV, MERS-CoV and SARS-CoV-2, wherein the polypeptides have a proline substitution.

In another embodiment, the present disclosure encompasses production of VLPs having envelopes that include a coronavirus polypeptide having a modified amino acid sequence and a premature conformation. In a specific embodiment, the modified envelope glycoprotein has a lysine and valine residue substituted for proline residues and lack a furin cleavage site. In some embodiments, the polypeptide having a proline substitution and lacking a furin cleavage site is from SARS-CoV. In some embodiments, the polypeptide having a proline substitution and lacking a furin cleavage site is from MERS-CoV. In some embodiments, the polypeptide having a proline substitution and lacking a furin cleavage site is from SARS-CoV-2. In some embodiments, the VLPs include polypeptides from more than one of SARS-CoV, MERS-CoV and SARS-CoV-2, wherein the polypeptides have a proline substitution and lack a furin cleavage site. In some embodiments, the VLPs include polypeptides from all three of SARS-CoV, MERS-CoV and SARS-CoV-2, wherein the polypeptides have a proline substitution and lack a furin cleavage site.

In a further embodiment, the modified envelope glycoprotein has been modified such that the transmembrane domain is replaced with the transmembrane domain of another virus. In a particularly preferred embodiment, the VLP has a modified envelope glycoprotein comprising an isolated coronavirus S protein, the transmembrane domain and cytoplasmic tail of which protein have been replaced with the transmembrane domain and cytoplasmic tail from vesicular stomatitis virus (VSV). In some embodiments, the polypeptide having a transmembrane domain and cytoplasmic tail from VSV is from SARS-CoV. In some embodiments, the polypeptide having a transmembrane domain and cytoplasmic tail from VSV is from MERS-CoV. In some embodiments, the polypeptide having a transmembrane domain and cytoplasmic tail from VSV is from SARS-CoV-2. In some embodiments, the VLPs include polypeptides from more than one of SARS-CoV, MERS-CoV and SARS-CoV-2, wherein the polypeptides have a transmembrane domain and cytoplasmic tail from VSV. In some embodiments, the VLPs include polypeptides from all three of SARS-CoV, MERS-CoV and SARS-CoV-2, wherein the polypeptides have a transmembrane domain and cytoplasmic tail from VSV. In some embodiments, the VLPS include one or more polypeptides from SARS-CoV, MERS-CoV and SARS-CoV-2, one or more of which have been modified as described herein and which have a transmembrane domain and cytoplasmic tail from VSV.

In a preferred embodiment, the present disclosure encompasses production of a VLP having an envelope that includes a SAR-CoV-2 spike polypeptide having a modified amino acid sequence and a premature conformation. The modified envelope glycoprotein has a lysine and valine residue substituted for proline residues and it lacks a furin cleavage site. Furthermore, the modified spike glycoprotein has been further modified such that the transmembrane domain and cytoplasmic tail have been replaced with the transmembrane domain and cytoplasmic tail from vesicular stomatitis virus (VSV).

The present disclosure further provides bivalent and trivalent VLPs comprising one or more modified human coronavirus envelope proteins and one or more wild type human coronavirus proteins.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

FIG. 3 discloses "RRAR" as SEQ ID NO: 43 and "GSAS" as SEQ ID NO: 44.

LISTING OF SEQUENCES

Figures 1, 2:
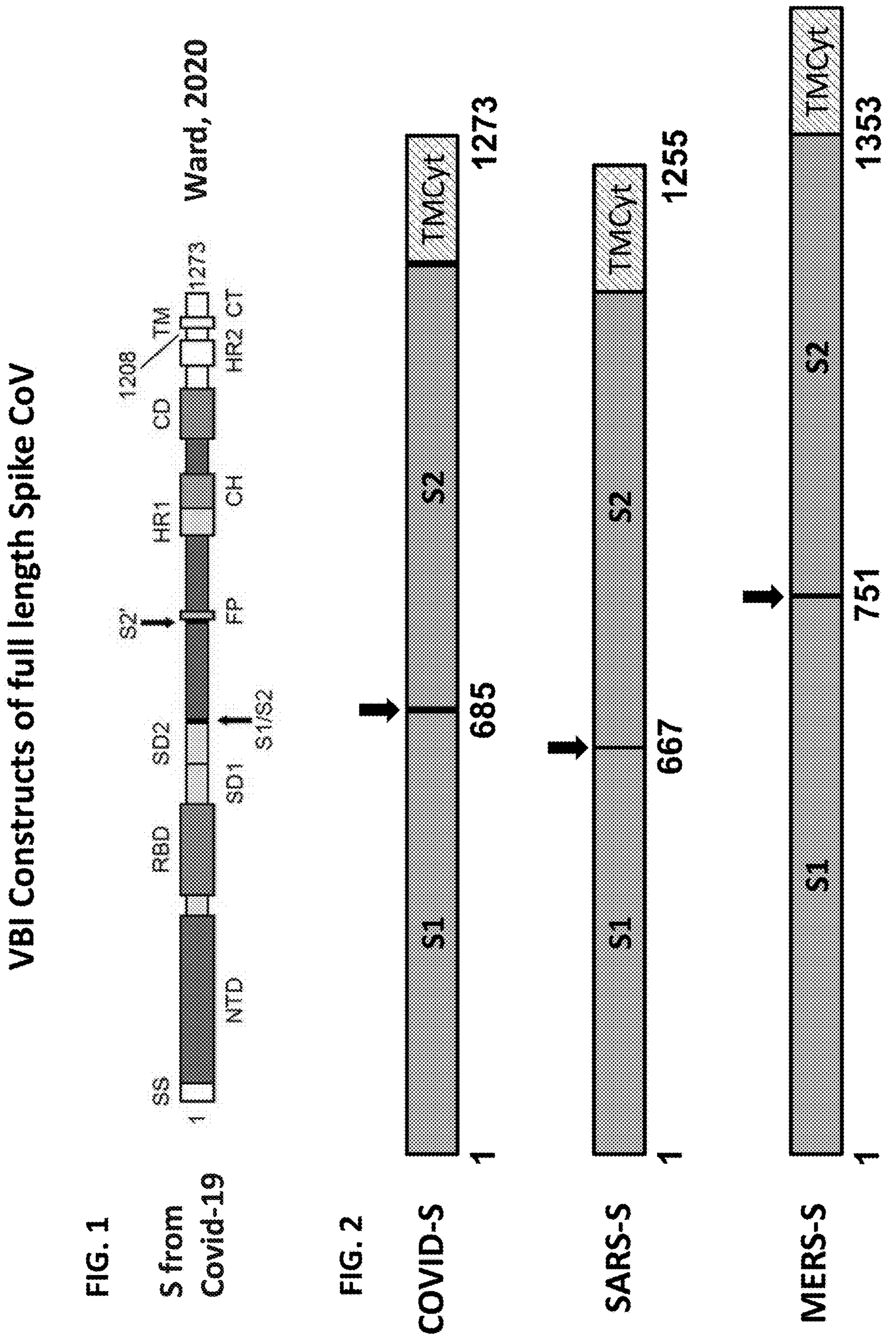
FIG. 1 is a diagram illustrating the structure of the SARS-CoV-2 envelope.
FIG. 2 the S1/S2 domains from SARS-CoV, SARS CoV-2 and MERS-CoV.
Figure 3:
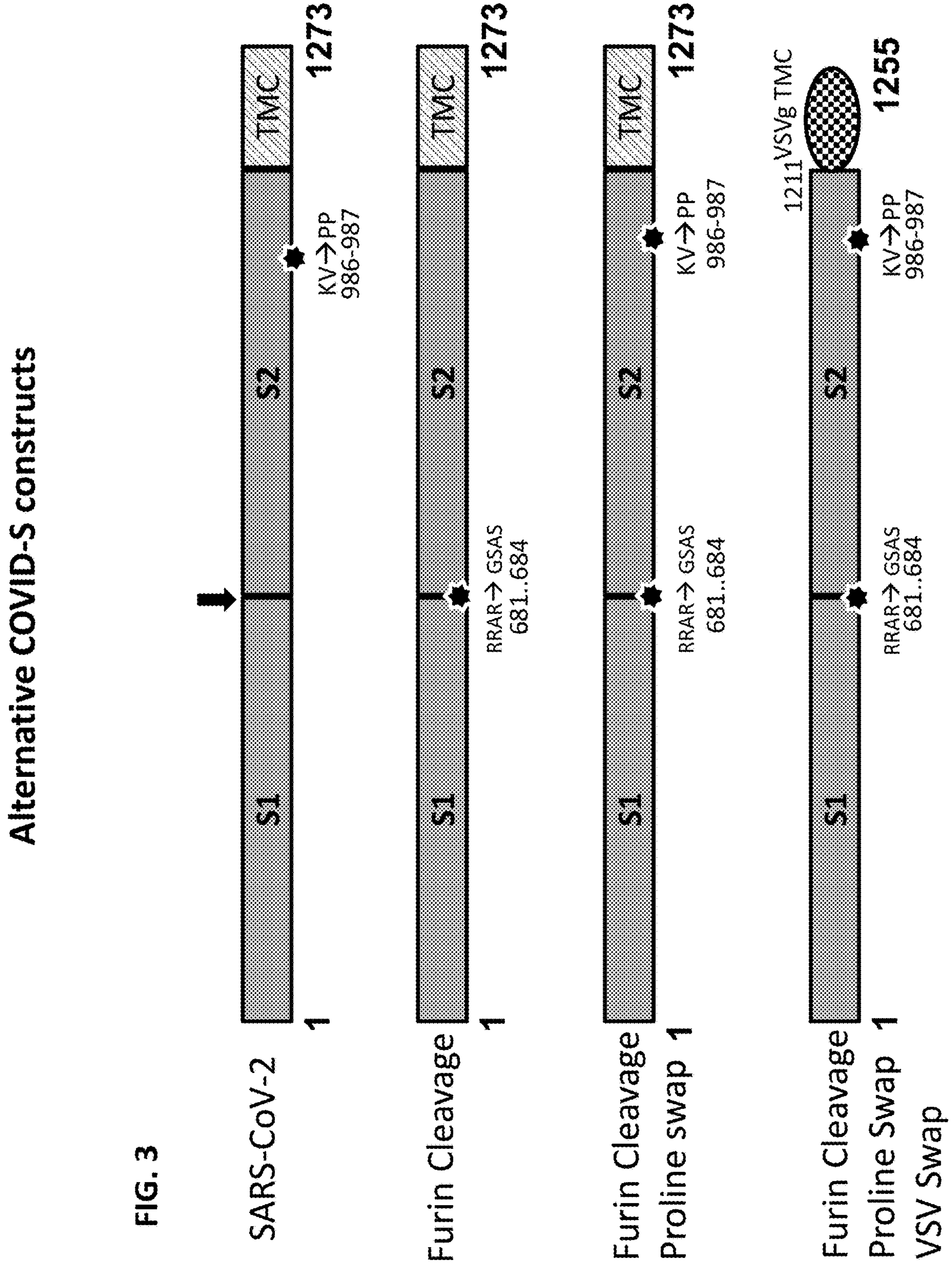
FIG. 3 is a diagram illustrating exemplary alternative COVID-S constructs.

The following is a list of sequences referred to herein:

SEQ ID NO: 1 is an MMLV-Gag Amino Acid Sequence

MGQTVTTPLSLTLGHWKDVERIAHNQSVDVKKRRWVTFCSAEWPTFNVGWPRDGTFNR
DLITQVKIKVFSPGPHGHPDQVPYIVTWEALAFDPPPWVKPFVHPKPPPPLPPSAPSLPLEP
PRSTPPRSSLYPALTPSLGAKPKPQVLSDSGGPLIDLLTEDPPPYRDPRPPPSDRDGNGGEA
TPAGEAPDPSPMASRLRGRREPPVADSTTSQAFPLRAGGNGQLQYWPFSSSDLYNWKNN
NPSFSEDPGKLTALIESVLITHQPTWDDCQQLLGTLLTGEEKQRVLLEARKAVRGDDGRP
TQLPNEVDAAFPLERPDWDYTTQAGRNHLVHYRQLLLAGLQNAGRSPTNLAKVKGITQ
GPNESPSAFLERLKEAYRRYTPYDPEDPGQETNVSMSFIWQSAPDIGRKLERLEDLKNKTL
GDLVREAEKIENKRETPEERREERIRRETEEKEERRRTEDEQKEKERDRRRHREMSKLLAT
VVSGQKQDRQGGERRRSQLDRDQCAYCKEKGHWAKDCPKKPRGPRGPRPQTSLLTLDD

SEQ ID NO: 2 is MMLV-Gag Nucleotide Sequence

ATGGGCCAGACTGTTACCACTCCCTTAAGTTTGACCTTAGGTCACTGGAAAGATGTCG
AGCGGATCGCTCACAACCAGTCGGTAGATGTCAAGAAGAGACGTTGGGTTACCTTCT
GCTCTGCAGAATGGCCAACCTTTAACGTCGGATGGCCGCGAGACGGCACCTTTAACC
GAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGG
GTCAAGCCCTTTGTACACCCTAAGCCTCCGCCTCCTCTTCCTCCATCCGCCCCGTCTCT
CCCCCTTGAACCTCCTCGTTCGACCCCGCCTCGATCCTCCCTTTATCCAGCCCTCACTC
CTTCTCTAGGCGCCAAACCTAAACCTCAAGTTCTTTCTGACAGTGGGGGGCCGCTCAT
CGACCTACTTACAGAAGACCCCCCGCCTTATAGGGACCCAAGACCACCCCCTTCCGA
CAGGGACGGAAATGGTGGAGAAGCGACCCCTGCGGGAGAGGCACCGGACCCCTCCC
CAATGGCATCTCGCCTACGTGGGAGACGGGAGCCCCCTGTGGCCGACTCCACTACCT
CGCAGGCATTCCCCCTCCGCGCAGGAGGAAACGGACAGCTTCAATACTGGCCGTTCT
CCTCTTCTGACCTTTACAACTGGAAAAATAATAACCCTTCTTTTTCTGAAGATCCAGG
TAAACTGACAGCTCTGATCGAGTCTGTTCTCATCACCCATCAGCCCACCTGGGACGAC
TGTCAGCAGCTGTTGGGGACTCTGCTGACCGGAGAAGAAAAACAACGGGTGCTCTTA
GAGGCTAGAAAGGCGGTGCGGGGCGATGATGGGCGCCCCACTCAACTGCCCAATGA
AGTCGATGCCGCTTTTCCCCTCGAGCGCCCAGACTGGGATTACACCACCCAGGCAGG
TAGGAACCACCTAGTCCACTATCGCCAGTTGCTCCTAGCGGGTCTCCAAAACGCGGG
CAGAAGCCCCACCAATTTGGCCAAGGTAAAAGGAATAACACAAGGGCCCAATGAGT
CTCCCTCGGCCTTCCTAGAGAGACTTAAGGAAGCCTATCGCAGGTACACTCCTTATGA
CCCTGAGGACCCAGGGCAAGAAACTAATGTGTCTATGTCTTTCATTTGGCAGTCTGCC
CCAGACATTGGGAGAAAGTTAGAGAGGTTAGAAGATTTAAAAAACAAGACGCTTGG
AGATTTGGTTAGAGAGGCAGAAAAGATCTTTAATAAACGAGAAACCCCGGAAGAAA
GAGAGGAACGTATCAGGAGAGAAACAGAGGAAAAAGAAGAACGCCGTAGGACAGA
GGATGAGCAGAAAGAGAAAGAAAGAGATCGTAGGAGACATAGAGAGATGAGCAAG
CTATTGGCCACTGTCGTTAGTGGACAGAAACAGGATAGACAGGGAGGAGAACGAAG
GAGGTCCCAACTCGATCGCGACCAGTGTGCCTACTGCAAAGAAAAGGGGCACTGGGC
TAAAGATTGTCCCAAGAAACCACGAGGACCTCGGGGACCAAGACCCCAGACCTCCCT
CCTGACCCTAGATGAC

SEQ ID NO: 3 is a Codon Optimized MMLV-Gag Nucleotide Sequence

ATGGGACAGACCGTCACAACACCCCTGAGCCTGACCCTGGGACATTGGAAAGACGTG

GAGAGGATCGCACATAACCAGAGCGTGGACGTGAAGAAACGGAGATGGGTCACATT

CTGCAGTGCTGAGTGGCCAACTTTTAATGTGGGATGGCCCCGAGACGGCACTTTCAA

CAGGGATCTGATCACCCAGGTGAAGATCAAGGTCTTTAGCCCAGGACCTCACGGACA

TCCAGACCAGGTGCCTTATATCGTCACCTGGGAGGCACTGGCCTTCGATCCCCCTCCA

TGGGTGAAGCCATTTGTCCACCCAAAACCACCTCCACCACTGCCTCCAAGTGCCCCTT

CACTGCCACTGGAACCACCCCGGAGCACACCACCCCGCAGCTCCCTGTATCCTGCTCT

GACTCCATCTCTGGGCGCAAAGCCAAAACCACAGGTGCTGAGCGACTCCGGAGGACC

ACTGATTGACCTGCTGACAGAGGACCCCCCACCATACCGAGATCCTCGGCCTCCACC

AAGCGACCGCGATGGAAATGGAGGAGAGGCTACTCCTGCCGGCGAAGCCCCTGACC

CATCTCCAATGGCTAGTAGGCTGCGCGGCAGGCGCGAGCCTCCAGTGGCAGATAGCA

CCACATCCCAGGCCTTCCCTCTGAGGGCTGGGGGAAATGGGCAGCTCCAGTATTGGC

CATTTTCTAGTTCAGACCTGTACAACTGGAAGAACAATAACCCCTCTTTCAGTGAGGA

CCCCGGCAAACTGACCGCCCTGATCGAATCCGTGCTGATTACCCATCAGCCCACATG

GGACGATTGTCAGCAGCTCCTGGGCACCCTGCTGACCGGAGAGGAAAAGCAGCGCGT

GCTGCTGGAGGCTCGCAAAGCAGTCCGAGGGGACGATGGACGGCCCACACAGCTCCC

TAATGAGGTGGACGCCGCTTTTCCACTGGAAAGACCCGACTGGGATTATACTACCCA

GGCAGGGAGAAACCACCTGGTCCATTACAGGCAGCTCCTGCTGGCAGGCCTGCAGAA

TGCCGGGAGATCCCCCACCAACCTGGCCAAGGTGAAAGGCATCACACAGGGGCCTAA

TGAGTCACCAAGCGCCTTTCTGGAGAGGCTGAAGGAAGCTTACCGACGGTATACCCC

ATACGACCCTGAGGACCCCGGACAGGAAACAAACGTCTCCATGTCTTTCATCTGGCA

GTCTGCCCCAGACATTGGGCGGAAGCTGGAGAGACTGGAAGACCTGAAGAACAAGA

CCCTGGGCGACCTGGTGCGGGAGGCTGAAAAGATCTTCAACAAACGGGAGACCCCCG

AGGAAAGAGAGGAAAGGATTAGAAGGGAAACTGAGGAAAAGGAGGAACGCCGACG

GACCGAGGACGAACAGAAGGAGAAAGAACGAGATCGGCGGCGGCACCGGGAGATG

TCAAAGCTGCTGGCCACCGTGGTCAGCGGACAGAAACAGGACAGACAGGGAGGAGA

GCGACGGAGAAGCCAGCTCGACAGGGATCAGTGCGCATACTGTAAGGAAAAAGGCC

ATTGGGCCAAGGATTGCCCCAAAAAGCCAAGAGGACCAAGAGGACCAAGACCACAG

ACATCACTGCTGACCCTGGACGAC

SEQ ID NO: 4 is a SARS-CoV-2 Spike Glycoprotein, Amino Acid Sequence

MFVFLVLLPLVSSQCVNLTTRTQLPPAYTNSFTRGVYYPDKVFRSSVLHSTQDLFLPFFSN

VTWFHAIHVSGTNGTKRFDNPVLPFNDGVYFASTEKSNIIRGWIFGTTLDSKTQSLLIVNN

ATNVVIKVCEFQFCNDPFLGVYYHKNNKSWMESEFRVYSSANNCTFEYVSQPFLMDLEG

KQGNFKNLREFVFKNIDGYFKIYSKHTPINLVRDLPQGFSALEPLVDLPIGINITRFQTLLAL

HRSYLTPGDSSSGWTAGAAAYYVGYLQPRTFLLKYNENGTITDAVDCALDPLSETKCTL

KSFTVEKGIYQTSNFRVQPTESIVRFPNITNLCPFGEVFNATRFASVYAWNRKRISNCVAD

YSVLYNSASFSTFKCYGVSPTKLNDLCFTNVYADSFVIRGDEVRQIAPGQTGKIADYNYK

-continued

LPDDFTGCVIAWNSNNLDSKVGGNYNYLYRLFRKSNLKPFERDISTEIYQAGSTPCNGVE

GFNCYFPLQSYGFQPTNGVGYQPYRVVVLSFELLHAPATVCGPKKSTKLVKNKCVNFNF

NGLTGTGVLTESNKKFLPFQQFGRDIADTTDAVRDPQTLEILDITPCSFGGVSVITPGTNTS

NQVAVLYQDVNCTEVPVAIHADQLTPTWRVYSTGSNVFQTRAGCLIGAEHVNNSYECDI

PIGAGICASYQTOTNSPRRARSVASOSIIAYTMSLGAENSVAYSNNSIAIPTNFTISVTTEILP

VSMTKTSVDCTMYICGDSTECSNLLLQYGSFCTOLNRALTGIAVEQDKNTOEVFAOVKQI

YKTPPIKDFGGFNFSQILPDPSKPSKRSFIEDLLFNKVTLADAGFIKQYGDCLGDIAARDLIC

AQKFNGLTVLPPLLTDEMIAQYTSALLAGTITSGWTFGAGAALOIPFAMQMAYRFNGIGV

TQNVLYENQKLIANQFNSAIGKIQDSLSSTASALGKLQDVVNQNAQALNTLVKQLSSNFG

AISSVLNDILSRLDKVEAEVQIDRLITGRLQSLQTYVTQQLIRAAEIRASANLAATKMSEC

VLGQSKRVDFCGKGYHLMSFPQSAPHGVVFLHVTYVPAQEKNFTTAPAICHDGKAHFPR

EGVFVSNGTHWFVTQRNFYEPQIITTDNTFVSGNCDVVIGIVNNTVYDPLQPELDSFKEEL

DKYFKNHTSPDVDLGDISGINASVVNIQKEIDRLNEVAKNLNESLIDLQELGKYEQYIKWP

WYIWLGFIAGLIAIVMVTIMLCCMTSCCSCLKGCCSCGSCCKFDEDDSEPVLKGVKLHYT

SEQ ID NO: 5 is a SARS-CoV-2 Spike Glycoprotein, Nucleotide Sequence (Wuhan-Hu-1: Genbank Ref: MN908947)

ATGTTTGTTTTTCTTGTTTTATTGCCACTAGTCTCTAGTCAGTGTGTTAATCTTACAAC

CAGAACTCAATTACCCCCTGCATACACTAATTCTTTCACACGTGGTGTTTATTACCCT

GACAAAGTTTTCAGATCCTCAGTTTTACATTCAACTCAGGACTTGTTCTTACCTTTCTT

TTCCAATGTTACTTGGTTCCATGCTATACATGTCTCTGGGACCAATGGTACTAAGAGG

TTTGATAACCCTGTCCTACCATTTAATGATGGTGTTTATTTTGCTTCCACTGAGAAGTC

TAACATAATAAGAGGCTGGATTTTTGGTACTACTTTAGATTCGAAGACCCAGTCCCTA

CTTATTGTTAATAACGCTACTAATGTTGTTATTAAAGTCTGTGAATTTCAATTTTGTAA

TGATCCATTTTTGGGTGTTTATTACCACAAAAACAACAAAAGTTGGATGGAAAGTGA

GTTCAGAGTTTATTCTAGTGCGAATAATTGCACTTTTGAATATGTCTCTCAGCCTTTTC

TTATGGACCTTGAAGGAAAACAGGGTAATTTCAAAAATCTTAGGGAATTTGTGTTTA

AGAATATTGATGGTTATTTTAAAATATATTCTAAGCACACGCCTATTAATTTAGTGCG

TGATCTCCCTCAGGGTTTTTCGGCTTTAGAACCATTGGTAGATTTGCCAATAGGTATT

AACATCACTAGGTTTCAAACTTTACTTGCTTTACATAGAAGTTATTTGACTCCTGGTG

ATTCTTCTTCAGGTTGGACAGCTGGTGCTGCAGCTTATTATGTGGGTTATCTTCAACCT

AGGACTTTTCTATTAAAATATAATGAAAATGGAACCATTACAGATGCTGTAGACTGT

GCACTTGACCCTCTCTCAGAAACAAAGTGTACGTTGAAATCCTTCACTGTAGAAAAA

GGAATCTATCAAACTTCTAACTTTAGAGTCCAACCAACAGAATCTATTGTTAGATTTC

CTAATATTACAAACTTGTGCCCTTTTGGTGAAGTTTTTAACGCCACCAGATTTGCATCT

GTTTATGCTTGGAACAGGAAGAGAATCAGCAACTGTGTTGCTGATTATTCTGTCCTAT

ATAATTCCGCATCATTTTCCACTTTTAAGTGTTATGGAGTGTCTCCTACTAAATTAAAT

GATCTCTGCTTTACTAATGTCTATGCAGATTCATTTGTAATTAGAGGTGATGAAGTCA

GACAAATCGCTCCAGGGCAAACTGGAAAGATTGCTGATTATAATTATAAATTACCAG

ATGATTTTACAGGCTGCGTTATAGCTTGGAATTCTAACAATCTTGATTCTAAGGTTGG

-continued

TGGTAATTATAATTACCTGTATAGATTGTTTAGGAAGTCTAATCTCAAACCTTTTGAG

AGAGATATTTCAACTGAAATCTATCAGGCCGGTAGCACACCTTGTAATGGTGTTGAA

GGTTTTAATTGTTACTTTCCTTTACAATCATATGGTTTCCAACCCACTAATGGTGTTGG

TTACCAACCATACAGAGTAGTAGTACTTTCTTTTGAACTTCTACATGCACCAGCAACT

GTTTGTGGACCTAAAAAGTCTACTAATTTGGTTAAAAACAAATGTGTCAATTTCAACT

TCAATGGTTTAACAGGCACAGGTGTTCTTACTGAGTCTAACAAAAAGTTTCTGCCTTT

CCAACAATTTGGCAGAGACATTGCTGACACTACTGATGCTGTCCGTGATCCACAGAC

ACTTGAGATTCTTGACATTACACCATGTTCTTTTGGTGGTGTCAGTGTTATAACACCA

GGAACAAATACTTCTAACCAGGTTGCTGTTCTTTATCAGGATGTTAACTGCACAGAAG

TCCCTGTTGCTATTCATGCAGATCAACTTACTCCTACTTGGCGTGTTTATTCTACAGGT

TCTAATGTTTTTCAAACACGTGCAGGCTGTTTAATAGGGGCTGAACATGTCAACAACT

CATATGAGTGTGACATACCCATTGGTGCAGGTATATGCGCTAGTTATCAGACTCAGAC

TAATTCTCCTCGGCGGGCACGTAGTGTAGCTAGTCAATCCATCATTGCCTACACTATG

TCACTTGGTGCAGAAAATTCAGTTGCTTACTCTAATAACTCTATTGCCATACCCACAA

ATTTTACTATTAGTGTTACCACAGAAATTCTACCAGTGTCTATGACCAAGACATCAGT

AGATTGTACAATGTACATTTGTGGTGATTCAACTGAATGCAGCAATCTTTTGTTGCAA

TATGGCAGTTTTTGTACACAATTAAACCGTGCTTTAACTGGAATAGCTGTTGAACAAG

ACAAAAACACCCAAGAAGTTTTTGCACAAGTCAAACAAATTTACAAAACACCACCAA

TTAAAGATTTTGGTGGTTTTAATTTTTCACAAATATTACCAGATCCATCAAAACCAAG

CAAGAGGTCATTTATTGAAGATCTACTTTTCAACAAAGTGACACTTGCAGATGCTGGC

TTCATCAAACAATATGGTGATTGCCTTGGTGATATTGCTGCTAGAGACCTCATTTGTG

CACAAAAGTTTAACGGCCTTACTGTTTTGCCACCTTTGCTCACAGATGAAATGATTGC

TCAATACACTTCTGCACTGTTAGCGGGTACAATCACTTCTGGTTGGACCTTTGGTGCA

GGTGCTGCATTACAAATACCATTTGCTATGCAAATGGCTTATAGGTTTAATGGTATTG

GAGTTACACAGAATGTTCTCTATGAGAACCAAAAATTGATTGCCAACCAATTTAATA

GTGCTATTGGCAAAATTCAAGACTCACTTTCTTCCACAGCAAGTGCACTTGGAAAACT

TCAAGATGTGGTCAACCAAAATGCACAAGCTTTAAACACGCTTGTTAAACAACTTAG

CTCCAATTTTGGTGCAATTTCAAGTGTTTTAAATGATATCCTTTCACGTCTTGACAAAG

TTGAGGCTGAAGTGCAAATTGATAGGTTGATCACAGGCAGACTTCAAAGTTTGCAGA

CATATGTGACTCAACAATTAATTAGAGCTGCAGAAATCAGAGCTTCTGCTAATCTTGC

TGCTACTAAAATGTCAGAGTGTGTACTTGGACAATCAAAAAGAGTTGATTTTTGTGGA

AAGGGCTATCATCTTATGTCCTTCCCTCAGTCAGCACCTCATGGTGTAGTCTTCTTGCA

TGTGACTTATGTCCCTGCACAAGAAAAGAACTTCACAACTGCTCCTGCCATTTGTCAT

GATGGAAAAGCACACTTTCCTCGTGAAGGTGTCTTTGTTTCAAATGGCACACACTGGT

TTGTAACACAAAGGAATTTTTATGAACCACAAATCATTACTACAGACAACACATTTGT

GTCTGGTAACTGTGATGTTGTAATAGGAATTGTCAACAACACAGTTTATGATCCTTTG

CAACCTGAATTAGACTCATTCAAGGAGGAGTTAGATAAATATTTTAAGAATCATACA

TCACCAGATGTTGATTTAGGTGACATCTCTGGCATTAATGCTTCAGTTGTAAACATTC

AAAAAGAAATTGACCGCCTCAATGAGGTTGCCAAGAATTTAAATGAATCTCTCATCG

ATCTCCAAGAACTTGGAAAGTATGAGCAGTATATAAAATGGCCATGGTACATTTGGC

TAGGTTTTATAGCTGGCTTGATTGCCATAGTAATGGTGACAATTATGCTTTGCTGTAT

-continued

GACCAGTTGCTGTAGTTGTCTCAAGGGCTGTTGTTCTTGTGGATCCTGCTGCAAATTT

GATGAAGACGACTCTGAGCCAGTGCTCAAAGGAGTCAAATTACATTACACATAA

SEQ ID NO: 6 is a SARS-CoV-2 Spike Glycoprotein, Nucleotide Sequence, Codon Optimized For Expression In Human Cell

ATGTTCGTGTTTCTGGTGCTGCTGCCTCTGGTGAGCTCCCAGTGCGTGAACCTGACCA

CAAGGACCCAGCTCCCCCCTGCCTATACCAATTCCTTCACACGGGGCGTGTACTATCC

CGACAAGGTGTTTAGATCTAGCGTGCTGCACTCCACACAGGATCTGTTTCTGCCTTTC

TTTTCTAACGTGACCTGGTTCCACGCCATCCATGTGAGCGGCACCAATGGCACAAAGC

GGTTCGACAATCCAGTGCTGCCCTTTAACGATGGCGTGTACTTCGCCTCCACCGAGAA

GTCTAACATCATCAGAGGCTGGATCTTTGGCACCACACTGGACAGCAAGACACAGTC

CCTGCTGATCGTGAACAATGCCACCAACGTGGTCATCAAGGTGTGCGAGTTCCAGTTT

TGTAATGATCCATTCCTGGGCGTGTACTATCACAAGAACAATAAGTCTTGGATGGAG

AGCGAGTTTCGCGTGTATTCCTCTGCCAACAATTGCACATTTGAGTACGTGTCCCAGC

CCTTCCTGATGGACCTGGAGGGCAAGCAGGGCAATTTCAAGAACCTGAGGGAGTTCG

TGTTTAAGAATATCGATGGCTACTTCAAGATCTACTCCAAGCACACCCCAATCAACCT

GGTGCGCGACCTGCCACAGGGCTTCTCTGCCCTGGAGCCACTGGTGGATCTGCCCATC

GGCATCAACATCACCCGGTTTCAGACACTGCTGGCCCTGCACAGAAGCTACCTGACA

CCAGGCGACAGCTCCTCTGGATGGACCGCCGGGGCCGCCGCCTACTATGTGGGCTAT

CTGCAGCCCAGGACCTTCCTGCTGAAGTACAACGAGAATGGCACCATCACAGACGCA

GTGGATTGCGCCCTGGACCCCCTGTCTGAGACCAAGTGTACACTGAAGAGCTTTACC

GTGGAGAAGGGCATCTATCAGACAAGCAATTTCAGGGTGCAGCCTACCGAGTCCATC

GTGCGCTTTCCCAATATCACAAACCTGTGCCCTTTTGGCGAGGTGTTCAACGCAACCA

GGTTCGCCAGCGTGTACGCATGGAATAGGAAGCGCATCTCCAACTGCGTGGCCGACT

ATTCTGTGCTGTACAACAGCGCCTCCTTCTCTACCTTTAAGTGCTATGGCGTGAGCCC

CACAAAGCTGAATGACCTGTGCTTTACCAACGTGTACGCCGATTCCTTCGTGATCAGG

GGCGACGAGGTGCGCCAGATCGCACCAGGACAGACAGGCAAGATCGCAGACTACAA

TTATAAGCTGCCTGACGATTTCACCGGCTGCGTGATCGCCTGGAACTCTAACAATCTG

GATAGCAAAGTGGGCGGCAACTACAATTATCTGTACCGGCTGTTTAGAAAGTCTAAT

CTGAAGCCATTCGAGAGGGACATCTCCACAGAGATCTACCAGGCCGGCTCTACCCCC

TGCAATGGCGTGGAGGGCTTTAACTGTTATTTCCCTCTGCAGAGCTACGGCTTCCAGC

CAACAAACGGCGTGGGCTATCAGCCCTACCGCGTGGTGGTGCTGTCTTTTGAGCTGCT

GCACGCACCTGCAACAGTGTGCGGACCAAAGAAGAGCACCAATCTGGTGAAGAACA

AGTGCGTGAACTTCAACTTCAACGGCCTGACCGGCACAGGCGTGCTGACCGAGTCCA

ACAAGAAGTTCCTGCCTTTTCAGCAGTTCGGCAGGGACATCGCAGATACCACAGACG

CCGTGCGCGACCCTCAGACCCTGGAGATCCTGGACATCACACCATGCTCCTTCGGCG

GCGTGTCTGTGATCACACCAGGCACCAATACAAGCAACCAGGTGGCCGTGCTGTATC

AGGACGTGAATTGTACCGAGGTGCCCGTGGCCATCCACGCAGATCAGCTCACCCCTA

CATGGCGGGTGTACTCTACCGGCAGCAACGTGTTCCAGACAAGAGCCGGCTGCCTGA

TCGGAGCCGAGCATGTGAACAATAGCTATGAGTGCGACATCCCTATCGGAGCCGGCA

-continued

TCTGTGCCTCCTACCAGACCCAGACAAACTCCCCACGGAGAGCCCGGTCTGTGGCCA

GCCAGTCCATCATCGCCTATACCATGAGCCTGGGGGCCGAGAACAGCGTGGCCTACT

CCAACAATTCTATCGCCATCCCTACCAACTTCACAATCTCCGTGACCACAGAGATCCT

GCCAGTGAGCATGACCAAGACATCCGTGGACTGCACAATGTATATCTGTGGCGATTC

CACCGAGTGCTCTAACCTGCTGCTGCAGTACGGCTCTTTTTGTACCCAGCTCAACAGA

GCCCTGACAGGCATCGCCGTGGAGCAGGACAAGAACACACAGGAGGTGTTCGCCCA

GGTGAAGCAGATCTACAAGACCCCACCCATCAAGGACTTTGGCGGCTTCAACTTCAG

CCAGATCCTGCCCGATCCTAGCAAGCCATCCAAGCGGTCTTTTATCGAGGACCTGCTG

TTCAACAAGGTGACCCTGGCCGATGCCGGCTTCATCAAGCAGTATGGCGATTGCCTG

GGCGACATCGCCGCCAGAGACCTGATCTGTGCCCAGAAGTTTAATGGCCTGACCGTG

CTGCCTCCACTGCTGACAGATGAGATGATCGCCCAGTACACATCTGCCCTGCTGGCCG

GCACCATCACAAGCGGATGGACCTTCGGGGCCGGGGCCGCCCTGCAGATCCCCTTTG

CCATGCAGATGGCCTATCGGTTCAACGGCATCGGCGTGACCCAGAATGTGCTGTACG

AGAACCAGAAGCTGATCGCCAATCAGTTTAACTCCGCCATCGGCAAGATCCAGGACT

CTCTGAGCTCCACAGCCAGCGCCCTGGGCAAGCTGCAGGATGTGGTGAATCAGAACG

CCCAGGCCCTGAATACCCTGGTGAAGCAGCTCAGCAGCAACTTCGGGGCCATCAGCA

GCGTGCTGAACGACATCCTGAGCCGGCTGGACAAGGTGGAGGCAGAGGTGCAGATC

GACCGGCTGATCACAGGCAGACTGCAGTCCCTGCAGACCTACGTGACACAGCAGCTC

ATCAGGGCCGCCGAGATCAGGGCCTCTGCCAATCTGGCCGCCACCAAGATGAGCGAG

TGCGTGCTGGGCCAGTCCAAGAGAGTGGACTTTTGTGGCAAGGGCTATCACCTGATG

AGCTTCCCACAGTCCGCCCCTCACGGAGTGGTGTTTCTGCATGTGACCTACGTGCCAG

CCCAGGAGAAGAACTTCACCACAGCCCCCGCAATCTGCCACGATGGCAAGGCACACT

TTCCCCGGGAGGGCGTGTTCGTGAGCAACGGCACCCACTGGTTTGTGACACAGCGCA

ATTTCTACGAGCCACAGATCATCACCACAGACAATACATTCGTGTCCGGCAACTGTG

ACGTGGTCATCGGCATCGTGAACAATACCGTGTATGATCCTCTGCAGCCAGAGCTGG

ACTCTTTTAAGGAGGAGCTGGATAAGTACTTCAAGAATCACACCAGCCCCGACGTGG

ATCTGGGCGACATCTCTGGCATCAATGCCAGCGTGGTGAACATCCAGAAGGAGATCG

ACAGGCTGAACGAGGTGGCCAAGAATCTGAACGAGTCCCTGATCGATCTGCAGGAGC

TGGGCAAGTATGAGCAGTACATCAAGTGGCCCTGGTATATCTGGCTGGGCTTCATCG

CCGGCCTGATCGCCATCGTGATGGTGACCATCATGCTGTGCTGTATGACAAGCTGCTG

TTCCTGCCTGAAGGGCTGCTGTTCTTGTGGCTCCTGCTGTAAGTTTGATGAGGACGAT

AGCGAGCCTGTGCTGAAGGGCGTGAAGCTGCACTACACCTGA

SEQ ID NO: 7 is a SARS-CoV Spike Glycoprotein, Amino Acid Sequence (HKU-39849, Genbank Ref: JN854286.1)

MFIFLLFLTLTSGSDLDRCTTFDDVQAPNYTQHTSSMRGVYYPDEIFRSDTLYLTQDLFLP

FYSNVTGFHTINHTFGNPVIPFKDGIYFAATEKSNVVRGWVFGSTMNNKSQSVIIINNSTN

VVIRACNFELCDNPFFAVSKPMGTQTHTMIFDNAFNCTFEYISDAFSLDVSEKSGNFKHLR

EFVFKNKDGFLYVYKGYQPIDVVRDLPSGFNTLKPIFKLPLGINITNFRAILTAFSPAQDIW

GTSAAAYFVGYLKPTTFMLKYDENGTITDAVDCSQNPLAELKCSVKSFEIDKGIYQTSNF

-continued

RVVPSGDVVRFPNITNLCPFGEVFNATKFPSVYAWERKKISNCVADYSVLYNSTFFSTFKC

YGVSATKLNDLCFSNVYADSFVVKGDDVRQIAPGQTGVIADYNYKLPDDFMGCVLAWN

TRNIDATSTGNYNYKYRYLRHGKLRPFERDISNVPFSPDGKPCTPPALNCYWPLNDYGFY

TTTGIGYQPYRVVVLSFELLNAPATVCGPKLSTDLIKNQCVNFNFNGLTGTGVLTPSSKRF

QPFQQFGRDVSDFTDSVRDPKTSEILDISPCSFGGVSVITPGTNASSEVAVLYQDVNCTDV

STAIHADQLTPAWRIYSTGNNVFQTQAGCLIGAEHVDTSYECDIPIGAGICASYHTVSLLR

STSQKSIVAYTMSLGADSSIAYSNNTIAIPTNFSISITTEVMPVSMAKTSVDCNMYICGDST

ECANLLLQYGSFCTQLNRALSGIAAEQDRNTREVFAQVKQMYKTPTLKYFGGFNFSQILP

DPLKPTKRSFIEDLLFNKVTLADAGFMKQYGECLGDINARDLICAQKFNGLTVLPPLLTD

DMIAAYTAALVSGTATAGWTFGAGAALQIPFAMQMAYRFNGIGVTQNVLYENQKQIAN

QFNKAISQIQESLTTTSTALGKLQDVVNQNAQALNTLVKQLSSNFGAISSVLNDILSRLDK

VEAEVQIDRLITGRLQSLQTYVTQQLIRAAEIRASANLAATKMSECVLGQSKRVDFCGKG

YHLMSFPQAAPHGVVFLHVTYVPSQERNFTTAPAICHEGKAYFPREGVFVFNGTSWFITQ

RNFFSPQIITTDNTFVSGNCDVVIGIINNTVYDPLQPELDSFKEELDKYFKNHTSPDVDLGD

ISGINASVVNIQKEIDRLNEVAKNLNESLIDLQELGKYEQYIKWPWYVWLGFIAGLIAIVM

VTILLCCMTSCCSCLKGACSCGSCCKFDEDDSEPVLKGVKLHYT

SEQ ID NO: 8 is a SARS-CoV Spike Glycoprotein, Nucleotide Sequence

ATGTTTATTTTCTTATTATTTCTTACTCTCACTAGTGGTAGTGACCTTGACCGGTGCAC

CACTTTTGATGATGTTCAAGCTCCTAATTACACTCAACATACTTCATCTATGAGGGGG

GTTTACTATCCTGATGAAATTTTTAGATCAGACACTCTTTATTTAACTCAGGATTTATT

TCTTCCATTTTATTCTAATGTTACAGGGTTTCATACTATTAATCATACGTTTGGCAACC

CTGTCATACCTTTTAAGGATGGTATTTATTTTGCTGCCACAGAGAAATCAAATGTTGT

CCGTGGTTGGGTTTTTGGTTCTACCATGAACAACAAGTCACAGTCGGTGATTATTATT

AACAATTCTACTAATGTTGTTATACGAGCATGTAACTTTGAATTGTGTGACAACCCTT

TCTTTGCTGTTTCTAAACCCATGGGTACACAGACACATACTATGATATTCGATAATGC

ATTTAATTGCACTTTCGAGTACATATCTGATGCCTTTTCGCTTGATGTTTCAGAAAAGT

CAGGTAATTTTAAACACTTACGAGAGTTTGTGTTTAAAAATAAAGATGGGTTTCTCTA

TGTTTATAAGGGCTATCAACCTATAGATGTAGTTCGTGATCTACCTTCTGGTTTTAAC

ACTTTGAAACCTATTTTTAAGTTGCCTCTTGGTATTAACATTACAAATTTTAGAGCCAT

TCTTACAGCCTTTTCACCTGCTCAAGACATTTGGGGCACGTCAGCTGCAGCCTATTTT

GTTGGCTATTTAAAGCCAACTACATTTATGCTCAAGTATGATGAAAATGGTACAATCA

CAGATGCTGTTGATTGTTCTCAAAATCCACTTGCTGAACTCAAATGCTCTGTTAAGAG

CTTTGAGATTGACAAAGGAATTTACCAGACCTCTAATTTCAGGGTTGTTCCCTCAGGA

GATGTTGTGAGATTCCCTAATATTACAAACTTGTGTCCTTTTGGAGAGGTTTTTAATG

CTACTAAATTCCCTTCTGTCTATGCATGGGAGAGAAAAAAAATTTCTAATTGTGTTGC

TGATTACTCTGTGCTCTACAACTCAACATTTTTTTCAACCTTTAAGTGCTATGGCGTTT

CTGCCACTAAGTTGAATGATCTTTGCTTCTCCAATGTCTATGCAGATTCTTTTGTAGTC

AAGGGAGATGATGTAAGACAAATAGCGCCAGGACAAACTGGTGTTATTGCTGATTAT

-continued

AATTATAAATTGCCAGATGATTTCATGGGTTGTGTCCTTGCTTGGAATACTAGGAACA

TTGATGCTACTTCAACTGGTAATTATAATTATAAATATAGGTATCTTAGACATGGCAA

GCTTAGGCCCTTTGAGAGAGACATATCTAATGTGCCTTTCTCCCCTGATGGCAAACCT

TGCACCCCACCTGCTCTTAATTGTTATTGGCCATTAAATGATTATGGTTTTTACACCAC

TACTGGCATTGGCTACCAACCTTACAGAGTTGTAGTACTTTCTTTTGAACTTTTAAATG

CACCGGCCACGGTTTGTGGACCAAAATTATCCACTGACCTTATTAAGAACCAGTGTGT

CAATTTTAATTTTAATGGACTCACTGGTACTGGTGTGTTAACTCCTTCTTCAAAGAGA

TTTCAACCATTTCAACAATTTGGCCGTGATGTTTCTGATTTCACTGATTCCGTTCGAGA

TCCTAAAACATCTGAAATATTAGACATTTCACCTTGCTCTTTTGGGGGTGTAAGTGTA

ATTACACCTGGAACAAATGCTTCATCTGAAGTTGCTGTTCTATATCAAGATGTTAACT

GCACTGATGTTTCTACAGCAATTCATGCAGATCAACTCACACCAGCTTGGCGCATATA

TTCTACTGGAAACAATGTATTCCAGACTCAAGCAGGCTGTCTTATAGGAGCTGAGCAT

GTCGACACTTCTTATGAGTGCGACATTCCTATTGGAGCTGGCATTTGTGCTAGTTACC

ATACAGTTTCTTTATTACGTAGTACTAGCCAAAAATCTATTGTGGCTTATACTATGTCT

TTAGGTGCTGATAGTTCAATTGCTTACTCTAATAACACCATTGCTATACCTACTAACTT

TTCAATTAGCATTACTACAGAAGTAATGCCTGTTTCTATGGCTAAAACCTCCGTAGAT

TGTAATATGTACATCTGCGGAGATTCTACTGAATGTGCTAATTTGCTTCTCCAATATG

GTAGCTTTTGCACACAACTAAATCGTGCACTCTCAGGTATTGCTGCTGAACAGGATCG

CAACACACGTGAAGTGTTCGCTCAAGTCAAACAAATGTACAAAACCCCAACTTTGAA

ATATTTTGGTGGTTTTAATTTTTCACAAATATTACCTGACCCTCTAAAGCCAACTAAG

AGGTCTTTTATTGAGGACTTGCTCTTTAATAAGGTGACACTCGCTGATGCTGGCTTCA

TGAAGCAATATGGCGAATGCCTAGGTGATATTAATGCTAGAGATCTCATTTGTGCGC

AGAAGTTCAATGGACTTACAGTGTTGCCACCTCTGCTCACTGATGATATGATTGCTGC

CTACACTGCTGCTCTAGTTAGTGGTACTGCCACTGCTGGATGGACATTTGGTGCTGGC

GCTGCTCTTCAAATACCTTTTGCTATGCAAATGGCATATAGGTTCAATGGCATTGGAG

TTACCCAAAATGTTCTCTATGAGAACCAAAAACAAATCGCCAACCAATTTAACAAGG

CGATTAGTCAAATTCAAGAATCACTTACAACAACATCAACTGCATTGGGCAAGCTGC

AAGACGTTGTTAACCAGAATGCTCAAGCATTAAACACACTTGTTAAACAACTTAGCT

CTAATTTTGGTGCAATTTCAAGTGTGCTAAATGATATCCTTTCGCGACTTGATAAAGT

CGAGGCGGAGGTACAAATTGACAGGTTAATTACAGGCAGACTTCAAAGCCTTCAAAC

CTATGTAACACAACAACTAATCAGGGCTGCTGAAATCAGGGCTTCTGCTAATCTTGCT

GCTACTAAAATGTCTGAGTGTGTTCTTGGACAATCAAAAAGAGTTGACTTTTGTGGAA

AGGGCTACCACCTTATGTCCTTCCCACAAGCAGCCCCGCATGGTGTTGTCTTCCTACA

TGTCACGTATGTGCCATCCCAGGAGAGGAACTTCACCACAGCGCCAGCAATTTGTCA

TGAAGGCAAAGCATACTTCCCTCGTGAAGGTGTTTTTGTGTTTAATGGCACTTCTTGG

TTTATTACACAGAGGAACTTCTTTTCTCCACAAATAATTACTACAGACAATACATTTG

TCTCAGGAAATTGTGATGTCGTTATTGGCATCATTAACAACACAGTTTATGATCCTCT

GCAACCTGAGCTTGACTCATTCAAAGAAGAGCTGGACAAGTACTTCAAAAATCATAC

ATCACCAGATGTTGATCTTGGCGACATTTCAGGCATTAACGCTTCTGTCGTCAACATT

CAAAAAGAAATTGACCGCCTCAATGAGGTCGCTAAAAATTTAAATGAATCACTCATT

GACCTTCAAGAATTGGGAAAATATGAGCAATATATTAAATGGCCTTGGTATGTTTGG

-continued

CTCGGCTTCATTGCTGGACTAATTGCCATCGTCATGGTTACAATCTTGCTTTGTTGCAT

GACTAGTTGTTGCAGTTGCCTCAAGGGTGCATGCTCTTGTGGTTCTTGCTGCAAGTTT

GATGAGGATGACTCTGAGCCAGTTCTCAAGGGTGTCAAATTACATTACACATAA

SEQ ID NO: 9 is a SARS-CoV Spike Glycoprotein, Nucleotide Sequence, Codon Optimized for Expression In Human Cells

ATGTTCATCTTTCTGCTGTTCCTGACCCTGACAAGCGGCTCCGACCTGG

ATAGGTGCACCACATTTGACGATGTGCAGGCCCCCAACTACACACAGCA

CACCAGCTCCATGAGGGGCGTGTACTATCCTGATGAGATCTTCCGCTCT

GACACACTGTACCTGACCCAGGACCTGTTCCTGCCTTTTTATAGCAATG

TGACAGGCTTCCACACCATCAATCACACATTTGGCAACCCCGTGATCCC

TTTCAAGGATGGCATCTACTTTGCCGCCACCGAGAAGTCTAACGTGGTG

CGGGGATGGGTGTTCGGCAGCACAATGAACAATAAGTCTCAGAGCGTGA

TCATCATCAACAATAGCACCAACGTGGTCATCAGAGCCTGCAATTTTGA

GCTGTGCGACAACCCCTTCTTTGCCGTGTCCAAGCCTATGGGCACCCAG

ACACACACCATGATCTTTGATAATGCCTTCAACTGTACCTTTGAGTACA

TCAGCGATGCCTTTTCCCTGGACGTGTCTGAGAAGTCCGGCAACTTCAA

GCACCTGAGGGAGTTCGTGTTTAAGAATAAGGACGGCTTCCTGTACGTG

TATAAGGGCTATCAGCCCATCGATGTGGTGCGCGACCTGCCTTCCGGCT

TCAACACCCTGAAGCCAATCTTTAAGCTGCCCCTGGGCATCAATATCAC

CAACTTCAGGGCCATCCTGACAGCCTTTAGCCCAGCACAGGACATCTGG

GGCACCAGCGCCGCCGCCTACTTCGTGGGCTATCTGAAGCCCACCACCT

TCATGCTGAAGTACGATGAGAACGGCACAATCACCGACGCCGTGGATTG

CAGCCAGAATCCACTGGCCGAGCTGAAGTGTTCCGTGAAGTCTTTCGAG

ATCGACAAGGGCATCTATCAGACCTCCAACTTTAGGGTGGTGCCATCTG

GCGATGTGGTGCGCTTCCCAAATATCACCAACCTGTGCCCCTTCGGCGA

GGTGTTTAATGCCACAAAGTTCCCCAGCGTGTACGCCTGGGAGCGCAAG

AAGATCAGCAACTGCGTGGCCGACTACTCCGTGCTGTATAATAGCACCT

TCTTCAGCACCTTCAAGTGCTACGGCGTGAGCGCCACCAAGCTGAATGA

CCTGTGCTTCTCTAACGTGTATGCCGATAGCTTTGTGGTGAAGGGCGAC

GATGTGAGGCAGATCGCACCTGGACAGACCGGCGTGATCGCAGACTACA

ACTATAAGCTGCCAGACGATTTCATGGGCTGCGTGCTGGCCTGGAATAC

ACGCAACATCGATGCCACATCCACCGGCAACTACAATTATAAGTACCGG

TATCTGAGACACGGCAAGCTGCGGCCCTTCGAGAGAGACATCTCCAATG

TGCCATTTTCTCCAGATGGCAAGCCATGCACCCCACCTGCCCTGAATTG

TTACTGGCCTCTGAACGACTACGGCTTCTATACCACAACCGGCATCGGC

TACCAGCCTTATAGGGTGGTGGTGCTGTCCTTTGAGCTGCTGAACGCAC

CTGCAACCGTGTGCGGACCAAAGCTGTCTACAGATCTGATCAAGAATCA

GTGCGTGAACTTCAACTTCAACGGCCTGACAGGCACCGGCGTGCTGACC

CCTTCTAGCAAGCGGTTCCAGCCATTTCAGCAGTTCGGCAGAGACGTGA

-continued

GCGATTTCACCGACTCCGTGCGCGACCCAAAGACATCCGAGATCCTGGA

CATCAGCCCCTGCTCCTTTGGCGGCGTGTCTGTGATCACACCTGGCACC

AACGCCTCCTCTGAGGTGGCCGTGCTGTACCAGGATGTGAATTGTACCG

ACGTGAGCACAGCAATCCACGCAGACCAGCTCACCCCAGCATGGCGGAT

CTATTCCACCGGCAACAACGTGTTCCAGACACAGGCAGGATGCCTGATC

GGAGCCGAGCATGTGGATACAAGCTACGAGTGCGACATCCCCATCGGAG

CCGGCATCTGTGCCTCTTATCACACCGTGAGCCTGCTGAGATCCACATC

TCAGAAGTCTATCGTGGCCTACACCATGAGCCTGGGGGCCGATAGCTCC

ATCGCCTATTCCAACAATACCATCGCCATCCCAACAAACTTCAGCATCT

CCATCACAACCGAAGTGATGCCCGTGTCCATGGCCAAGACCTCTGTGGA

CTGCAACATGTACATCTGTGGCGATAGCACAGAGTGCGCCAATCTGCTG

CTGCAGTATGGCTCCTTTTGTACCCAGCTCAACCGGGCCCTGTCTGGAA

TCGCCGCCGAGCAGGACAGGAATACACGCGAGGTGTTCGCCCAGGTGAA

GCAGATGTACAAGACACCTACCCTGAAGTATTTTGGCGGCTTCAACTTT

TCTCAGATCCTGCCTGATCCACTGAAGCCAACCAAGCGGAGCTTCATCG

AGGACCTGCTGTTTAATAAGGTGACACTGGCCGATGCCGGCTTCATGAA

GCAGTACGGCGAGTGCCTGGGCGACATCAACGCCAGAGACCTGATCTGT

GCCCAGAAGTTTAATGGCCTGACCGTGCTGCCACCCCTGCTGACAGACG

ATATGATCGCAGCATATACCGCCGCCCTGGTGTCCGGCACAGCCACCGC

CGGCTGGACCTTCGGGGCCGGGGCCGCCCTGCAGATCCCTTTCGCCATG

CAGATGGCCTACCGGTTTAACGGCATCGGCGTGACCCAGAATGTGCTGT

ATGAGAACCAGAAGCAGATCGCCAATCAGTTTAACAAGGCCATCAGCCA

GATCCAGGAGTCCCTGACAACCACATCTACCGCCCTGGGCAAGCTGCAG

GACGTGGTGAATCAGAACGCCCAGGCCCTGAATACACTGGTGAAGCAGC

TCAGCAGCAACTTCGGGGCCATCAGCAGCGTGCTGAACGACATCCTGAG

CCGGCTGGACAAGGTGGAGGCAGAGGTGCAGATCGATAGGCTGATCACC

GGCAGACTGCAGTCTCTGCAGACATACGTGACCCAGCAGCTCATCAGGG

CCGCCGAGATCAGAGCCAGCGCCAACCTGGCCGCCACAAAGATGTCCGA

GTGCGTGCTGGGCCAGTCTAAGAGGGTGGACTTCTGTGGCAAGGGCTAC

CACCTGATGTCCTTTCCACAGGCCGCCCCTCACGGAGTGGTGTTCCTGC

ATGTGACCTATGTGCCTTCTCAGGAGCGCAACTTTACCACAGCCCCAGC

AATCTGCCACGAGGGCAAGGCATACTTCCCCCGGGAGGGCGTGTTCGTG

TTTAACGGCACCTCCTGGTTTATCACACAGAGAAATTTCTTTTCCCCTC

AGATCATCACCACAGACAATACCTTCGTGAGCGGCAACTGTGACGTGGT

CATCGGCATCATCAACAATACAGTGTACGATCCTCTGCAGCCAGAGCTG

-continued

```
GACAGCTTCAAGGAGGAGCTGGATAAGTACTTCAAGAACCACACCTCCC
CCGACGTGGATCTGGGCGACATCAGCGGCATCAATGCCTCCGTGGTGAA
CATCCAGAAGGAGATCGACAGACTGAATGAGGTGGCCAAGAATCTGAAC
GAGTCCCTGATCGATCTGCAGGAGCTGGGCAAGTACGAGCAGTATATCA
AGTGGCCATGGTACGTGTGGCTGGGCTTCATCGCCGGCCTGATCGCCAT
CGTGATGGTGACCATCCTGCTGTGCTGTATGACATCTTGCTGTAGCTGC
CTGAAGGGAGCCTGCTCCTGTGGCTCTTGCTGTAAGTTTGACGAGGACG
ATAGCGAGCCCGTGCTGAAGGGCGTGAAGCTGCACTATACCTGA
```

SEQ ID NO: 10 is a MERS-CoV Spike Glycoprotein, Amino Acid Sequence

```
MIHSVFLLMFLLTPTESYVDVGPDSVKSACIEVDIQQTFFDKTWPRPID
VSKADGITYPQGRTYSNITITYQGLFPYQGDHGDMYVYSAGHATGTTPQ
KLFVANYSQDVKQFANGFVVRIGAAANSTGTVIISPSTSATIRKIYPAF
MLGSSVGNFSDGKMGRFFNHTLVLLPDGCGTLLRAFYCILEPRSGNHCP
AGNSYTSFATYHTPATDCSDGNYNRNASLNSFKEYFNLRNCTFMYTYNI
TEDEILEWFGITQTAQGVHLFSSRYVDLYGGNMFQFATLPVYDTIKYYS
IIPHSIRSIQSDRKAWAAFYVYKLQPLTFLLDFSVDGYIRRAIDCGFND
LSQLHCSYESFDVESGVYSVSSFEAKPSGSVVEQAEGVECDFSPLLSGT
PPQVYNFKRLVFTNCNYNLTKLLSLFSVNDFTCSQISPAAIASNCYSSL
ILDYFSYPLSMKSDLSVSSAGPISQFNYKQSFSNPTCLILATVPHNLTT
ITKPLKYSYINKCSRLLSDDRTEVPQLVNANQYSPCVSIVPSTVWEDGD
YYRKQLSPLEGGGWLVASGSTVAMTEQLQMGFGITVQYGTDTNSVCPKL
EFANDTKIASQLGNCVEYSLYGVSGRGVFQNCTAVGVRQQRFVYDAYQN
LVGYYSDDGNYYCLRACVSVPVSVIYDKETKTHATLFGSVACEHISSTM
SQYSRSTRSMLKRRDSTYGPLQTPVGCVLGLVNSSLFVEDCKLPLGQSL
CALPDTPSTLTPRSVRSVPGEMRLASIAFNHPIQVDQLNSSYFKLSIPT
NFSFGVTQEYIQTTIQKVTVDCKQYVCNGFQKCEQLLREYGQFCSKINQ
ALHGANLRQDDSVRNLFASVKSSQSSPIIPGFGGDFNLTLLEPVSISTG
SRSARSAIEDLLFDKVTIADPGYMQGYDDCMQQGPASARDLICAQYVAG
YKVLPPLMDVNMEAAYTSSLLGSIAGVGWTAGLSSFAAIPFAQSIFYRL
NGVGITQQVLSENQKLIANKFNQALGAMQTGFTTTNEAFQKVQDAVNNN
AQALSKLASELSNTFGAISASIGDIIQRLDVLEQDAQIDRLINGRLTTL
NAFVAQQLVRSESAALSAQLAKDKVNECVKAQSKRSGFCGQGTHIVSFV
VNAPNGLYFMHVGYYPSNHIEVVSAYGLCDAANPTNCIAPVNGYFIKTN
NTRIVDEWSYTGSSFYAPEPITSLNTKYVAPQVTYQNISTNLPPPLLGN
STGIDFQDELDEFFKNVSTSIPNFGSLTQINTTLLDLTYEMLSLQQVVK
ALNESYIDLKELGNYTYYNKWPWYIWLGFIAGLVALALCVFFILCCTGC
GTNCMGKLKCNRCCDRYEEYDLEPHKVHVH
```

SEQ ID NO: 11 is a MERS-CoV Spike Glycoprotein, Nucleotide Sequence (EMC/2012, Genbank Ref: JX869059.2)

```
ATGATACACTCAGTGTTTCTACTGATGTTCTTGTTAACACCTACAGAAA
GTTACGTTGATGTAGGGCCAGATTCTGTTAAGTCTGCTTGTATTGAGGT
TGATATACAACAGACTTTCTTTGATAAAACTTGGCCTAGGCCAATTGAT
GTTTCTAAGGCTGACGGTATTATATACCCTCAAGGCCGTACATATTCTA
ACATAACTATCACTTATCAAGGTCTTTTTCCCTATCAGGGAGACCATGG
TGATATGTATGTTTACTCTGCAGGACATGCTACAGGCACAACTCCACAA
AAGTTGTTTGTAGCTAACTATTCTCAGGACGTCAAACAGTTTGCTAATG
GGTTTGTCGTCCGTATAGGAGCAGCTGCCAATTCCACTGGCACTGTTAT
TATTAGCCCATCTACCAGCGCTACTATACGAAAAATTTACCCTGCTTTT
ATGCTGGGTTCTTCAGTTGGTAATTTCTCAGATGGTAAAATGGGCCGCT
TCTTCAATCATACTCTAGTTCTTTTGCCCGATGGATGTGGCACTTTACT
TAGAGCTTTTTATTGTATTCTAGAGCCTCGCTCTGGAAATCATTGTCCT
GCTGGCAATTCCTATACTTCTTTTGCCACTTATCACACTCCTGCAACAG
ATTGTTCTGATGGCAATTACAATCGTAATGCCAGTCTGAACTCTTTTAA
GGAGTATTTTAATTTACGTAACTGCACCTTTATGTACACTTATAACATT
ACCGAAGATGAGATTTTAGAGTGGTTTGGCATTACACAAACTGCTCAAG
GTGTTCACCTCTTCTCATCTCGGTATGTTGATTTGTACGGCGGCAATAT
GTTTCAATTTGCCACCTTGCCTGTTTATGATACTATTAAGTATTATTCT
ATCATTCCTCACAGTATTCGTTCTATCCAAAGTGATAGAAAAGCTTGGG
CTGCCTTCTACGTATATAAACTTCAACCGTTAACTTTCCTGTTGGATTT
TTCTGTTGATGGTTATATACGCAGAGCTATAGACTGTGGTTTTAATGAT
TTGTCACAACTCCACTGCTCATATGAATCCTTCGATGTTGAATCTGGAG
TTTATTCAGTTTCGTCTTTCGAAGCAAAACCTTCTGGCTCAGTTGTGGA
ACAGGCTGAAGGTGTTGAATGTGATTTTTCACCTCTTCTGTCTGGCACA
CCTCCTCAGGTTTATAATTTCAAGCGTTTGGTTTTTACCAATTGCAATT
ATAATCTTACCAAATTGCTTTCACTTTTTTCTGTGAATGATTTTACTTG
TAGTCAAATATCTCCAGCAGCAATTGCTAGCAACTGTTATTCTTCACTG
ATTTTGGATTACTTTTCATACCCACTTAGTATGAAATCCGATCTCAGTG
TTAGTTCTGCTGGTCCAATATCCCAGTTTAATTATAAACAGTCCTTTTC
TAATCCCACATGTTTGATTTTAGCGACTGTTCCTCATAACCTTACTACT
ATTACTAAGCCTCTTAAGTACAGCTATATTAACAAGTGCTCTCGTCTTC
TTTCTGATGATCGTACTGAAGTACCTCAGTTAGTGAACGCTAATCAATA
CTCACCCTGTGTATCCATTGTCCCATCCACTGTGTGGGAAGACGGTGAT
TATTATAGGAAACAACTATCTCCACTTGAAGGTGGTGGCTGGCTTGTTG
CTAGTGGCTCAACTGTTGCCATGACTGAGCAATTACAGATGGGCTTTGG
TATTACAGTTCAATATGGTACAGACACCAATAGTGTTTGCCCCAAGCTT
GAATTTGCTAATGACACAAAAATTGCCTCTCAATTAGGCAATTGCGTGG
AATATTCCCTCTATGGTGTTTCGGGCCGTGGTGTTTTTCAGAATTGCAC
AGCTGTAGGTGTTCGACAGCAGCGCTTTGTTTATGATGCGTACCAGAAT
TTAGTTGGCTATTATTCTGATGATGGCAACTACTACTGTTTGCGTGCTT
GTGTTAGTGTTCCTGTTTCTGTCATCTATGATAAAGAAACTAAAACCCA
```

```
CGCTACTCTATTTGGTAGTGTTGCATGTGAACACATTTCTTCTACCATG
TCTCAATACTCCCGTTCTACGCGATCAATGCTTAAACGGCGAGATTCTA
CATATGGCCCCCTTCAGACACCTGTTGGTTGTGTCCTAGGACTTGTTAA
TTCCTCTTTGTTCGTAGAGGACTGCAAGTTGCCTCTTGGTCAATCTCTC
TGTGCTCTTCCTGACACACCTAGTACTCTCACACCTCGCAGTGTGCGCT
CTGTTCCAGGTGAAATGCGCTTGGCATCCATTGCTTTTAATCATCCTAT
TCAGGTTGATCAACTTAATAGTAGTTATTTTAAATTAAGTATACCCACT
AATTTTTCCTTTGGTGTGACTCAGGAGTACATTCAGACAACCATTCAGA
AAGTTACTGTTGATTGTAAACAGTACGTTTGCAATGGTTTCCAGAAGTG
TGAGCAATTACTGCGCGAGTATGGCCAGTTTTGTTCCAAAATAAACCAG
GCTCTCCATGGTGCCAATTTACGCCAGGATGATTCTGTACGTAATTTGT
TTGCGAGCGTGAAAAGCTCTCAATCATCTCCTATCATACCAGGTTTTGG
AGGTGACTTTAATTTGACACTTCTAGAACCTGTTTCTATATCTACTGGC
AGTCGTAGTGCACGTAGTGCTATTGAGGATTTGCTATTTGACAAAGTCA
CTATAGCTGATCCTGGTTATATGCAAGGTTACGATGATTGCATGCAGCA
AGGTCCAGCATCAGCTCGTGATCTTATTTGTGCTCAATATGTGGCTGGT
TACAAAGTATTACCTCCTCTTATGGATGTTAATATGGAAGCCGCGTATA
CTTCATCTTTGCTTGGCAGCATAGCAGGTGTTGGCTGGACTGCTGGCTT
ATCCTCCTTTGCTGCTATTCCATTTGCACAGAGTATCTTTTATAGGTTA
AACGGTGTTGGCATTACTCAACAGGTTCTTTCAGAGAACCAAAAGCTTA
TTGCCAATAAGTTTAATCAGGCTCTGGGAGCTATGCAAACAGGCTTCAC
TACAACTAATGAAGCTTTTCAGAAGGTTCAGGATGCTGTGAACAACAAT
GCACAGGCTCTATCCAAATTAGCTAGCGAGCTATCTAATACTTTTGGTG
CTATTTCCGCCTCTATTGGAGACATCATACAACGTCTTGATGTTCTCGA
ACAGGACGCCCAAATAGACAGACTTATTAATGGCCGTTTGACAACACTA
AATGCTTTTGTTGCACAGCAGCTTGTTCGTTCCGAATCAGCTGCTCTTT
CCGCTCAATTGGCTAAAGATAAAGTCAATGAGTGTGTCAAGGCACAATC
CAAGCGTTCTGGATTTTGCGGTCAAGGCACACATATAGTGTCCTTTGTT
GTAAATGCCCCTAATGGCCTTTACTTCATGCATGTTGGTTATTACCCTA
GCAACCACATTGAGGTTGTTTCTGCTTATGGTCTTTGCGATGCAGCTAA
CCCTACTAATTGTATAGCCCCTGTTAATGGCTACTTTATTAAAACTAAT
AACACTAGGATTGTTGATGAGTGGTCATATACTGGCTCGTCCTTCTATG
CACCTGAGCCCATTACCTCCCTTAATACTAAGTATGTTGCACCACAGGT
GACATACCAAAACATTTCTACTAACCTCCCTCCTCCTCTTCTCGGCAAT
TCCACCGGGATTGACTTCCAAGATGAGTTGGATGAGTTTTTCAAAAATG
TTAGCACCAGTATACCTAATTTTGGTTCCCTAACACAGATTAATACTAC
ATTACTCGATCTTACCTACGAGATGTTGTCTCTTCAACAAGTTGTTAAA
GCCCTTAATGAGTCTTACATAGACCTTAAAGAGCTTGGCAATTATACTT
ATTACAACAAATGGCCGTGGTACATTTGGCTTGGTTTCATTGCTGGGCT
TGTTGCCTTAGCTCTATGCGTCTTCTTCATACTGTGCTGCACTGGTTGT
GGCACAAACTGTATGGGAAAACTTAAGTGTAATCGTTGTTGTGATAGAT
ACGAGGAATACGACCTCGAGCCGCATAAGGTTCATGTTCACTAA
```

SEQ ID NO: 12 is a MERS-CoV Spike Glycoprotein, Nucleotide Sequence, Codon Optimized For Expression In Human Cells

```
ATGATCCACAGCGTGTTCCTGCTGATGTTTCTGCTGACACCTACCGAGT
CCTACGTGGATGTGGGCCCAGACTCTGTGAAGAGCGCCTGCATCGAGGT
GGACATCCAGCAGACATTCTTTGACAAGACCTGGCCCAGACCCATCGAC
GTGAGCAAGGCAGACGGAATCATCTACCCACAGGGACGCACATATAGCA
ACATCACAATCACCTACCAGGGCCTGTTCCCTTATCAGGGCGACCACGG
CGATATGTACGTGTATAGCGCCGGCCACGCAACCGGCACCACACCACAG
AAGCTGTTTGTGGCCAATTATTCCCAGGACGTGAAGCAGTTCGCCAACG
GATTTGTGGTGCGGATCGGGGCCGCCGCCAACAGCACAGGCACCGTGAT
CATCTCTCCCAGCACATCCGCCACCATCAGAAAGATCTACCCTGCCTTT
ATGCTGGGCAGCTCCGTGGGCAACTTCTCCGATGGCAAGATGGGCAGGT
TCTTTAATCACACACTGGTGCTGCTGCCAGACGGATGCGGCACCCTGCT
GAGGGCCTTCTACTGTATCCTGGAGCCCCGCTCTGGAAATCACTGCCCT
GCCGGCAACTCCTACACCTCTTTTGCCACATATCACACCCCTGCCACAG
ACTGTTCCGATGGCAATTATAACCGGAATGCCAGCCTGAACTCCTTCAA
GGAGTACTTTAATCTGAGAAACTGCACCTTCATGTACACATATAATATC
ACCGAGGATGAGATCCTGGAGTGGTTCGGCATCACACAGACCGCCCAGG
GCGTGCACCTGTTTTCTAGCAGATACGTGGATCTGTATGGCGGCAACAT
GTTCCAGTTTGCCACACTGCCAGTGTATGACACCATCAAGTACTATAGC
ATCATCCCCCACTCTATCCGGAGCATCCAGTCCGACAGAAAGGCCTGGG
CCGCCTTCTACGTGTATAAGCTGCAGCCCCTGACCTTCCTGCTGGATTT
TTCCGTGGACGGCTACATCCGGAGAGCCATCGATTGCGGCTTTAACGAC
CTGTCTCAGCTCCACTGTTCTTATGAGAGCTTCGATGTGGAGTCTGGCG
TGTACAGCGTGTCCTCTTTTGAGGCCAAGCCATCTGGCAGCGTGGTGGA
GCAGGCAGAGGGAGTGGAGTGCGACTTCTCCCCACTGCTGTCTGGCACA
CCACCTCAGGTGTATAATTTCAAGAGGCTGGTGTTTACAAACTGTAATT
ACAACCTGACCAAGCTGCTGTCCCTGTTCTCTGTGAACGACTTTACCTG
CAGCCAGATCTCCCCTGCCGCCATCGCCTCCAATTGTTATAGCTCCCTG
ATCCTGGATTACTTCTCTTATCCCCTGTCTATGAAGAGCGACCTGTCCG
TGTCTAGCGCCGGCCCTATCAGCCAGTTTAATTACAAGCAGTCCTTCTC
TAACCCCACATGCCTGATCCTGGCCACCGTGCCTCACAACCTGACCACA
ATCACAAAGCCACTGAAGTACTCCTATATCAATAAGTGCAGCAGGCTGC
TGTCCGACGATCGCACCGAGGTGCCTCAGCTCGTGAACGCCAACCAGTA
CTCTCCATGCGTGAGCATCGTGCCATCCACCGTGTGGGAGGACGGCGAT
TACTATAGAAAGCAGCTCAGCCCACTGGAGGGAGGAGGATGGCTGGTGG
CCAGCGGCTCCACAGTGGCCATGACCGAGCAGCTCCAGATGGGCTTCGG
CATCACAGTGCAGTACGGCACAGATACCAATAGCGTGTGCCCCAAGCTG
```

-continued

```
GAGTTTGCCAACGACACCAAGATCGCCTCCCAGCTCGGCAATTGCGTGG
AGTACTCCCTGTATGGCGTGTCTGGCAGAGGCGTGTTCCAGAACTGTAC
AGCCGTGGGCGTGCGGCAGCAGCGGTTCGTGTACGATGCCTATCAGAAC
CTGGTGGGCTACTATAGCGACGATGGCAATTACTATTGCCTGAGGGCAT
GCGTGAGCGTGCCCGTGAGCGTGATCTACGACAAGGAGACAAAGACCCA
CGCCACCCTGTTCGGCTCCGTGGCCTGCGAGCACATCTCCTCTACAATG
TCTCAGTATTCTAGGAGCACCCGCTCTATGCTGAAGAGGCGCGACAGCA
CATACGGACCACTGCAGACCCCTGTGGGATGCGTGCTGGGCCTGGTGAA
CAGCAGCCTGTTTGTGGAGGATTGCAAGCTGCCACTGGGCCAGTCTCTG
TGCGCACTGCCAGACACCCCCAGCACACTGACCCCACGGTCTGTGAGAA
GCGTGCCCGGAGAGATGAGACTGGCCAGCATCGCCTTCAATCACCCTAT
CCAGGTGGATCAGCTCAACAGCAGCTACTTTAAGCTGAGCATCCCAACA
AACTTCTCCTTTGGCGTGACCCAGGAGTATATCCAGACCACAATCCAGA
AGGTGACCGTGGACTGCAAGCAGTACGTGTGCAATGGCTTCCAGAAGTG
CGAGCAGCTCCTGAGGGAGTATGGCCAGTTTTGTTCCAAGATCAATCAG
GCCCTGCACGGAGCCAACCTGAGGCAGGACGATTCCGTGAGAAACCTGT
TCGCCTCTGTGAAGTCCTCTCAGAGCTCCCCTATCATCCCAGGCTTCGG
CGGCGACTTCAACCTGACCCTGCTGGAGCCCGTGTCCATCTCTACCGGC
AGCAGGTCCGCCCGCAGCGCCATCGAGGATCTGCTGTTTGACAAGGTGA
CCATCGCCGACCCAGGCTACATGCAGGGCTATGACGATTGCATGCAGCA
GGGACCAGCCTCCGCCCGCGATCTGATCTGTGCCCAGTACGTGGCCGGC
TATAAGGTGCTGCCACCCCTGATGGACGTGAACATGGAGGCCGCCTATA
CATCTAGCCTGCTGGGCAGCATCGCAGGAGTGGGATGGACCGCCGGCCT
GTCCTCTTTCGCCGCAATCCCTTTTGCCCAGTCTATCTTCTACCGGCTG
AACGGCGTGGGCATCACACAGCAGGTGCTGAGCGAGAATCAGAAGCTGA
TCGCCAATAAGTTCAACCAGGCCCTGGGGGCCATGCAGACCGGCTTTAC
CACAACCAACGAGGCCTTCCAGAAGGTGCAGGATGCCGTGAACAATAAC
GCACAGGCCCTGTCCAAGCTGGCCTCCGAGCTGTCTAATACCTTCGGGG
CCATCAGCGCCAGCATCGGCGACATCATCCAGCGCCTGGACGTGCTGGA
GCAGGATGCCCAGATCGACAGGCTGATCAATGGCCGCCTGACAACCCTG
AACGCCTTTGTGGCACAGCAGCTCGTGCGGAGCGAGTCTGCCGCCCTGA
GCGCCCAGCTCGCCAAGGACAAGGTGAACGAGTGCGTGAAGGCCCAGAG
CAAGCGGTCCGGCTTTTGTGGCCAGGGCACCCACATCGTGTCCTTCGTG
GTGAATGCCCCTAACGGCCTGTACTTTATGCATGTGGGCTACTATCCAA
GCAACCACATCGAGGTGGTGTCCGCCTATGGCCTGTGCGATGCCGCCAA
TCCTACAAACTGTATCGCCCCAGTGAATGGCTACTTCATCAAGACCAAT
AACACACGGATCGTGGACGAGTGGTCCTACACCGGCAGCTCCTTTTATG
CCCCCGAGCCTATCACATCTCTGAACACCAAGTACGTGGCCCCACAGGT
GACATATCAGAATATCAGCACCAACCTGCCTCCACCCCTGCTGGGCAAT
TCCACCGGCATCGACTTCCAGGATGAGCTGGACGAGTTCTTTAAGAATG
```

-continued

```
TGAGCACATCCATCCCCAACTTTGGCAGCCTGACCCAGATCAACACAAC
CCTGCTGGATCTGACATACGAGATGCTGTCTCTGCAGCAGGTGGTGAAG
GCCCTGAATGAGAGCTACATCGACCTGAAGGAGCTGGGCAATTATACCT
ACTATAACAAGTGGCCTTGGTACATCTGGCTGGGCTTCATCGCAGGCCT
GGTGGCCCTGGCCCTGTGCGTGTTCTTTATCCTGTGCTGTACAGGCTGC
GGCACCAATTGTATGGGCAAGCTGAAGTGTAACCGGTGCTGTGATAGAT
ACGAGGAGTATGACCTGGAGCCACACAAGGTGCATGTGCACTGA
```

SEQ ID NO: 13 is a SARS-CoV-2 "Proline Modified" Spike Glycoprotein, Amino Acid Sequence MFVFLVLLPLVSSQCVNLTTRTQLPPAYTNSFTRGVYYPDKVFRSSVLH
STQDLFLPFFSNVTWFHAIHVSGTNGTKRFDNPVLPFNDGVYFASTEKS
NIIRGWIFGTTLDSKTQSLLIVNNATNVVIKVCEFQFCNDPFLGVYYHK
NNKSWMESEFRVYSSANNCTFEYVSQPFLMDLEGKQGNFKNLREFVFKN
IDGYFKIYSKHTPINLVRDLPQGFSALEPLVDLPIGINITRFQTLLALH
RSYLTPGDSSSGWTAGAAAYYVGYLQPRTFLLKYNENGTITDAVDCALD
PLSETKCTLKSFTVEKGIYQTSNFRVQPTESIVRFPNITNLCPFGEVFN
ATRFASVYAWNRKRISNCVADYSVLYNSASFSTFKCYGVSPTKLNDLCF
TNVYADSFVIRGDEVRQIAPGQTGKIADYNYKLPDDFTGCVIAWNSNNL
DSKVGGNYNYLYRLFRKSNLKPFERDISTEIYQAGSTPCNGVEGFNCYF
PLQSYGFQPTNGVGYQPYRVVVLSFELLHAPATVCGPKKSTNLVKNKCV
NFNFNGLTGTGVLTESNKKFLPFQQFGRDIADTTDAVRDPQTLEILDIT
PCSFGGVSVITPGTNTSNQVAVLYQDVNCTEVPVAIHADQLTPTWRVYS
TGSNVFQTRAGCLIGAEHVNNSYECDIPIGAGICASYQTQTNSPRRARS
VASQSIIAYTMSLGAENSVAYSNNSIAIPTNFTISVTTEILPVSMTKTS
VDCTMYICGDSTECSNLLLQYGSFCTQLNRALTGIAVEQDKNTQEVFAQ
VKQIYKTPPIKDFGGFNFSQILPDPSKPSKRSFIEDLLFNKVTLADAGF
IKQYGDCLGDIAARDLICAQKFNGLTVLPPLLTDEMIAQYTSALLAGTI
TSGWTFGAGAALQIPFAMQMAYRFNGIGVTQNVLYENQKLIANQFNSAI
GKIQDSLSSTASALGKLQDVVNQNAQALNTLVKQLSSNFGAISSVLNDI
LSRLDPPEAEVQDRLITGRLQSLQTYVTQQLIRAAEIRASANLAATKMS
ECVLGQSKRVDFCGKGYHLMSFPQSAPHGVVFLHVTYVPAQEKNFTTAP
AICHDGKAHFPREGVFVSNGTHWFVTQRNFYEPQIITTDNTFVSGNCDV
VIGIVNNTVYDPLQPELDSFKEELDKYFKNHTSPDVDLGDISGINASVV
NIQKEIDRLNEVAKNLNESLIDLQELGKYEQYIKWPWYIWLGFIAGLIA
IVMVTIMLCCMTSCCSCLKGCCSCGSCCKFDEDDSEPVLKGVKLHYT SEQ ID NO: 14 is a SARS-CoV-2 "Proline Modified" Spike Glycoprotein, Nucleotide Sequence

```
ATGTTTGTTTTTCTTGTTTTATTGCCACTAGTCTCTAGTCAGTGTGTTA
ATCTTACAACCAGAACTCAATTACCCCCTGCATACACTAATTCTTTCAC
ACGTGGTGTTTATTACCCTGACAAAGTTTTCAGATCCTCAGTTTTACAT
```

-continued

TCAACTCAGGACTTGTTCTTACCTTTCTTTTCCAATGTTACTTGGTTCC
ATGCTATACATGTCTCTGGGACCAATGGTACTAAGAGGTTTGATAACCC
TGTCCTACCATTTAATGATGGTGTTTATTTTGCTTCCACTGAGAAGTCT
AACATAATAAGAGGCTGGATTTTTGGTACTACTTTAGATTCGAAGACCC
AGTCCCTACTTATTGTTAATAACGCTACTAATGTTGTTATTAAAGTCTG
TGAATTTCAATTTTGTAATGATCCATTTTTGGGTGTTTATTACCACAAA
AACAACAAAAGTTGGATGGAAAGTGAGTTCAGAGTTTATTCTAGTGCGA
ATAATTGCACTTTTGAATATGTCTCTCAGCCTTTTCTTATGGACCTTGA
AGGAAAACAGGGTAATTTCAAAAATCTTAGGGAATTTGTGTTTAAGAAT
ATTGATGGTTATTTTAAAATATATTCTAAGCACACGCCTATTAATTTAG
TGCGTGATCTCCCTCAGGGTTTTTCGGCTTTAGAACCATTGGTAGATTT
GCCAATAGGTATTAACATCACTAGGTTTCAAACTTTACTTGCTTTACAT
AGAAGTTATTTGACTCCTGGTGATTCTTCTTCAGGTTGGACAGCTGGTG
CTGCAGCTTATTATGTGGGTTATCTTCAACCTAGGACTTTTCTATTAAA
ATATAATGAAAATGGAACCATTACAGATGCTGTAGACTGTGCACTTGAC
CCTCTCTCAGAAACAAAGTGTACGTTGAAATCCTTCACTGTAGAAAAAG
GAATCTATCAAACTTCTAACTTTAGAGTCCAACCAACAGAATCTATTGT
TAGATTTCCTAATATTACAAACTTGTGCCCTTTTGGTGAAGTTTTTAAC
GCCACCAGATTTGCATCTGTTTATGCTTGGAACAGGAAGAGAATCAGCA
ACTGTGTTGCTGATTATTCTGTCCTATATAATTCCGCATCATTTTCCAC
TTTTAAGTGTTATGGAGTGTCTCCTACTAAATTAAATGATCTCTGCTTT
ACTAATGTCTATGCAGATTCATTTGTAATTAGAGGTGATGAAGTCAGAC
AAATCGCTCCAGGGCAAACTGGAAAGATTGCTGATTATAATTATAAATT
ACCAGATGATTTTACAGGCTGCGTTATAGCTTGGAATTCTAACAATCTT
GATTCTAAGGTTGGTGGTAATTATAATTACCTGTATAGATTGTTTAGGA
AGTCTAATCTCAAACCTTTTGAGAGAGATATTTCAACTGAAATCTATCA
GGCCGGTAGCACACCTTGTAATGGTGTTGAAGGTTTTAATTGTTACTTT
CCTTTACAATCATATGGTTTCCAACCCACTAATGGTGTTGGTTACCAAC
CATACAGAGTAGTAGTACTTTCTTTTGAACTTCTACATGCACCAGCAAC
TGTTTGTGGACCTAAAAAGTCTACTAATTTGGTTAAAAACAAATGTGTC
AATTTCAACTTCAATGGTTTAACAGGCACAGGTGTTCTTACTGAGTCTA
ACAAAAAGTTTCTGCCTTTCCAACAATTTGGCAGAGACATTGCTGACAC
TACTGATGCTGTCCGTGATCCACAGACACTTGAGATTCTTGACATTACA
CCATGTTCTTTTGGTGGTGTCAGTGTTATAACACCAGGAACAAATACTT
CTAACCAGGTTGCTGTTCTTTATCAGGATGTTAACTGCACAGAAGTCCC
TGTTGCTATTCATGCAGATCAACTTACTCCTACTTGGCGTGTTTATTCT
ACAGGTTCTAATGTTTTTCAAACACGTGCAGGCTGTTTAATAGGGGCTG
AACATGTCAACAACTCATATGAGTGTGACATACCCATTGGTGCAGGTAT
ATGCGCTAGTTATCAGACTCAGACTAATTCTCCTCGGCGGGCACGTAGT
GTAGCTAGTCAATCCATCATTGCCTACACTATGTCACTTGGTGCAGAAA

-continued

ATTCAGTTGCTTACTCTAATAACTCTATTGCCATACCCACAAATTTTAC
TATTAGTGTTACCACAGAAATTCTACCAGTGTCTATGACCAAGACATCA
GTAGATTGTACAATGTACATTTGTGGTGATTCAACTGAATGCAGCAATC
TTTTGTTGCAATATGGCAGTTTTTGTACACAATTAAACCGTGCTTTAAC
TGGAATAGCTGTTGAACAAGACAAAAACACCCAAGAAGTTTTTGCACAA
GTCAAACAAATTTACAAAACACCACCAATTAAAGATTTTGGTGGTTTTA
ATTTTTCACAAATATTACCAGATCCATCAAAACCAAGCAAGAGGTCATT
TATTGAAGATCTACTTTTCAACAAAGTGACACTTGCAGATGCTGGCTTC
ATCAAACAATATGGTGATTGCCTTGGTGATATTGCTGCTAGAGACCTCA
TTTGTGCACAAAAGTTTAACGGCCTTACTGTTTTGCCACCTTTGCTCAC
AGATGAAATGATTGCTCAATACACTTCTGCACTGTTAGCGGGTACAATC
ACTTCTGGTTGGACCTTTGGTGCAGGTGCTGCATTACAAATACCATTTG
CTATGCAAATGGCTTATAGGTTTAATGGTATTGGAGTTACACAGAATGT
TCTCTATGAGAACCAAAAATTGATTGCCAACCAATTTAATAGTGCTATT
GGCAAAATTCAAGACTCACTTTCTTCCACAGCAAGTGCACTTGGAAAAC
TTCAAGATGTGGTCAACCAAAATGCACAAGCTTTAAACACGCTTGTTAA
ACAACTTAGCTCCAATTTTGGTGCAATTTCAAGTGTTTTAAATGATATC
CTTTCACGTCTTGACCCTCCTGAGGCTGAAGTGCAAATTGATAGGTTGA
TCACAGGCAGACTTCAAAGTTTGCAGACATATGTGACTCAACAATTAAT
TAGAGCTGCAGAAATCAGAGCTTCTGCTAATCTTGCTGCTACTAAAATG
TCAGAGTGTGTACTTGGACAATCAAAAAGAGTTGATTTTTGTGGAAAGG
GCTATCATCTTATGTCCTTCCCTCAGTCAGCACCTCATGGTGTAGTCTT
CTTGCATGTGACTTATGTCCCTGCACAAGAAAAGAACTTCACAACTGCT
CCTGCCATTTGTCATGATGGAAAAGCACACTTTCCTCGTGAAGGTGTCT
TTGTTTCAAATGGCACACACTGGTTTGTAACACAAAGGAATTTTTATGA
ACCACAAATCATTACTACAGACAACACATTTGTGTCTGGTAACTGTGAT
GTTGTAATAGGAATTGTCAACAACACAGTTTATGATCCTTTGCAACCTG
AATTAGACTCATTCAAGGAGGAGTTAGATAAATATTTTAAGAATCATAC
ATCACCAGATGTTGATTTAGGTGACATCTCTGGCATTAATGCTTCAGTT
GTAAACATTCAAAAAGAAATTGACCGCCTCAATGAGGTTGCCAAGAATT
TAAATGAATCTCTCATCGATCTCCAAGAACTTGGAAAGTATGAGCAGTA
TATAAAATGGCCATGGTACATTTGGCTAGGTTTTATAGCTGGCTTGATT
GCCATAGTAATGGTGACAATTATGCTTTGCTGTATGACCAGTTGCTGTA
GTTGTCTCAAGGGCTGTTGTTCTTGTGGATCCTGCTGCAAATTTGATGA
AGACGACTCTGAGCCAGTGCTCAAAGGAGTCAAATTACATTACACATAA

SEQ ID NO: 15 is a SARS-CoV-2 "Proline Modified" Spike Glycoprotein, Nucleotide Sequence, Codon Optimized for Expression In Human Cells ATGTTCGTGTTTCTGGTGCTGCTGCCTCTGGTGAGCTCCCAGTGCGTGA
ACCTGACCACAAGGACCCAGCTCCCCCCTGCCTATACCAATTCCTTCAC
ACGGGGCGTGTACTATCCAGACAAGGTGTTTAGATCTAGCGTGCTGCAC -continued TCCACACAGGATCTGTTTCTGCCCTTCTTTTCTAACGTGACCTGGTTCC
ACGCCATCCATGTGAGCGGCACCAATGGCACAAAGCGGTTCGACAATCC
TGTGCTGCCCTTCAACGATGGCGTGTACTTCGCCTCCACCGAGAAGTCT
AACATCATCAGAGGCTGGATCTTTGGCACCACACTGGACAGCAAGACAC
AGTCCCTGCTGATCGTGAACAATGCCACCAACGTGGTCATCAAGGTGTG
CGAGTTCCAGTTTTGTAATGATCCTTTCCTGGGCGTGTACTATCACAAG
AACAATAAGTCTTGGATGGAGAGCGAGTTTCGCGTGTATTCCTCTGCCA
ACAATTGCACATTTGAGTACGTGTCCCAGCCATTCCTGATGGACCTGGA
GGGCAAGCAGGGCAATTTCAAGAACCTGAGGGAGTTCGTGTTTAAGAAT
ATCGATGGCTACTTCAAGATCTACTCCAAGCACACCCCTATCAACCTGG
TGCGCGACCTGCCACAGGGCTTCTCTGCCCTGGAGCCTCTGGTGGATCT
GCCAATCGGCATCAACATCACCCGGTTTCAGACACTGCTGGCCCTGCAC
AGAAGCTACCTGACACCTGGCGACAGCTCCTCTGGATGGACCGCCGGGG
CCGCCGCCTACTATGTGGGCTATCTGCAGCCAAGGACCTTCCTGCTGAA
GTACAACGAGAATGGCACCATCACAGACGCAGTGGATTGCGCCCTGGAC
CCCCTGTCTGAGACCAAGTGTACACTGAAGAGCTTTACCGTGGAGAAGG
GCATCTATCAGACAAGCAATTTCAGGGTGCAGCCCACCGAGTCCATCGT
GCGCTTTCCAAATATCACAAACCTGTGCCCCTTTGGCGAGGTGTTCAAC
GCAACCAGGTTCGCCAGCGTGTACGCATGGAATAGGAAGCGCATCTCCA
ACTGCGTGGCCGACTATTCTGTGCTGTACAACAGCGCCTCCTTCTCTAC
CTTTAAGTGCTATGGCGTGAGCCCCACAAAGCTGAATGACCTGTGCTTT
ACCAACGTGTACGCCGATTCCTTCGTGATCAGGGGCGACGAGGTGCGCC
AGATCGCACCAGGACAGACAGGCAAGATCGCCGACTACAATTATAAGCT
GCCCGACGATTTCACCGGCTGCGTGATCGCCTGGAACTCTAACAATCTG
GATAGCAAAGTGGGCGGCAACTACAATTATCTGTACCGGCTGTTTAGAA
AGTCTAATCTGAAGCCTTTCGAGAGGGACATCTCCACAGAGATCTACCA
GGCCGGCTCTACCCCATGCAATGGCGTGGAGGGCTTTAACTGTTATTTC
CCCCTGCAGAGCTACGGCTTCCAGCCTACAAACGGCGTGGGCTATCAGC
CATACCGCGTGGTGGTGCTGTCTTTTGAGCTGCTGCACGCACCAGCAAC
AGTGTGCGGACCTAAGAAGAGCACCAATCTGGTGAAGAACAAGTGCGTG
AACTTCAACTTCAACGGCCTGACCGGCACAGGCGTGCTGACCGAGTCCA
ACAAGAAGTTCCTGCCCTTTCAGCAGTTCGGCAGGGACATCGCAGATAC
CACAGACGCCGTGCGCGACCCCCAGACCCTGGAGATCCTGGACATCACA
CCTTGCTCCTTCGGCGGCGTGTCTGTGATCACACCTGGCACCAATACAA
GCAACCAGGTGGCCGTGCTGTATCAGGACGTGAATTGTACCGAGGTGCC
AGTGGCCATCCACGCCGATCAGCTCACCCCCACATGGCGGGTGTACTCT
ACCGGCAGCAACGTGTTCCAGACAAGAGCCGGCTGCCTGATCGGAGCCG
AGCATGTGAACAATAGCTATGAGTGCGACATCCCCATCGGAGCCGGCAT
CTGTGCCTCCTACCAGACCCAGACAAACTCCCCTCGGAGAGCCCGGTCT
GTGGCCAGCCAGTCCATCATCGCCTATACCATGAGCCTGGGGGCCGAGA -continued ACAGCGTGGCCTACTCCAACAATTCTATCGCCATCCCCACCAACTTCAC
AATCTCCGTGACCACAGAGATCCTGCCTGTGAGCATGACCAAGACATCC
GTGGACTGCACAATGTATATCTGTGGCGATTCCACCGAGTGCTCTAACC
TGCTGCTGCAGTACGGCTCTTTTTGTACCCAGCTCAACAGAGCCCTGAC
AGGCATCGCCGTGGAGCAGGACAAGAACACACAGGAGGTGTTCGCCCAG
GTGAAGCAGATCTACAAGACCCCACCCATCAAGGACTTTGGCGGCTTCA
ACTTCAGCCAGATCCTGCCAGATCCCAGCAAGCCTTCCAAGCGGTCTTT
TATCGAGGACCTGCTGTTCAACAAGGTGACCCTGGCCGATGCCGGCTTC
ATCAAGCAGTATGGCGATTGCCTGGGCGACATCGCCGCCAGAGACCTGA
TCTGTGCCCAGAAGTTTAATGGCCTGACCGTGCTGCCTCCACTGCTGAC
AGATGAGATGATCGCCCAGTACACATCTGCCCTGCTGGCCGGCACCATC
ACAAGCGGATGGACCTTCGGGGCCGGGGCCGCCCTGCAGATCCCATTTG
CCATGCAGATGGCCTATCGGTTCAACGGCATCGGCGTGACCCAGAATGT
GCTGTACGAGAACCAGAAGCTGATCGCCAATCAGTTTAACTCCGCCATC
GGCAAGATCCAGGACTCTCTGAGCTCCACAGCCAGCGCCCTGGGCAAGC
TGCAGGATGTGGTGAATCAGAACGCCCAGGCCCTGAATACCCTGGTGAA
GCAGCTCAGCAGCAACTTCGGGGCCATCAGCAGCGTGCTGAACGACATC
CTGAGCCGGCTGGACCCCCCTGAGGCAGAGGTGCAGATCGACCGGCTGA
TCACAGGCAGACTGCAGTCCCTGCAGACCTACGTGACACAGCAGCTCAT
CAGGGCCGCCGAGATCAGGGCCTCTGCCAATCTGGCCGCCACCAAGATG
AGCGAGTGCGTGCTGGGCCAGTCCAAGAGAGTGGACTTTTGTGGCAAGG
GCTATCACCTGATGAGCTTCCCACAGTCCGCCCCCCACGGAGTGGTGTT
TCTGCATGTGACCTACGTGCCTGCCCAGGAGAAGAACTTCACCACAGCC
CCAGCCATCTGCCACGATGGCAAGGCCCACTTTCCCAGGGAGGGCGTGT
TCGTGAGCAACGGCACCCACTGGTTTGTGACACAGCGCAATTTCTACGA
GCCTCAGATCATCACCACAGACAATACATTCGTGTCCGGCAACTGTGAC
GTGGTCATCGGCATCGTGAACAATACCGTGTATGATCCCCTGCAGCCTG
AGCTGGACTCTTTTAAGGAGGAGCTGGATAAGTACTTCAAGAATCACAC
CAGCCCCGACGTGGATCTGGGCGACATCTCTGGCATCAATGCCAGCGTG
GTGAACATCCAGAAGGAGATCGACAGGCTGAACGAGGTGGCCAAGAATC
TGAACGAGTCCCTGATCGATCTGCAGGAGCTGGGCAAGTATGAGCAGTA
CATCAAGTGGCCATGGTATATCTGGCTGGGCTTCATCGCCGGCCTGATC
GCCATCGTGATGGTGACCATCATGCTGTGCTGTATGACAAGCTGCTGTT
CCTGCCTGAAGGGCTGCTGTTCTTGTGGCTCCTGCTGTAAGTTTGATGA
GGACGATAGCGAGCCCGTGCTGAAGGGCGTGAAGCTGCACTACACCTGA SEQ ID NO: 16 is a SARS-CoV-2 "Furin Cleavage Modified" Spike Glycoprotein, Amino Acid Sequence MFVFLVLLPLVSSQCVNLTTRTQLPPAYTNSFTRGVYYPDKVFRSSVLH
STQDLFLPFFSNVTWFHAIHVSGTNGTKRFDNPVLPFNDGVYFASTEKS
NIIRGWIFGTTLDSKTQSLLIVNNATNVVIKVCEFQFCNDPFLGVYYHK -continued

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPGSASS

VASQSIIAYTMSLGAENSVAYSNNSIAIPTNFTISVTTEILPVSMTKTS

VDCTMYICGDSTECSNLLLQYGSFCTQLNRALTGIAVEQDKNTQEVFAQ

VKQIYKTPPIKDFGGFNFSQILPDPSKPSKRSFIEDLLFNKVTLADAGF

IKQYGDCLGDIAARDLICAQKFNGLTVLPPLLTDEMIAQYTSALLAGTI

TSGWTFGAGAALQIPFAMQMAYRFNGIGVTQNVLYENQKLIANQFNSAI

GKIQDSLSSTASALGKLQDVVNQNAQALNTLVKQLSSNFGAISSVLNDI

LSRLDKVEAEVQIDRLITGRLQSLQTYVTQQLIRAAEIRASANLAATKM

SECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCD

VVIGIVNNTVYDPLQPELDSFKEELDKYFKNHTSPDVDLGDISGINASV

VNIQKEIDRLNEVAKNLNESLIDLQELGKYEQYIKWPWYIWLGFIAGLI

AIVMVTIMLCCMTSCCSCLKGCCSCGSCCKFDEDDSEPVLKGVKLHYT

SEQ ID NO: 17 is a SARS-CoV-2 “Furin Cleavage Modified” Spike Glycoprotein, Nucleotide Sequence

ATGTTTGTTTTTCTTGTTTTATTGCCACTAGTCTCTAGTCAGTGTGTTA

ATCTTACAACCAGAACTCAATTACCCCCTGCATACACTAATTCTTTCAC

ACGTGGTGTTTATTACCCTGACAAAGTTTTCAGATCCTCAGTTTTACAT

TCAACTCAGGACTTGTTCTTACCTTTCTTTTCCAATGTTACTTGGTTCC

ATGCTATACATGTCTCTGGGACCAATGGTACTAAGAGGTTTGATAACCC

TGTCCTACCATTTAATGATGGTGTTTATTTTGCTTCCACTGAGAAGTCT

AACATAATAAGAGGCTGGATTTTTGGTACTACTTTAGATTCGAAGACCC

AGTCCCTACTTATTGTTAATAACGCTACTAATGTTGTTATTAAAGTCTG

TGAATTTCAATTTTGTAATGATCCATTTTTGGGTGTTTATTACCACAAA

AACAACAAAAGTTGGATGGAAAGTGAGTTCAGAGTTTATTCTAGTGCGA

ATAATTGCACTTTTGAATATGTCTCTCAGCCTTTTCTTATGGACCTTGA

AGGAAAACAGGGTAATTTCAAAAATCTTAGGGAATTTGTGTTTAAGAAT

ATTGATGGTTATTTTAAAATATATTCTAAGCACACGCCTATTAATTTAG

TGCGTGATCTCCCTCAGGGTTTTTCGGCTTTAGAACCATTGGTAGATTT

GCCAATAGGTATTAACATCACTAGGTTTCAAACTTTACTTGCTTTACAT

-continued

AGAAGTTATTTGACTCCTGGTGATTCTTCTTCAGGTTGGACAGCTGGTG

CTGCAGCTTATTATGTGGGTTATCTTCAACCTAGGACTTTTCTATTAAA

ATATAATGAAAATGGAACCATTACAGATGCTGTAGACTGTGCACTTGAC

CCTCTCTCAGAAACAAAGTGTACGTTGAAATCCTTCACTGTAGAAAAAG

GAATCTATCAAACTTCTAACTTTAGAGTCCAACCAACAGAATCTATTGT

TAGATTTCCTAATATTACAAACTTGTGCCCTTTTGGTGAAGTTTTTAAC

GCCACCAGATTTGCATCTGTTTATGCTTGGAACAGGAAGAGAATCAGCA

ACTGTGTTGCTGATTATTCTGTCCTATATAATTCCGCATCATTTTCCAC

TTTTAAGTGTTATGGAGTGTCTCCTACTAAATTAAATGATCTCTGCTTT

ACTAATGTCTATGCAGATTCATTTGTAATTAGAGGTGATGAAGTCAGAC

AAATCGCTCCAGGGCAAACTGGAAAGATTGCTGATTATAATTATAAATT

ACCAGATGATTTTACAGGCTGCGTTATAGCTTGGAATTCTAACAATCTT

GATTCTAAGGTTGGTGGTAATTATAATTACCTGTATAGATTGTTTAGGA

AGTCTAATCTCAAACCTTTTGAGAGAGATATTTCAACTGAAATCTATCA

GGCCGGTAGCACACCTTGTAATGGTGTTGAAGGTTTTAATTGTTACTTT

CCTTTACAATCATATGGTTTCCAACCCACTAATGGTGTTGGTTACCAAC

CATACAGAGTAGTAGTACTTTCTTTTGAACTTCTACATGCACCAGCAAC

TGTTTGTGGACCTAAAAAGTCTACTAATTTGGTTAAAAACAAATGTGTC

AATTTCAACTTCAATGGTTTAACAGGCACAGGTGTTCTTACTGAGTCTA

ACAAAAAGTTTCTGCCTTTCCAACAATTTGGCAGAGACATTGCTGACAC

TACTGATGCTGTCCGTGATCCACAGACACTTGAGATTCTTGACATTACA

CCATGTTCTTTTGGTGGTGTCAGTGTTATAACACCAGGAACAAATACTT

CTAACCAGGTTGCTGTTCTTTATCAGGATGTTAACTGCACAGAAGTCCC

TGTTGCTATTCATGCAGATCAACTTACTCCTACTTGGCGTGTTTATTCT

ACAGGTTCTAATGTTTTTCAAACACGTGCAGGCTGTTTAATAGGGGCTG

AACATGTCAACAACTCATATGAGTGTGACATACCCATTGGTGCAGGTAT

ATGCGCTAGTTATCAGACTCAGACTAATTCTCCTGGTAGTGCAAGTAGT

GTAGCTAGTCAATCCATCATTGCCTACACTATGTCACTTGGTGCAGAAA

ATTCAGTTGCTTACTCTAATAACTCTATTGCCATACCCACAAATTTTAC

TATTAGTGTTACCACAGAAATTCTACCAGTGTCTATGACCAAGACATCA

GTAGATTGTACAATGTACATTTGTGGTGATTCAACTGAATGCAGCAATC

TTTTGTTGCAATATGGCAGTTTTTGTACACAATTAAACCGTGCTTTAAC

TGGAATAGCTGTTGAACAAGACAAAAACACCCAAGAAGTTTTTGCACAA

GTCAAACAAATTTACAAAACACCACCAATTAAAGATTTTGGTGGTTTTA

ATTTTTCACAAATATTACCAGATCCATCAAAACCAAGCAAGAGGTCATT

TATTGAAGATCTACTTTTCAACAAAGTGACACTTGCAGATGCTGGCTTC

ATCAAACAATATGGTGATTGCCTTGGTGATATTGCTGCTAGAGACCTCA

TTTGTGCACAAAAGTTTAACGGCCTTACTGTTTTGCCACCTTTGCTCAC

AGATGAAATGATTGCTCAATACACTTCTGCACTGTTAGCGGGTACAATC

ACTTCTGGTTGGACCTTTGGTGCAGGTGCTGCATTACAAATACCATTTG

CTATGCAAATGGCTTATAGGTTTAATGGTATTGGAGTTACACAGAATGT

-continued

TCTCTATGAGAACCAAAAAATTGATTGCCAACCAATTTAATAGTGCTATT

GGCAAAATTCAAGACTCACTTTCTTCCACAGCAAGTGCACTTGGAAAAC

TTCAAGATGTGGTCAACCAAAATGCACAAGCTTTAAACACGCTTGTTAA

ACAACTTAGCTCCAATTTTGGTGCAATTTCAAGTGTTTTAAATGATATC

CTTTCACGTCTTGACAAAGTTGAGGCTGAAGTGCAAATTGATAGGTTGA

TCACAGGCAGACTTCAAAGTTTGCAGACATATGTGACTCAACAATTAAT

TAGAGCTGCAGAAATCAGAGCTTCTGCTAATCTTGCTGCTACTAAAATG

TCAGAGTGTGTACTTGGACAATCAAAAAGAGTTGATTTTTGTGGAAAGG

GCTATCATCTTATGTCCTTCCCTCAGTCAGCACCTCATGGTGTAGTCTT

CTTGCATGTGACTTATGTCCCTGCACAAGAAAAGAACTTCACAACTGCT

CCTGCCATTTGTCATGATGGAAAAGCACACTTTCCTCGTGAAGGTGTCT

TTGTTTCAAATGGCACACACTGGTTTGTAACACAAAGGAATTTTTATGA

ACCACAAATCATTACTACAGACAACACATTTGTGTCTGGTAACTGTGAT

GTTGTAATAGGAATTGTCAACAACACAGTTTATGATCCTTTGCAACCTG

AATTAGACTCATTCAAGGAGGAGTTAGATAAATATTTTAAGAATCATAC

ATCACCAGATGTTGATTTAGGTGACATCTCTGGCATTAATGCTTCAGTT

GTAAACATTCAAAAAGAAATTGACCGCCTCAATGAGGTTGCCAAGAATT

TAAATGAATCTCTCATCGATCTCCAAGAACTTGGAAAGTATGAGCAGTA

TATAAAATGGCCATGGTACATTTGGCTAGGTTTTATAGCTGGCTTGATT

GCCATAGTAATGGTGACAATTATGCTTTGCTGTATGACCAGTTGCTGTA

GTTGTCTCAAGGGCTGTTGTTCTTGTGGATCCTGCTGCAAATTTGATGA

AGACGACTCTGAGCCAGTGCTCAAAGGAGTCAAATTACATTACACATAA

SEQ ID NO: 18 is a SARS-CoV-2 "Furin Cleavage Modified" Spike Glycoprotein, Nucleotide Sequence, Codon Optimized For Expression In Human Cells

ATGTTCGTGTTTCTGGTGCTGCTGCCTCTGGTGAGCTCCCAGTGCGTGA

ACCTGACCACAAGGACCCAGCTCCCCCCTGCCTATACCAATTCCTTCAC

AAGGGGCGTGTACTATCCCGACAAGGTGTTTCGCTCTAGCGTGCTGCAC

AGCACACAGGATCTGTTTCTGCCTTTCTTTTCCAACGTGACCTGGTTCC

ACGCCATCCATGTGAGCGGCACCAATGGCACAAAGAGGTTCGACAATCC

AGTGCTGCCCTTTAACGATGGCGTGTACTTCGCCTCTACCGAGAAGAGC

AACATCATCCGCGGCTGGATCTTTGGCACCACACTGGACTCCAAGACAC

AGTCTCTGCTGATCGTGAACAATGCCACCAACGTGGTCATCAAGGTGTG

CGAGTTCCAGTTTTGTAATGATCCATTCCTGGGCGTGTACTATCACAAG

AACAATAAGAGCTGGATGGAGTCCGAGTTTCGCGTGTATTCCTCTGCCA

ACAATTGCACATTTGAGTACGTGTCCCAGCCCTTCCTGATGGACCTGGA

GGGCAAGCAGGGCAATTTCAAGAACCTGCGGGAGTTCGTGTTTAAGAAT

ATCGATGGCTACTTCAAGATCTACAGCAAGCACACCCCAATCAACCTGG

TGAGAGACCTGCCACAGGGCTTCTCCGCCCTGGAGCCACTGGTGGATCT

GCCCATCGGCATCAACATCACCAGGTTTCAGACACTGCTGGCCCTGCAC

-continued

CGCAGCTACCTGACACCAGGCGACAGCTCCTCTGGATGGACCGCCGGGG

CCGCCGCCTACTATGTGGGCTATCTGCAGCCCCGGACCTTCCTGCTGAA

GTACAACGAGAATGGCACCATCACAGACGCAGTGGATTGCGCCCTGGAC

CCCCTGTCCGAGACCAAGTGTACACTGAAGTCTTTTACCGTGGAGAAGG

GCATCTATCAGACATCTAATTTCCGGGTGCAGCCTACCGAGAGCATCGT

GAGATTTCCCAATATCACAAACCTGTGCCCTTTTGGCGAGGTGTTCAAC

GCCACCAGATTCGCCAGCGTGTACGCCTGGAATCGGAAGAGAATCAGCA

ACTGCGTGGCCGACTATTCCGTGCTGTACAACTCTGCCAGCTTCTCCAC

CTTTAAGTGCTATGGCGTGTCTCCCACAAAGCTGAATGACCTGTGCTTT

ACCAACGTGTACGCCGATAGCTTCGTGATCAGGGGCGACGAGGTGAGAC

AGATCGCACCAGGACAGACAGGCAAGATCGCAGACTACAATTATAAGCT

GCCTGACGATTTCACCGGCTGCGTGATCGCCTGGAACAGCAACAATCTG

GATTCCAAAGTGGGCGGCAACTACAATTATCTGTACAGGCTGTTTCGCA

AGTCCAATCTGAAGCCATTCGAGCGGGACATCAGCACAGAGATCTACCA

GGCAGGCTCCACCCCATGCAATGGAGTGGAGGGCTTTAACTGTTATTTC

CCTCTGCAGTCTTACGGCTTCCAGCCAACAAACGGCGTGGGCTATCAGC

CCTACAGAGTGGTGGTGCTGTCCTTTGAGCTGCTGCACGCACCTGCAAC

AGTGTGCGGACCAAAGAAGTCTACCAATCTGGTGAAGAACAAGTGCGTG

AACTTCAACTTCAACGGCCTGACCGGCACAGGCGTGCTGACCGAGTCCA

ACAAGAAGTTCCTGCCTTTTCAGCAGTTCGGCAGAGACATCGCCGATAC

CACAGACGCCGTGAGAGACCCTCAGACCCTGGAGATCCTGGACATCACA

CCATGCTCTTTCGGCGGCGTGAGCGTGATCACACCAGGCACCAATACAA

GCAACCAGGTGGCCGTGCTGTATCAGGACGTGAATTGTACCGAGGTGCC

CGTGGCCATCCACGCAGATCAGCTCACCCCTACATGGAGGGTGTACTCC

ACCGGCTCTAACGTGTTCCAGACACGCGCCGGATGCCTGATCGGAGCCG

AGCATGTGAACAATTCTTATGAGTGCGACATCCCTATCGGAGCCGGCAT

CTGTGCCAGCTACCAGACCCAGACAAACAGCCCAGGCTCCGCCAGCTCC

GTGGCCTCTCAGAGCATCATCGCCTATACCATGAGCCTGGGGGCCGAGA

ATAGCGTGGCCTACTCTAACAATAGCATCGCCATCCCTACCAACTTCAC

AATCTCCGTGACCACAGAGATCCTGCCAGTGTCCATGACCAAGACATCT

GTGGACTGCACAATGTATATCTGTGGCGATTCTACCGAGTGCAGCAACC

TGCTGCTGCAGTACGGCAGCTTTTGTACCCAGCTCAACCGGGCCCTGAC

AGGAATCGCAGTGGAGCAGGACAAGAACACACAGGAGGTGTTCGCCCAG

GTGAAGCAGATCTACAAGACCCCACCCATCAAGGACTTTGGCGGCTTCA

ACTTCAGCCAGATCCTGCCCGATCCTTCCAAGCCATCTAAGAGGAGCTT

TATCGAGGACCTGCTGTTCAACAAGGTGACCCTGGCCGATGCCGGCTTC

ATCAAGCAGTATGGCGATTGCCTGGGCGACATCGCAGCCCGCGACCTGA

TCTGTGCCCAGAAGTTTAATGGCCTGACCGTGCTGCCTCCACTGCTGAC

AGATGAGATGATCGCACAGTACACATCCGCCCTGCTGGCCGGCACCATC

ACATCTGGATGGACCTTCGGGGCCGGGGCCGCCCTGCAGATCCCCTTTG

CCATGCAGATGGCCTATAGATTCAACGGCATCGGCGTGACCCAGAATGT

-continued

GCTGTACGAGAACCAGAAGCTGATCGCCAATCAGTTTAACTCCGCCATC
GGCAAGATCCAGGACTCCCTGTCTAGCACAGCCTCTGCCCTGGGCAAGC
TGCAGGATGTGGTGAATCAGAACGCCCAGGCCCTGAATACCCTGGTGAA
GCAGCTCAGCAGCAACTTCGGGGCCATCAGCAGCGTGCTGAACGACATC
CTGAGCCGGCTGGACAAGGTGGAGGCAGAGGTGCAGATCGACAGGCTGA
TCACAGGCCGCCTGCAGAGCCTGCAGACCTACGTGACACAGCAGCTCAT
CAGGGCCGCCGAGATCAGAGCCTCCGCCAATCTGGCCGCCACCAAGATG
TCTGAGTGCGTGCTGGGCCAGAGCAAGCGCGTGGACTTTTGTGGCAAGG
GCTATCACCTGATGTCCTTCCCACAGTCTGCCCCTCACGGAGTGGTGTT
TCTGCATGTGACCTACGTGCCAGCCCAGGAGAAGAACTTCACCACAGCC
CCCGCAATCTGCCACGATGGCAAGGCACACTTTCCTCGGGAGGGCGTGT
TCGTGTCTAACGGCACCCACTGGTTTGTGACACAGAGAAATTTCTACGA
GCCACAGATCATCACCACAGACAATACATTCGTGAGCGGCAACTGTGAC
GTGGTCATCGGCATCGTGAACAATACCGTGTATGATCCTCTGCAGCCAG
AGCTGGACTCCTTTAAGGAGGAGCTGGATAAGTACTTCAAGAATCACAC
CTCTCCCGACGTGGATCTGGGCGACATCAGCGGCATCAATGCCTCCGTG
GTGAACATCCAGAAGGAGATCGACAGGCTGAACGAGGTGGCCAAGAATC
TGAACGAGTCCCTGATCGATCTGCAGGAGCTGGGCAAGTATGAGCAGTA
CATCAAGTGGCCCTGGTATATCTGGCTGGGCTTCATCGCCGGCCTGATC
GCCATCGTGATGGTGACCATCATGCTGTGCTGTATGACATCCTGCTGTT
CTTGCCTGAAGGGCTGCTGTAGCTGTGGCTCCTGCTGTAAGTTTGATGA
GGACGATAGCGAGCCTGTGCTGAAGGGCGTGAAGCTGCACTACACCTGA

SEQ ID NO: 19 is a SARS-CoV-2 "Proline & Furin Cleavage Modified" Spike Glycoprotein, Amino Acid Sequence MFVFLVLLPLVSSQCVNLTTRTQLPPAYTNSFTRGVYYPDKVFRSSVLH
STQDLFLPFFSNVTWFHAIHVSGTNGTKRFDNPVLPFNDGVYFASTEKS
NIIRGWIFGTTLDSKTQSLLIVNNATNVVIKVCEFQFCNDPFLGVYYHK
NNKSWMESEFRVYSSANNCTFEYVSQPFLMDLEGKQGNFKNLREFVFKN
IDGYFKIYSKHTPINLVRDLPQGFSALEPLVDLPIGINITRFQTLLALH
RSYLTPGDSSSGWTAGAAAYYVGYLQPRTFLLKYNENGTITDAVDCALD
PLSETKCTLKSFTVEKGIYQTSNFRVQPTESIVRFPNITNLCPFGEVFN
ATRFASVYAWNRKRISNCVADYSVLYNSASFSTFKCYGVSPTKLNDLCF
TNVYADSFVIRGDEVRQIAPGQTGKIADYNYKLPDDFTGCVIAWNSNNL
DSKVGGNYNYLYRLFRKSNLKPFERDISTEIYQAGSTPCNGVEGFNCYF
PLQSYGFQPTNGVGYQPYRVVVLSFELLHAPATVCGPKKSTNLVKNKCV
NFNFNGLTGTGVLTESNKKFLPFQQFGRDIADTTDAVRDPQTLEILDIT
PCSFGGVSVITPGTNTSNQVAVLYQDVNCTEVPVAIHADQLTPTWRVYS
TGSNVFQTRAGCLIGAEHVNNSYECDIPIGAGICASYQTQTNSPGSASS
VASQSIIAYTMSLGAENSVAYSNNSIAIPTNFTISVTTEILPVSMTKTS -continued VDCTMYICGDSTECSNLLLQYGSFCTQLNRALTGIAVEQDKNTQEVFAQ
VKQIYKTPPIKDFGGFNFSQILPDPSKPSKRSFIEDLLFNKVTLADAGF
IKQYGDCLGDIAARDLICAQKFNGLTVLPPLLTDEMIAQYTSALLAGTI
TSGWTFGAGAALQIPFAMQMAYRFNGIGVTQNVLYENQKLIANQFNSAI
GKIQDSLSSTASALGKLQDVVNQNAQALNTLVKQLSSNFGAISSVLNDI
LSRLDPPLEAEVQIDRLITGRLQSLQTYVTQQLIRAAEIRASANLAATK
MSECVLGQSKRVDFCGKGYHLMSFPQSAPHGVVFLHVTYVPAQEKNFTT
APAICHDGKAHFPREGVFVSNGTHWFVTQRNFYEPQIITTDNTFVSGNC
DVVIGIVNNTVYDPLQPELDSFKEELDKYFKNHTSPDVDLGDISGINAS
VVNIQKEIDRLNEVAKNLNESLIDLQELGKYEQYIKWPWYIWLGFIAGL
IAIVMVTIMLCCMTSCCSCLKGCCSCGSCCKFDEDDSEPVLKGVKLHYT SEQ ID NO: 20 is a SARS-CoV-2 "Proline & Furin Cleavage Modified" Spike Glycoprotein, Nucleotide Sequence ATGTTTGTTTTTCTTGTTTTATTGCCACTAGTCTCTAGTCAGTGTGTTA
ATCTTACAACCAGAACTCAATTACCCCCTGCATACACTAATTCTTTCAC
ACGTGGTGTTTATTACCCTGACAAAGTTTTCAGATCCTCAGTTTTACAT
TCAACTCAGGACTTGTTCTTACCTTTCTTTTCCAATGTTACTTGGTTCC
ATGCTATACATGTCTCTGGGACCAATGGTACTAAGAGGTTTGATAACCC
TGTCCTACCATTTAATGATGGTGTTTATTTTGCTTCCACTGAGAAGTCT
AACATAATAAGAGGCTGGATTTTTGGTACTACTTTAGATTCGAAGACCC
AGTCCCTACTTATTGTTAATAACGCTACTAATGTTGTTATTAAAGTCTG
TGAATTTCAATTTTGTAATGATCCATTTTTGGGTGTTTATTACCACAAA
AACAACAAAAGTTGGATGGAAAGTGAGTTCAGAGTTTATTCTAGTGCGA
ATAATTGCACTTTTGAATATGTCTCTCAGCCTTTTCTTATGGACCTTGA
AGGAAAACAGGGTAATTTCAAAAATCTTAGGGAATTTGTGTTTAAGAAT
ATTGATGGTTATTTTAAAATATATTCTAAGCACACGCCTATTAATTTAG
TGCGTGATCTCCCTCAGGGTTTTTCGGCTTTAGAACCATTGGTAGATTT
GCCAATAGGTATTAACATCACTAGGTTTCAAACTTTACTTGCTTTACAT
AGAAGTTATTTGACTCCTGGTGATTCTTCTTCAGGTTGGACAGCTGGTG
CTGCAGCTTATTATGTGGGTTATCTTCAACCTAGGACTTTTCTATTAAA
ATATAATGAAAATGGAACCATTACAGATGCTGTAGACTGTGCACTTGAC
CCTCTCTCAGAAACAAAGTGTACGTTGAAATCCTTCACTGTAGAAAAAG
GAATCTATCAAACTTCTAACTTTAGAGTCCAACCAACAGAATCTATTGT
TAGATTTCCTAATATTACAAACTTGTGCCCTTTTGGTGAAGTTTTTAAC
GCCACCAGATTTGCATCTGTTTATGCTTGGAACAGGAAGAGAATCAGCA
ACTGTGTTGCTGATTATTCTGTCCTATATAATTCCGCATCATTTTCCAC
TTTTAAGTGTTATGGAGTGTCTCCTACTAAATTAAATGATCTCTGCTTT
ACTAATGTCTATGCAGATTCATTTGTAATTAGAGGTGATGAAGTCAGAC
AAATCGCTCCAGGGCAAACTGGAAAGATTGCTGATTATAATTATAAATT
ACCAGATGATTTTACAGGCTGCGTTATAGCTTGGAATTCTAACAATCTT -continued

```
GATTCTAAGGTTGGTGGTAATTATAATTACCTGTATAGATTGTTTAGGA
AGTCTAATCTCAAACCTTTTGAGAGAGATATTTCAACTGAAATCTATCA
GGCCGGTAGCACACCTTGTAATGGTGTTGAAGGTTTTAATTGTTACTTT
CCTTTACAATCATATGGTTTCCAACCCACTAATGGTGTTGGTTACCAAC
CATACAGAGTAGTAGTACTTTCTTTTGAACTTCTACATGCACCAGCAAC
TGTTTGTGGACCTAAAAAGTCTACTAATTTGGTTAAAAACAAATGTGTC
AATTTCAACTTCAATGGTTTAACAGGCACAGGTGTTCTTACTGAGTCTA
ACAAAAAGTTTCTGCCTTTCCAACAATTTGGCAGAGACATTGCTGACAC
TACTGATGCTGTCCGTGATCCACAGACACTTGAGATTCTTGACATTACA
CCATGTTCTTTTGGTGGTGTCAGTGTTATAACACCAGGAACAAATACTT
CTAACCAGGTTGCTGTTCTTTATCAGGATGTTAACTGCACAGAAGTCCC
TGTTGCTATTCATGCAGATCAACTTACTCCTACTTGGCGTGTTTATTCT
ACAGGTTCTAATGTTTTTCAAACACGTGCAGGCTGTTTAATAGGGGCTG
AACATGTCAACAACTCATATGAGTGTGACATACCCATTGGTGCAGGTAT
ATGCGCTAGTTATCAGACTCAGACTAATTCTCCTGGTAGTGCAAGTAGT
GTAGCTAGTCAATCCATCATTGCCTACACTATGTCACTTGGTGCAGAAA
ATTCAGTTGCTTACTCTAATAACTCTATTGCCATACCCACAAATTTTAC
TATTAGTGTTACCACAGAAATTCTACCAGTGTCTATGACCAAGACATCA
GTAGATTGTACAATGTACATTTGTGGTGATTCAACTGAATGCAGCAATC
TTTTGTTGCAATATGGCAGTTTTTGTACACAATTAAACCGTGCTTTAAC
TGGAATAGCTGTTGAACAAGACAAAAACACCCAAGAAGTTTTTGCACAA
GTCAAACAAATTTACAAAACACCACCAATTAAAGATTTTGGTGGTTTTA
ATTTTTCACAAATATTACCAGATCCATCAAAACCAAGCAAGAGGTCATT
TATTGAAGATCTACTTTTCAACAAAGTGACACTTGCAGATGCTGGCTTC
ATCAAACAATATGGTGATTGCCTTGGTGATATTGCTGCTAGAGACCTCA
TTTGTGCACAAAAGTTTAACGGCCTTACTGTTTTGCCACCTTTGCTCAC
AGATGAAATGATTGCTCAATACACTTCTGCACTGTTAGCGGGTACAATC
ACTTCTGGTTGGACCTTTGGTGCAGGTGCTGCATTACAAATACCATTTG
CTATGCAAATGGCTTATAGGTTTAATGGTATTGGAGTTACACAGAATGT
TCTCTATGAGAACCAAAAATTGATTGCCAACCAATTTAATAGTGCTATT
GGCAAAATTCAAGACTCACTTTCTTCCACAGCAAGTGCACTTGGAAAAC
TTCAAGATGTGGTCAACCAAAATGCACAAGCTTTAAACACGCTTGTTAA
ACAACTTAGCTCCAATTTTGGTGCAATTTCAAGTGTTTTAAATGATATC
CTTTCACGTCTTGACCCTCCTGAGGCTGAAGTGCAAATTGATAGGTTGA
TCACAGGCAGACTTCAAAGTTTGCAGACATATGTGACTCAACAATTAAT
TAGAGCTGCAGAAATCAGAGCTTCTGCTAATCTTGCTGCTACTAAAATG
TCAGAGTGTGTACTTGGACAATCAAAAAGAGTTGATTTTTGTGGAAAGG
GCTATCATCTTATGTCCTTCCCTCAGTCAGCACCTCATGGTGTAGTCTT
CTTGCATGTGACTTATGTCCCTGCACAAGAAAAGAACTTCACAACTGCT
CCTGCCATTTGTCATGATGGAAAAGCACACTTTCCTCGTGAAGGTGTCT
```

-continued

```
TTGTTTCAAATGGCACACACTGGTTTGTAACACAAAGGAATTTTTATGA
ACCACAAATCATTACTACAGACAACACATTTGTGTCTGGTAACTGTGAT
GTTGTAATAGGAATTGTCAACAACACAGTTTATGATCCTTTGCAACCTG
AATTAGACTCATTCAAGGAGGAGTTAGATAAATATTTTAAGAATCATAC
ATCACCAGATGTTGATTTAGGTGACATCTCTGGCATTAATGCTTCAGTT
GTAAACATTCAAAAAGAAATTGACCGCCTCAATGAGGTTGCCAAGAATT
TAAATGAATCTCTCATCGATCTCCAAGAACTTGGAAAGTATGAGCAGTA
TATAAAATGGCCATGGTACATTTGGCTAGGTTTTATAGCTGGCTTGATT
GCCATAGTAATGGTGACAATTATGCTTTGCTGTATGACCAGTTGCTGTA
GTTGTCTCAAGGGCTGTTGTTCTTGTGGATCCTGCTGCAAATTTGATGA
AGACGACTCTGAGCCAGTGCTCAAAGGAGTCAAATTACATTACACATAA
```

SEQ ID NO: 21 is a SARS-Cov-2 “Proline & Furin Cleavage Modified” Spike Glycoprotein, Nucleotide Sequence, Codon Optimized for Expression in Human Cells

```
ATGTTCGTGTTTCTGGTGCTGCTGCCTCTGGTGAGCTCCCAGTGCGTGA
ACCTGACCACAAGGACCCAGCTCCCCCCTGCCTATACCAATTCCTTCAC
AAGGGGCGTGTACTATCCAGACAAGGTGTTTCGCTCTAGCGTGCTGCAC
AGCACACAGGATCTGTTTCTGCCCTTCTTTTCCAACGTGACCTGGTTCC
ACGCCATCCATGTGAGCGGCACCAATGGCACAAAGAGGTTCGACAATCC
TGTGCTGCCCTTCAACGATGGCGTGTACTTCGCCTCTACCGAGAAGAGC
AACATCATCCGCGGCTGGATCTTTGGCACCACACTGGACTCCAAGACAC
AGTCTCTGCTGATCGTGAACAATGCCACCAACGTGGTCATCAAGGTGTG
CGAGTTCCAGTTTTGTAATGATCCTTTCCTGGGCGTGTACTATCACAAG
AACAATAAGAGCTGGATGGAGTCCGAGTTTCGCGTGTATTCCTCTGCCA
ACAATTGCACATTTGAGTACGTGTCCCAGCCATTCCTGATGGACCTGGA
GGGCAAGCAGGGCAATTTCAAGAACCTGCGGGAGTTCGTGTTTAAGAAT
ATCGATGGCTACTTCAAGATCTACAGCAAGCACACCCCTATCAACCTGG
TGAGAGACCTGCCACAGGGCTTCTCCGCCCTGGAGCCTCTGGTGGATCT
GCCAATCGGCATCAACATCACCAGGTTTCAGACACTGCTGGCCCTGCAC
CGCAGCTACCTGACACCTGGCGACAGCTCCTCTGGATGGACCGCCGGGG
CCGCCGCCTACTATGTGGGCTATCTGCAGCCACGGACCTTCCTGCTGAA
GTACAACGAGAATGGCACCATCACAGACGCAGTGGATTGCGCCCTGGAC
CCCCTGTCCGAGACCAAGTGTACACTGAAGTCTTTTACCGTGGAGAAGG
GCATCTATCAGACATCTAATTTCCGGGTGCAGCCCACCGAGAGCATCGT
GAGATTTCCAAATATCACAAACCTGTGCCCCTTTGGCGAGGTGTTCAAC
GCCACCAGATTCGCCAGCGTGTACGCCTGGAATCGGAAGAGAATCAGCA
ACTGCGTGGCCGACTATTCCGTGCTGTACAACTCTGCCAGCTTCTCCAC
CTTTAAGTGCTATGGCGTGTCTCCCACAAAGCTGAATGACCTGTGCTTT
ACCAACGTGTACGCCGATAGCTTCGTGATCAGGGGCGACGAGGTGAGAC
AGATCGCACCAGGCCAGACAGGCAAGATCGCCGACTACAATTATAAGCT
GCCCGACGATTTCACCGGCTGCGTGATCGCCTGGAACAGCAACAATCTG
```

-continued

```
GATTCCAAAGTGGGCGGCAACTACAATTATCTGTACAGGCTGTTTCGCA
AGTCCAATCTGAAGCCTTTCGAGCGGGACATCAGCACAGAGATCTACCA
GGCCGGCTCCACCCCATGCAATGGCGTGGAGGGCTTTAACTGTTATTTC
CCCCTGCAGTCTTACGGCTTCCAGCCTACAAACGGCGTGGGCTATCAGC
CATACAGAGTGGTGGTGCTGTCCTTTGAGCTGCTGCACGCACCAGCAAC
AGTGTGCGGACCTAAGAAGTCTACCAATCTGGTGAAGAACAAGTGCGTG
AACTTCAACTTCAACGGCCTGACCGGCACAGGCGTGCTGACCGAGTCCA
ACAAGAAGTTCCTGCCCTTTCAGCAGTTCGGCAGAGACATCGCCGATAC
CACAGACGCCGTGAGAGACCCCCAGACCCTGGAGATCCTGGACATCACA
CCTTGCTCTTTCGGCGGCGTGAGCGTGATCACACCTGGCACCAATACAA
GCAACCAGGTGGCCGTGCTGTATCAGGACGTGAATTGTACCGAGGTGCC
AGTGGCCATCCACGCCGATCAGCTCACCCCCACATGGAGGGTGTACTCC
ACCGGCTCTAACGTGTTCCAGACACGCGCCGGATGCCTGATCGGAGCCG
AGCATGTGAACAATTCTTATGAGTGCGACATCCCCATCGGAGCCGGCAT
CTGTGCCAGCTACCAGACCCAGACAAACAGCCCTGGCTCCGCCAGCTCC
GTGGCCTCTCAGAGCATCATCGCCTATACCATGAGCCTGGGGGCCGAGA
ATAGCGTGGCCTACTCTAACAATAGCATCGCCATCCCCACCAACTTCAC
AATCTCCGTGACCACAGAGATCCTGCCCGTGAGCATGACCAAGACATCT
GTGGACTGCACAATGTATATCTGTGGCGATTCTACCGAGTGCAGCAACC
TGCTGCTGCAGTACGGCAGCTTTTGTACCCAGCTCAACCGGGCCCTGAC
AGGAATCGCAGTGGAGCAGGACAAGAACACACAGGAGGTGTTCGCCCAG
GTGAAGCAGATCTACAAGACCCCACCCATCAAGGACTTTGGCGGCTTCA
ACTTCAGCCAGATCCTGCCAGATCCCTCCAAGCCTTCTAAGAGGAGCTT
TATCGAGGACCTGCTGTTCAACAAGGTGACCCTGGCCGATGCCGGCTTC
ATCAAGCAGTATGGCGATTGCCTGGGCGACATCGCAGCCCGCGACCTGA
TCTGTGCCCAGAAGTTTAATGGCCTGACCGTGCTGCCTCCACTGCTGAC
AGATGAGATGATCGCACAGTACACATCCGCCCTGCTGGCCGGCACCATC
ACATCTGGATGGACCTTCGGGGCCGGGGCCGCCCTGCAGATCCCATTTG
CCATGCAGATGGCCTATAGATTCAACGGCATCGGCGTGACCCAGAATGT
GCTGTACGAGAACCAGAAGCTGATCGCCAATCAGTTTAACTCCGCCATC
GGCAAGATCCAGGACTCCCTGTCTAGCACAGCCTCTGCCCTGGGCAAGC
TGCAGGATGTGGTGAATCAGAACGCCCAGGCCCTGAATACCCTGGTGAA
GCAGCTCAGCAGCAACTTCGGGGCCATCAGCAGCGTGCTGAACGACATC
CTGAGCCGGCTGGACCCCCCTGAGGCAGAGGTGCAGATCGACAGGCTGA
TCACAGGCCGCCTGCAGAGCCTGCAGACCTACGTGACACAGCAGCTCAT
CAGGGCCGCCGAGATCAGAGCCTCCGCCAATCTGGCCGCCACCAAGATG
TCTGAGTGCGTGCTGGGCCAGAGCAAGCGCGTGGACTTTTGTGGCAAGG
GCTATCACCTGATGTCCTTCCCACAGTCTGCCCCCCACGGAGTGGTGTT
TCTGCATGTGACCTACGTGCCTGCCCAGGAGAAGAACTTCACCACAGCC
CCAGCCATCTGCCACGATGGCAAGGCACACTTTCCCCGGGAGGGCGTGT
```

-continued

```
TCGTGTCTAACGGCACCCACTGGTTTGTGACACAGAGAAATTTCTACGA
GCCTCAGATCATCACCACAGACAATACATTCGTGAGCGGCAACTGTGAC
GTGGTCATCGGCATCGTGAACAATACCGTGTATGATCCCCTGCAGCCTG
AGCTGGACTCCTTTAAGGAGGAGCTGGATAAGTACTTCAAGAATCACAC
CTCTCCCGACGTGGATCTGGGCGACATCAGCGGCATCAATGCCTCCGTG
GTGAACATCCAGAAGGAGATCGACAGGCTGAACGAGGTGGCCAAGAATC
TGAACGAGTCCCTGATCGATCTGCAGGAGCTGGGCAAGTATGAGCAGTA
CATCAAGTGGCCATGGTATATCTGGCTGGGCTTCATCGCCGGCCTGATC
GCCATCGTGATGGTGACCATCATGCTGTGCTGTATGACATCCTGCTGTT
CTTGCCTGAAGGGCTGCTGTAGCTGTGGCTCCTGCTGTAAGTTTGATGA
GGACGATAGCGAGCCCGTGCTGAAGGGCGTGAAGCTGCACTACACCTGA
```

SEQ ID NO: 22 is a SARS-CoV-2 "Proline & Furin Cleavage Modified & VSV-G TMCyt Swap" Spike Glycoprotein, Amino Acid Sequence

```
MFVFLVLLPLVSSQCVNLTTRTQLPPAYTNSFTRGVYYPDKVFRSSVLH
STQDLFLPFFSNVTWFHAIHVSGTNGTKRFDNPVLPFNDGVYFASTEKS
NIIRGWIFGTTLDSKTQSLLIVNNATNVVIKVCEFQFCNDPFLGVYYHK
NNKSWMESEFRVYSSANNCTFEYVSQPFLMDLEGKQGNFKNLREFVFKN
IDGYFKIYSKHTPINLVRDLPQGFSALEPLVDLPIGINITRFQTLLALH
RSYLTPGDSSSGWTAGAAAYYVGYLQPRTFLLKYNENGTITDAVDCALD
PLSETKCTLKSFTVEKGIYQTSNFRVQPTESIVRFPNITNLCPFGEVFN
ATRFASVYAWNRKRISNCVADYSVLYNSASFSTFKCYGVSPTKLNDLCF
TNVYADSFVIRGDEVRQIAPGQTGKIADYNYKLPDDFTGCVIAWNSNNL
DSKVGGNYNYLYRLFRKSNLKPFERDISTEIYQAGSTPCNGVEGFNCYF
PLQSYGFQPTNGVGYQPYRVVVLSFELLHAPATVCGPKKSTNLVKNKCV
NFNFNGLTGTGVLTESNKKFLPFQQFGRDIADTTDAVRDPQTLEILDIT
PCSFGGVSVITPGTNTSNQVAVLYQDVNCTEVPVAIHADQLTPTWRVYS
TGSNVFQTRAGCLIGAEHVNNSYECDIPIGAGICASYQTQTNSPGSASS
VASQSIIAYTMSLGAENSVAYSNNSIAIPTNFTISVTTEILPVSMTKTS
VDCTMYICGDSTECSNLLLQYGSFCTQLNRALTGIAVEQDKNTQEVFAQ
VKQIYKTPPIKDFGGFNFSQILPDPSKPSKRSFIEDLLFNKVTLADAGF
IKQYGDCLGDIAARDLICAQKFNGLTVLPPLLTDEMIAQYTSALLAGTI
TSGWTFGAGAALQIPFAMQMAYRFNGIGVTQNVLYENQKLIANQFNSAI
GKIQDSLSSTASALGKLQDVVNQNAQALNTLVKQLSSNFGAISSVLNDI
LSRLDPPEAEVQIDRLITGRLQSLQTYVTQQLIRAAEIRASANLAATKM
SECV LGQSKRVDFCGKGYHLMSFPQSAPHGVVFLHVTYVPAQEKNFTT
APAICHDGKAHFPREGVFVSNGTHWFVTQRNFYEPQIITTDNTFVSGNC
DVVIGIVNNTVYDPLQPELDSFKEELDKYFKNHTSPDVDLGDISGINAS
VVNIQKEIDRLNEVAKNLNESLIDLQELGKYEQYIKFFFIIGLIIGLFL
VERVGIIILCIKLKEITKKRQIYTDIEMNREGK
```

SEQ ID NO: 23 is a SARS CoV-2 “Proline & Furin Cleavage Modified & VSV-G TMCyt SWAP” Spike Glycoprotein, Nucleotide Sequence ATGTTTGTTTTTCTTGTTTTATTGCCACTAGTCTCTAGTCAGTGTGTTA
ATCTTACAACCAGAACTCAATTACCCCCTGCATACACTAATTCTTTCAC
ACGTGGTGTTTATTACCCTGACAAAGTTTTCAGATCCTCAGTTTTACAT
TCAACTCAGGACTTGTTCTTACCTTTCTTTTCCAATGTTACTTGGTTCC
ATGCTATACATGTCTCTGGGACCAATGGTACTAAGAGGTTTGATAACCC
TGTCCTACCATTTAATGATGGTGTTTATTTTGCTTCCACTGAGAAGTCT
AACATAATAAGAGGCTGGATTTTTGGTACTACTTTAGATTCGAAGACCC
AGTCCCTACTTATTGTTAATAACGCTACTAATGTTGTTATTAAAGTCTG
TGAATTTCAATTTTGTAATGATCCATTTTTGGGTGTTTATTACCACAAA
AACAACAAAAGTTGGATGGAAAGTGAGTTCAGAGTTTATTCTAGTGCGA
ATAATTGCACTTTTGAATATGTCTCTCAGCCTTTTCTTATGGACCTTGA
AGGAAAACAGGGTAATTTCAAAAATCTTAGGGAATTTGTGTTTAAGAAT
ATTGATGGTTATTTTAAAATATATTCTAAGCACACGCCTATTAATTTAG
TGCGTGATCTCCCTCAGGGTTTTTCGGCTTTAGAACCATTGGTAGATTT
GCCAATAGGTATTAACATCACTAGGTTTCAAACTTTACTTGCTTTACAT
AGAAGTTATTTGACTCCTGGTGATTCTTCTTCAGGTTGGACAGCTGGTG
CTGCAGCTTATTATGTGGGTTATCTTCAACCTAGGACTTTTCTATTAAA
ATATAATGAAAATGGAACCATTACAGATGCTGTAGACTGTGCACTTGAC
CCTCTCTCAGAAACAAAGTGTACGTTGAAATCCTTCACTGTAGAAAAAG
GAATCTATCAAACTTCTAACTTTAGAGTCCAACCAACAGAATCTATTGT
TAGATTTCCTAATATTACAAACTTGTGCCCTTTTGGTGAAGTTTTTAAC
GCCACCAGATTTGCATCTGTTTATGCTTGGAACAGGAAGAGAATCAGCA
ACTGTGTTGCTGATTATTCTGTCCTATATAATTCCGCATCATTTTCCAC
TTTTAAGTGTTATGGAGTGTCTCCTACTAAATTAAATGATCTCTGCTTT
ACTAATGTCTATGCAGATTCATTTGTAATTAGAGGTGATGAAGTCAGAC
AAATCGCTCCAGGGCAAACTGGAAAGATTGCTGATTATAATTATAAATT
ACCAGATGATTTTACAGGCTGCGTTATAGCTTGGAATTCTAACAATCTT
GATTCTAAGGTTGGTGGTAATTATAATTACCTGTATAGATTGTTTAGGA
AGTCTAATCTCAAACCTTTTGAGAGAGATATTTCAACTGAAATCTATCA
GGCCGGTAGCACACCTTGTAATGGTGTTGAAGGTTTTAATTGTTACTTT
CCTTTACAATCATATGGTTTCCAACCCACTAATGGTGTTGGTTACCAAC
CATACAGAGTAGTAGTACTTTCTTTTGAACTTCTACATGCACCAGCAAC
TGTTTGTGGACCTAAAAAGTCTACTAATTTGGTTAAAAACAAATGTGTC
AATTTCAACTTCAATGGTTTAACAGGCACAGGTGTTCTTACTGAGTCTA
ACAAAAAGTTTCTGCCTTTCCAACAATTTGGCAGAGACATTGCTGACAC
TACTGATGCTGTCCGTGATCCACAGACACTTGAGATTCTTGACATTACA
CCATGTTCTTTTGGTGGTGTCAGTGTTATAACACCAGGAACAAATACTT
CTAACCAGGTTGCTGTTCTTTATCAGGATGTTAACTGCACAGAAGTCCC -continued TGTTGCTATTCATGCAGATCAACTTACTCCTACTTGGCGTGTTTATTCT
ACAGGTTCTAATGTTTTTCAAACACGTGCAGGCTGTTTAATAGGGGCTG
AACATGTCAACAACTCATATGAGTGTGACATACCCATTGGTGCAGGTAT
ATGCGCTAGTTATCAGACTCAGACTAATTCTCCTGGTAGTGCAAGTAGT
GTAGCTAGTCAATCCATCATTGCCTACACTATGTCACTTGGTGCAGAAA
ATTCAGTTGCTTACTCTAATAACTCTATTGCCATACCCACAAATTTTAC
TATTAGTGTTACCACAGAAATTCTACCAGTGTCTATGACCAAGACATCA
GTAGATTGTACAATGTACATTTGTGGTGATTCAACTGAATGCAGCAATC
TTTTGTTGCAATATGGCAGTTTTTGTACACAATTAAACCGTGCTTTAAC
TGGAATAGCTGTTGAACAAGACAAAAACACCCAAGAAGTTTTTGCACAA
GTCAAACAAATTTACAAAACACCACCAATTAAAGATTTTGGTGGTTTTA
ATTTTTCACAAATATTACCAGATCCATCAAAACCAAGCAAGAGGTCATT
TATTGAAGATCTACTTTTCAACAAAGTGACACTTGCAGATGCTGGCTTC
ATCAAACAATATGGTGATTGCCTTGGTGATATTGCTGCTAGAGACCTCA
TTTGTGCACAAAAGTTTAACGGCCTTACTGTTTTGCCACCTTTGCTCAC
AGATGAAATGATTGCTCAATACACTTCTGCACTGTTAGCGGGTACAATC
ACTTCTGGTTGGACCTTTGGTGCAGGTGCTGCATTACAAATACCATTTG
CTATGCAAATGGCTTATAGGTTTAATGGTATTGGAGTTACACAGAATGT
TCTCTATGAGAACCAAAAATTGATTGCCAACCAATTTAATAGTGCTATT
GGCAAAATTCAAGACTCACTTTCTTCCACAGCAAGTGCACTTGGAAAAC
TTCAAGATGTGGTCAACCAAAATGCACAAGCTTTAAACACGCTTGTTAA
ACAACTTAGCTCCAATTTTGGTGCAATTTCAAGTGTTTTAAATGATATC
CTTTCACGTCTTGACCCTCCTGAGGCTGAAGTGCAAATTGATAGGTTGA
TCACAGGCAGACTTCAAAGTTTGCAGACATATGTGACTCAACAATTAAT
TAGAGCTGCAGAAATCAGAGCTTCTGCTAATCTTGCTGCTACTAAAATG
TCAGAGTGTGTACTTGGACAATCAAAAAGAGTTGATTTTTGTGGAAAGG
GCTATCATCTTATGTCCTTCCCTCAGTCAGCACCTCATGGTGTAGTCTT
CTTGCATGTGACTTATGTCCCTGCACAAGAAAAGAACTTCACAACTGCT
CCTGCCATTTGTCATGATGGAAAAGCACACTTTCCTCGTGAAGGTGTCT
TTGTTTCAAATGGCACACACTGGTTTGTAACACAAAGGAATTTTTATGA
ACCACAAATCATTACTACAGACAACACATTTGTGTCTGGTAACTGTGAT
GTTGTAATAGGAATTGTCAACAACACAGTTTATGATCCTTTGCAACCTG
AATTAGACTCATTCAAGGAGGAGTTAGATAAATATTTTAAGAATCATAC
ATCACCAGATGTTGATTTAGGTGACATCTCTGGCATTAATGCTTCAGTT
GTAAACATTCAAAAAGAAATTGACCGCCTCAATGAGGTTGCCAAGAATT
TAAATGAATCTCTCATCGATCTCCAAGAACTTGGAAAGTATGAGCAGTA
TATAAAATTTTTCTTTATCATAGGGTTAATCATTGGACTATTCTTGGTT
CTCCGAGTTGGTATCCATCTTTGCATTAAATTAAAGCACACCAAGAAAA
GACAGATTTATACAGACATAGAGATGAACCGACTTGGAAAGTAA SEQ ID NO: 24 is a SARS CoV-2 "Proline & Furin Cleavage Modified & VSV-G TMCyt SWAP" Spike Glycoprotein, Nucleotide Sequence, Codon Optimized For Expression In Human Cells

ATGTTCGTGTTCCTGGTGCTGCTGCCTCTGGTGAGCTCCCAGTGCGTGA

ACCTGACCACAAGGACCCAGCTCCCCCCTGCCTATACCAATTCCTTTAC

AAGGGGCGTGTACTATCCAGACAAGGTGTTCCGCTCTAGCGTGCTGCAC

TCTACACAGGATCTGTTCCTGCCCTTCTTTAGCAACGTGACCTGGTTTC

ACGCCATCCATGTGAGCGGCACCAATGGCACAAAGCGGTTTGACAATCC

TGTGCTGCCATTCAACGATGGCGTGTACTTTGCCTCCACCGAGAAGTCT

AACATCATCAGAGGCTGGATCTTCGGCACCACACTGGACAGCAAGACAC

AGTCCCTGCTGATCGTGAACAATGCCACCAACGTGGTCATCAAGGTGTG

CGAGTTTCAGTTCTGTAATGATCCTTTTCTGGGCGTGTACTATCACAAG

AACAATAAGTCTTGGATGGAGAGCGAGTTCCGCGTGTATTCCTCTGCCA

ACAATTGTACATTCGAGTACGTGTCCCAGCCATTTCTGATGGACCTGGA

GGGCAAGCAGGGCAACTTCAAGAACCTGCGGGAGTTCGTGTTCAAGAAT

ATCGATGGCTATTTCAAGATCTACTCTAAGCACACCCCTATCAACCTGG

TGCGCGACCTGCCACAGGGCTTTAGCGCCCTGGAGCCTCTGGTGGATCT

GCCAATCGGCATCAACATCACCAGGTTCCAGACACTGCTGGCCCTGCAC

CGCAGCTACCTGACACCTGGCGACAGCTCCTCTGGATGGACCGCCGGGG

CCGCCGCCTACTATGTGGGCTATCTGCAGCCACGGACCTTTCTGCTGAA

GTACAACGAGAATGGCACCATCACAGACGCAGTGGATTGCGCCCTGGAC

CCCCTGAGCGAGACCAAGTGTACACTGAAGTCCTTCACCGTGGAGAAGG

GCATCTATCAGACATCCAATTTTCGGGTGCAGCCCACCGAGTCTATCGT

GAGATTCCCAAATATCACAAACCTGTGCCCCTTCGGCGAGGTGTTTAAC

GCCACCAGATTCGCCAGCGTGTACGCCTGGAATCGGAAGAGAATCTCTA

ACTGCGTGGCCGACTATAGCGTGCTGTACAACTCTGCCAGCTTTTCCAC

CTTCAAGTGCTATGGCGTGTCCCCCACAAAGCTGAATGACCTGTGCTTC

ACCAACGTGTACGCCGATTCTTTTGTGATCAGGGGCGACGAGGTGAGAC

AGATCGCACCAGGCCAGACAGGCAAGATCGCCGACTACAATTATAAGCT

GCCCGACGATTTCACCGGCTGCGTGATCGCCTGGAACTCTAACAATCTG

GATAGCAAAGTGGGCGGCAACTACAATTATCTGTACAGGCTGTTCCGCA

AGAGCAATCTGAAGCCTTTTGAGCGGGACATCTCTACAGAGATCTACCA

GGCCGGCAGCACCCCATGCAATGGCGTGGAGGGCTTCAACTGTTATTTT

CCCCTGCAGTCCTACGGCTTTCAGCCTACCAACGGCGTGGGCTATCAGC

CATACAGAGTGGTGGTGCTGAGCTTCGAGCTGCTGCACGCACCAGCAAC

AGTGTGCGGACCTAAGAAGTCCACCAATCTGGTGAAGAACAAGTGCGTG

AACTTCAACTTCAACGGCCTGACCGGCACAGGCGTGCTGACCGAGTCCA

ATAAGAAGTTTCTGCCCTTCCAGCAGTTTGGCCGGGACATCGCCGATAC

CACAGACGCCGTGAGAGACCCCCAGACCCTGGAGATCCTGGACATCACA

CCTTGCTCCTTCGGCGGCGTGTCTGTGATCACACCTGGCACCAATACAA

GCAACCAGGTGGCCGTGCTGTATCAGGACGTGAATTGTACCGAGGTGCC

-continued

AGTGGCCATCCACGCCGATCAGCTCACCCCCACATGGCGGGTGTACTCC

ACCGGCTCTAACGTGTTCCAGACAAGAGCCGGCTGCCTGATCGGAGCCG

AGCATGTGAACAATTCCTATGAGTGCGACATCCCCATCGGAGCCGGCAT

CTGTGCCTCTTACCAGACCCAGACAAACAGCCCTGGCTCCGCCAGCTCC

GTGGCCTCTCAGAGCATCATCGCCTATACCATGAGCCTGGGGGCCGAGA

ACAGCGTGGCCTACTCTAACAATAGCATCGCCATCCCCACCAACTTTAC

AATCTCTGTGACCACAGAGATCCTGCCTGTGAGCATGACCAAGACATCC

GTGGACTGCACAATGTATATCTGTGGCGATTCCACCGAGTGCTCTAACC

TGCTGCTGCAGTACGGCAGCTTCTGTACCCAGCTCAACCGGGCCCTGAC

AGGAATCGCAGTGGAGCAGGACAAGAACACACAGGAGGTGTTTGCCCAG

GTGAAGCAGATCTACAAGACCCCACCCATCAAGGACTTCGGCGGCTTTA

ATTTCTCCCAGATCCTGCCAGATCCCTCCAAGCCATCTAAGCGGAGCTT

CATCGAGGACCTGCTGTTTAACAAGGTGACCCTGGCCGATGCCGGCTTT

ATCAAGCAGTATGGCGATTGCCTGGGCGACATCGCCGCCAGAGACCTGA

TCTGTGCCCAGAAGTTCAATGGCCTGACCGTGCTGCCTCCACTGCTGAC

AGATGAGATGATCGCACAGTACACAAGCGCCCTGCTGGCCGGCACCATC

ACATCCGGATGGACCTTCGGGGCCGGGGCCGCCCTGCAGATCCCCTTCG

CCATGCAGATGGCCTATAGGTTTAACGGCATCGGCGTGACCCAGAATGT

GCTGTACGAGAACCAGAAGCTGATCGCCAATCAGTTCAACTCCGCCATC

GGCAAGATCCAGGACAGCCTGTCTAGCACAGCCTCCGCCCTGGGCAAGC

TGCAGGATGTGGTGAATCAGAACGCCCAGGCCCTGAATACCCTGGTGAA

GCAGCTCAGCAGCAACTTCGGGGCCATCAGCAGCGTGCTGAACGACATC

CTGAGCCGGCTGGACCCCCCTGAGGCAGAGGTGCAGATCGACAGGCTGA

TCACAGGCCGCCTGCAGTCTCTGCAGACCTATGTGACACAGCAGCTCAT

CAGGGCCGCCGAGATCAGAGCCAGCGCCAATCTGGCCGCCACCAAGATG

TCCGAGTGCGTGCTGGGCCAGTCTAAGCGCGTGGACTTCTGTGGCAAGG

GCTATCACCTGATGAGCTTTCCACAGTCCGCCCCCCACGGAGTGGTGTT

CCTGCATGTGACCTACGTGCCTGCCCAGGAGAAGAACTTTACCACAGCC

CCAGCCATCTGCCACGATGGCAAGGCACACTTCCCCAGGGAGGGCGTGT

TCGTGAGCAACGGCACCCACTGGTTCGTGACACAGCGCAACTTCTACGA

GCCTCAGATCATCACCACAGACAATACATTCGTGTCTGGCAACTGTGAC

GTGGTCATCGGCATCGTGAACAATACCGTGTATGATCCCCTGCAGCCTG

AGCTGGACAGCTTCAAGGAGGAGCTGGATAAGTACTTTAAGAATCACAC

CTCCCCCGACGTGGATCTGGGCGACATCTCTGGCATCAATGCCAGCGTG

GTGAACATCCAGAAGGAGATCGACAGGCTGAACGAGGTGGCCAAGAATC

TGAACGAGAGCCTGATCGATCTGCAGGAGCTGGGCAAGTATGAGCAGTA

CATCAAGTTCTTTTTCATCATCGGCCTGATCATCGGCCTGTTCCTGGTG

CTGCGCGTGGGCATCCACCTGTGCATCAAGCTGAAGCACACCAAGAAGA

GGCAGATCTACACAGACATCGAGATGAACCGCCTGGGCAAGTGA

SEQ ID NO: 25 is a SARS-CoV-2 Spike Glycoprotein, with VSV-G TMCyt SWAP Amino Acid Sequence MFVFLVLLPLVSSQCVNLTTRTQLPPAYTNSFTRGVYYPDKVFRSSVLH
STQDLFLPFFSNVTWFHAIHVSGTNGTKRFDNPVLPFNDGVYFASTEKS
NIIRGWIFGTTLDSKTQSLLIVNNATNVVIKVCEFQFCNDPFLGVYYHK
NNKSWMESEFRVYSSANNCTFEYVSQPFLMDLEGKQGNFKNLREFVFKN
IDGYFKIYSKHTPINLVRDLPQGFSALEPLVDLPIGINITRFQTLLALH
RSYLTPGDSSSGWTAGAAAYYVGYLQPRTFLLKYNENGTITDAVDCALD
PLSETKCTLKSFTVEKGIYQTSNFRVQPTESIVRFPNITNLCPFGEVFN
ATRFASVYAWNRKRISNCVADYSVLYNSASFSTFKCYGVSPTKLNDLCF
TNVYADSFVIRGDEVRQIAPGQTGKIADYNYKLPDDFTGCVIAWNSNNL
DSKVGGNYNYLYRLFRKSNLKPFERDISTEIYQAGSTPCNGVEGFNCYF
PLQSYGFQPTNGVGYQPYRVVVLSFELLHAPATVCGPKKSTNLVKNKCV
NFNFNGLTGTGVLTESNKKFLPFQQFGRDIADTTDAVRDPQTLEILDIT
PCSFGGVSVITPGTNTSNQVAVLYQDVNCTEVPVAIHADQLTPTWRVYS
TGSNVFQTRAGCLIGAEHVNNSYECDIPIGAGICASYQTQTNSPRRARS
VASQSIIAYTMSLGAENSVAYSNNSIAIPTNFTISVTTEILPVSMTKTS
VDCTMYICGDSTECSNLLLQYGSFCTQLNRALTGIAVEQDKNTQEVFAQ
VKQIYKTPPIKDFGGFNFSQILPDPSKPSKRSFIEDLLFNKVTLADAGF
IKQYGDCLGDIAARDLICAQKFNGLTVLPPLLTDEMIAQYTSALLAGTI
TSGWTFGAGAALQIPFAMQMAYRFNGIGVTQNVLYENQKLIANQFNSAI
GKIQDSLSSTASALGKLQDVVNQNAQALNTLVKQLSSNFGAISSVLNDI
LSRLDKVEAEVQIDRLITGRLQSLQTYVTQQLIRAAEIRASANLAATKM
SECVLGQSKRVDFCGKGYHLMSFPQSAPHGVVFLHVTYVPAQEKNFTTA
PAICHDGKAHFPREGVFVSNGTHWFVTQRNFYEPQIITTDNTFVSGNCD
VVIGIVNNTVYDPLQPELDSFKEELDKYFKNHTSPDVDLGDISGINASV
VNIQKEIDRLNEVAKNLNESLIDLQELGKYEQYIKFIIGLIIGLFLVLR
VGIHLCIKLKHTKKRQIYTDIEMNRLGK

SEQ ID NO: 26 is a SARS-CoV-2 Spike Glycoprotein with VSV-G TMCyt SWAP, Nucleotide Sequence CTCGAGGTTTAAACGAATTCCGCCACCATGTTTGTTTTTCTTGTTTTAT
TGCCACTAGTCTCTAGTCAGTGTGTTAATCTTACAACCAGAACTCAATT
ACCCCCTGCATACACTAATTCTTTCACACGTGGTGTTTATTACCCTGAC
AAAGTTTTCAGATCCTCAGTTTTACATTCAACTCAGGACTTGTTCTTAC
CTTTCTTTTCCAATGTTACTTGGTTCCATGCTATACATGTCTCTGGGAC
CAATGGTACTAAGAGGTTTGATAACCCTGTCCTACCATTTAATGATGGT
GTTTATTTTGCTTCCACTGAGAAGTCTAACATAATAAGAGGCTGGATTT
TTGGTACTACTTTAGATTCGAAGACCCAGTCCCTACTTATTGTTAATAA
CGCTACTAATGTTGTTATTAAAGTCTGTGAATTTCAATTTTGTAATGAT
CCATTTTTGGGTGTTTATTACCACAAAAACAACAAAAGTTGGATGGAAA
GTGAGTTCAGAGTTTATTCTAGTGCGAATAATTGCACTTTTGAATATGT
CTCTCAGCCTTTTCTTATGGACCTTGAAGGAAAACAGGGTAATTTCAAA -continued AATCTTAGGGAATTTGTGTTTAAGAATATTGATGGTTATTTTAAAATAT
ATTCTAAGCACACGCCTATTAATTTAGTGCGTGATCTCCCTCAGGGTTT
TTCGGCTTTAGAACCATTGGTAGATTTGCCAATAGGTATTAACATCACT
AGGTTTCAAACTTTACTTGCTTTACATAGAAGTTATTTGACTCCTGGTG
ATTCTTCTTCAGGTTGGACAGCTGGTGCTGCAGCTTATTATGTGGGTTA
TCTTCAACCTAGGACTTTTCTATTAAAATATAATGAAAATGGAACCATT
ACAGATGCTGTAGACTGTGCACTTGACCCTCTCTCAGAAACAAAGTGTA
CGTTGAAATCCTTCACTGTAGAAAAAGGAATCTATCAAACTTCTAACTT
TAGAGTCCAACCAACAGAATCTATTGTTAGATTTCCTAATATTACAAAC
TTGTGCCCTTTTGGTGAAGTTTTTAACGCCACCAGATTTGCATCTGTTT
ATGCTTGGAACAGGAAGAGAATCAGCAACTGTGTTGCTGATTATTCTGT
CCTATATAATTCCGCATCATTTTCCACTTTTAAGTGTTATGGAGTGTCT
CCTACTAAATTAAATGATCTCTGCTTTACTAATGTCTATGCAGATTCAT
TTGTAATTAGAGGTGATGAAGTCAGACAAATCGCTCCAGGGCAAACTGG
AAAGATTGCTGATTATAATTATAAATTACCAGATGATTTTACAGGCTGC
GTTATAGCTTGGAATTCTAACAATCTTGATTCTAAGGTTGGTGGTAATT
ATAATTACCTGTATAGATTGTTTAGGAAGTCTAATCTCAAACCTTTTGA
GAGAGATATTTCAACTGAAATCTATCAGGCCGGTAGCACACCTTGTAAT
GGTGTTGAAGGTTTTAATTGTTACTTTCCTTTACAATCATATGGTTTCC
AACCCACTAATGGTGTTGGTTACCAACCATACAGAGTAGTAGTACTTTC
TTTTGAACTTCTACATGCACCAGCAACTGTTTGTGGACCTAAAAAGTCT
ACTAATTTGGTTAAAAACAAATGTGTCAATTTCAACTTCAATGGTTTAA
CAGGCACAGGTGTTCTTACTGAGTCTAACAAAAAGTTTCTGCCTTTCCA
ACAATTTGGCAGAGACATTGCTGACACTACTGATGCTGTCCGTGATCCA
CAGACACTTGAGATTCTTGACATTACACCATGTTCTTTTGGTGGTGTCA
GTGTTATAACACCAGGAACAAATACTTCTAACCAGGTTGCTGTTCTTTA
TCAGGATGTTAACTGCACAGAAGTCCCTGTTGCTATTCATGCAGATCAA
CTTACTCCTACTTGGCGTGTTTATTCTACAGGTTCTAATGTTTTTCAAA
CACGTGCAGGCTGTTTAATAGGGGCTGAACATGTCAACAACTCATATGA
GTGTGACATACCCATTGGTGCAGGTATATGCGCTAGTTATCAGACTCAG
ACTAATTCTCCTCGGCGGGCACGTAGTGTAGCTAGTCAATCCATCATTG
CCTACACTATGTCACTTGGTGCAGAAAATTCAGTTGCTTACTCTAATAA
CTCTATTGCCATACCCACAAATTTTACTATTAGTGTTACCACAGAAATT
CTACCAGTGTCTATGACCAAGACATCAGTAGATTGTACAATGTACATTT
GTGGTGATTCAACTGAATGCAGCAATCTTTTGTTGCAATATGGCAGTTT
TTGTACACAATTAAACCGTGCTTTAACTGGAATAGCTGTTGAACAAGAC
AAAAACACCCAAGAAGTTTTTGCACAAGTCAAACAAATTTACAAAACAC
CACCAATTAAAGATTTTGGTGGTTTTAATTTTTCACAAATATTACCAGA
TCCATCAAAACCAAGCAAGAGGTCATTTATTGAAGATCTACTTTTCAAC
AAAGTGACACTTGCAGATGCTGGCTTCATCAAACAATATGGTGATTGCC
TTGGTGATATTGCTGCTAGAGACCTCATTTGTGCACAAAAGTTTAACGG -continued CCTTACTGTTTTGCCACCTTTGCTCACAGATGAAATGATTGCTCAATAC
ACTTCTGCACTGTTAGCGGGTACAATCACTTCTGGTTGGACCTTTGGTG
CAGGTGCTGCATTACAAATACCATTTGCTATGCAAATGGCTTATAGGTT
TAATGGTATTGGAGTTACACAGAATGTTCTCTATGAGAACCAAAAATTG
ATTGCCAACCAATTTAATAGTGCTATTGGCAAAATTCAAGACTCACTTT
CTTCCACAGCAAGTGCACTTGGAAAACTTCAAGATGTGGTCAACCAAAA
TGCACAAGCTTTAAACACGCTTGTTAAACAACTTAGCTCCAATTTTGGT
GCAATTTCAAGTGTTTTAAATGATATCCTTTCACGTCTTGACAAAGTTG
AGGCTGAAGTGCAAATTGATAGGTTGATCACAGGCAGACTTCAAAGTTT
GCAGACATATGTGACTCAACAATTAATTAGAGCTGCAGAAATCAGAGCT
TCTGCTAATCTTGCTGCTACTAAAATGTCAGAGTGTGTACTTGGACAAT
CAAAAAGAGTTGATTTTTGTGGAAAGGGCTATCATCTTATGTCCTTCCC
TCAGTCAGCACCTCATGGTGTAGTCTTCTTGCATGTGACTTATGTCCCT
GCACAAGAAAAGAACTTCACAACTGCTCCTGCCATTTGTCATGATGGAA
AAGCACACTTTCCTCGTGAAGGTGTCTTTGTTTCAAATGGCACACACTG
GTTTGTAACACAAAGGAATTTTTATGAACCACAAATCATTACTACAGAC
AACACATTTGTGTCTGGTAACTGTGATGTTGTAATAGGAATTGTCAACA
ACACAGTTTATGATCCTTTGCAACCTGAATTAGACTCATTCAAGGAGGA
GTTAGATAAATATTTTAAGAATCATACATCACCAGATGTTGATTTAGGT
GACATCTCTGGCATTAATGCTTCAGTTGTAAACATTCAAAAAGAAATTG
ACCGCCTCAATGAGGTTGCCAAGAATTTAAATGAATCTCTCATCGATCT
CCAAGAACTTGGAAAGTATGAGCAGTATATAAAATGGCCATTTTTCTTT
ATCATAGGGTTAATCATTGGACTATTCTTGGTTCTCCGAGTTGGTATCC
ATCTTTGCATTAAATTAAAGCACACCAAGAAAAGACAGATTTATACAGA
CATAGAGATGAACCGACTTGGAAAGTAAGAATTCCACGTGGGATCC SEQ ID NO: 27 is a SARS CoV-2 Spike Glycoprotein with VSV-G TMCyt SWAP, Nucleotide Sequence, Codon Optimized For Expression In Human Cells CTCGAGGTTTAAACGAATTCCGCCACCATGTTCGTGTTCCTGGTGCTGC
TGCCCCTGGTGTCCAGCCAGTGCGTGAATCTGACCACCCGGACCCAACT
GCCTCCCGCCTACACAAACTCTTTCACCAGAGGGGTTTATTACCCCGAT
AAGGTGTTCAGAAGCTCAGTGCTTCATTCTACCCAGGACCTGTTTCTGC
CTTTTTTCAGCAACGTCACATGGTTCCACGCCATCCACGTCAGCGGAAC
CAACGGCACGAAGCGGTTCGACAATCCTGTGCTGCCTTTTAACGACGGC
GTCTACTTTGCCAGCACGGAAAAGAGCAACATTATCCGGGGATGGATCT
TCGGCACCACCCTGGACTCTAAAACCCAGAGCCTGTTGATCGTGAACAA
CGCAACCAATGTGGTGATCAAGGTCTGCGAGTTCCAATTTTGCAACGAT
CCTTTCCTGGGCGTGTACTACCACAAGAACAACAAGTCTTGGATGGAAT
CTGAGTTCCGCGTCTACAGCAGCGCAAACAACTGCACATTTGAGTACGT
GTCTCAGCCTTTTCTGATGGACCTGGAAGGAAAGCAGGGAAATTTCAAG -continued AACCTGCGGGAGTTCGTGTTCAAGAACATCGACGGCTACTTCAAGATCT
ACAGCAAGCACACCCCCATCAACCTCGTGAGAGACCTGCCCCAGGGCTT
CAGCGCCCTGGAACCCCTGGTGGACCTTCCCATAGGAATCAACATCACA
CGGTTCCAGACACTGCTGGCCCTGCATAGAAGCTACCTGACCCCTGGAG
ATTCTAGCAGCGGCTGGACCGCCGGCGCTGCCGCTTACTACGTCGGATA
CCTGCAGCCTAGAACCTTCCTGTTGAAGTACAACGAGAACGGCACCATC
ACAGATGCCGTGGACTGCGCCCTGGACCCCCTGAGCGAGACAAAGTGCA
CCCTGAAGAGCTTCACCGTGGAGAAGGGCATCTACCAGACAAGCAACTT
CAGAGTGCAGCCTACCGAGTCAATCGTGAGATTCCCAAACATCACCAAC
CTTTGTCCTTTCGGCGAGGTATTTAACGCCACCCGGTTCGCCAGCGTGT
ACGCCTGGAATAGGAAGCGGATCAGCAACTGCGTGGCCGATTACAGCGT
GCTCTATAACAGCGCCAGTTTTAGCACTTTCAAGTGCTACGGAGTCTCT
CCTACAAAGCTGAACGACCTGTGCTTCACCAACGTGTATGCCGACAGCT
TCGTCATCCGGGGCGACGAGGTGCGACAGATCGCTCCTGGCCAGACCGG
CAAGATAGCCGACTACAACTACAAGCTGCCTGACGACTTCACAGGCTGC
GTGATCGCTTGGAACAGCAACAATCTGGATAGCAAAGTGGGCGGCAACT
ATAACTACCTGTACAGACTGTTCCGGAAGTCCAATCTCAAGCCGTTTGA
GAGAGACATCAGCACCGAAATCTACCAGGCTGGATCTACACCCTGCAAC
GGCGTCGAAGGCTTCAATTGTTACTTCCCTCTGCAATCTTACGGCTTCC
AGCCCACCAACGGCGTGGGCTACCAGCCCTACAGAGTGGTTGTGCTGAG
CTTCGAGCTGCTGCACGCCCCAGCTACAGTGTGCGGCCCTAAGAAATCT
ACAAACCTGGTCAAGAACAAGTGTGTGAACTTCAACTTCAATGGCCTGA
CGGGCACCGGCGTGCTGACAGAGAGCAACAAGAAGTTCCTGCCTTTCCA
GCAATTTGGCAGAGACATCGCCGACACCACCGACGCCGTGCGCGACCCT
CAGACCCTGGAAATTCTGGACATCACCCCATGTTCTTTCGGCGGCGTGT
CCGTCATTACGCCAGGCACCAATACCAGCAACCAGGTGGCCGTGCTTTA
TCAGGATGTGAATTGTACCGAAGTTCCTGTTGCAATCCACGCCGACCAA
CTGACCCCCACATGGAGAGTGTACTCTACCGGCAGCAACGTGTTCCAAA
CGAGAGCCGGATGCCTGATTGGAGCTGAGCATGTGAACAACAGCTACGA
GTGCGATATTCCAATCGGAGCCGGCATCTGCGCCTCCTACCAAACACAA
ACCAACTCCCCTCGTAGAGCGAGAAGCGTGGCCTCTCAGAGCATCATCG
CCTACACCATGAGCCTGGGTGCCGAAAACTCCGTGGCTTACTCCAACAA
CAGCATCGCCATCCCTACAAATTTCACCATCAGCGTGACAACCGAGATC
CTGCCTGTGTCCATGACCAAGACCAGCGTGGACTGCACGATGTACATCT
GCGGAGATAGCACCGAGTGCAGCAATCTGCTACTGCAGTATGGCAGCTT
CTGCACCCAACTGAACAGAGCACTGACCGGCATTGCTGTGGAACAGGAC
AAGAATACCCAGGAGGTGTTCGCCCAAGTGAAGCAGATTTACAAGACAC
CCCCTATCAAGGACTTCGGAGGCTTCAACTTCAGCCAGATCCTGCCTGA
CCCTAGCAAGCCAAGCAAAAGATCCTTTATCGAAGATCTGCTGTTTAAC
AAGGTGACACTGGCCGATGCCGGCTTTATCAAGCAGTACGGCGACTGCC
TGGGAGACATCGCCGCCAGAGACCTGATCTGTGCTCAGAAATTTAACGG -continued

```
GCTGACCGTGCTGCCACCTCTGCTGACAGATGAGATGATCGCTCAGTAC

ACCAGCGCCCTGCTGGCCGGCACAATTACCTCCGGCTGGACCTTCGGAG

CCGGAGCCGCCCTGCAGATCCCCTTCGCCATGCAGATGGCCTACCGGTT

CAATGGCATCGGCGTCACCCAAAACGTGCTCTATGAGAACCAGAAGCTG

ATCGCAAACCAGTTCAACTCCGCCATCGGTAAGATCCAGGACAGTCTGA

GCAGCACGGCGTCTGCCCTGGGCAAGCTCCAGGACGTGGTGAACCAGAA

CGCCCAGGCCCTTAACACCCTGGTGAAACAACTGAGCAGCAACTTCGGT

GCCATTTCCAGCGTTCTCAATGACATCCTGAGCAGACTGGATAAGGTGG

AAGCCGAGGTGCAGATCGACCGGCTGATCACCGGACGGCTGCAGAGCCT

GCAGACGTACGTGACCCAGCAATTAATCAGAGCTGCCGAGATCAGAGCC

AGCGCCAATCTGGCTGCCACCAAAATGAGCGAATGTGTGCTGGGCCAGT

CAAAGAGAGTGGATTTTTGTGGCAAAGGCTACCACCTGATGTCCTTCCC

TCAGTCTGCCCCTCACGGCGTGGTGTTCCTCCATGTGACCTATGTGCCT

GCTCAGGAGAAGAACTTTACCACAGCCCCTGCTATCTGCCACGACGGAA

AGGCCCACTTCCCCAGAGAGGGCGTGTTTGTGTCCAATGGCACACACTG

GTTCGTGACCCAAAGAAACTTCTACGAGCCCCAGATCATCACCACAGAC

AACACCTTCGTGAGCGGCAACTGCGACGTGGTGATCGGCATCGTGAACA

ACACAGTGTACGACCCCCTGCAACCTGAGCTGGACAGCTTCAAAGAGGA

ACTGGACAAATACTTCAAGAATCACACCAGCCCTGATGTGGATCTGGGC

GACATCAGCGGCATCAACGCCAGCGTCGTGAACATCCAGAAGGAAATCG

ACAGACTGAACGAAGTGGCCAAGAACCTGAACGAGAGCCTCATCGATCT

GCAGGAGCTGGGCAAGTACGAGCAGTACATCAAATGGCCTTTCTTCTTC

ATCATCGGCCTGATTATCGGCCTGTTCCTCGTGCTGAGAGTGGGCATCC

ACCTGTGCATCAAGCTTAAGCACACAAAAAAGCGGCAGATTTACACCGA

CATCGAGATGAACCGGCTGGGCAAATGAGAATTCCACGTGGGATCC
```

DETAILED DESCRIPTION OF THE EMBODIMENTS

Coronaviruses, such as SARS-CoV, MERS-CoV and SARS-Cov-2, are enveloped viruses having an RNA genome of about 30,000 bases. They fall within the beta genus of coronaviruses. They contain a nucleocapsid surrounded by a lipid bilayer derived from the host cell. An envelope-anchored spike protein (called "S") mediates the entry of the coronavirus into host cells by binding a host receptor and then fusing viral and host membranes. A defined receptor binding domain is the receptor for angiotensin converting enzyme 2 (ACE2). (Wan et al., J. Vir. (2020) 94: 1). Coronavirus S proteins contain three copies of an 51 subunit and three copies of an S2 subunit. Coronavirus S proteins are cleaved into 51 and S2 subunits by furin during protein biosynthesis. The two subunits trimerize and fold into a metastable prefusion conformation. The 51 subunit is responsible for receptor binding while the S2 subunit mediates membrane fusion.

SARS-CoV and SARS-CoV-2 spike protein share about 76% sequence homology, suggesting that these two viruses share the same receptor, ACE2. There is lower sequence similarity between SARS-CoV-2 and MERS-CoV.

Studies on the genomes of SARS-CoV-2 isolated from patients over the span of four months from December 2019 to March 2020 showed that the overall similarity of the human strains declined over the four month period indicating mutation of the virus had occurred within the human population to 0.988468, corresponding to an average of 348.33 nucleotide differences. Such changes imply evolutional changes of this virus, which might result in attenuation or more virulent strains (Li et al 2020. Xidan University). Subsequently, the viral variant which was predominant prior to March 2020, D614, was overtaken by another variant which has a single amino acid change to the spike protein, G614, even in areas where D614 was well established (Korber et al, (2020) Cell, 4:812-827). Subsequently, in late 2020, an unexpected rise in reported COVID-19 cases was attributed to the emergence of the new variants, B.1.1.7 in the UK and 501Y.V2 in South Africa (Fontanet et al, (2021) the Lancet, 397: 952-954). Both variants have a mutation (N501Y) in the receptor-binding domain of the spike protein that is reported to contribute to increased transmission, with estimates ranging between 40% and 70% for increased transmission. The 501Y.V2 variant has two additional mutations (E484K and K417N) in the spike protein that confer a potential immune escape to antibodies. A further variant of concern, P.1 has emerged in Brazil with another set of mutations (N501Y, E484K, and K417T).

An important concern is whether the currently available COVID-19 vaccines will be able to protect against infection or disease from the SARS-CoV-2 variants. Preliminary research suggests sera from individuals immunized with the mRNA COVID-19 vaccines neutralized a pseudovirus analogous to the U.K. variant but were less effective against a pseudovirus analogous to the South Africa variant (Yang et al (2021) Nature, doi.org/10.1038/s41586-021-03324-6). Moreover, preliminary results of studies using viral vector vaccines demonstrated good efficacy against the UK variant but poor efficacy against the South Africa variant (Madhi et al (2021) N.E.J.M. DOI: 10.1056/NEJMoa2102214). Therefore, it appears that a vaccine which is capable of inducing production of broadly reactive antibodies would be required to provide protection from infection by variant strains of coronavirus which include multiple mutations.

The inventors herein have made vaccines against beta coronavirus which comprises a VLP. VLPs are multiprotein structures which are generally composed of one or more viral proteins. VLP's mimic the conformation of viruses but lack genetic material, and therefore are not infectious. They can form (or "self-assemble") upon expression of a viral structural protein under appropriate circumstances. VLP vaccines overcome some of the disadvantages of more traditional vaccines prepared using attenuated viruses because they can be produced without the need to have any live virus present during the production process. A wide variety of VLPs have been prepared. For example, VLPs including single or multiple capsid proteins either with or without envelope proteins and/or surface glycoproteins have been prepared. In some cases, VLPs are non-enveloped and assemble by expression of just one major capsid protein. In other cases, VLPs are enveloped and can comprise multiple antigenic proteins found in the corresponding native virus. Self-assembly of enveloped VLPs is more complex than non-enveloped VLPs because of the complex reactions required for fusion with the host cell membrane (Garrone et al., 2011 Science Trans. Med. 3: 1-8) and "budding" of the VLP to form a fully enveloped separate particle. Accordingly, self-assembly of enveloped VLPs may not be successful and the formation and stability of enveloped VLP particles is difficult to predict. Formation of intact VLPs can be confirmed by imaging of the particles using electron microscopy.

VLPs typically resemble their corresponding native virus and can be multivalent particulate structures. The present disclosure encompasses the recognition that presentation of surface glycoproteins in the context of a VLP is advantageous for induction of neutralizing antibodies against such polypeptide as compared to other forms of antigen presentation, e.g., soluble antigens not associated with a VLP. Neutralizing antibodies most often recognize tertiary or quaternary structures; this often requires presenting antigenic proteins, like envelope glycoproteins, in their native viral conformation. VLP's present epitopes in a highly structured, repetitive array that enables efficient crosslinking of B cell receptors, leading to activation and expansion of high affinity B cells and subsequent antibody production (Bachmann, 1993). Indeed, VLP expression of a B cell antigen improved neutralizing titers by over 10-fold relative to immunization with the same amount of recombinant protein (Kirchmeier, 2014). Accordingly, use of VLPs as a vaccine modality may expand higher affinity B cell repertoires relative to recombinant protein or DNA/mRNA-based approaches, the latter approach being used in two widely used COVID-19 vaccines.

The VLPs of the invention comprise retroviral vectors. Retroviruses are enveloped RNA viruses that belong to the family Retroviridae. After infection of a host cell by a retrovirus, RNA is transcribed into DNA via the enzyme reverse transcriptase. DNA is then incorporated into the host cell's genome by an integrase enzyme and thereafter replicates as part of the host cell's DNA. The Retroviridae family includes the following genera Alpharetrovirus, Betaretrovirus, Gammearetrovirus, Deltaretrovirus, Epsilonretrovirus, Lentivirus and Spumavirus. The hosts for this family of retroviruses generally are vertebrates. Retroviruses produce an infectious virion containing a spherical nucleocapsid (the viral genome in complex with viral structural proteins) surrounded by a lipid bilayer derived from the host cell membrane.

Retroviral vectors can be used to generate VLPs that lack a retrovirus-derived genome and are therefore non-replicating. This is accomplished by replacement of most of the coding regions of the retrovirus with genes or nucleotide sequences to be transferred; so that the vector is incapable of making proteins required for additional rounds of replication. Depending on the properties of the glycoproteins present on the surface of the particles, VLPs have limited ability to bind to and enter the host cell but cannot propagate. Therefore, VLPs can be administered safely as an immunogenic composition (e.g., a vaccine).

The present invention utilizes VLPs comprising one or more retroviral structural proteins. In some embodiments, a structural protein for use in accordance with the present invention is Alpharetrovirus (e.g., Avian Leukosis Virus), Betaretrovirus (Mouse Mammary Tumor Virus), Gammearetrovirus (Murine Leukemia Virus), Deltaretrovirus (Bovine Leukemia Virus), Epsilonretrovirus (Walley Dermal Sarcoma Virus), Lentivirus (Human Immunodeficiency Virus 1) or Spumavirus (Chimpanzee Foamy Virus) structural protein. In certain embodiments, a structural polyprotein is a Murine Leukemia Virus (MLV) structural protein. In an embodiment of the invention the structural protein in a Moloney Murine Leukemia Virus (MMLV). Genomes of these retroviruses are readily available in databases.

In some embodiments, the retroviral structural protein for use in accordance with the present invention is a Gag polypeptide. The Gag proteins of retroviruses have an overall structural similarity and, within each group of retroviruses, are conserved at the amino acid level. Retroviral Gag proteins primarily function in viral assembly. Expression of Gag of some viruses (e.g., murine leukemia viruses, such as MMLV) in some host cells, can result in self-assembly of the expression product into VLPs. The Gag gene expression product in the form of a polyprotein gives rise to the core structural proteins of the VLP. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. In general, the form of the Gag protein that mediates viral particle assembly is the polyprotein. Retroviruses assemble an immature capsid composed of the Gag polyprotein but devoid of other viral elements like viral protease with Gag as the structural protein of the immature virus particle.

A suitable Gag polypeptide for use in the invention is substantially homologous to a known retroviral Gag polypeptide. The MMLV-Gag gene encodes a 65 kDa polyprotein precursor which is proteolytically cleaved into 4 structural proteins (Matrix (MA); p12; Capsid (CA); and Nucleocapsid (NC)), by MLV protease, in the mature virion. In the absence of MLV protease, the polyprotein remains uncleaved and the resulting particle remains in an immature form. The morphology of the immature particle is different from that of the mature particle. In some embodiments of the invention, the Gag sequence does not include a gene encoding MLV protease. The gene encoding the MMLV nucleic acid is SEQ ID NO: 2. An exemplary codon optimized sequence of MMLV nucleic acid is provided as SEQ ID NO: 3.

Therefore, in some embodiments, a Gag polypeptide suitable for the present invention is substantially homologous to an MMLV-Gag polypeptide (SEQ ID NO:1). In some embodiments, a Gag polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a Gag polypeptide suitable for the present invention is substantially identical to, or identical to SEQ ID NO: 1.

In some embodiments, a suitable MMLV-Gag polypeptide is encoded by a nucleic acid sequence having at least 80%, 85%, 90%, 91%, 92%, 93%, 94%, 95%, 96%, 97%, 98%, 99% sequence identity to SEQ ID NO:2. In some embodiments, a suitable MMLV-Gag polypeptide is encoded by a nucleic acid sequence having SEQ ID NO: 2 or a codon degenerate version thereof.

As is well known to those of skill in the art, it is possible to improve the expression of a nucleic acid sequence in a host organism by replacing the nucleic acids coding for a particular amino acid (i.e. a codon) with another codon which is better expressed in the host organism. One reason that this effect arises is due to the fact that different organisms show preferences for different codons. The process of altering a nucleic acid sequence to achieve better expression based on codon preference is called codon optimization. Various methods are known in the art to analyze codon use bias in various organisms and many computer algorithms have been developed to implement these analyses in the design of codon optimized gene sequences. Therefore, in some embodiments, a suitable MMLV-Gag polypeptide is encoded by a codon optimized version of a nucleic acid sequence encoding MMLV-Gag and having at least 80%, 85%, 90%, 91%, 92%, 93%, 94%, 95%, 96%, 97%, 98%, 99% sequence identity to SEQ ID NO:3. In some embodiments, a suitable MMLV-Gag polypeptide is encoded by a nucleic acid sequence which is substantially identical to, or identical to, SEQ ID NO: 3.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Examples of such programs are described in Altschul, et al., 1990, *J. Mol. Biol.*, 215(3): 403-410; Altschul, et al., 1996, *Methods in Enzymology* 266:460-480; Altschul, et al., 1997 *Nucleic Acids Res.* 25:3389-3402; Baxevanis, et al., 1998, *Bioinformatics: A Practical Guide to the Analysis of Genes and Proteins*, Wiley; and Misener, et al., (eds.), 1999, *Bioinformatics Methods and Protocols* (Methods in Molecular Biology, Vol. 132), Humana Press. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Alternatively, the Gag polypeptide used in the invention may be a modified retroviral Gag polypeptide containing one or more amino acid substitutions, deletions, and/or insertions as compared to a wild-type or naturally-occurring Gag polypeptide while retaining substantial self-assembly activity. Typically, in nature, a Gag protein includes a large C-terminal extension which may contain retroviral protease, reverse transcriptase, and integrase enzymatic activity. Assembly of VLPs, however, generally does not require the presence of such components. In some cases, a retroviral Gag protein alone (e.g., lacking a C-terminal extension, lacking one or more of genomic RNA, reverse transcriptase, viral protease, or envelope protein) can self-assemble to form VLPs both in vitro and in vivo (Sharma S et al., 1997, Proc. Natl. Acad. Sci. USA 94: 10803-8).

The inventors of the present application have made VLPs which express beta coronavirus envelope glycoproteins on the surface which can cause an immune response in a subject. A humoral immune response is an immune response mediated by antibody molecules. Certain antibodies, called neutralizing antibodies, defend cells from infection by a virus and associated biological effects by recognizing and binding to a particular protein or antigen expressed by the virus. The envelope protein of coronaviruses are important targets for production of neutralizing antibodies. It is well known to those in the art that retroviral Gag-based enveloped VLPs can be used to express a variety of envelope glycoproteins for the purpose of eliciting neutralizing antibody responses. More specifically, evidence exists for expression of Class I viral fusion proteins such as HIV-1 gp120, metapneumovirus and Influenza HA, as well as Class III fusion proteins such as VSV G protein and CMV gB protein (Mammano et al., 1997, J. Virol. 71:3341-3345; Levy et al., 2013, Vaccine 31:2778-2785; Lemaitre et al., 2011, Clin. Microbiol. Infect. 1:732-737; Garrone et al, 2011; Kirchmeier et al., 2014, CVI 21: 174-180). However, there is little known about expression of coronavirus spike proteins, particularly with MLV-derived Gag. In U.S. Pat. No. 8,920,812, Example 1 describes a failure to express RSV F glycoprotein, a class II viral fusion protein, on the surface of a VLP produced using MLV Gag. The inventor hypothesized that the presence of the RSV F glycoprotein interfered with budding of the Gag viral particle through the cell membrane (see column 41, line 50). It was therefore not predictable that a retroviral Gag-based enveloped virus-like particle could be used to successfully express the coronavirus spike protein. Nevertheless, the present inventors have made several different embodiments of a beta coronavirus vaccine comprising one or more spike polypeptide antigens (e.g., from SARS CoV-2, SARS CoV and MERS-CoV) on the surface of a VLP. In some embodiments, the spike polypeptide antigens comprise modified polypeptides. In some embodiments, the spike polypeptide antigens have more than one genetic modification.

In some embodiments, a VLP of the invention includes a fusion protein of a spike polypeptide from a beta coronavirus (e.g., all or part of an extracellular portion of an beta coronavirus spike polypeptide) and a transmembrane and/or cytoplasmic domain that is not found in nature in the beta coronavirus protein (e.g., from another virus). In some embodiments, a fusion protein includes a spike polypeptide from a beta coronavirus (e.g., all or part of an extracellular portion of the spike polypeptide) and a transmembrane domain and/or cytoplasmic domain found in nature in the glycoprotein G from VSV which is referred to as VSV-G. The nucleotide and amino acid sequences of the VSV-G protein are known in the art.

The transmembrane domain of VSV-G can function to target the viral glycoprotein to the cell membrane (Compton T et al., 1989, Proc Natl Acad Sci USA 86:4112-4116). Swapping the transmembrane and cytoplasmic domains of VSV-G for the transmembrane and cytoplasmic domains of another protein has been used to increase the yield of the protein of interest in the VLP preparation and increase immunogenicity to neutralizing antibody response (Garrone et al., 2011). This modification was successful to increase yield and activity of a VLP expressing HCV-E1 protein (Garrone et al, 2011) and CMV-gB protein (Kirchmeier et al, 2014). However, this modification has also been associated with a significant loss of immunogenicity when used with certain viral antigens. In addition, expression of some glycoproteins has decreased after replacement of the transmembrane/cytoplasmic domain of the antigenic glycoprotein with the transmembrane/cytoplasmic domain from VSV. For example, loss of glycoprotein was reported in SARS virus (Broer et al., 2006, J. Vir. 80, 1302-1310). In RSV, a significant loss of immunogenicity was observed when the antigenic surface protein was modified to replace the transmembrane component with a sequence from VSV (See Example 6).

In some embodiments, an immunogenic composition of the present invention comprises a VLP comprising a wild type spike polypeptide from SARS-CoV-2, the sequence of which is SEQ ID NO: 4 or a codon degenerate version of SEQ ID NO: 4. A nucleic acid which encodes for the polypeptide is shown as SEQ ID NO: 5. A codon optimized version of SEQ ID NO: 5 is shown as SEQ ID NO: 6. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 4. In some embodiments, the present invention comprises an immunogenic composition comprising a VLP comprising a polypeptide having an amino acid sequence which is SEQ ID NO: 4 or a codon degenerate version of SEQ ID NO: 4. In some embodiments, the polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 5. In some embodiments, the polypeptide is encoded by a codon optimized version of the nucleic acid sequence of SEQ ID NO: 5, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 6. In some embodiments, the polypeptide is encoded by a nucleic acid sequence having SEQ ID NO: 6.

In some embodiments, an immunogenic composition of the present invention comprises a VLP comprising a modified spike polypeptide from SARS-CoV-2 which has been modified to replace the transmembrane and cytoplasmic segments with corresponding segments from VSV, the sequence of which is SEQ ID NO: 26 or a codon degenerate version of SEQ ID NO: 26. A nucleic acid which encodes for the polypeptide is shown as SEQ ID NO: 25. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 25. In some embodiments, the present invention comprises an immunogenic composition comprising a VLP comprising a polypeptide having an amino acid sequence which is SEQ ID NO: 25 or a codon degenerate version of SEQ ID NO: 25. In some embodiments, the polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 26. In some embodiments, the mutated polypeptide is encoded by a nucleic acid sequence having SEQ ID NO: 26. In some embodiments, the polypeptide is encoded by a codon optimized version of the nucleic acid sequence of SEQ ID NO: 26, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 27.

In some embodiments, an immunogenic composition of the present invention comprises a VLP comprising a wild type spike polypeptide from SARS-CoV, the sequence of which is SEQ ID NO: 7 or a codon degenerate version of SEQ ID NO: 7. A nucleic acid which encodes for the polypeptide is shown as SEQ ID NO: 8. A codon optimized version of SEQ ID NO: 8 is shown as SEQ ID NO: 9. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 7. In some embodiments, the present invention comprises an immunogenic composition comprising a VLP comprising a polypeptide having an amino acid sequence which is SEQ ID NO: 7 or a codon degenerate version of SEQ ID NO: 7. In some embodiments, the polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 8. In some embodiments, the polypeptide is encoded by a codon optimized version of the nucleic acid sequence of SEQ ID NO: 8, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 9. In some embodiments, the polypeptide is encoded by a nucleic acid sequence having SEQ ID NO: 9.

In some embodiments, an immunogenic composition of the present invention comprises a VLP comprising a wild type spike polypeptide from MERS-CoV, the sequence of which is SEQ ID NO: 10 or a codon degenerate version of SEQ ID NO: 10. A nucleic acid which encodes for the polypeptide is shown as SEQ ID NO: 11. A codon optimized version of SEQ ID NO:11 is shown as SEQ ID NO: 12. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 10. In some embodiments, the present invention comprises an immunogenic composition comprising a VLP comprising a polypeptide having an amino acid sequence which is SEQ ID NO: 10 or a codon degenerate version of SEQ ID NO: 10. In some embodiments, the polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 11. In some embodiments, the polypeptide is encoded by a codon optimized version of the nucleic acid sequence of SEQ ID NO: 11, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 12. In some embodiments, the polypeptide is encoded by a nucleic acid sequence having SEQ ID NO: 12.

In some embodiments, immunogenic compositions of the present invention comprise VLPs comprising variants of beta coronavirus spike glycoproteins. In some embodiments, a variant spike glycoprotein has been modified to delete the furin cleavage site from the spike polypeptide. In some embodiments, the spike glycoprotein has been modified to replace lysine (986) and valine (987) residues with proline residues. In some embodiments, the spike glycoprotein has been modified to delete the furin cleavage site and to replace lysine (986) and valine (987) residues with proline residues. Each such modification is further described below.

It is known that the coronavirus spike protein includes a site where the protease, furin, cleaves the S polypeptide into S1 and S2 subunits during the process of virion maturation. A modified spike protein construct was produced wherein the amino acid sequence was modified to remove the furin cleavage site, thus retaining the spike polypeptide in its immature form. It is possible that the furin-cleavage site mutated version of the spike protein, which does not undergo normal cleavage and maturation, will show enhanced cell receptor binding and cell entry, indicating that immunity against this structure may result in humoral immunity with greater neutralizing activity.

In some embodiments, an immunogenic composition of the invention comprises a VLP comprising a modified SARS-CoV-2 spike polypeptide with a mutated furin cleavage site as compared to a wild-type or naturally-occurring SARS-CoV-2 spike polypeptide. The sequence for an exemplary modified SARS-CoV-2 polypeptide is shown as SEQ ID NO: 16. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 16. In some embodiments, the present invention comprises an immunogenic composition comprising a VLP comprising a polypeptide having an amino acid sequence which is SEQ ID NO: 16 or a codon degenerate version of SEQ ID NO: 16. In some embodiments, the modified polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 17. In some embodiments, the modified polypeptide is encoded by a codon optimized version of the nucleic acid sequence of SEQ ID NO: 17, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 18. In some embodiments, the mutated polypeptide is encoded by a nucleic acid sequence having SEQ ID NO: 18.

It is known from previous studies of SARS-CoV and MERS-CoV that substitution of two amino acid residues with proline residues results in stabilisation of the S2 subunit in its prefusion conformation (Pallesen et al., 2017 PNAS. 114:35; Wrapp et al (2020) Science: 367: 1260-1263). Therefore, it is possible that such a mutation could enhance the immune response to coronavirus. Accordingly, a SARS-CoV-2 polypeptide construct was prepared which has been modified to replace lysine (986) and valine (987) residues with proline residues. In some embodiments, an immunogenic composition of the invention comprises a VLP comprising a SARS-CoV-2 polypeptide which has been modified to replace lysine (986) and valine (987) residues with proline residues as compared to a wild-type or naturally-occurring SARS-CoV-2 polypeptide. The sequence of an exemplary modified polypeptide is shown in SEQ ID NO: 13. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 13. In some embodiments, the present invention comprises an immunogenic composition comprising a VLP comprising a polypeptide having an amino acid sequence which is SEQ ID NO: 13 or a codon degenerate version of SEQ ID NO: 13. In some embodiments, the modified polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 14. In some embodiments, the modified polypeptide is encoded by a codon optimized version of the nucleic acid sequence of SEQ ID NO: 14, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO:15. In some embodiments, the modified polypeptide is encoded by a nucleic acid sequence having SEQ ID NO: 15.

In a further variation, a SARS-CoV-2 polypeptide construct was prepared which has been modified to replace lysine (986) and valine (987) residues with proline residues and which have been further modified to remove the furin cleavage site. In some embodiments, an immunogenic composition of the invention comprises a VLP comprising a SARS-CoV-2 polypeptide which has been modified to replace lysine (986) and valine (987) residues with proline residues and to remove the furin cleavage site as compared to a wild-type or naturally-occurring SARS-CoV-2 polypeptide. The sequence of an exemplary modified polypeptide is shown in SEQ ID NO: 19. In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 19. In some embodiments, the present invention comprises an immunogenic composition comprising a VLP comprising a polypeptide having an amino acid sequence which is SEQ ID NO: 19 or a codon degenerate version of SEQ ID NO: 19. In some embodiments, the modified polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 20. In some embodiments, the modified polypeptide is encoded by a codon optimized version of the nucleic acid sequence of SEQ ID NO: 20, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO:21. In some embodiments, the modified polypeptide is encoded by a nucleic acid sequence having SEQ ID NO: 21.

In some embodiments, a VLP described herein comprises a fusion protein comprising an extracellular domain (or a portion thereof) of a coronavirus spike polypeptide, and a transmembrane domain and cytoplasmic tail from an envelope protein from VSV. In some embodiments, the immunogenic composition of the invention comprises a VLP comprising a coronavirus spike polypeptide modified to replace the transmembrane domain and cytoplasmic tail with the transmembrane domain and cytoplasmic tail from VSV. Any of the coronavirus spike proteins described herein may be modified to replace the transmembrane domain and cytoplasmic tail with a transmembrane domain and cytoplasmic tail from VSV.

In one particular embodiment, the inventors have constructed a SARS-CoV-2 spike protein which protein has been modified to replace the transmembrane domain and cytoplasmic tail with a transmembrane domain and cytoplasmic tail from VSV; to replace lysine (986) and valine (987) residues with proline residues; and to remove the furin cleavage site. This triple modified SARS-CoV-2 protein includes the double proline mutation directed to enhanced stability and a mutated furin cleavage site, which is associated with enhanced receptor binding. Further, it includes the transmembrane domain and cytoplasmic tail from VSV, which are associated with improved expression on the VLP envelope. The sequence of this triple modified coronavirus spike polypeptide is shown as SEQ ID NO: 22 (shown above with the portion from VSV in bold text at the end of the sequence). In some embodiments, the present invention comprises an immunogenic composition comprising a VLP comprising a polypeptide having an amino acid sequence which is at least 80%, 85%, 90%, 91%, 92%, 93%, 94%, 95%, 96%, 97%, 98%, 99% or more homologous to SEQ ID NO: 22. In some embodiments, the modified polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 23. In some embodiments, the modified polypeptide is encoded by a codon optimized version of the nucleic acid sequence of SEQ ID NO: 23, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 23. In some embodiments, the modified polypeptide is encoded by a nucleic acid sequence having SEQ ID NO: 24.

Mixtures of antigens can induce broad reactive immunity therefore, combinations of coronavirus antigens can be used to enhance the breadth of the immune response. VLPs can be used to express two (bivalent) or three (trivalent) viral antigens in their native conformation, thus inducing a potent B cell response. Previous studies using Zika viral epitopes demonstrated that the combination of two antigens on a single bivalent VLP generated a significantly more potent immune response than two monovalent VLPs expressing the same antigens (U.S. Pat. No. 8,920,812).

Accordingly, the VLPs of the present disclosure include bivalent VLPs containing two wild type coronavirus spike proteins, two modified coronavirus spike proteins described herein or any combination of the wild type and modified coronavirus spike proteins described herein. The VLPs of the present disclosure also include trivalent VLPs containing three wild type coronavirus spike proteins, three modified coronavirus spike proteins described herein or any combination of the wild type and modified coronavirus spike proteins described herein. One or more of any of the wild type or modified spike proteins expressed on a bivalent or a trivalent VLP may be further modified to replace the transmembrane domain and the cytoplasmic tail with the transmembrane domain and cytoplasmic tail from VSV.

In a preferred embodiment, the VLP of the present disclosure is a trivalent VLP comprising a spike protein from SARS-CoV-2, a spike protein from SARS-CoV and a spike protein from MERS-CoV. One or more of the spike proteins may be modified to replace the transmembrane domain and the cytoplasmic tail with the transmembrane domain and cytoplasmic tail from VSV.

In some embodiments, an immunogenic composition of the present invention comprises a trivalent VLP comprising a wild type spike polypeptide from SARS-CoV-2, the sequence of which is SEQ ID NO: 4 or a codon degenerate version of SEQ ID NO: 4; a spike polypeptide from SARS-CoV the sequence of which is SEQ ID NO: 7 or a codon degenerate version of SEQ ID NO: 7; and a spike polypeptide from MERS the sequence of which is SEQ ID NO: 10 or a codon degenerate version of SEQ ID NO: 10. A nucleic acid which encodes for the SARS-CoV-2 polypeptide is shown as SEQ ID NO: 5. A codon optimized version of SEQ ID NO: 5 is shown as SEQ ID NO: 6. A nucleic acid which encodes for the SARS-CoV polypeptide is shown as SEQ ID NO: 8. A codon optimized version of SEQ ID NO: 8 is shown as SEQ ID NO: 9. A nucleic acid which encodes for the MERS polypeptide is shown as SEQ ID NO: 11. A codon optimized version of SEQ ID NO:11 is shown as SEQ ID NO: 12. In some embodiments, the present invention comprises an immunogenic composition comprising a VLP comprising polypeptides having an amino acid sequence which is at least 80%, 85%, 90%, 91%, 92%, 93%, 94%, 95%, 96%, 97%, 98%, 99% or more homologous to SEQ ID NO: 4, 80%, 85%, 90%, 91%, 92%, 93%, 94%, 95%, 96%, 97%, 98%, 99% or more homologous to SEQ ID NO: 7 and 80%, 85%, 90%, 91%, 92%, 93%, 94%, 95%, 96%, 97%, 98%, 99% or more homologous to SEQ ID NO: 10. In some embodiments, the SARS-CoV-2 polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 5. In some embodiments, the polypeptide is encoded by a codon optimized version of the nucleic acid sequence of SEQ ID NO: 5, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 6. In some embodiments, the polypeptide is encoded by a nucleic acid sequence having SEQ ID NO: 6. In some embodiments, the SAR-CoV polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 8. In some embodiments, the polypeptide is encoded by a codon optimized version of the nucleic acid sequence of SEQ ID NO: 8, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 9. In some embodiments, the polypeptide is encoded by a nucleic acid sequence having SEQ ID NO: 9. In some embodiments, the MERS polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 11. In some embodiments, the polypeptide is encoded by a codon optimized version of the nucleic acid sequence of SEQ ID NO: 11, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 12. In some embodiments, the polypeptide is encoded by a nucleic acid sequence having SEQ ID NO: 12.

In some embodiments, an immunogenic composition of the present invention comprises a trivalent VLP comprising a modified spike polypeptide from SARS-CoV-2, the sequence of which is SEQ ID NO: 22 or a codon degenerate version of SEQ ID NO: 22; a spike polypeptide from SARS-CoV the sequence of which is SEQ ID NO: 7 or a codon degenerate version of SEQ ID NO: 7; and a spike polypeptide from MERS the sequence of which is SEQ ID NO: 10 or a codon degenerate version of SEQ ID NO: 10. A nucleic acid which encodes for the SARS-CoV-2 polypeptide is shown as SEQ ID NO: 5. A codon optimized version of SEQ ID NO: 5 is shown as SEQ ID NO: 6. A nucleic acid which encodes for the SARS-CoV polypeptide is shown as SEQ ID NO: 8. A codon optimized version of SEQ ID NO: 8 is shown as SEQ ID NO: 9. A nucleic acid which encodes for the MERS polypeptide is shown as SEQ ID NO: 11. A codon optimized version of SEQ ID NO:11 is shown as SEQ ID NO: 12. In some embodiments, the present invention comprises an immunogenic composition comprising a VLP comprising polypeptides having an amino acid sequence which is at least 80%, 85%, 90%, 91%, 92%, 93%, 94%, 95%, 96%, 97%, 98%, 99% or more homologous to SEQ ID NO: 22, 80%, 85%, 90%, 91%, 92%, 93%, 94%, 95%, 96%, 97%, 98%, 99% or more homologous to SEQ ID NO: 7 and 80%, 85%, 90%, 91%, 92%, 93%, 94%, 95%, 96%, 97%, 98%, 99% or more homologous to SEQ ID NO: 10. In some embodiments, the SARS-CoV-2 polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 23. In some embodiments, the polypeptide is encoded by a codon optimized version of the nucleic acid sequence of SEQ ID NO: 23, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 24. In some embodiments, the polypeptide is encoded by a nucleic acid sequence having SEQ ID NO: 24. In some embodiments, the SAR-CoV polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 8. In some embodiments, the polypeptide is encoded by a codon optimized version of the nucleic acid sequence of SEQ ID NO: 8, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 9. In some embodiments, the polypeptide is encoded by a nucleic acid sequence having SEQ ID NO: 9. In some embodiments, the MERS polypeptide is encoded by a nucleic acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO: 11. In some embodiments, the polypeptide is encoded by a codon optimized version of the nucleic acid sequence of SEQ ID NO: 11, which is at least 50%, 55%, 60%, 65%, 70%, 75%, 80%, 85%, 90%, 91%, 92%, 93%, 94%, 95%, 96%, 97%, 98%, 99% or more homologous to the SEQ ID NO: 12. In some embodiments, the polypeptide is encoded by a nucleic acid sequence having SEQ ID NO: 12.

As can be seen in the Examples, the VLPs of the invention were able to elicit a strong immune response to SARS-CoV-2. In particular, each of the modified spike variants described herein was effective to induce a strong immune response (see Example 5). The trivalent VLPs of the invention (see Example 6) induced an antibody response against SARS-Cov-2, SARS-CoV and MERS. Moreover, immunization with the trivalent VLPs of the invention induced antibodies that recognized a related seasonal human coronavirus, OC43, not included within the vaccine, demonstrating that the trivalent VLP has an ability to broaden immunity against coronaviruses. Unexpectedly, relative to immunization with a monovalent VLP, trivalent VLPs enriched the induction of antibodies with functional, neutralizing activity. This enrichment of neutralizing antibodies in shown in Table 8, which shows the ratio of endpoint neutralizing antibody titer to the endpoint antibody binding titer, using sera obtained from vaccinated mice.

The monovalent VLP which expresses the triple modified SARS-CoV-2 spike protein provides significant protection against infection by SARS-CoV-2 as demonstrated by a challenge study in golden hamster (Example 7). As shown in Example 7, the hamsters which were vaccinated with the VLP had significantly lower levels of viral RNA and improved clinical presentation as shown by body weight. Furthermore, the immunized hamsters were able to mount a stronger cytokine response than the unvaccinated hamsters.

The VLPs of the invention have demonstrated a broad immune response that is effective against a variant of SARS-CoV-2. As described in Example 9, a trivalent VLP expressing the triple modified SARS-CoV-2 spike protein, a native MERS spike protein and a native SARS-CoV protein and a monovalent VLP expressing the triple modified SARS-CoV-2 spike protein were evaluated for their ability to induce antibodies against the 501Y.V2 (South Africa) variant of SARS-CoV-2 in mice. Surprisingly, both the trivalent and the monovalent constructs elicited antibodies to the 501Y.V2 variant. Even more surprising was the fact that the antibody titres were similar for the 501Y.V2 strain and the original L strain of SARS-CoV-2. Accordingly, both the trivalent and the monovalent VLPs expressing the triple modified SARS-CoV-2 spike protein were unexpectedly effective at inducing a potent antibody response to a SARS-CoV-2 variant which has demonstrated significant escape from other COVID-19 vaccines.

The VLPs of the invention also had an effect on the nature of the antibody response. As shown in Example 10, mice immunized with a monovalent VLP of the invention expressing wild type SARS-CoV-2 spike protein produced a higher amount of IgG2b than those immunized with a recombinant spike protein. Higher IgG2b is associated with a TH1 immune response and may result in a higher level of cell-mediated immunity. Therefore, presentation of the spike protein on an VLP resulted in a response correlated to cell-mediated immunity.

It will be appreciated that a composition comprising VLPs will typically include a mixture of VLPs with a range of sizes. It is to be understood that the diameter values listed below correspond to the most frequent diameter within the mixture. In some embodiments >90% of the vesicles in a composition will have a diameter which lies within 50% of the most frequent value (e.g., 1000±500 nm). In some embodiments, the distribution may be narrower, e.g., >90% of the vesicles in a composition may have a diameter which lies within 40, 30, 20, 10 or 5% of the most frequent value. In some embodiments, sonication or ultra-sonication may be used to facilitate VLP formation and/or to alter VLP size. In some embodiments, filtration, dialysis and/or centrifugation may be used to adjust the VLP size distribution.

In general, VLPs produced in accordance with the methods of the present disclosure may be of any size. In certain embodiments, the composition may include VLPs with diameters in the range of about 20 nm to about 300 nm. In some embodiments, a VLP is characterized in that it has a diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs within a population show an average diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs in a population have a polydispersity index that is less than 0.5 (e.g., less than 0.45, less than 0.4, or less than 0.3). In some embodiments, VLP diameter is determined by nanosizing. In some embodiments, VLP diameter is determined by electron microscopy.

VLPs in accordance with the present invention may be prepared according to general methodologies known to the skilled person. For example, nucleic acid molecules, reconstituted vectors or plasmids may be prepared using sequences which are known in the art. Such sequences are available from banks, and material may be obtained from various collections, published plasmids, etc. These elements can be isolated and manipulated using techniques well known to the skilled artisan, or available in the art. Various synthetic or artificial sequences may also be produced from computer analysis or through (high throughput) screening of libraries. Recombinant expression of the polypeptides for VLPs requires construction of an expression vector containing a polynucleotide that encodes one or more polypeptide(s). Once a polynucleotide encoding one or more polypeptides has been obtained, the vector for production of the polypeptide may be produced by recombinant DNA technology using techniques known in the art. Expression vectors that may be utilized in accordance with the present invention include, but are not limited to mammalian and avian expression vectors, bacculovirus expression vectors, plant expression vectors (e.g., Cauliflower Mosaic Virus (CaMV), Tobacco Mosaic Virus (TMV)), plasmid expression vectors (e.g., Ti plasmid), among others.

The VLPs of the invention may be produced in any available protein expression system. Typically, the expression vector is transferred to a host cell by conventional techniques and the transfected cells are then cultured by conventional techniques to produce VLPs. In some embodiments, VLPs are produced using transient transfection of cells. In some embodiments, VLPs are produced using stably transfected cells. Typical cell lines that may be utilized for VLP production include, but are not limited to, mammalian cell lines such as human embryonic kidney (HEK) 293, WI 38, Chinese hamster ovary (CHO), monkey kidney (COS), HT1080, C10, HeLa, baby hamster kidney (BHK), 3T3, C127, CV-1, HaK, NS/O, and L-929 cells. Specific non-limiting examples include, but are not limited to, BALB/c mouse myeloma line (NSO/l, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 cells subcloned for growth in suspension culture, Graham et al., *J. Gen Virol.,* 36:59 (1977)); baby hamster kidney cells (BHK, ATCC CCL 10); Chinese hamster ovary cells+/−DHFR (CHO, Urlaub and Chasin, *Proc. Natl. Acad. Sci. USA,* 77:4216 (1980)); mouse sertoli cells (TM4, *Mather, Biol. Reprod.,* 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 (1982)); MRC 5 cells; FS4 cells; and a human hepatoma line (Hep G2). In some embodiments, cell lines that may be utilized for VLP production include insect (e.g., Sf-9, Sf-21, Tn-368, Hi5) or plant (e.g., *Leguminosa*, cereal, or tobacco) cells. It will be appreciated in some embodiments, particularly when glycosylation is important for protein function, mammalian cells are preferable for protein expression and/or VLP production (see, e.g., Roldao A et al., 2010 Expt Rev Vaccines 9:1149-76).

It will be appreciated that a cell strain may be chosen which modulates the expression of the inserted sequences, or modifies and processes the gene product in a specific way. Such modifications (e.g., glycosylation) and processing (e.g., cleavage or transport to the membrane) of protein products may be important for generation of a VLP or function of a VLP polypeptide or additional polypeptide (e.g., an adjuvant or additional antigen). Different cells have characteristic and specific mechanisms for post-translational processing and modification of proteins and gene products. Appropriate cell lines or host systems can be chosen to ensure the correct modification and processing of the foreign protein expressed. Generally, eukaryotic host cells (also referred to as packaging cells (e.g., 293T human embryo kidney cells)) which possess appropriate cellular machinery for proper processing of the primary transcript, glycosylation and phosphorylation of the gene product may be used in accordance with the present invention.

VLPs may be purified according to known techniques, such as centrifugation, gradients, sucrose-gradient ultracentrifugation, tangential flow filtration and chromatography (e.g., ion exchange (anion and cation), affinity and sizing column chromatography), or differential solubility, among others. Alternatively, or additionally, cell supernatant may be used directly, with no purification step. Additional entities, such as additional antigens or adjuvants may be added to purified VLPs.

In accordance with the present invention, cells may be transfected with a single expression vector. In some embodiments, a single expression vector encodes more than one element of a VLP (e.g., more than one of structural polyprotein, coronavirus spike protein, etc.). For example, in some embodiments, a single expression vector encodes two or more elements of a VLP. In some embodiments, a single expression vector encodes three of more elements of a VLP. In an embodiment of the invention, a single expression vector encodes a Gag polypeptide and a coronavirus spike glycoprotein.

In some embodiments, cells are transfected with two or more expression vectors. For example, in some embodiments, cells are transfected with a first vector encoding a Gag polypeptide and a second vector encoding a coronavirus spike glycoprotein and "monovalent" VLPs comprising a coronavirus spike glycoprotein are produced. In some embodiments, cells are transfected with a first vector encoding a Gag polypeptide, a second vector encoding a coronavirus spike glycoprotein and a third vector encoding another coronavirus spike glycoprotein. In such embodiments, "bivalent" VLPs comprising two coronavirus spike glycoproteins are produced. In some embodiments, cells are transfected with a first vector encoding a Gag polypeptide, a second vector encoding a coronavirus spike glycoprotein, and a third vector encoding two coronavirus spike glycoproteins. In such embodiments, "trivalent" VLPs comprising three coronavirus spike glycoproteins are produced.

As further demonstrated in the Examples, modification of the SARS-CoV-2 spike protein had a significant effect on the yield of the VLPs. Referring to Table 1, in Example 3, the VLP expressing the triple modified SARS-CoV-2 spike protein (Group 3) showed significantly higher spike protein yield that other monovalent VLPs expressing SARS-CoV-2 spike proteins. Accordingly, this embodiment of the VLP can be manufactured in higher volumes, which is important for addressing demand in pandemic situations.

In some embodiments, monovalent, bivalent, or trivalent VLPs are admixed. For example, in some embodiments, monovalent and bivalent VLPs are admixed to form a trivalent VLP mixture. In some embodiments two monovalent VLPs are admixed to form a bivalent VLP mixture.

The present invention provides pharmaceutical compositions comprising the VLPs described herein and, optionally, further comprising the glycoproteins and glycoprotein variants described herein. In some embodiments, the present invention provides a VLP and at least one pharmaceutically acceptable excipient, adjuvant and/or carrier. Such pharmaceutical compositions may optionally comprise and/or be administered in combination with one or more additional therapeutically active substances. The provided pharmaceutical compositions are useful as prophylactic agents (i.e., vaccines) in the prevention of SARS, MERS or COVID-19 infection or of negative ramifications associated or correlated with SARS, MERS or COVID-19 infection. The provided pharmaceutical compositions are also useful as prophylactic agents against certain variants of SARS-CoV-2. In some embodiments, pharmaceutical compositions are formulated for administration to humans.

Pharmaceutical compositions provided here may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). Suitable excipients include, for example, water, saline, dextrose, sucrose, trehalose, glycerol, ethanol, or similar, and combinations thereof. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention. In some embodiments, pharmaceutical compositions comprise one or more preservatives. In some embodiments, pharmaceutical compositions comprise no preservative.

In some embodiments, a pharmaceutical composition is sufficiently immunogenic as a vaccine (e.g., in the absence of an adjuvant). In some embodiments, immunogenicity of a pharmaceutical composition is enhanced by including an adjuvant. Any adjuvant may be used in accordance with the present invention. A large number of adjuvants are known; a useful compendium of many such compounds is prepared by the National Institutes of Health and can be found (www.niaid.nih.gov/daids/vaccine/pdf/compendium.pdf). See also Allison, 1998, Dev. Biol. Stand., 92:3-11, Unkeless et al., 1998, Annu. Rev. Immunol., 6:251-281, and Phillips et al., 1992, Vaccine, 10:151-158. Hundreds of different adjuvants are known in the art and may be employed in the practice of the present invention. Exemplary adjuvants that can be utilized in accordance with the invention include, but are not limited to, cytokines, gel-type adjuvants (e.g., aluminum hydroxide, aluminum phosphate, calcium phosphate, etc.), microbial adjuvants (e.g., immunomodulatory DNA sequences that include CpG motifs; endotoxins such as monophosphoryl lipid A; exotoxins such as cholera toxin, *E. coli* heat labile toxin, and pertussis toxin; muramyl dipeptide, etc.), oil-emulsion and emulsifier-based adjuvants (e.g., Freund's Adjuvant, MF59 [Novartis], SAF, etc.), particulate adjuvants (e.g., liposomes, biodegradable microspheres, saponins, etc.), synthetic adjuvants (e.g., nonionic block copolymers, muramyl peptide analogues, polyphosphazene, synthetic polynucleotides, etc.) and/or combinations thereof. Other exemplary adjuvants include some polymers (e.g., polyphosphazenes; described in U.S. Pat. No. 5,500,161, Q57, QS21, squalene, tetrachlorodecaoxide, etc.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of VLP formulations for longer than the specified time results in VLP degradation.

A pharmaceutical composition in accordance with the invention may be prepared, packaged, and/or sold as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject and/or depending upon the route by which the composition is to be administered. By way of example, the composition may comprise between 0.1% and 100% (w/w) active ingredient.

Provided compositions and methods of the present disclosure are useful for prophylaxis and/or treatment of SARS, MERS or COVID-19 infection in a subject, including human adults and children. In general however they may be used with any animal. If desired, the methods herein may also be used with farm animals, such as ovine, avian, bovine, porcine and equine breeds. For the purposes of the present disclosure, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Compositions described herein will generally be administered in such amounts and for such a time as is necessary or sufficient to induce an immune response. Dosing regimens may consist of a single dose or a plurality of doses over a period of time. The exact amount of an immunogenic composition (e.g., VLP) to be administered may vary from subject to subject and may depend on several factors. Thus, it will be appreciated that, in general, the precise dose used will depend not only on the weight of the subject and the route of administration, but also on the age of the subject. In certain embodiments a particular amount of a VLP composition is administered as a single dose. In certain embodiments, a particular amount of a VLP composition is administered as more than one dose (e.g., 1-3 doses that are separated by 1-12 months).

In some embodiments, a provided composition is administered in an initial dose and in at least one booster dose. In some embodiments, a provided composition is administered in an initial dose and two, three or four booster doses. In some embodiments, a provided composition is administered in an initial dose and in at least one booster dose about one month, about two months, about three months, about four months, about five months, or about six months following the initial dose. In some embodiments, a provided composition is administered in a second booster dose about six months, about seven months, about eight months, about nine months, about ten months, about eleven months, or about one year following the initial dose. In some embodiments, a provided composition is administered in a booster dose every 1 year, 2 years, 3 years, 4 years, 5 years, 6 years, 7 years, 8 years, 9 years, or 10 years.

In certain embodiments, provided compositions may be formulated for delivery parenterally, e.g., by injection. In such embodiments, administration may be, for example, intravenous, intramuscular, intradermal, or subcutaneous, or via by infusion or needleless injection techniques. In certain embodiments, the compositions may be formulated for peroral delivery, oral delivery, intranasal delivery, buccal delivery, sublingual delivery, transdermal delivery, transcutaneous delivery, intraperitoneal delivery, intravaginal delivery, rectal delivery or intracranial delivery.

In some embodiments, upon administration to a subject, provided VLPs induce a humoral immune response in the subject. In some embodiments, the humoral immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 28 months, at least about 32 months, at least about 36 months, at least about 40 months, at least about 44 months, at least about 48 months, or longer.

In some embodiments, upon administration to a subject, provided VLPs induce a cellular immune response in the subject. In some embodiments, the cellular immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least 12 months.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

EXAMPLES

The following examples describe some exemplary modes of making and practicing certain compositions that are described herein. It should be understood that these examples are for illustrative purposes only and are not meant to limit the scope of the compositions and methods described herein.

Example 1: Construction of DNA Expression Plasmids

This Example describes development of expression plasmids and constructs for expression of recombinant coronavirus spike gene sequences. A standard expression plasmid generally consists of a promoter sequence of mammalian origin, an intron sequence, a PolyAdenylation signal sequence (PolyA), a pUC origin of replication sequence (pUC—pBR322 is a colE1 origin/site of replication initiation and is used to replicate plasmid in bacteria such as *E. coli* (DH5α)), and an antibiotic resistance gene as a selectable marker for plasmid plaque selection. Within the plasmid following the intron are a variety of restriction enzyme sites that can be used to splice in a gene or partial gene sequence of interest.

The Propol II expression plasmid contains the pHCMV (early promoter for HCMV), a Beta-Globin Intron (BGL Intron), a rabbit Globin polyAdenylation signal sequence (PolyA), a pUC origin of replication sequence (pUC—pBR322 is a colE1 origin/site of replication initiation and is used to replicate plasmid in bacteria such as *E. coli* (DH5α)), and an ampicillin resistance gene β-lactamase (Amp R—selectable marker for plasmid confers resistance to ampicillin (100 μg/ml).

To develop a Gag MMLV expression construct ("MLV-Gag"), a complementary DNA (cDNA) sequence encoding a Gag polyprotein of MMLV (Gag without its C terminus Pol sequence) (SEQ ID NO: 3) was cloned in a Propol II expression vector. To develop all of coronavirus expression constructs, each of the following sequences:

i) SARS-CoV-2 (SEQ ID NO: 6);
ii) SARS-CoV (SEQ ID NO: 9);
iii) MERS (SEQ ID NO: 12);
iv) SARS-CoV-2 Proline Modified Spike Glycoprotein (SEQ ID NO: 15);
v) SARS-CoV-2 Furin Cleavage Modified (SEQ ID NO: 18);
vi) SARS-CoV-2 Proline and Furin Cleavage Modified (SEQ ID NO: 21);
vii) SARS-CoV-2 Proline and Furin Cleavage Modified with TM/Cyt from VSV (SEQ ID NO: 24); and
viii) SARS-CoV-2 modified with TM/Cyt from VSV (SEQ ID NO: 26) was cloned in a Propol II expression vector. The SARS-CoV-2 sequence was from the L strain of the virus that was originally identified in Wuhan China.

DNA plasmids were amplified in competent *E. coli* (DH5α) and purified with endotoxin-free preparation kits according to standard protocols.

Example 2: Production of Virus-Like Particles

This Example describes methods for production of virus-like particles containing various recombinant coronavirus spike antigens described in Example 1.

293 SF-3F6 cell line derived from HEK 293 cells are a proprietary suspension cell culture grown in serum-free chemically defined media (CA 2,252,972 and U.S. Pat. No. 6,210,922). HEK 293 SF-3F6 cells were scaled up in shaker flasks at 37° C., 5% $CO_2$ at a speed of 80 rpm and subsequently seeded in a bioreactor using HyQSF4 Transfx293 media supplemented with L-glutamine (GE Bioscience) to obtain a target cell density of 0.9 to 1.2 million cells/ml and high viability (>90%). The cells were co-transfected at cell density of about ~1 million cells/ml with different ratios of plasmids encoding coronavirus envelope polypeptides, plasmids encoding Gag and using high quality polyethyleneimine (PEIpro™) as transfection agent. The DNA plasmids and transfection agent were prepared in OptiPRO SFM medium (GE Biosciences). The bioreactor was monitored daily (~24 hrs and 48 hrs post transfection) and cell density, viability and cell diameters recorded. The production broth was harvested at 48 hrs post transfection.

Total protein was determined on an aliquot by a Bradford assay quantification kit (BioRad). The Bradford Protein assay is based on the observation that the absorbance maximum for an acidic solution of Coomassie Brilliant Blue G-250 shifts from 465 nm to 595 nm when binding to protein occurs. Both hydrophobic and ionic interactions stabilize the anionic form of the dye, causing a visible color change. A spectrophotometer was used to measure the absorbance of the sample and Bradford Protein Reagent dye at 595 nm.

Example 3: Production of Monovalent Vaccine Candidates

Four different monovalent virus like particles were produced using the method described in Example 2. The virus like particles were transfected with one of the four following SARS-CoV-2 nucleotide sequences:

1. Native form of SARS-CoV-2 (SEQ ID NO: 6);
2. SARS-CoV-2 Proline and Furin Cleavage Modified (SEQ ID NO: 21);
3. SARS-CoV-2 Proline and Furin Cleavage Modified with TM/Cyt from VSV (SEQ ID NO: 24); or 4. SARS-CoV-2 modified with TM/Cyt from VSV (SEQ ID NO: 26).

The total antigen content of the resulting products was measured and the results are shown in Table 1.

TABLE 1

Monovalent SARS-CoV-2 Virus Like Particle Yields

| Group | Monovalent VLP Description | Gag (μg) | SARS-CoV-2 spike protein (μg) |
|---|---|---|---|
| 1 | Native SARS-Cov-2 (SEQ ID #6) | 23,157 | 16.2 |
| 2 | SARS-CoV-2 Proline and Furin Cleavage Modified (SEQ ID NO: 21) | 32,220 | 229.9 |
| 3 | SARS-CoV-2 Proline and Furin Cleavage Modified with TM/Cyt from VSV (SEQ ID NO: 24) | 22,916 | 639.2 |
| 4 | SARS-CoV-2 modified with TM/Cyt from VSV (SEQ ID NO: 26) | 19,332 | 49.95 |

As can be seen from the data in Table 1, a significantly higher yield was obtained using Group 3, the SARS-CoV-2 sequence which had been modified by replacing the cytoplasmic and transmembrane segments with the corresponding segments form VSV.

Example 4: Production of Trivalent Vaccine Candidates

Four different trivalent virus like particles were produced using the method described in Example 2. Each particle was transfected with plasmids encoding Gag, an antigenic sequence from MERS (SEQ ID NO: 12), an antigenic sequence from SARS-CoV (SEQ ID NO: 9) and one of the two following SARS-CoV-2 sequences:

1. Native form of SARS-CoV-2 envelope polypeptide (SEQ ID NO: 6); or
2. SARS-CoV-2 Proline and Furin Cleavage Modified with TM/Cyt from VSV (SEQ ID NO: 24).

The antigen content of the resulting products was measured and the results are shown in Table 2.

TABLE 2

Trivalent Coronavirus Virus Like Particle Yields

| Group | Trivalent VLP - SARS-CoV-2 Spike Protein | Gag (μg) | SARS-CoV-2 spike protein (μg) |
|---|---|---|---|
| 1 | Native SARS-Cov-2 (SEQ ID #6) | 20,358 | 28.8 |
| 2 | SARS-CoV-2 Proline and Furin Cleavage Modified with TM/Cyt from VSV (SEQ ID NO: 24) | 17,382 | 404.4 |

As can be seen from the data in Table 2, a significantly higher yield of trivalent VLPs was obtained using Group 2, the SARS-CoV-2 sequence with a stabilized prefusion form of the spike protein which was further modified with the TM/Cyt from VSV G protein (SEQ ID NO: 24).

Example 5: Evaluation of the Potency of Monovalent SARS-CoV-2 VLP Vaccine Constructs Naïve 6-8 week-old C57/BL6 mice (n=10) were immunized twice with approximately $\frac{1}{20}^{th}$ to $\frac{1}{50}^{th}$ the human dose of the SARS-CoV-2 VLP vaccine formulations shown below in Table 3. Immunization took place at day 0 and day 21. Animals were sacrificed 14 days after immunization and their serum was collected for subsequent analysis of anti-spike protein antibody titers, and neutralizing antibodies.

The SARS-CoV-2 VLPs were formulated with aluminum phosphate adjuvant (Adjuphos®) as shown in Table 3.

TABLE 3

Monovalent SARS-CoV-2 VLP Vaccine Formulations

| Group | Monovalent SARS-CoV-2 | μg SARS-CoV-2 Spike/dose | μg Gag/dose | Al+++ μg/dose | Dose volume/ Animal (μL) |
|---|---|---|---|---|---|
| 1 | SARS-CoV-2 native Spike protein VLP | 0.07 | 100.1 | 125 | 500 |
| 2 | SARS-CoV-2 Proline and Furin | 0.14 | 19.6 | 125 | 500 |
| 3 | Cleavage Modified (SEQ ID NO: 21) | 0.7 | 98.1 | 125 | 500 |
| 4 | SARS-CoV-2 Proline and Furin | 0.14 | 5.0 | 125 | 500 |
| 5 | Cleavage Modified with TM/Cyt from VSV (SEQ ID NO: 24) | 0.7 | 25.05 | 125 | 500 |
| 6 | SARS-CoV-2 modified with | 0.07 | 27.1 | 125 | 500 |
| 7 | TM/Cyt from VSV (SEQ ID NO: 26) | 0.14 | 54.2 | 125 | 500 |

Anti-Spike SARS-CoV-2 antibody titers were measured as follows: 96 well plates were coated overnight at 4° C., with SARS-COV-2 Spike Protein (S1+S2) (Sinobiological, Cat #40589-V08B1) (0.1 μg/ml in DPBS). The following day, plates were blocked with 5% milk in ELISA wash buffer, for 1 hour at 37° C. Plates were washed with wash buffer, followed by addition of 2 fold dilutions of individual mouse sera starting at 1:10,000 to 1:1,200,000. Plates were incubated for 1.5 hours at 37° C., followed by plate washing and addition of Secondary Antibody: Goat anti-Mouse IgG1 (Bethyl, Cat #A90-131P), diluted 1:5,000 in 1% milk in ELISA wash buffer. Plates were incubated for 1 hour at 37° C. Plates were added with TMB One component Microwell substrate, incubated at room temperature for 10 minutes and then added with Stop solution. Absorbance was read at 450 nm using a MAXline plate reader. Results are shown below in Table 4.

The anti-spike total IgG binding titers reported in Table 4 represent the highest dilution of sera that still had an optical density of 0.1 or greater by ELISA measurement against recombinant SARS-CoV-2 spike protein. Unexpectedly, immunization of mice with just a single dose of VLPs expressing the stabilized prefusion form of the SARS-CoV-2 spike protein further modified with the TM/Cyt from the VSV-G protein (Group 4) induced antibody responses which were dramatically stronger than immunization of mice with VLPs expressing similar doses of SARS-CoV-2 spike protein but in different presentations (Groups 2, 7).

The antibody titers from the mice 14 days after each vaccination are shown in Table 4. P1 and P2 refer to the first and second vaccination. Results were pooled among individual animals.

TABLE 4

Monovalent SARS-CoV-2 VLP Vaccine Antibody Titres

| Group | Vaccination | Anti- SARS-CoV-2 Spike Total IgG Binding Titers |
|---|---|---|
| Pooled Group 1 | P1Vd14 | 9,099 |
| | P2Vd14 | 310,103 |
| Pooled Group 2 | P1Vd14 | 74,612 |
| | P2Vd14 | 424,883 |
| Pooled Group 3 | P1Vd14 | 262,689 |
| | P2Vd14 | 321,427 |
| Pooled Group 4 | P1Vd14 | 341,493 |
| | P2Vd14 | 670,735 |
| Pooled Group 5 | P1Vd14 | 619,766 |
| | P2Vd14 | 359,528 |
| Pooled Group 6 | P1Vd14 | 1,108 |
| | P2Vd14 | 302,500 |
| Pooled Group 7 | P1Vd14 | 4,093 |
| | P2Vd14 | 221,990 |

As is shown in Table 4, each of the monovalent VLP vaccine formulations induced a strong antibody response in mice. In almost all formulations, the response was strongly enhanced by a second vaccination. One group, group 5 consisting of a vaccine formulation based on SARS-CoV-2 Proline and Furin Cleavage Modified with TM/Cyt from VSV (SEQ ID NO: 24), showed a reduced response after second vaccination. However, the response was very high after first vaccination, raising the possibility that the second vaccination exhausted the immune response in mice. It is possible that this response may not be seen in larger mammals such as humans.

Neutralizing antibodies were tested as follows. A constant amount of virus consisting of 100 plaque forming units (pfu) of a Canadian isolate of SARS-CoV-2 virus was mixed with 2-fold dilutions of the mouse serum specimens being tested, the dilutions ranging from 40 to 5120 times, followed by plating of the mixture onto cells of an appropriate cell line for the individual virus. The concentration of plaque forming units is determined by the number of plaques formed after a few days. A vital dye (e.g. crystal violet or neutral red) was then added for visualization of the plaques and the number of plaques in an individual plate with test serum was divided by the number of plaques present in a negative control sera to calculate the percentage neutralization. The plaque forming units were measured by microscopic observations or by observation of specific dyes that react with the infected cell. Interpretation is typically based on 50% neutralization, which is the last dilution of serum capable of inhibiting 50% of the total plaques (virions). Plaque reduction neutralization test (PRNT) thresholds of 80 and 90 represent dilutions of sera capable of reducing plaques by 80% or 90% respectively. The results are shown in Table 5.

TABLE 5

Monovalent SARS-CoV-2 VLP Vaccine Neutralizing Antibodies

| Test Group | PRNT50 | PRNT80 | PRNT90 |
|---|---|---|---|
| POV (before vaccination) | ** | | |
| P1VD14 Group 1 | ** | | |
| P2VD14 Group 1 | 2560 | 1280 | 640 |
| P1VD14 Group 2 | 320 | 160 | 80 |
| P2VD14 Group 2 | *** | 5120 | 2560 |
| P1VD14 Group 3 | 320 | 285 | 160 |
| P2VD14 Group 3 | 5120 | 2560 | 1280 |
| P1VD14 Group 4 | 640 | 320 | 160 |
| P2VD14 Group 4 | *** | 5120 | 2560 |
| P1VD14 Group 5 | 2560 | 640 | 320 |
| P2VD14 Group 5 | 5120 | 2276 | 1280 |
| P1VD14 Group 6 | ** | | |
| P2VD14 Group 6 | 5120 | 2560 | 640 |
| P1VD14 Group 7 | 160 | 80 | ** |
| P2VD14 Group 7 | 2560 | 1280 | 320 |

** below lowest dilution limit of PRNT (titer 40);

*** above highest dilution range of PRNT (titer 5120)

As shown in Table 5, all of the monovalent vaccine constructs induced a neutralizing antibody response. This response was very potent, as demonstrated by the data from the stringent PRNT 90 threshold.

Example 6: Evaluation of the Potency of a Trivalent SARS-CoV-2 VLP Vaccine Construct A trivalent VLP was prepared using the method in Example 2 with antigen plasmids including all of the following sequences:

i) SARS-CoV-2 (SEQ ID NO: 6);

ii) SARS-CoV (SEQ ID NO: 9); and iii) MERS (SEQ ID NO: 12).

Vaccine formulations comprising the trivalent VLP, a monovalent VLP (expressing native SARS-CoV-2 (SEQ ID NO. 6), a recombinant SARS-CoV-2 (SEQ ID NO: 25) and Gag protein alone (SEQ ID NO:1) were tested in vivo in mice. The recombinant SARS-CoV-2 (SEQ ID NO: 25) was provided by the National Research Council of Canada. The vaccines were formulated with aluminum phosphate adjuvant (Adjuphos®) as shown in Table 6.

Forty naïve 6-8 week-old C57/BL6 mice (4 groups of 10) were immunized three times with approximately $1/20^{th}$ to $1/50^{th}$ of a human dose of the vaccine formulations shown below in Table 6. Immunization took place at day 0, day 21 and day 42. Animals were sacrificed 14 days after the last immunization and their serum was collected for subsequent analysis of anti-spike protein antibody titers and neutralizing antibodies.

TABLE 6

| Vaccine Formulations | | | | | |
|---|---|---|---|---|---|
| Test Group | Description | µg SARS-CoV-2 Spike/dose | µg Gag/dose | Al+++ pg/dose | Dose volume/ Animal (µL) |
| 1 | Monovalent SARS-CoV-2 native spike protein VLP | 0.1 | 50 | 125 | 250 |
| 2 | Trivalent SARS-CoV-2 (native spike protein); SARS-CoV; MERS-CoV VLP | 0.1 | 50 | 125 | 250 |
| 3 | SARS-CoV-2 spike recombinant | 0.1 | N/A | 125 | 250 |
| 4 | Empty Gag | N/A | 50 | 125 | 250 |

Anti-Spike SARS-CoV-2, anti-SARS and anti-MERS antibody titers were measured for each group using the technique described in Example 5 with the following capture antigens (SARS-COV-2 Spike Protein (S1+S2), Sino Biological, Cat #40589-V08B1, SARS-COVSpike Protein (S1+S2), MyBioSource, Cat #MBS434077 and MERS-CoV Spike Protein (S1+S2), Sino Biological, Cat #40069-V08B). The results are shown in Table 7.

TABLE 7

| Coronavirus Antibody Titres | | | | |
|---|---|---|---|---|
| Group | Time Point | Anti SARS-CoV2 Spike binding titre | Anti SARS-CoV Spike binding titre | Anti MERS Spike binding titre |
| Pooled Group 1 | P1Vd14 | 2700 | 300 | negative |
| Monovalent | P2Vd14 | 72900 | 8100 | 100 |
| VLP | P3Vd14 | 218700 | 24300 | negative |
| Pooled Group 2 | P1Vd14 | 2700 | 900 | >2700 |
| Trivalent | P2Vd14 | 24300 | 24300 | >72900 |
| VLP | P3Vd14 | >72900 (72900~218700) | 72900 | 656100 |

TABLE 7-continued

| Coronavirus Antibody Titres | | | | |
|---|---|---|---|---|
| Group | Time Point | Anti SARS-CoV2 Spike binding titre | Anti SARS-CoV Spike binding titre | Anti MERS Spike binding titre |
| Pooled Group 3 | P1Vd14 | 2700 | 900 | negative |
| Stabilized | P2Vd14 | 72900 | 24300 | 900 |
| Recombinant SARS-CoV2 | P3Vd14 | 218700 | 24300 | negative |
| Pooled Group 4 | P1Vd14 | negative | negative | negative |
| Empty Gag | P2Vd14 | negative | negative | negative |
| VLP | P3Vd14 | negative | negative | negative |

As shown in Table 7, the trivalent VLP (Group 2) induced antibody responses against all three coronaviruses: SARS-CoV-2, SARS and MERS. This demonstrates that a trivalent vaccine candidate has the potential to provide immunological protection again all three major coronaviruses.

Anti-SARS-CoV-2 binding and PRNT 80 neutralizing titres for individual animals after the third vaccination are shown in Table 8 below. Neutralizing antibodies were measured using the method described in Example 5.

TABLE 8

| Anti-SARS-CoV-2 Binding and Neutralizing Titres for Individual Mice | | | | | | | |
|---|---|---|---|---|---|---|---|
| Group # | Description | Mouse # | Anti SARS-CoV2 binding titre | Anti SARS-CoV2 binding titre Geometric Mean | Anti SARS-CoV2 Neutralizing Antibodies (PRNT 80) | Neutralizing Antibodies Geometric Mean | nAb/ Binding Titres Ratio |
| 1 | SARS-CoV-2 native Spike protein eVLP | 6 | 1,057,003 | 355538 | 2560 | 1810 | 0.002 |
| | | 7 | 221,691 | | 640 | | 0.003 |
| | | 8 | 515,381 | | 1280 | | 0.002 |
| | | 9 | 240,199 | | 5120 | | 0.021 |
| | | 10 | 124,759 | | 1280 | | 0.01 |
| | | 11 | 1,320,203 | | 5120 | | 0.004 |
| | | 12 | 258,417 | | 1280 | | 0.005 |
| | | 13 | 252,174 | | 640 | | 0.003 |
| | | 14 | 454,574 | | 5120 | | 0.011 |
| | | 15 | 228,032 | | 1280 | | 0.006 |
| 2 | SARS-CoV-2 + SARS-CoV- + MERS-CoV Native Spike protein eVLP | 21 | 333,263 | 247080 | >5120 | >5120 | 0.015 |
| | | 22 | 299,575 | | >5120 | | 0.017 |
| | | 23 | 208,191 | | >5120 | | 0.024 |
| | | 24 | 142,458 | | >5120 | | 0.036 |
| | | 25 | 294,434 | | >5120 | | 0.017 |
| | | 26 | 129,136 | | >5120 | | 0.04 |
| | | 27 | 322,558 | | >5120 | | 0.016 |
| | | 28 | 390,847 | | >5120 | | 0.013 |
| | | 29 | 278,663 | | >5120 | | 0.019 |
| | | 30 | 214,394 | | >5120 | | 0.024 |

As can be seen from the data shown in Table 8 demonstrates that the trivalent VLP induced higher neutralizing antibody responses than the monovalent SARS-CoV-2 VLP even though the binding titres were lower. This is particularly evident when by observing the ratio f neutralizing antibodies to binding antibody titres in the last column of Table 8. This demonstrates that the trivalent vaccine candidate has the potential to provide stronger immunological protection against COVID-19.

The serum obtained from mice fourteen (14) days after each vaccination was tested for cross reactivity with a different coronavirus which is known to infect humans and cause a common cold (HCoV-OC43). Antibody titres were measured using ELISA as described above using human coronavirus (HCoV-OC43) spike protein (S1+S2 ECD, His Tag), Sino, Cat #40607-V08B, stock 0.25 mg/mL as the capture antigen. The results are shown below in Table 9 below.

TABLE 9

Cross Reactivity of Mouse Serum against HCoV-OC43 Spike Protein

| Group | Vaccination Number | Anti-HCoV-OC43 Spike Total IgG Binding Titres |
|---|---|---|
| Pooled Group 1 | P1VD14 | negative |
| Monovalent VLPs | P2VD14 | 100 |
| | P3VD14 | 300 |
| Pooled Group 2 | P1VD14 | negative |
| Trivalent VLPs | P2Vd14 | 900 |
| | P3VD14 | 2700 |
| Pooled Group 3 NRC | P1VD14 | negative |
| Stabilized Recombinant | P2VD14 | 300 |
| SARS-CoV2 | P3Vd14 | 300 |
| Pooled Group 4 Empty | P1VD14 | negative |
| eVLP | P2VD14 | negative |
| | P3VD14 | negative |

As can be seen from Table 9 above, the trivalent VLP vaccine candidate (Group 2) demonstrated higher cross reactivity against a human coronavirus which causes common cold. As such, the trivalent candidate demonstrated the potential for broader protection against coronavirus than the monovalent VLP or the recombinant SARS-CoV-2 spike protein alone.

In order to evaluate the efficacy of the vaccine formulations, the neutralizing antibodies were also measured in human serum (HS) collected from four recovered COVID-19 patients and the results were compared to the neutralizing antibodies induced by the four different test groups shown in Table 6. PRNT 50 and PRNT 90 was determined following the first and second vaccination using the method described in Example 5. Pooled results for each group are shown in Table 10 below.

TABLE 10

Anti-SARS-CoV-2 Neutralizing Antibodies

| Sample | PRNT50 | PRNT90 |
|---|---|---|
| HS1 | 80 | ** |
| HS2 | 160 | 40 |
| HS3 | 1280 | 320 |
| HS4 | 160 | 80 |
| POV (BEFORE VACCINATION) | ** | ** |
| P1VD14 GR1 | ** | ** |
| P1VD14 GR2 | ** | ** |
| P1VD14 GR3 | 40 | ** |
| P1VD14 GR4 | ** | ** |
| P2VD14 GR1 | 640 | 160 |
| P2VD14 GR2 | 320 | ** |
| P2VD14 GR3 | 640 | 80 |
| P2VD14 GR4 | ** | ** |

** below lowest dilution limit of PRNT (titer 40);

As can be seen in Table 10, the monovalent VLP vaccine induced more neutralizing antibodies than COVID-19 infection in three out of four human patients as measured by PRNT 50 and 90. The trivalent VLP vaccine induced more neutralizing antibodies than COVID-19 infection in three out of four human patients as measured by PRNT 50. Accordingly, the vaccine constructs at least as effective, and potentially more effective, at inducing immune protection than exposure to SARS-CoV-2.

Example 7: Evaluation of Protective Effect of a Monovalent SARS-CoV-2 VLP Vaccine Construct Syrian golden hamsters (males, aged approximately 5-6 weeks old) were divided into two groups and immunized with two doses of the formulations shown below in Table 11, specifically a test sample comprising a triple modified SARS-CoV2 VLP (SEQ ID: 24) formulated with aluminum phosphate adjuvant (Adjuphos®) (Group B) and a saline control (Group A). Immunizations took place at day 0 and day 21, via intramuscular injection. At day 42, all animals were challenged intranasally with 50 µl of SARS-CoV-2 via both nares, at a challenge virus dose of $1\times10^5$ $TCID_{50}$ per animal. SST (serum separation tube) blood samples (approximately 0.5 ml each) were collected on day 0 prior to the prime immunization, day 14 and day 35, respectively. Final blood samples were collected at necropsy. Nasal washes were collected on days 35, 43, 44, 45, 47, 49, 51, 53 and 56. Half of the animals in each group were euthanized at three days post-challenge, and the remaining animals were euthanized at 14 days post-challenge.

TABLE 11

Monovalent SARS-CoV-2 VLP Vaccine Formulations

| Group | Test Article | µg SARS-CoV-2 Spike/dose | Al+++ µg/dose | Dose volume/ Animal (µL) |
|---|---|---|---|---|
| A | Saline control | N/A | N/A | 100 |
| B | SARS-CoV-2 Proline and Furin Cleavage Modified with TM/Cyt from VSV (SEQ ID NO: 24) | 1 | 125 | 100 |

At necropsy, gross lung pathology was evaluated and the proportion of lung lobe that contained lesions was estimated. Lung tissues were analyzed for viral load by qRT-PCR and viral cell culture. Similarly, nasal turbinates were collected for viral load by qRT-PCR and viral cell culture.

Extraction of RNA from nasal washes was performed using Qiagen reagents (QIAamp Viral RNA Mini Kit Cat No./ID: 52906). Briefly, 140 µl of nasal wash was added into 560 µl viral lysis buffer (Buffer AVL). The mixture was incubated at room temperature for 10 min. After brief centrifugation, the solution was transferred to a fresh tube containing 560 μL of 100% ethanol, and the tube was incubated at room temperature for 10 min. RNA was then purified and eluted with 60 μl of RNase Free water containing 0.04% sodium azide (elution buffer AVE).

Extraction of RNA from lung lobes and nasal turbinates was completed using approximately 100 μg of tissue. The tissues were homogenized in 600 μl of lysis buffer (RLT Qiagen) with a sterile stainless steel bead in the TissueLyserII (Qiagen) for 6 min, at 30 Hz. The solution was centrifuged at 5000×g for 5 min. Supernatant was transferred to a fresh tube containing 600 μl of 70% ethanol, and the tube was incubated at room temperature for 10 min. Viral RNA was then purified using Qiagen RNeasy Mini Kit (Cat No/ID: 74106) and eluted with 50 μL elution buffer.

qRT-PCR assays were performed on RNA from samples of nasal washes, lung tissues and nasal turbinates using SARS-CoV-2 specific primers (Table 12). The primers had an annealing temperature of approximately 60° C. Qiagen Quantifast RT-PCR Probe kits were used for qRT-PCR, and the qRT-PCR reactions were conducted using the OneStep Plus (Applied Biosystems) machine. The qRT-PCR results were expressed in copy number per reaction, by producing a standard curve with a sample of a linearized plasmid DNA that contains the env gene of SARS-CoV-2. The Ct values for individual samples were used with the standard curve to determine the copy number in each sample.

TABLE 12

Sequence of Primers Used

| Primer | Sequence | SEQ ID NO: |
|---|---|---|
| Forward Primer (Fwd) | ACAGGTACGTTAATAGTTAATAGCGT | 28 |
| Reverse Primer (Rev) | ATATTGCAGCAGTACGCACACA | 29 |
| Labelled Probe | ACACTAGCCATCCTTACTGCGCTTCG | 30 |

Viral titration assays were performed to assess infectious virus. The assays were conducted in 96-well plates using Vero'76 cells (ATCC CRL-1587). Median tissue culture infectious dose ($TCID_{50}$) was determined by microscopic observation of the cytopathic effect (CPE) of cells. The virus was quantified and reported in $TCID_{50}$/ml or $TCID_{50}$/gram. $TCID_{50}$ values were calculated using the Spearman & Karber algorithm in Excel.

Anti-Spike SARS-CoV-2 antibody titers were measured by ELISA performed on serum samples. Plates were coated with spike S1+S2 Ag (Cat #40589-V08B1, Sino Biological Inc.). The coating concentration was 0.1 ug/mL. Plates were blocked with 5% non-fat skim milk powder in PBS containing 0.05% Tween 20. Fourfold dilutions of serum were used. Goat anti-Hamster IgG HRP from ThermoFisher (PA1-29626) was used as the secondary antibody at 1:7000. Plates were developed with OPD peroxidase substrate (0.5 mg/ml) (Thermo Scientific Pierce 34006). The reaction was stopped with 2.5 M sulfuric acid and absorbance was measured at 490 nm. Throughout the assay, plates were washed with PBS containing 0.05% Tween 20. The assay was performed in duplicate. The titres were reported as the end point of the dilutions.

Antibodies to the spike protein receptor binding domain ("RBD") were measured as follows. Anti-SARS-CoV-2 spike S1 RBD IgG antibody binding titer was determined from serum samples using an indirect ELISA. Recombinant SARS-CoV-2 spike S1 RBD protein was adsorbed on a microtiter plate overnight and plates were then blocked with a solution of 5% skim milk in wash buffer for 1 hour. After blocking and washing, samples were added to the microplates and incubated for 1.5 hours. An HRP-conjugated goat anti-Syrian Hamster IgG-Fc was used as a detection antibody, and incubated on the microplates for 1 hour. The signal was developed with Tetramethylbenzidine (TMB) substrate solution and the reaction stopped by addition of 450 μL Liquid Stop Solution for TMB Microwell Substrate. The absorbance was read at 450 nm using an ELISA microwell plate reader.

Viral neutralization assays against the challenge SARS-CoV-2 virus were performed on the serum samples using the cell line Vero'76. The serum samples were heat-inactivated for 30 min at 56° C. The serum samples were serially diluted (2-fold serial dilutions). The experiment was conducted in technical duplicates. The virus was diluted in medium to a concentration of 25 $TCID_{50}$ in 50 μl per well (the inoculum size=25 $TCID_{50}$). Then 60 μl of the virus solution was mixed with 60 μl serially diluted serum samples. The mixture was incubated for 1 hr at 37° C., with 5% $CO_2$. The pre-incubated virus-serum mixtures ($100_1 1.1$) were transferred to the wells of the 96-well flat-bottom plates containing 90% confluent pre-seeded Vero'76 cells. The plates were incubated at 37° C., with 5% $CO_2$ for five days. The plates were observed using a microscope on day 1 post-infection (dpi) for contamination and on days 3 and 5 post-infection for cytopathic effect. The serum dilution factor for the wells with no CPE at 5 dpi was defined as the serum neutralization titre. The initial serum dilution factor was 1:20.

Neutralizing antibodies were tested as follows. Vero cells were seeded at $8\times10^5$ cells/well in 6-well plates 48 h prior to infection. Sera were heat-inactivated at 56° C. for 30 min then transferred on ice. Sera were diluted 1:10 with virus infection media then each diluted serum was used to carry out ½× fold serial dilutions to give 1:20 to 1:40960 (8 subsequent dilutions). Equal volumes of diluted serum and virus (100 pfu per serum dilution) were mixed and incubated at 37° C. for 1 h. No sera and no virus controls were included. Cells were washed with PBS and each virus/serum were transferred and mixed to each well containing cells, and incubated at 37° C. for 1 h, with interval rocking of the plates. After the 1 h adsorption, excess inoculum was removed and a 2 ml virus infection media/agarose mix were overlaid onto the cells. The overlay was allowed to solidify and plates were incubated at 37° C. for 72 h. Cells were stained with crystal violet at 72 h post-infection. Plaques were quantified for all dilutions and PRNT titer was calculated. The % plaque reduction for all the dilutions based on the no serum control, was calculate using the Reed-Muench formula to determine the PRNT titers 50, 80, and 90.

Lung tissues were also quantified for cytokine gene expression collected at necropsy. The gene expression of IL-4, IL-10, IL-13, TNF-alpha and IFN-gamma was determined in the right cranial and right caudal lung lobe by qRT-PCR using the primers shown in Table 13. The beta-actin gene expression was used for reference.

TABLE 13

| Primer Sequence | | | | |
|---|---|---|---|---|
| Gene Target | Forward Primer 5'->3' | SEQ ID NO: | Reverse Primer 5'->3' | SEQ ID NO: |
| IL-4 | CCACGGAGAAAGA CCTCATCTG | 31 | GGGTCACCTCAT GTTGGAAATAAA | 32 |
| IL-10 | GTTGCCAAACCTT ATCAGAAATGA | 33 | TTCTGGCCCGTG GTTCTCT | 34 |
| IL-13 | AAATGGCGGGTTC TGTGC | 35 | AATATCCTCTGGG TCTTGTAGATGG | 36 |
| TNF-alpha | GGAGTGGCTGAGC CATCGT | 37 | AGCTGGTTGTCTT TGAGAGACATG | 38 |
| IFN-gamma | GGCCATCCAGAGG AGCATAG | 39 | TTTCTCCATGCTG CTGTTGAA | 40 |
| Beta-actin | ACTGCCGCATCCT CTTCCT | 41 | TCGTTGCCAATGG TGATGAC | 42 |

Lung tissues were collected in RNAlater and the RNA was isolated using Qiagen RNeasy Mini extraction kits using RLT lysis buffer (Qiagen RNeasy Mini Kit, Cat No/ID:74106). RNA concentration and the 260/280 ratio as an indicator of purity was determined by a nanodrop spectrophotometer. cDNA was synthesized using iScript™ Reverse Transcription Supermix with 500 ng of RNA as template. cDNA was synthesized following a program of 5 min at 25° C., 20 min at 46° C., and 95° C. for 1 min. Master mix was prepared for each gene of interest as well as a house keeping gene at 10% overage: 1.84 μl Nuclease Free $H_2O$; Forward Primer 0.08 μL; Reverse Primer 0.08 μl; and SYBR 10 μl [SYBR® Green PCR Master Mix (SsoAdvanced™ Universal SYBR® Green Supermix #1725275)]. Twelve μl of the master mix was combined with 8 μl of RNA for each PCR reaction. After loading, the plate was centrifuged at 1500 RPM for 1 min to bring all liquid back into base of well. The qPCR was performed using a Bio-Rad Thermocycler (Bio-Rad CX1000). Data was analyzed using the Bio-Rad CFX Maestro software. Data is exported in the form of Ct values to an excel spreadsheet for fold change calculation by ΔΔCt Formula in Excel.

Results based on clinical observation of animals indicated that all animals were healthy throughout the immunization phase. All animals had normal activity levels and had no clinical signs. The body weight increases were normal in the group vaccinated with test article (Group B) when compared to the Saline control group (Group A).

Immune response to vaccination as measured by antibody titres to SARS-CoV-2 spike protein are shown in Table 14 fourteen days after the first vaccination and fourteen days after the second vaccination (P1 and P2 refer to the first and second vaccination). Results shown are Geo means of the animals in each group.

TABLE 14

| SARS-CoV-2 VLP Vaccine Antibody Titres | | | | |
|---|---|---|---|---|
| | First Vaccination (day 14) | | Second Vaccination (day 14) | |
| | Anti-SARS-CoV-2 S1 RBD | Anti-SARS-CoV-2 Spike total IgG | Anti-SARS-CoV-2 S1 RBD | Anti-SARS-CoV-2 Spike Total IgG |
| Group A (control) | — | 3 | — | 3 |
| Group B (SARS-CoV-2 Proline and Furin Cleavage Modified with TM/Cyt from VSV (SEQ ID NO: 24) | 7,446 | 1,222 | 268,399 | 22,868 |

The Group B animals (immunized with the triple modified monovalent SARS-CoV-2 VLP vaccine) produced high levels of anti-spike antibody two weeks after the second vaccination. At two weeks after the first vaccination, 10 out of 12 animals in Group B produced anti-spike antibodies (data not shown). Group A animals (Saline control) did not have anti-spike antibody production. The triple modified monovalent SARS-CoV-2 VLP vaccine also induced detectable level of anti-SARS-CoV-2-S1 RBD IgG antibody at 14 days after the first immunization. A substantial increase in antibody titres was observed on day 14 after the $2^{nd}$ immunization. No anti-SARS-CoV-2-S1 RBD IgG were detected in control Group A.

The neutralizing antibodies, as determined by PRNT, for each group fourteen days after the first vaccination are shown in Table 15 (average values shown). Values indicate reciprocal of highest dilution that showed inhibition of 50% (PRNT50), 80% (PRNT80), or 90% (PRNT90) of input virus, respectively.

TABLE 15

| SARS-CoV-2 VLP Vaccine Neutralizing Antibodies | | | |
|---|---|---|---|
| Test Group - Fourteen days after first vaccination | PRNT50 | PRNT80 | PRNT90 |
| Group A Pooled (Control) | ** | (N/A) | (N/A) |
| Group B (SARS-CoV-2 Proline and Furin Cleavage Modified with TM/Cyt from VSV (SEQ ID NO: 24) | 441 | 241 | 198 |

** below lowest dilution limit of PRNT (titer 40)

All Group B animals produced virus neutralizing antibodies at two weeks post-immunization as shown in Table 15. The Group A animals did not produce any neutralizing antibodies as shown in Table 15.

At three days post-challenge (dpc), all animals Group B, and only one animal in Group A, produced neutralizing antibodies (data not shown). At 14 dpc, all the animals in Group A and B produced neutralizing antibodies. (data not shown).

During the challenge phase, all animals except for two were active and had normal activity levels, and did not have abnormal nasal signs.

Animals were weighed each day post challenge. After challenge, Group A animals lost approximately 15% of their initial body weight, peaking at 6-8 dpc. The means of % body weight changes of the Group B animals were only about 1-2% and peaked at two dpc. Body weight data is shown in Table 16 below at Day 0 and at Day 3 and 6 after challenge.

TABLE 16

Body Weight of Hamsters following Viral Challenge

| Group | Animal ID | Day 0 BW | Day 0 BW Average | Day 3 BW | Day 3 BW Average | Day 6 BW | Day 6 BW Average |
|---|---|---|---|---|---|---|---|
| A (control) | 401 | 175.1 | 171.5 ± 14.5 | 160.9 | 160.9 ± 13.9 | Euth | 155.5 ± 11.5 |
| | 403 | 182.1 | | 167.3 | | 155.4 | |
| | 408 | 172.6 | | 160.7 | | Euth | |
| | 412 | 173.6 | | 161 | | 149.1 | |
| | 416* | 165.9 | | 163.2 | | 137.1 | |
| | 422 | 196.3 | | 185.8 | | 170.5 | |
| | 423 | 162.8 | | 149.6 | | Euth | |
| | 429 | 185.2 | | 171.6 | | 159.6 | |
| | 434 | 174.8 | | 170.00 | | 161.5 | |
| | 435 | 156.4 | | 143.7 | | Euth | |
| | 440 | 174.3 | | 164.9 | | Euth | |
| | 443 | 139.4 | | 132.1 | | Euth | |
| B (SARS-CoV-2 Proline and Furin Cleavage Modified with TM/Cyt from VSV (SEQ ID NO: 24) | 402 | 159.5 | 174.2 ± 14.3 | 155.7 | 171.6 ± 14.3 | Euth | 180.3 ± 7.9 |
| | 404 | 181.2 | | 177.1 | | 179.6 | |
| | 410 | 161.4 | | 160.1 | | Euth | |
| | 411 | 190.0 | | 183.6 | | 182.1 | |
| | 418 | 181.3 | | 179.1 | | 185.1 | |
| | 421* | 188.4 | | 189.5 | | 191.6 | |
| | 426 | 160.0 | | 159.0 | | Euth | |
| | 428 | 175.8 | | 173.3 | | 172.8 | |
| | 431 | 172.3 | | 169.1 | | 170.3 | |
| | 436 | 152.7 | | 147.3 | | Euth | |
| | 442 | 199.1 | | 195.4 | | Euth | |
| | 446 | 168.8 | | 169.9 | | Euth | |

Euthanized on day 3 as planned or humane euthanized
*(416 and 421)

As can be seen in Table 16, animals given the Saline solution lost considerable weight three days and six days after challenge whereas the animals that had received the vaccine lost considerably less weight at day 3 and were had gained weight by day 6.

Viral RNA as measured in nasal washes post challenge is shown in Table 17. In all days examined, the vaccinated (Group B) animals had lower viral RNA levels in nasal washes than the Group A animals (control group), as depicted in Table 17 (showing copies/Rxn for each day post-challenge). Only during day two after challenge were the viral RNA levels significantly lower in Groups B compared to Group A (p=0.0206).

TABLE 17

Viral RNA in nasal washes

| Group ID | Table 16 Day post-challenge Viral RNA Averages (copies/Rxn) 0 | 2 | 3 | 5 | 7 | 9 | 11 | 14 |
|---|---|---|---|---|---|---|---|---|
| Group A | 0.1 | 3708602 | 340897 | 94932 | 12409 | 6231 | 130 | 3146 |
| Group B | 0.1 | 205616 | 105469 | 31861 | 93 | 20 | 2461 | 2 |

Viral RNA at 3 days post-challenge in various tissues for control (Group A) and vaccinated (Group B) animals are shown in Table 18 (showing values for copies/gram). At three days post-challenge, viral RNA was detectable in the right cranial lobe (RCra) and the right caudal lobe (RCau) of the lung and the nasal turbinates in all animals. When compared to Group A, the levels of viral RNA in the RCra of Group B were significantly lower. Similarly, the levels of RNA in RCau were significantly lower in Group B than Group A. In the nasal turbinates, viral RNA levels in Group B was significantly lower than in Group A.

TABLE 18

Viral RNA in tissues at 3 days post-challenge

| Group ID | Right cranial lobe | Right caudal lobe | Nasal turbinates |
|---|---|---|---|
| Group A (control) | 2613650533 | 1608083300 | 2099767910 |

TABLE 18-continued

| Viral RNA in tissues at 3 days post-challenge | | | |
|---|---|---|---|
| Group ID | Right cranial lobe | Right caudal lobe | Nasal turbinates |
| Group B (SARS-CoV-2 Proline and Furin Cleavage Modified with TM/Cyt from VSV (SEQ ID NO: 24) | 108006 | 42465 | 1205108163 |

Viral RNA at 14 days post-challenge in various tissues for the control (Group A) and vaccinated (Group B) animals are shown in Table 19 (showing values for copies/gram). At 14 days post-challenge, viral RNA was detectable in all Group A animals and some animals in Group B in the RCra, RCau or nasal turbinates. The levels of RNA in RCra and RCau were significantly different in Group B than those in Group A.

TABLE 19

| Viral RNA in Tissues at 14 days Post-challenge | | | |
|---|---|---|---|
| Group ID | Right cranial lobe | Right caudal lobe | Nasal turbinates |
| Group A (control) | 127855.5 | 62075.0 | 3104415.2 |
| Group B (SARS-CoV-2 Proline and Furin Cleavage Modified with TM/Cyt from VSV (SEQ ID NO: 24) | 99.43 | 105.78 | 100398.57 |

Infectious virus in various tissues at 3 days post-challenge for control (Group A) and vaccinated (Group B) animals are shown in Table 20 (showing values for $TCID_{50}$/gram). At three days post-challenge, infectious virus was detectable in all animals of Group A in the right cranial and right caudal lobes of the lung and in nasal turbinates. The titres of infectious virus in Group B was significantly lower than those in Group A. At 14 days post-challenge, infectious virus was not detected in any of the animals (data not shown).

TABLE 20

| Infectious Virus in tissues at 3 days post-challenge (TCID50/gram) | | | | | | |
|---|---|---|---|---|---|---|
| | Right cranial lobe | | Right caudal lobe | | Nasal turbinates | |
| Group ID | TCID50/gram | Average | TCID50/gram | Average | TCID50/gram | Average |
| Group A (control) | 1.51E+07 | 2.63E+07 | 6.71E+02 | 1.65E+06 | 1.15E+07 | 2.00E+07 |
| | 1.03E+07 | | 3.94E+05 | | 2.39E+06 | |
| | 3.89E+07 | | 3.45E+05 | | 3.76E+07 | |
| | 1.30E+07 | | 1.23E+06 | | 4.66E+05 | |
| | 1.32E+06 | | 5.99E+06 | | 2.47E+07 | |
| Group B (SARS-CoV-2 Proline and Furin Cleavage Modified with TM/Cyt from VSV (SEQ ID NO: 24) | 1.79E+01 | 1.48E+01 | 8.78E+00 | 3.45E+00 | 1.26E+02 | 3.58E+06 |
| | 1.49E+01 | | 2.56E+00 | | 5.43E+05 | |
| | 2.39E+01 | | 2.28E+00 | | 5.86E+01 | |
| | 9.05E+00 | | 2.42E+00 | | 2.09E+07 | |
| | 1.12E+01 | | 2.59E+00 | | 6.85E+00 | |

Heavier lungs is associated with more advanced disease. Therefore, the ratio of lung weight to body is correlated with more severe disease states. Table 21 shows the lung weight to body weight ratios for animals in the control (Group A) and vaccinated (Group B) animals three days post challenge. Animals in group Group B animals had significantly lower lung weight to body weight ratios.

TABLE 21

| Ratios of lung weight to body weight (%) | | | | |
|---|---|---|---|---|
| Group ID | Lung Weight (g) | Body Weight (g) | Lung weight/ Body Weight Ratio | Average ± SD |
| Group A (control) | 1.4 | 160.9 | 0.87 | 0.76 ± 0.15 |
| | 1.2 | 170.1 | 0.71 | |
| | 1.5 | 160.7 | 0.93 | |
| | 1.1 | 160.9 | 0.68 | |
| | 0.88 | 137.1 | 0.64 | |
| | 1.4 | 183.7 | 0.76 | |
| | 1.6 | 149.6 | 1.07 | |
| | 1.3 | 183.6 | 0.71 | |
| | 1 | 182.3 | 0.55 | |
| | 1.1 | 143.7 | 0.77 | |
| | 1.3 | 164.9 | 0.79 | |
| | 0.8 | 132.1 | 0.61 | |
| Group B (SARS-CoV-2 Proline and Furin Cleavage Modified with TM/Cyt from VSV (SEQ ID NO: 24) | 0.9 | 155.7 | 0.58 | 0.56 ± 0.07 |
| | 1 | 188.2 | 0.53 | |
| | 1 | 160.1 | 0.62 | |
| | 0.9 | 188.2 | 0.48 | |
| | 0.9 | 195.2 | 0.46 | |
| | 0.98 | 191.6 | 0.51 | |
| | 1 | 159 | 0.63 | |
| | 0.9 | 180.1 | 0.50 | |
| | 1 | 183.6 | 0.54 | |
| | 1 | 147.3 | 0.68 | |
| | 1.2 | 195.4 | 0.61 | |
| | NA | 169.9 | missing | |

Following necropsy, lung tissues were fixed in formalin, embedded, sectioned and stained with hematoxylin and eosin (H&E). Slides were examined by a board-certified pathologist and scored on a scale of 0-4 as shown in Table 22.

TABLE 22

| Lung Histology Scores (median) | | | | | | |
|---|---|---|---|---|---|---|
| Group ID | Days Post-Challenge | Proportion of parenchyma affected | Intensity of the inflammatory infiltrate in affected areas | Extent of hypertrophy of alveolar pneumocytes | Interalveolar hemorrhage | Extent of emphysema |
| Group A (control) | 3 | 3 | 3 | 0 | 2 | 0 |
| | | 3 | 3 | 0 | 1 | 0 |
| | | 3 | 3 | 0 | 2 | 0 |
| | | 1 | 3 | 0 | 3 | 0 |
| | | 1 | 3 | 0 | 2 | 0 |
| | | 1 | 2 | 0 | 1 | 0 |
| | 14 | 1 | 2 | 3 | 0 | 0 |
| | | 1 | 2 | 2 | 0 | 0 |
| | | 4 | 4 | 3 | 4 | 0 |
| | | 4 | 2 | 2 | 0 | 0 |
| | | 2 | 3 | 2 | 0 | 0 |
| | | 1 | 2 | 1 | 0 | 0 |
| Group B (SARS-CoV-2 Proline and Furin Cleavage Modified with TM/Cyt from VSV (SEQ ID NO: 24) | 3 | 0 | 0 | 0 | 0 | 1 |
| | | 1 | 2 | 0 | 0 | 0 |
| | | 1 | 1 | 0 | 0 | 0 |
| | | 1 | 2 | 0 | 0 | 0 |
| | | 1 | 1 | 0 | 1 | 0 |
| | | 1 | 1 | 0 | 0 | 0 |
| | 14 | 0 | 0 | 0 | 0 | 0 |
| | | 0 | 0 | 0 | 0 | 0 |
| | | 0 | 0 | 0 | 0 | 0 |
| | | 1 | 1 | 0 | 0 | 0 |
| | | 0 | 0 | 0 | 0 | 0 |
| | | 0 | 0 | 0 | 0 | 0 |

As can be seen in Table 22, animals in the control group (Group A) showed significant disease pathology following challenge at days 3 and 14. By way of contrast, the vaccinated animals (Group B) showed some minor pathology at day 3 but were mostly recovered by day 14. Accordingly, the vaccine provided significant protection against disease induced lung pathology.

Immunohistochemical staining was conducted to observe SARS-CoV-2 virus in the lung tissues, specifically the parenchyma and bronchioles/bronchi. Staining was observed and scores for the two groups of animals is shown in Table 23.

TABLE 23

| Immunohistochemical scores (median) of the lung for SARS-CoV-2 | | | | | |
|---|---|---|---|---|---|
| | | Parenchyma IHC | | Bronchioles/bronchi | |
| Group ID | Days post-challenge | Individual Score | Median | Individual Score | Median |
| Group A (Control) | 3 | 4 | 4 ± 0.84 | 2 | 3 ± 0.52 |
| | | 4 | | 3 | |
| | | 4 | | 2 | |
| | | 4 | | 3 | |
| | | 3 | | 3 | |
| | | 2 | | 3 | |
| | 14 | 0 | 0±1.21 | 2 | 2±0.75 |
| | | 0 | | 2 | |
| | | 3 | | 1 | |
| | | 1 | | 1 | |
| | | 0 | | 3 | |
| | | 0 | | 2 | |
| Group B (SARS-CoV-2 Proline and Furin Cleavage Modified with TM/Cyt from | 3 | 0 | 0 ± 0 | 2 | 1 ± 0.89 |
| | | 0 | | 1 | |
| | | 0 | | 2 | |
| | | 0 | | 0 | |
| | | 0 | | 1 | |
| | | 0 | | 0 | |

TABLE 23-continued

| Immunohistochemical scores (median) of the lung for SARS-CoV-2 | | | | | |
|---|---|---|---|---|---|
| | | Parenchyma IHC | | Bronchioles/bronchi | |
| Group ID | Days post-challenge | Individual Score | Median | Individual Score | Median |
| VSV (SEQ ID NO: 24) | 14 | 0 | 0 ± 0 | 0 | 1 ± 0.63 |
| | | 0 | | 1 | |
| | | 0 | | 2 | |
| | | 0 | | 1 | |
| | | 0 | | 1 | |
| | | 0 | | 1 | |

Vaccinated animals had significantly less virus stain in both parenchyma and bronchioles/bronchi than those of the saline control animals (Group A). At 14 days post-challenge, virus stain was similar among the groups in either parenchyma or bronchioles/bronchi although still a little lower in the vaccinated group.

The transcriptional levels of cytokines IL-4, IL-10, IL-13, TNF-alpha and IFN-gamma in the right cranial lung, right caudal lung and the nasal turbinates were determined by qRT-PCR. At 3 days post-challenge, IL-10, IL-13 and IFN-gamma displayed differential expression in the right cranial lobe and the right caudal lobe in Group B (shown in Tables 24 and 25). In nasal turbinates, IL-10 and IFN-gamma exhibited differential expression (shown in Table 26). At 14 days post-challenge, the transcriptional levels of IL-4, IL-10, IL-13, TNF-alpha and IFN-gamma in the right cranial lung, right caudal lung and the nasal turbinates were similar across the groups (shown in Tables 27-29).

TABLE 24

| Transcriptional profiles of cytokines in right cranial lobe 3 days post-challenge (fold changes) | | | | | |
|---|---|---|---|---|---|
| Group ID | IL-4 | IL-10 | IL-13 | TNF-alpha | IFN-gamma |
| Group A | 1.04 | 1.09 | 1.3 | 1.07 | 1.14 |
| Group B | 1.8 | 0.37 | 7.1 | 0.61 | 0.27 |

TABLE 25

| Transcriptional profiles of cytokines in right caudal lobe 3 days post-challenge (fold changes) | | | | | |
|---|---|---|---|---|---|
| Group ID | IL-4 | IL-10 | IL-13 | TNF-alpha | IFN-gamma |
| Group A | 1.02 | 1.03 | 1.33 | 1.04 | 1.21 |
| Group B | 0.88 | 0.33 | 2.4 | 0.55 | 0.35 |

TABLE 26

| Transcriptional profiles of cytokines in nasal turbinates 3 days post-challenge (fold changes) | | | | | |
|---|---|---|---|---|---|
| Group ID | IL-4 | IL-10 | IL-13 | TNF-alpha | IFN-gamma |
| Group A | 1.22 | 1.05 | 1.26 | 1.16 | 1.09 |
| Group B | 1.44 | 0.84 | 2.87 | 0.45 | 0.82 |

TABLE 27

| Transcriptional profiles of cytokines in right cranial lobe 14 days post-challenge (fold changes) | | | | | |
|---|---|---|---|---|---|
| Group ID | IL-4 | IL-10 | IL-13 | TNF-alpha | IFN-gamma |
| Group A | 1.07 | 1.25 | 1.57 | 1.34 | 1.24 |
| Group B | 1.37 | 0.92 | 2.22 | 0.77 | 0.61 |

TABLE 28

| Transcriptional profiles of cytokines in right caudal lobe 14 days post-challenge (fold changes) | | | | | |
|---|---|---|---|---|---|
| Group ID | IL-4 | IL-10 | IL-13 | TNF-alpha | IFN-gamma |
| Group A | 1.09 | 1.51 | 1.13 | 1.11 | 1.31 |
| Group B | 1.38 | 0.78 | 0.63 | 0.94 | 0.65 |

TABLE 29

| Transcriptional profiles of cytokines in nasal turbinates 14 days post-challenge (fold changes) | | | | | |
|---|---|---|---|---|---|
| Group ID | IL-4 | IL-10 | IL-13 | TNF-alpha | IFN-gamma |
| Group A | 1.46 | 1.45 | 1.43 | 1.41 | 1.46 |
| Group B | 0.73 | 0.72 | 1.40 | 0.65 | 0.57 |

Example 8: Evaluation of Potency and Protective Effect of Single Dose of Monovalent SARS-CoV-2 VLP Vaccine Construct Syrian golden hamsters (males, aged approximately 6-7 weeks old) were immunized with the monovalent triple modified SARS-CoV-2 VLP vaccine formulations shown below in Table 30. Immunizations took place only at day 21 via intramuscular injection. Serum was collected at day 0 and day 35 for subsequent analysis of neutralizing antibodies.

TABLE 30

| Monovalent SARS-CoV-2 VLP Vaccine Formulations | | | | |
|---|---|---|---|---|
| Group | Test Article | μg SARS-CoV-2 Spike/dose | Al+++ μg/dose | Dose volume/Animal (μL) |
| A | Saline control | N/A | N/A | 100 |
| B | SARS-CoV-2 Proline and Furin Cleavage Modified with TM/Cyt from VSV (SEQ ID NO: 24) | 1.4 | 125 | 100 |

Neutralizing antibodies were tested using the plaque reduction neutralization test (PRNT), as described in Example 7 for animals in Group B. The results are shown in Table 31 (average values shown).

TABLE 31

| Monovalent SARS-CoV-2 VLP Vaccine Neutralizing Antibodies | | | |
|---|---|---|---|
| Test Group | PRNT50 | PRNT80 | PRNT90 |
| Day 0 (before vaccination) | ** | — | — |
| Day 14 after vaccination Group B | 190 | 65 | 45 |

** below lowest dilution limit of PRNT (titer 40)

Compared to Group B of Example 7 (where animals received immunizations of 1 μg SARS-CoV-2 Spike/dose at day 0 and day 21), animals in Group B of this Example 8 (where animals received a single immunization of 1.4 μg SARS-CoV-2 Spike/dose at day 21) exhibited a higher serum neutralizing antibody response. These data support effective immunization with only a single dose of monovalent SARS-CoV-2 VLP vaccine.

Challenge studies were performed on day 42, as described in Example 7. Table 32 shows average body weights (grams) of animals before challenge.

TABLE 32

| Pre-Challenge Average Body Weights of Animals | | |
|---|---|---|
| Day | Group A | Group B |
| −1 | 113.8 | 116.6 |
| 7 | 131.7 | 134.6 |
| 10 | 136.3 | 139.9 |
| 22 | 154.5 | 157.6 |
| 28 | 160.4 | 164.0 |
| 35 | 168.4 | 172.0 |
| 42 | 174 | 178.5 |

Table 33 shows average body weights (grams) of animals post-challenge. As can be seen in Table 33, animals who received a single dose of vaccine lost less weight than those who received saline.

TABLE 33

| Post-Challenge Average Body Weights of Animals | | |
|---|---|---|
| Day | Group A | Group B |
| 1 | 172.1 | 174.6 |
| 2 | 168.3 | 172.6 |
| 3 | 165.3 | 173.4 |
| 4 | 163.7 | 168.5 |
| 5 | 159.1 | 168.5 |
| 6 | 155.7 | 168.5 |
| 7 | 154.7 | 170.1 |
| 8 | 157.5 | 171.7 |
| 9 | 162.9 | 173.8 |
| 10 | 164.4 | 174.0 |
| 11 | 166.6 | 175.3 |
| 12 | 169.4 | 177.1 |
| 13 | 172.0 | 177.8 |
| 14 | 173.5 | 178.9 |

Table 34 shows average % change in body weights of animals post-challenge.

TABLE 34

| Post-Challenge Average % Body Weight Change of Animals | | |
|---|---|---|
| Day | Group A | Group B |
| 1 | −1.09 | −2.24 |
| 2 | −3.29 | −3.30 |
| 3 | −5.08 | −2.90 |
| 4 | −6.51 | −2.10 |
| 5 | −9.14 | −2.15 |
| 6 | −11.11 | −2.11 |
| 7 | −11.64 | −1.22 |
| 8 | −10.05 | −0.31 |
| 9 | −7.03 | 0.87 |
| 10 | −6.22 | 0.93 |
| 11 | −4.94 | 1.63 |
| 12 | −3.35 | 2.69 |
| 13 | −1.89 | 3.09 |
| 14 | −1.00 | 3.74 |

These data demonstrate that a single immunization of 1.4 μg SARS-CoV-2 Spike/dose at day 21 was effective at preventing reduction in body weight following viral challenge, relative to control.

Example 9: Evaluation of Monovalent and Trivalent SARS-CoV-2 VLP Vaccine Constructs for Antibody Titers Against South African SARS-CoV-2 Variant Monovalent and trivalent SARS-CoV-2 VLP vaccine constructs which have the triple modified SARS-CoV-2 spike protein were assessed for production of antibodies against South African SARS-CoV-2 variant. Mice were immunized IP twice (on day 0 and day 21, as described in Example 6) with the SARS-CoV-2 VLP vaccine formulations shown below in Table 35. Animals were sacrificed 14 days after immunization and their serum was collected for subsequent analysis of anti-spike protein antibody titers.

The SARS-CoV-2 VLPs were formulated with aluminum phosphate adjuvant (Adjuphos®) as shown in Table 35.

TABLE 35

| SARS-CoV-2 VLP Vaccine Formulations | | | | |
|---|---|---|---|---|
| Group | Test Article | μg SARS-CoV-2 Spike/dose | Al+++ μg/dose | Dose volume/ Animal (μL) |
| 1 | Monovalent VLP - SARS-CoV-2 Proline and Furin Cleavage Modified with TM/Cyt from VSV (SEQ ID NO: 24) | 0.2 | 125 | 500 |
| 2 | Trivalent VLP (v4) - SARS-CoV-2 Spike Protein (described in Example 4) | 0.2 | 125 | 500 |

Antibody titers were assessed by ELISA, as described in Example 7, except that well plates were coated with SARS-COV-2 Spike Protein from South African variant. Antibody titers at 14 days after the second immunizations are shown in Table 36. Results shown are Geo means of the animals in each group.

TABLE 36

| SARS-CoV-2 VLP Vaccine Antibody Titres | | | |
|---|---|---|---|
| Group | Days post Second Vaccination | Anti- SARS-CoV-2 Spike Total IgG Binding Titers | Anti- SARS-CoV-2 African Variant Spike Total IgG Binding Titers |
| Group 1 | 14 | 128,850 | 121,511 |
| Group 2 | 14 | 215,232 | 211,080 |

These data demonstrate that mice injected with the monovalent and trivalent vaccines produced antibodies which bind to the South African variant of the Spike protein of SARS-CoV.

Example 10: Evaluation of Isotype Antibody Titer of Monovalent SARS-CoV-2 VLP Vaccine Construct In another study, the isotype of antibody titers were assessed, following immunization of mice with the vaccine constructs shown in Table 37.

TABLE 37

| SARS-CoV-2 VLP Vaccine Antibody Titres | | | | |
|---|---|---|---|---|
| Group | | μg SARS-CoV-2 Spike/dose | Al+++ μg/dose | Dose volume/ Animal (μL) |
| 1 | Monovalent Native SARS-Cov-2 (SEQ ID NO: 6) VLP | 0.2 | 125 | 500 |
| 2 | Stabilized Recombinant SARS-CoV2 spike protein (non-VLP) | 0.2 | 125 | 500 |

Mice were immunized IP twice (on day 0 and day 21, as described in Example 6). Animals were sacrificed 14 days after immunization and their serum was collected for subsequent analysis of anti-spike protein antibody titers.

As shown in Table 38, unexpectedly, when VLPs were formulated with the same amount/concentration of alum as recombinant spike protein, a balanced antibody response was seen (IgG1/IgG2b). Increased production of IgG2b is associated with a TH1 immune response, which is indicative of cell-mediated immunity. This indicates that the VLP construct resulted in elevated levels of IgG2b expression which is correlated to the more effective TH1 immune response.

TABLE 38

SARS-CoV-2 VLP Vaccine Antibody Titres

| Group | Days post second vaccination | Anti- SARS-CoV-2 Spike IgG1 Binding Titers | Anti- SARS-CoV-2 Spike IgG2b Binding Titers |
|---|---|---|---|
| Group 1 | 14 | 172,105 | 116,633 |
| Group 2 | 14 | 198,469 | 9,674 |

What is claimed is:

1. An immunogenic composition comprising a virus-like particle (VLP) comprising:

a first polypeptide that is a gag protein found in murine leukemia virus (MLV) having at least 95% identity with the amino acid sequence of SEQ ID NO:1;

at least one additional polypeptide which is a spike glycoprotein from a beta coronavirus; and a pharmaceutically acceptable carrier.

2. The immunogenic composition of claim 1 wherein the at least one additional polypeptide is a spike glycoprotein from SARS-CoV-2, SARS-CoV or MERS-CoV.

3. The immunogenic composition of claim 2 wherein the spike glycoprotein is a wild type protein.

4. The immunogenic composition of claim 2 wherein the spike glycoprotein is a modified protein.

5. The immunogenic composition of claim 2 comprising two spike glycoproteins.

6. The immunogenic composition of claim 2 comprising three spike glycoproteins.

7. The immunogenic composition of claim 4 wherein the modified protein has a deletion at a furin cleavage site.

8. The immunogenic composition of claim 7 wherein the modified protein has a transmembrane domain from VSV.

9. The immunogenic composition of claim 4 wherein the modified protein has a lysine residue and a valine residue replaced with proline residues.

10. The immunogenic composition of claim 9 wherein the modified protein has a transmembrane domain from VSV.

11. The immunogenic composition of claim 4 wherein the modified protein has a lysine residue and a valine residue replaced with proline residues and has a deletion at a furin cleavage site.

12. The immunogenic composition of claim 4 wherein the modified protein has a lysine residue and a valine residue replaced with proline residues and has a deletion at a furin cleavage site and has a transmembrane domain from VSV.

13. The immunogenic composition of claim 1, wherein the additional polypeptide has an amino acid sequence sequence of SEQ ID NO: 22.

14. The immunogenic composition of claim 1, further comprising an adjuvant.

15. The immunogenic composition of claim 14, wherein the adjuvant is selected from the group consisting of cytokines, gel-type adjuvants, microbial adjuvants, oil-emulsion and emulsifier-based adjuvants, particulate adjuvants, synthetic adjuvants, polymer adjuvants, and/or combinations thereof.

16. The immunogenic composition of claim 15, wherein the particulate adjuvant is an aluminum salt.

17. The immunogenic composition of claim 1, wherein the VLP is produced by co-transfecting a host cell with a first vector comprising a nucleotide sequence of SEQ ID NO: 3 and a second vector comprising a nucleotide sequence of SEQ ID NO: 6, 9, 12, 15, 18, 21, 24 or 27; and cultivating the host cell in a suitable medium under conditions allowing the expression of the proteins encoded by the vectors.

18. The immunogenic composition of claim 1, wherein the VLP is produced by co-transfecting a host cell with a first vector comprising a nucleotide sequence of SEQ ID NO: 3, a second vector comprising a nucleotide sequence of SEQ ID NO: 6; a third vector comprising a nucleotide sequence of SEQ ID NO: 9 and a fourth vector comprising a nucleotide sequence of SEQ ID NO: 12; and cultivating the host cell in a suitable medium under conditions allowing the expression of the proteins encoded by the vectors.

19. The immunogenic composition of claim 1, wherein the VLP is produced by co-transfecting a host cell with a first vector comprising a nucleotide sequence of SEQ ID NO: 3 and a second vector comprising a nucleotide sequence of SEQ ID NO: 25; and cultivating the host cell in a suitable medium under conditions allowing the expression of the proteins encoded by the vectors.

20. A method of treating a subject having or at risk for coronavirus infection, comprising administering to the subject the pharmaceutical composition of claim 1.

* * * * *